(12) United States Patent
Tamura et al.

(10) Patent No.: US 8,784,787 B2
(45) Date of Patent: Jul. 22, 2014

(54) CO-MODIFIED ORGANOPOLYSILOXANE

(75) Inventors: Seiki Tamura, Ichihara (JP); Tomohiro Iimura, Sodegaura (JP); Akito Hayashi, Ichihara (JP); Tatsuo Souda, Ichihara (JP); Haruhiko Furukawa, Chiba (JP)

(73) Assignee: Dow Corning Toray Co., Ltd., Chiyoda-Ku, Tokyo (JP)

( * ) Notice: Subject to any disclaimer, the term of this patent is extended or adjusted under 35 U.S.C. 154(b) by 0 days.

(21) Appl. No.: 13/503,455

(22) PCT Filed: Oct. 25, 2010

(86) PCT No.: PCT/JP2010/069249
§ 371 (c)(1),
(2), (4) Date: Jul. 10, 2012

(87) PCT Pub. No.: WO2011/049248
PCT Pub. Date: Apr. 28, 2011

(65) Prior Publication Data
US 2012/0269875 A1    Oct. 25, 2012

(30) Foreign Application Priority Data

Oct. 23, 2009   (JP) ................................ 2009-244975
Oct. 25, 2010   (WO) .................. PCT/JP2010/069249

(51) Int. Cl.
| | | |
|---|---|---|
| *A61K 8/25* | (2006.01) | |
| *C07F 7/08* | (2006.01) | |
| *C08G 77/46* | (2006.01) | |
| *C08L 83/16* | (2006.01) | |
| *A61Q 19/00* | (2006.01) | |
| *C08G 77/50* | (2006.01) | |
| *A61K 8/06* | (2006.01) | |
| *A61K 8/04* | (2006.01) | |
| *C09C 1/30* | (2006.01) | |
| *A61K 8/02* | (2006.01) | |
| *A61K 8/894* | (2006.01) | |
| *C09C 3/12* | (2006.01) | |
| *C08G 77/38* | (2006.01) | |
| *A61Q 1/10* | (2006.01) | |
| *A61Q 1/02* | (2006.01) | |
| *A61Q 1/12* | (2006.01) | |
| *A61Q 1/08* | (2006.01) | |
| *A61Q 17/04* | (2006.01) | |
| *A61Q 15/00* | (2006.01) | |
| *A61Q 1/04* | (2006.01) | |

(52) U.S. Cl.
CPC ... *C09C 3/12* (2013.01); *A61Q 1/10* (2013.01); *C08G 77/46* (2013.01); *C08L 83/16* (2013.01); *A61Q 19/00* (2013.01); *C08G 77/50* (2013.01); *A61Q 1/02* (2013.01); *A61K 8/06* (2013.01); *A61Q 1/12* (2013.01); *A61Q 1/08* (2013.01); *A61K 8/044* (2013.01); *A61K 2800/10* (2013.01); *C09C 1/3081* (2013.01); *A61K 8/022* (2013.01); *A61Q 17/04* (2013.01); *A61K 8/894* (2013.01); *A61Q 15/00* (2013.01); *C08G 77/38* (2013.01); *A61Q 1/04* (2013.01)
USPC .......................... 424/70.19; 556/439; 556/444

(58) Field of Classification Search
None
See application file for complete search history.

(56) References Cited

U.S. PATENT DOCUMENTS

| | | |
|---|---|---|
| 4,431,789 A | 2/1984 | Okazaki et al. |
| 4,616,076 A | 10/1986 | Ona et al. |
| 4,631,208 A | 12/1986 | Westall |
| 4,698,178 A | 10/1987 | Huttinger et al. |
| 5,144,054 A | 9/1992 | Shioya et al. |
| 5,472,686 A | 12/1995 | Tsubaki et al. |
| 5,484,950 A | 1/1996 | Crivello |
| 5,654,362 A | 8/1997 | Schulz, Jr. et al. |
| 5,660,819 A | 8/1997 | Tsubaki et al. |
| 5,874,069 A | 2/1999 | Mendolia et al. |
| 5,889,108 A | 3/1999 | Zhang |
| 5,919,441 A | 7/1999 | Mendolia et al. |
| 5,929,163 A | 7/1999 | Harashima |
| 5,981,680 A | 11/1999 | Petroff et al. |
| 6,168,782 B1 | 1/2001 | Lin et al. |
| 6,184,407 B1 | 2/2001 | Yoshitake et al. |
| 6,534,072 B2 | 3/2003 | Mondet et al. |
| 6,576,623 B1 | 6/2003 | Nakanishi et al. |
| 6,660,281 B1 | 12/2003 | Nakanishi et al. |
| 7,001,971 B2 | 2/2006 | Nakanishi |
| 7,482,419 B2 | 1/2009 | Caprasse et al. |
| 7,507,775 B2 | 3/2009 | Leatherman et al. |
| 7,601,680 B2 | 10/2009 | Wang et al. |

(Continued)

FOREIGN PATENT DOCUMENTS

| | | |
|---|---|---|
| CA | 2291284 A1 | 5/2000 |
| EP | 1031592 A2 | 8/2000 |

(Continued)

OTHER PUBLICATIONS

English language abstract for JP 2001-039819 extracted from the espacenet.com database on Jul. 17, 2012, 29 pages.

(Continued)

*Primary Examiner* — Robert A Wax
*Assistant Examiner* — H. Sarah Park
(74) *Attorney, Agent, or Firm* — Howard & Howard Attorneys PLLC

(57) ABSTRACT

A novel organopolysiloxane having a hydrophilic group, which can be produced easily and is not susceptible to two-phase separation, sedimentation of unreacted materials or the like after production, while being chemically stable and excellently practical, is disclosed. A method for producing the organopolysiloxane; and uses of the organopolysiloxane are also disclosed. The organopolysiloxane is a co-modified organopolysiloxane which has a group having a siloxane dendron structure and a hydrophilic group.

25 Claims, No Drawings

(56) References Cited

U.S. PATENT DOCUMENTS

| | | |
|---|---|---|
| 7,612,051 B2 | 11/2009 | Kamei et al. |
| 7,655,744 B2 | 2/2010 | Miyanaga |
| 7,771,709 B2 | 8/2010 | Nakanishi et al. |
| 7,998,903 B2 | 8/2011 | Nakanishi et al. |
| 8,034,891 B2 | 10/2011 | Okawa |
| 2005/0261133 A1 | 11/2005 | Nakanishi et al. |
| 2009/0203802 A1 | 8/2009 | Kamei et al. |
| 2010/0190871 A1 | 7/2010 | Araki et al. |
| 2011/0182846 A1 | 7/2011 | Ikeda et al. |
| 2012/0269747 A1 | 10/2012 | Iimura et al. |
| 2012/0269748 A1 | 10/2012 | Tamura et al. |

FOREIGN PATENT DOCUMENTS

| | | | |
|---|---|---|---|
| EP | 2014701 A2 | 1/2009 | |
| EP | 2174985 A1 | 4/2010 | |
| EP | 2180028 A1 | 4/2010 | |
| JP | 50-004199 A | 1/1975 | |
| JP | 57-139123 A | 8/1982 | |
| JP | 57-149290 A | 9/1982 | |
| JP | 61-090732 A | 5/1986 | |
| JP | 61-123635 A | 6/1986 | |
| JP | 61-127733 A | 6/1986 | |
| JP | 61-293903 A | 12/1986 | |
| JP | 61-293904 A | 12/1986 | |
| JP | 62-034039 B | 7/1987 | |
| JP | 62-187406 A | 8/1987 | |
| JP | 62-195389 A | 8/1987 | |
| JP | 62-215510 A | 9/1987 | |
| JP | 62-216635 A | 9/1987 | |
| JP | 4108795 A | 4/1992 | |
| JP | 4134013 A | 5/1992 | |
| JP | 04-211605 A | 8/1992 | |
| JP | 04-234307 A | 8/1992 | |
| JP | 05-112424 A | 5/1993 | |
| JP | 05-163436 A | 6/1993 | |
| JP | 05-186596 A | 7/1993 | |
| JP | 05-311076 A | 11/1993 | |
| JP | 06-157236 A | 6/1994 | |
| JP | 06-305933 A | 11/1994 | |
| JP | 6089147 B | 11/1994 | |
| JP | 07-025728 A | 1/1995 | |
| JP | 07-033622 A | 2/1995 | |
| JP | 07-100358 A | 4/1995 | |
| JP | 07-187945 A | 7/1995 | |
| JP | 08-217626 A | 8/1996 | |
| JP | 08-268831 A | 10/1996 | |
| JP | 08-268832 A | 10/1996 | |
| JP | 02-583412 B2 | 2/1997 | |
| JP | 09-071504 A | 3/1997 | |
| JP | 09-194323 A | 7/1997 | |
| JP | 09-194594 A | 7/1997 | |
| JP | 02-719303 B2 | 2/1998 | |
| JP | 10-167946 A | 6/1998 | |
| JP | 10-245317 A | 9/1998 | |
| JP | 10-310504 A | 11/1998 | |
| JP | 10-310505 A | 11/1998 | |
| JP | 10-310506 A | 11/1998 | |
| JP | 10-310507 A | 11/1998 | |
| JP | 10-310508 A | 11/1998 | |
| JP | 10-310509 A | 11/1998 | |
| JP | 10-316536 A | 12/1998 | |
| JP | 11-049957 A | 2/1999 | |
| JP | 2000-063225 A | 2/2000 | |
| JP | 2000-072784 A | 3/2000 | |
| JP | 2000-239390 A | 9/2000 | |
| JP | 2001-011281 A | 1/2001 | |
| JP | 2001-039819 A | 2/2001 | |
| JP | 2001-072891 A | 3/2001 | |
| JP | 2001-316473 A | 11/2001 | |
| JP | 2002-038013 A | 2/2002 | |
| JP | 2002-179797 A | 6/2002 | |
| JP | 2002-179798 A | 6/2002 | |
| JP | 2004-169015 A | 6/2004 | |
| JP | 2004-182680 A | 7/2004 | |
| JP | 2004-231608 A | 8/2004 | |
| JP | 2004-339244 A | 12/2004 | |
| JP | 2005-042097 A | 2/2005 | |
| JP | 2005-089494 A | 4/2005 | |
| JP | 2005-194523 A | 7/2005 | |
| JP | 2005-344076 A | 12/2005 | |
| JP | 2006-218472 A | 8/2006 | |
| JP | 2007-532754 A | 11/2007 | |
| JP | 2009-511710 A | 3/2009 | |
| JP | 2009-511712 A | 3/2009 | |
| WO | WO 03/041664 A1 | 5/2003 | |
| WO | WO 03/075864 A1 | 9/2003 | |
| WO | WO 2007/135771 A1 | 11/2007 | |
| WO | WO 2009/022621 A1 | 2/2009 | |
| WO | WO 2009/025146 A1 | 2/2009 | |

OTHER PUBLICATIONS

English language abstract for JP 2001-072891 extracted from the espacenet.com database on Jul. 17, 2012, 23 pages.

English language abstract and machine-assisted translation for JP 2001-316473 extracted from the PAJ database on Jul. 26, 2012, 45 pages.

English language abstract for JP 2002-038013 extracted from the espacenet.com database on Jul. 16, 2012, 19 pages.

English language abstract and machine-assisted translation for JP 2002-179797 extracted from PAJ database on Jul. 13, 2012, 67 pages.

English language abstract for JP 2002-179798 extracted from the espacenet.com database on Jul. 12, 2012, 27 pages.

English language abstract for JP 2004-169015 extracted from the espacenet.com database on Jul. 16, 2012, 43 pages.

English language abstract and machine-assisted translation for JP 2004-182680 extracted from the PAJ database on Jul. 26, 2012, 96 pages.

English language abstract and machine-assisted translation for JP 2004-231608 extracted from the PAJ database on Jul. 26, 2012, 75 pages.

English language abstract for JP 2004-339244 extracted from the espacenet.com database on Jul. 12, 2012, 45 pages.

English language abstract for JP 2005-042097 extracted from the espacenet.com database on Jul. 12, 2012, 59 pages.

English language abstract and machine-assisted translation for JP 2005-089494 extracted from the PAJ database on Jul. 12, 2012, 47 pages.

English language abstract and machine-assisted translation for JP 2005-194523 extracted from the PAJ database on Jul. 26, 2012, 53 pages.

English language abstract for JP 2005-344076 extracted from the espacenet.com database on Jul. 26, 2012, 18 pages.

English language abstract not available for JP 2007-532754; however, see English equivalent US 7,482,419. Original document extracted from espacenet.com database on Jul. 16, 2012, 39 pages.

English language abstract not available for JP 2009-511710; however, see English equivalent US 7,507,775. Orginal document extracted from the espacenet.com database on Jul. 26, 2012, 29 pages.

English language abstract not available for JP 2009-511712; however, see English equivalent US 7,601,680, Original document extracted from the espacenet.com database on Jul. 26, 2012, 29 pages.

English language abstract for WO 03/041664 extracted from the espacenet.com database on Jul. 26, 2012, 71 pages.

English language abstract for WO 03/075864 extracted from the espacenet.com database on Jul. 16, 2012, 38 pages.

English language abstract for WO 2007/135771 extracted from the espacenet.com database on Jul. 17, 2012, 160 pages.

English language abstract for WO 2009/022621 extracted from the espacenet.com database on Jul. 26, 2012, 53 pages.

English language abstract for WO 2009/025146 extracted from the espacenet.com database on Jul. 26, 2012, 48 pages.

English language abstract for JP 62-195389 extracted from the espacenet.com database on Nov. 26, 2012, 5 pages.

(56) References Cited

OTHER PUBLICATIONS

English language abstract and machine-assisted English translation for JP 10-167946 extracted from the PAJ database on Nov. 26, 2012, 27 pages.
International Search Report for Application No. PCT/JP2010/069237 dated Jan. 11, 2011, 6 pages.
International Search Report for Application No. PCT/JP2010/069249 dated Jan. 11, 2011, 6 pages.
International Search Report for Application No. PCT/JP2010/069248 dated Jan. 11, 2011, 4 pages.
English language abstract and machine-assisted English translation for JP 09-194594 extracted from the PAJ database on Nov. 26, 2012, 56 pages.
English language abstract for JP 02-583412 extracted from the espacenet.com and machine-assisted translation extracted from the PAJ database on Jul. 12, 2012, 22 pages.
English language abstract for JP 02-719303 extracted from the espacenet.com database and machine-assisted translation extracted from the PAJ database on Jul. 16, 2012, 24 pages.
English language abstract for JP 4134013 extracted from the espacenet.com database on Nov. 26, 2012, 19 pages.
English language abstract for JP 04-211605 extracted from the espacenet.com database on Jul. 26, 2012, 8 pages.
English language abstract for JP 04-234307 extracted from the espacenet.com database on Jul. 26, 2012, 9 pages.
English language abstract and machine-assisted translation for JP 05-112424 extracted from the PAJ database on Jul. 16, 2012, 80 pages.
English language abstract and machine-assisted translation for JP 05-163436 extracted from the PAJ database on Jul. 26, 2012, 26 pages.
English language abstract and machine-assisted translation for JP 05-186596 extracted from the PAJ database on Jul. 12, 2012, 52 pages.
English language abstract for JP 05-311076 extracted from the espacenet.com database on Jul. 26, 2012, 14 pages.
English language abstract for JP 62-034039 extracted from the espacenet.com database on Nov. 26, 2012, 14 pages.
English language abstract and machine-assisted translation for JP 06-157236 extracted from the PAJ database on Jul. 13, 2012, 26 pages.
English language abstract and machine-assisted translation for JP 06-305933 extracted from the PAJ database on Jul. 16, 2012, 36 pages.
English language abstract and machine-assisted translation for JP 07-025728 extracted from the PAJ database on Jul. 16, 2012, 39 pages.
English language abstract and machine-assisted translation for JP 07-033622 extracted from the PAJ database on Jul. 16, 2012, 40 pages.
English language abstract and machine-assisted translation for JP 07-100358 extracted from the PAJ database on Jul. 26, 2012, 29 pages.
English language abstract and machine-assisted translation for JP 07-187945 extracted from the PAJ database on Jul. 13, 2012, 56 pages.
English language abstract for JP 2006218472 extracted from the espacenet.com database on Nov. 26, 2012, 14 pages.
English language abstract and machine-assisted translation for JP 08-217626 extracted from the PAJ database on Jul. 26, 2012, 53 pages.
English language abstract and machine-assisted translation for JP 08-268831 extracted from the PAJ database on Jul. 26, 2012, 35 pages.
English language abstract and machine-assisted translation for JP 08-268832 extracted from the PAJ database on Jul. 26, 2012, 47 pages.
English language abstract and machine-assisted translation for JP 09-071504 extracted from the PAJ database on Jul. 13, 2012, 29 pages.
English language abstract and machine-assisted translation for JP 09-194323 extracted from the PAJ database on Jul. 26, 2012, 31 pages.
English language abstract and machine-assisted translation for JP 10-245317 extracted from the PAJ database on Jul. 26, 2012, 39 pages.
English language abstract and machine-assisted translation for JP 10-310504 extracted from the PAJ database on Jul. 13, 2012, 33 pages.
English language abstract and machine-assisted translation for JP 10-310505 extracted from the PAJ database on Jul. 13, 2012, 28 pages.
English language abstract and machine-assisted translation for JP 10-310506 extracted from the PAJ database on Jul. 13, 2012, 29 pages.
English language abstract and machine-assisted translation for JP 10-310507 extracted from the PAJ database on Jul. 13, 2012, 30 pages.
English language abstract and machine-assisted translation for JP 10-310508 extracted from the PAJ database on Jul. 13, 2012, 33 pages.
English language abstract and machine-assisted translation for JP 10-310509 extracted from the PAJ database on Jul. 13, 2012, 33 pages.
English language abstract and machine-assisted translation for JP 10-316536 extracted from the PAJ database on Jul. 16, 2012, 29 pages.
English language abstract for JP 11-049957 extracted from the espacenet.com database on Jul. 16, 2012, 9 pages.
English language abstract for JP 57-149290 extracted from the espacenet.com database on Jul. 17, 2012, 12 pages.
English language abstract not available for JP 61-090732; however, see English language equivalent US 4,698,178. Original Document extracted-from the espacenet.com database on Jul. 13, 2012, 9 pages.
English language abstract not available for JP 61-123635; however, see English language equivalent US 4,631,208. Original Document extracted from the espacenet.com database on Jul. 26, 2012, 7 pages.
English language abstract for JP 61-127733 extracted from the espacenet.com database on Jul. 26, 2012, 12 pages.
English language abstract for JP 61-293903 extracted from the espacenet.com database on Jul. 12, 2012, 13 pages.
English language abstract for JP 61-293904 extracted from the espacenet.com database on Jul. 12, 2012, 15 pages.
English language abstract and machine-assisted English Translation for JP 6089147 extracted from the espacenet.com database on Nov. 26, 2012, 54 pages.
English language abstract for JP 62-187406 extracted from the espacenet.com database on Jul. 12, 2012, 11 pages.
English language abstract for JP 62-215510 extracted from the espacenet.com database on Jul. 12, 2012, 16 pages.
English language abstract for JP 62-216635 extracted from the espacenet.com database on Jul. 12, 2012, 13 pages.
English language abstract and machine-assisted translation for JP 2000-063225 extracted from the PAJ database on Jul. 16, 2012, 61 pages.
English language abstract for JP 2000-072784 extracted from the espacenet.com database on Jul. 17, 2012, 13 pages.
English language abstract for JP 2000-239390 extracted from the espacenet.com database on Jul. 17, 2012, 14 pages.
English language abstract for JP 2001-011281 extracted from the espacenet.com database on Jul. 16, 2012, 14 pages.
English language abstract for JP 4108795 extracted from the espacenet.com database on Nov. 26, 2012, 21 pages.
Supplementary European Search Report for Application No. EP 10 82 5093 dated May 16, 2013; 2 pages.
Supplementary European Search Report for Application No. EP 10 82 5094 completed on Dec. 11, 2013, 2 pages.

CO-MODIFIED ORGANOPOLYSILOXANE

RELATED APPLICATIONS

This application claims priority to and all the advantages of International Patent Application No. PCT/JP2010/069249, filed on Oct. 25, 2010, which claims priority to Japanese Patent Application No. JP2009-244975, filed on Oct. 23, 2009.

TECHNICAL FIELD

The present invention relates to a novel co-modified organopolysiloxane having a group with a siloxane dendron structure and a hydrophilic group, and a method for producing the same; a surfactant and a powder treatment agent comprising the co-modified organopolysiloxane; and a cosmetic composition comprising the co-modified organopolysiloxane. Novel co-modified silicone having a siloxane dendron structure has a variety of functional aspects, one of which is an aspect as an oil agent that imparts superior feel and texture when compounded in a cosmetic composition that includes water. Another aspect is that of a superior emulsification aid or an emulsifier by which various oil agents can be stably emulsified. Yet another aspect is that of a superior dispersing agent or powder surface treatment agent for stably dispersing/compounding a powder in a cosmetic composition.

BACKGROUND ART

Conventionally, various modified silicone compounds are known as silicones having hydrophilic groups and, conventionally polyether-modified silicones have been used as non-ionic silicones. Other than these, (poly)glycerin-modified silicones (Patent Documents 1 to 9), a sugar and polysaccharide-modified silicone compound (Patent Document 10), and the like have been proposed.

Polyether-modified silicones are ordinarily produced by adding a polyether having a reactive unsaturated group to an organohydrogensiloxane, and are beneficial in that these have a structural design with a high degree of freedom. For this reason, compatibility between a copolymer that is a reaction product and the unreacted polyether ordinarily included in the modified silicone is comparatively excellent and, therefore, in many cases, even when in a form of a mixture, polyether-modified silicones do not separate into two phases.

In contrast, silicones modified by polyglycerine, sugars, or polysaccharides have a low degree of freedom with respect to structural design, and this leads to the problem of the scope of use not being able to be expanded. Such polyhydric alcohol-modified silicones are ordinarily produced by adding a polyhydric alcohol derivative having a reactive unsaturated group to an organohydrogensiloxane. However, in many cases, compatibility between the remaining polyhydric alcohol derivative and the copolymer that is a reaction product is low, and such silicones separate into two phases within a short period of time following production.

Additionally, compatibility between organohydrogensiloxanes and such polyhydric alcohol derivatives is fundamentally low and, therefore, when the design is such that molecular weight of the copolymer exceeds about 5,000, the addition reaction does not complete even if a solvent is added, thus, in many cases, leading to difficulties in producing the target product. Even when the molecular weight is about 3,000, the unreacted product gradually separates or precipitates. This necessitates a task of removing the separated or precipitated material and is a large obstruction from the perspective of production efficiency as well. (Patent Documents 1, 6, 9, and 10)

Even when a compound is used in which a form of the hydroxyl group is protected as the polyhydric alcohol derivative, deprotection is required following completion of the reaction and, therefore, the problem of separation into two phases cannot be avoided. Additionally, heavy acidizing conditions must be introduced due to the deprotection in this method, and the desired product cannot be obtained in an easily reproducible manner as a result of disconnections of the silicone backbone occurring. (Patent Document 3)

Recently, Patent Document 8 has proposed a novel alternating copolymer of organopolysiloxane with polyglycerine derivative, and suggests that a high molecular weight polyglycerine-modified silicone can be obtained without the problem of white turbidness, and the like, caused by the unreacted raw material occurring. However, it is clear from the chemical structure that this compound has a hydrophilic group portion incorporated on its backbone. As a result, this copolymer has properties completely different that those of conventional general-use hydrophilic silicones such as polyether-modified silicone and the like and, therefore, a high level of technical skill is necessary to stably compound this copolymer in delicate formulations such as cosmetic products and the like, leading to the problem of the field of use being limited.

Patent Document 7 proposes a method for producing a branched polyglycerol-modified silicone obtained by adding/graft polymerizing a silicone having at least one functional group selected from the group consisting of hydroxy groups, carboxy groups, amino groups, imino groups, mercapto groups, and epoxy groups, with 2,3-epoxy-1-propanol in the presence of an acidic or basic catalyst. However, with this method, the siloxane backbone disconnects during the graft polymerization, which results in two or more components having different properties being prone to be produced as the copolymer. This leads to a multitude of problems related to product quality, refining processes, and the like.

For these reasons, there are few practical products among the conventional polyhydric alcohol-modified silicones, and, to-date, variation on chemical structure has been limited. Thus, there is a need for the development of a stable polyhydric alcohol-modified silicone that is easy to produce, and in which little separation into two phases and/or sedimentation or the like of the unreacted raw material occurs after production; and a method for producing said polyhydric alcohol-modified silicone.

Next, considering the interaction between various cosmetic raw materials and these silicones that have a hydrophilic group, it is understood first and foremost that various oil agents are compounded in cosmetic compositions and that each type of oil composition has strengths and weaknesses.

For example, silicone oils have strengths of a light feel and superior spreadability, superior water repellency, and a high degree of safety, but lack moisturizing feel. Moreover, problems exist such as that silicone oils with high volatility leave a dry feeling after application and silicone oils with low volatility impart an unnatural feeling of residue on the skin. In either case, it is difficult to attain a natural skin feel after application.

On the other hand, while ester oils have a problem in that they feel heavy and oily when applying, they have the strength of providing a natural skin feel after application. However, due to its high degree of oiliness, cosmetic compositions comprising ester oils have problems attaining moisturizing feel after application or, in other words, providing silky-smooth moisturization when applying and maintaining that feel thereafter.

Additionally, hydrocarbon oils have the strengths of being easily compounded in a cosmetic composition and spreading well, and hydrocarbon oils with high volatility provide a refreshing, light feel when applied. However, hydrocarbon oils are prone to break down sebum, causing the skin to whiten after application, which, in some cases, leads to a feeling of pulling or itchiness due to desiccation, and irritation. Hydrocarbon oils with low volatility have problems of feeling heavy when applying and feeling extremely oily.

In many cases, combinations of these oil agents are used in cosmetic composition formulations, whereby strengths thereof are promoted and weaknesses thereof are compensated for and, by further adding water, value as a cosmetic composition from the perspectives of skin care and the like due to feel and hydration increases. This is because oiliness is suppressed by the effects of water and, compared to cases where water is not added, and a clean skin feeling can easily be obtained.

Ordinarily, emulsification using a surfactant is performed in order to stably compound an oil agent and water in a cosmetic composition. From the perspectives of being difficult to obtain a stable emulsion using an organic surfactant and the sensation during use of the cosmetic composition being easily negatively affected when the oil agent system comprises a silicone oil, research into a silicone-based surfactant that is beneficial in terms of feel is actively being carried out.

Patent Documents 11 to 15 propose a method in which a polyoxyalkylene-modified organopolysiloxane (a polyether-modified silicone) having good compatibility with silicone oil is used as a surfactant for a water-in-oil emulsion. However, in some cases, emulsion stability of the polyether-modified silicone in mixed oil agent systems and the like is insufficient, and care is needed when formulating the cosmetic composition.

A method in which an organopolysiloxane (alkyl/polyether co-modified silicone) having both a long chain alkyl group and a polyoxyalkylene group is used as an emulsifier (see Patent Document 16), and a method in which a silicone branched polyether-modified silicone compound (e.g. an alkyl/linear siloxane branch/polyether co-modified silicone) is used as an emulsifier (see Patent Document 17) are proposed as methods to solve these problems.

Other examples of non-ionic silicone-based surfactants that have been proposed include various glycerin-modified silicones, and it is suggested that theses surfactants improve the squeaky feel and poor compatibility on the skin unique to silicone. Examples of the oil agent are recited in Patent Documents 18 and 19 and in Patent Documents 20 to 25, which are related to fluorine alkyl co-modification; examples of the surfactant are described in Patent Documents 1, 4, 5, and the like, in which glycerin-modified silicone compounds are recited; and examples of cosmetic compositions thereof are recited in Patent Documents 26 to 28. Recently, a silicone branched polyhydric alcohol-modified silicone (e.g. an alkyl/linear siloxane branch/polyglycerine co-modified silicone) has been proposed, and it is suggested that a cosmetic composition comprising this silicone has superior adhesion to the skin, is not sticky, has a clean feel after application, and has superior emulsion stability. (Patent Document 6)

All of these techniques take the approach of attempting to increase functionality as an oil or surfactant by introducing a modified group for the purpose of improving compatibility with the oil agent system in the structure of the silicone. Thus, the standpoint of taking advantage of the compounding effect of water described above is not prominent, and a cosmetic composition having excellent effects of providing the skin with silky-smooth moisture, and maintaining that feel thereafter has not been obtained. That is, the effect of suppressing the oiliness of conventional silicone-based surfactants is insufficient.

On the other hand, titanium oxide, zinc oxide, red iron oxide, and other exemplary pigments, and powders such as mica, sericite, and the like are widely used as basic cosmetic products, sunscreens, nail colors, nail coatings, foundations, mascaras, eye liners, and similar cosmetic compositions. However, with untreated powders, agglomeration due to electric charge or polarity of the powder surface, trace amounts of impurities, and the like occurs easily and, therefore, generally powders that have been surface treated with various treatment agents are used for the purpose enhancing the dispersibility and stability of the powder, and improving feel, water resistance, sebum resistance and the like when used in a cosmetic composition.

Known examples of such treatments include lipophilization treatments using an oil agent, a metal soap, or the like; hydrophilization treatments using a surfactant, water-soluble polymer, or the like; treatments using silicone compounds; silica treatments; alumina treatments; and the like. Particularly, in recent years, there have been many cases where treatment using a silicone compound having a reactive portion in the molecule have been performed. This is because of the following reasons. This treatment forms a chemical bond with the surface of the powder and, therefore, it is useful not only for improving the surface of the powder but, at the same time, also for sealing surface activity; treatment is carried out reliably; the treatment agent will not separate from the powder surface, even when used on a solvent-based cosmetic composition; and efficiency is good because changes in properties caused by treatment can be reduced.

For example, Patent Document 29 discloses a method of surface treating in which 12 to 60 parts by weight of methylhydrogenpolysiloxane are used per 100 parts by weight of a powder. However, in this method, unreacted Si—H groups still remain even after the treating of the surface of the powder and, therefore, there is a problem when this powder is compounded in a cosmetic composition because hydrogen gas is produced due to the liquid conditions of the powder.

Patent Document 30 proposes a method in which a polyether-modified silicone having an HLB value of greater than or equal to 2 and less than or equal to 7 is used as a dispersing aid for a powder. However, while this technique is effective when the oil agent is only a silicone system, in cases of a mixed oil agent system comprising an organic system, dispersion stability may be insufficient.

Patent Document 31 recites an improved powder treated using a polyglycerine-modified silicone. However, with this technology, dispersibility in oil agents is insufficient, the treated powder is prone to separation over time, and redispersibility is poor, which may lead to worsening of the quality and feel after application of the cosmetic composition.

Patent Document 32 describes a powder composition that is treated using a modified silicone that has an alcoholic OH group, and proposes an example of a triglycerin variant. However, in this case, there are the following problems. It is necessary to addition react a triglycerin derivative in which a hydroxyl group is protected by acetal with silicone and, thereafter, perform a reaction to remove the acetone. The production process is lengthened and reaction conditions of the deprotection group following the addition reaction are severe.

The desired product cannot be obtained in an easily reproducible manner as a result of disconnections of the silicone backbone occurring.

Patent Document 33 recites a powder composition that is treated using a silicone branched polyglycerine-modified silicone (e.g. an alkyl/linear siloxane branch/polyglycerine co-modified silicone) and a powder in oil dispersion comprising the same. With this technology, when a method is used in which a powder is dispersed in the oil agent dispersing medium using the modified silicone, compared with the same method using the polyether-modified silicone described above, a stable powder in oil dispersion can be obtained. Additionally, dispersion stability in mixed oil agent systems is also improved. However, when using a method in which the powder composition, obtained by treating the powder surface using the modified silicone, is dispersed in the oil agent dispersing medium, the powder tends to easily agglomerate and/or precipitate.

Patent Document 34 recites a powder dispersion stabilizer comprising a two-end silicone modified glycerin and a powder dispersion composition in which the powder dispersion stabilizer is compounded. However, while this dispersion stabilizer displays superior effects when the oil agent is only a silicone system, there is a problem in that when the oil system is a mixed oil system comprising an organic system, the effects are insignificant.

In other words, with conventional technology related to powder dispersion and surface treatment, dispersion stability in mixed oil agent systems is insufficient. Additionally, from the perspective of providing a superior powder in oil dispersion with stability such that the powder does not agglomerate or precipitate after preparation of a powder composition obtained by treating a powder surface using a treatment agent, even in cases where a method is used in which the powder composition is dispersed in an oil agent dispersing medium, the degree of achievement of conventional technology is insufficient.

Furthermore, cosmetic compositions that have a small water content such as oil-based cosmetic compositions and the like generally have the following problems. 1) Easily produces discomfort related to such points as being extremely oily, being sticky or heavy, leaving a heavy coated feeling, and the like. 2) Moreover, lipsticks, eye shadows, eye liners, oil-based foundations, and similar oil-based makeup cosmetic compositions have poor cosmetic retainability after application to skin, and easily transfer or soak into clothing.

Compounding a silicone oil having superior spreadability, smoothness, and light feel is effective in mitigating the prominent oiliness of 1). However, when compounding a silicone oil, new problems arise such as an unnatural feeling on the skin unique to silicone oil, insufficient moisturizing feel, and the like. Moreover, there is a tendency for the feel of adherence to the skin, which is a characteristic of oil-based cosmetic compositions, to be inhibited.

Thus, from the perspective of improving the negative aspects of silicone oil as an oil agent, a cosmetic composition comprising a glycerin-modified silicone compound as an oil agent (Patent Document 18), an oil-based cosmetic composition comprising a polyglycerine-modified silicone compound having an alkyl group with 1 to 10 carbons as an oil agent component (Patent Document 19), an oil-based cosmetic composition comprising a polyglycerine-modified silicone compound including a long chain alkyl group having from 11 to 30 carbons (Patent Document 35), and similar development has been carried out.

On the other hand, with regards to the problem of cosmetic retainability described in 2), an oil-based solid cosmetic composition comprising one or at least two types of alkyl glyceryl ether-modified silicones (Patent Document 36), an oil-based cosmetic composition comprising a polyoxyalkylene-modified silicone and an alkyl glyceryl ether-modified silicone (Patent Document 37), Patent Document 38, and similar research has been performed. It is suggested that, after application, moisture is supplied into the applied layers of these oil-based cosmetic compositions from the skin, exhalation, or the like, and the viscosity of the alkyl glyceryl ether-modified silicone in the applied layer increases, leading to an increase in the viscosity of the applied layer and, thus, greater retainability of the cosmetic.

However, with these technologies, oiliness remains prominent and it has not been possible to obtain an oil-based cosmetic composition that can impart a natural feeling on the skin without discomfort and sufficient moisturizing feel after application (a cosmetic composition that is substantially water-free or has a small water content).

Patent Document 1: Japanese Patent Publication No. S-62-34039

Patent Document 2: Japanese Unexamined Patent Application Publication No. 5-62-195389 (Japanese Patent No. 2583412)

Patent Document 3: Japanese Patent Publication No. H-06-089147 (Japanese Patent No. 1956013)

Patent Document 4: Japanese Patent No. 2613124 (Japanese Unexamined Patent Application Publication No. JP04-108795)

Patent Document 5: Japanese Patent No. 2844453 (Japanese Unexamined Patent Application Publication No. JP09-194594)

Patent Document 6: Japanese Patent No. 3976226 (Japanese Unexamined Patent Application Publication No. 2002-179798)

Patent Document 7: Japanese Unexamined Patent Application Publication No. 2004-339244

Patent Document 8: Japanese Unexamined Patent Application Publication No. 2005-042097

Patent Document 9: Japanese Unexamined Patent Application Publication No. 2005-089494

Patent Document 10: Japanese Unexamined Patent Application Publication No. H-05-186596

Patent Document 11: Japanese Unexamined Patent Application Publication No. S-61-293903

Patent Document 12: Japanese Unexamined Patent Application Publication No. S-61-293904

Patent Document 13: Japanese Unexamined Patent Application Publication No. S-62-187406

Patent Document 14: Japanese Unexamined Patent Application Publication No. S-62-215510

Patent Document 15: Japanese Unexamined Patent Application Publication No. S-62-216635

Patent Document 16: Japanese Unexamined Patent Application Publication No. S-61-90732

Patent Document 17: Japanese Unexamined Patent Application Publication No. 2002-179797

Patent Document 18: Japanese Unexamined Patent Application Publication No. H-06-157236 (Japanese Patent No. 3389271)

Patent Document 19: Japanese Unexamined Patent Application Publication No. H-09-71504 (Japanese Patent No. 3513682)

Patent Document 20: Japanese Unexamined Patent Application Publication No. H-10-310504

Patent Document 21: Japanese Unexamined Patent Application Publication No. H-10-310505

Patent Document 22: Japanese Unexamined Patent Application Publication No. H-10-310506

Patent Document 23: Japanese Unexamined Patent Application Publication No. H-10-310507

Patent Document 24: Japanese Unexamined Patent Application Publication No. H-10-310508

Patent Document 25: Japanese Unexamined Patent Application Publication No. H-10-310509

Patent Document 26: Japanese Patent Publication No. H-08-22811

Patent Document 27: Japanese Unexamined Patent Application Publication No. H-07-187945 (Japanese Patent No. 2587797)

Patent Document 28: Japanese Unexamined Patent Application Publication No. H-05-112424 (Japanese Patent No. 2601738)

Patent Document 29: Japanese Patent No. 2719303

Patent Document 30: Japanese Unexamined Patent Application Publication No. H-10-167946

Patent Document 31: Japanese Unexamined Patent Application Publication No. H-10-316536

Patent Document 32: Japanese Unexamined Patent Application Publication No. 2002-38013

Patent Document 33: Japanese Unexamined Patent Application Publication No. 2004-169015

Patent Document 34: Japanese Unexamined Patent Application Publication No. 2006-218472

Patent Document 35: WO2003-075864 (Japanese Patent No. 3625471)

Patent Document 36: Japanese Unexamined Patent Application Publication No. H-06-305933 (Japanese Patent No. 3477222)

Patent Document 37: Japanese Unexamined Patent Application Publication No. H-07-25728 (Japanese Patent No. 3160427)

Patent Document 38: Japanese Unexamined Patent Application Publication No. H-07-33622 (Japanese Patent No. 3200247)

DISCLOSURE OF THE INVENTION

Summary of the Invention

The purpose of the present invention is to resolve the problems described above. An object of the present invention is to provide a novel organopolysiloxane having a hydrophilic group, that is easy to produce, is chemically stable, has superior utility, and in which separation into two phases and sedimentation of unreacted raw material following production occurs only minimally; and a method of manufacturing the same.

Another object of the present invention is to provide a surfactant comprising the organopolysiloxane, which can stably emulsify various oil agents and impart a unique texture to an emulsion.

Yet another object of the present invention is to provide a powder treatment agent comprising the organopolysiloxane, which has excellent dispersion stability in mixed oil agent systems and, after preparing a powder composition obtained by treating the powder surface using a treatment agent, even when a method is used where the powder composition is dispersed in an oil agent dispersing medium, a powder in oil dispersion having superior stability is provided in which the powder does not agglomerate or settle.

Still another object of the present invention is to provide an external use preparation of the organopolysiloxane, particularly for use as a raw material of a cosmetic composition; and a cosmetic composition comprising the organopolysiloxane. Specifically, an object of the present invention is to provide a cosmetic composition that works to promote the effects of water and suppress oiliness in cases when compounded in a cosmetic composition comprising water and an oil agent and which, as a result, has superior effects of imparting silky-smooth moisturization to the skin and maintaining that feel. Particularly, an object of the present invention is to provide a cosmetic composition that optionally ensures optical transparency and has superior storage stability when compounded in an emulsion-type cosmetic composition.

Yet another object of the present invention is to provide a substantially water-free cosmetic composition comprising the organopolysiloxane and an oil agent.

Means to Resolve the Problems

As a result of intensive investigation aimed at achieving the above objects, the present inventors arrived at the present invention. Specifically, the objects of the present invention are achieved by: a novel co-modified organopolysiloxane having a group that has a carbosiloxane dendron structure and a hydrophilic group such as a polyether group or the like in the molecule; a surfactant comprising the co-modified organopolysiloxane; a powder treatment agent comprising the co-modified organopolysiloxane; and an external use preparation, particularly a cosmetic composition, comprising the same.

More specifically, an object of the present invention is achieved by: a co-modified organopolysiloxane having a group that has a siloxane dendron structure and a hydrophilic group, expressed by the following general formula (1):

a surfactant comprising the co-modified organopolysiloxane; a powder treatment agent comprising the co-modified organopolysiloxane; and an external use preparation, particularly a cosmetic composition, comprising the same.

In general formula (1), $R^1$ is a monovalent organic group (with the exception of groups corresponding to L1 or Q) or a hydrogen atom; and $L^1$ is a silylalkyl group having a siloxane dendron structure expressed by the following general formula (2) when i=1.

General Formula (2)

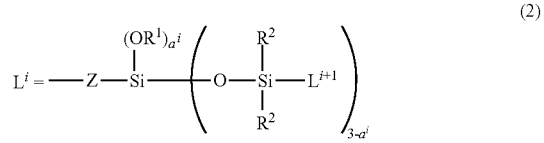

In general formula (2), $R^2$ is a phenyl group or an alkyl group having from 1 to 6 carbons, and Z is a divalent organic group. i represents a generation of the silylalkyl group represented by $L^i$, and is an integer of 1 to c when c is a number of generations that is a number of repetitions of the silylalkyl group. The number of generations c is an integer from 1 to 10, and $L^{i+1}$ is the silylalkyl group when i is less than c and is a methyl group or a phenyl group when i=c. $a^i$ is a number in a range of 0 to 3, and Q is a hydrophilic group bonded to the silicon atom via a linking group that is at least divalent, and comprises at least one hydrophilic unit selected from hydrophilic units expressed by the following structural formulae (3-1) to (3-4).

In structural formula 3-1, r is a number in a range of 1 to 6.

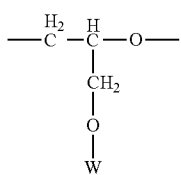
(3-2)

In structural formula 3-2, W is a hydrogen atom or an alkyl group having from 1 to 20 carbons.

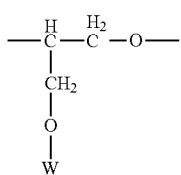
(3-3)

In structural formula 3-3, W is synonymous with the group described above.

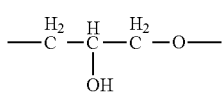
(3-4)

In structural formula 3-4, a, b, and c are in ranges so that $1.0 \leq a \leq 2.5$, $0.001 \leq b \leq 1.5$, and $0.001 \leq c \leq 1.5$.

Yet more specifically, the objects described above are achieved by, firstly, the invention of the novel co-modified organopolysiloxane having the group that has the siloxane dendron structure and the hydrophilic group, described in [1] to [8] below.

[1] A co-modified organopolysiloxane having a group that has a siloxane dendron structure and a hydrophilic group, expressed by the following general formula (1):

(1).

In general formula (1),
$R^1$ is a monovalent organic group (with the exception of groups corresponding to $L^1$ or Q) or a hydrogen atom, and $L^1$ is a silylalkyl group having a siloxane dendron structure expressed by the following general formula (2) when i=1.

General Formula (2):

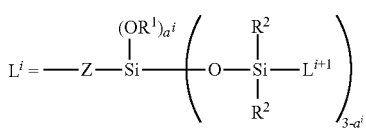
(2)

In general formula (2), $R^2$ is a phenyl group or an alkyl group having from 1 to 6 carbons, and Z is a divalent organic group; i represents a generation of the silylalkyl group represented by $L^i$, and is an integer of 1 to c when c is a number of generations that is a number of repetitions of the silylalkyl group; the number of generations c is an integer from 1 to 10, and $L^{i+1}$ is the silylalkyl group when i is less than c and is a methyl group or a phenyl group when i=c; $a^i$ is a number in a range of 0 to 3; and $R^1$ is a group that is synonymous with that described above and, in the general formula (2), is preferably a hydrogen atom, or a substituted or unsubstituted monovalent hydrocarbon group having from 1 to 30 carbons.

Q is a hydrophilic group bonded to the silicon atom via a linking group that is at least divalent, and comprises at least one hydrophilic unit selected from hydrophilic units expressed by the following structural formulae (3-1) to (3-4).

(3-1)

In structural formula 3-1, r is a number in a range of 1 to 6.

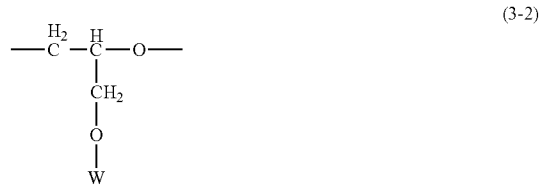
(3-2)

In structural formula 3-2, W is a hydrogen atom or an alkyl group having from 1 to 20 carbons.

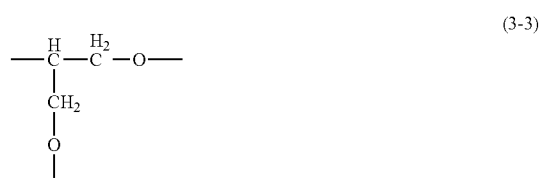
(3-3)

In structural formula 3-3, W is synonymous with the group described above.

(3-4)

In structural formula 3-4, a, b, and c are in ranges so that $1.0 \leq a \leq 2.5$, $0.001 \leq b \leq 1.5$, and $0.001 \leq c \leq 1.5$.

[2] The co-modified organopolysiloxane described in [1], wherein in the general formula (1), $L^1$ is a functional group expressed by the following general formula (2-1) or general formula (2-2).

General Formula (2-1):

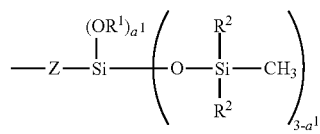
(2-1)

-continued

General Formula (2-2):

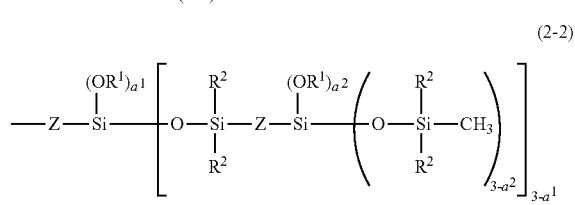

(2-2)

In these formulae, $R^1$, $R^2$, and Z are synonymous with the groups described above, and $a^1$ and $a^2$ are each independently numbers in a range of 0 to 3.

[3] The co-modified organopolysiloxane described in [1] or [2], wherein in the general formula (1), Q is a hydrophilic segment bonded to the silicon atom via a linking group that is at least divalent, comprising at least one linearly bonded hydrophilic unit selected from hydrophilic units expressed by the following structural formulae (3-1) to (3-4); or Q is a hydrophilic group bonded to the silicon atom via a linking group that is at least divalent, comprising not less than two of at least one hydrophilic unit selected from hydrophilic units expressed by structural formulae (3-1) to (3-4) above, and a branch unit selected from groups expressed by structural formulae (3-5) to (3-7) below.

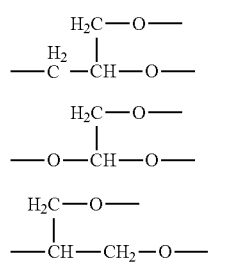

(3-5)

(3-6)

(3-7)

[4] The co-modified organopolysiloxane described in any one of [1] to [3], wherein Q is a hydrophilic group expressed by general formulae (4-1) to (4-4) below.

General Formula (4-1):

$$—R^3(—O—X^1{}_m—R^4)_p \qquad (4\text{-}1)$$

In general formula (4-1), $R^3$ is an organic group having (p+1) valency, and p is a number that is greater than or equal to 1 and less than or equal to 3; $X^1$ are each independently at least one hydrophilic unit selected from the hydrophilic units expressed by the general formulae (3-1) to (3-4) above, and m is a number in a range of 1 to 100; and $R^4$ is a hydrogen atom or a group selected from the group consisting of glycidyl groups, acyl groups, and alkyl groups having from 1 to 20 carbons.

General Formula (4-2):

$$—R^3(—O—X^2)_p \qquad (4\text{-}2)$$

In general formula (4-2), $R^3$ is a group synonymous with the groups described above, p is a number synonymous with the number described above; and $X^2$ is a hydrophilic group expressed by structural formula (4-2-1) below.

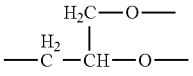

(4-2-1)

In structural formula (4-2-1), the at least one hydrophilic unit selected from the hydrophilic units expressed by the general formulae (3-1) to (3-4) is bonded to two oxygen atoms, each independently.

General Formula (4-3):

$$—R^3(—O—X^3)_p \qquad (4\text{-}3)$$

In general formula (4-3), $R^3$ is a group synonymous with the groups described above, p is a number synonymous with the number described above; and $X^3$ is a hydrophilic group expressed by structural formula (4-3-1) below:

(4-3-1)

In structural formula (4-3-1), the at least one hydrophilic unit selected from the hydrophilic units expressed by the general formulae (3-1) to (3-4) is bonded to two oxygen atoms, each independently.

General Formula (4-4):

$$—R^3(—O—X^4)_p \qquad (4\text{-}4)$$

In general formula (4-4), $R^3$ is a group synonymous with the groups described above, p is a number synonymous with the number described above; and $X^4$ is a hydrophilic group expressed by structural formula (4-4-1) below:

(4-4-1)

In structural formula (4-4-1), the at least one hydrophilic unit selected from the hydrophilic units expressed by the general formulae (3-1) to (3-4) is bonded to two oxygen atoms, each independently.

[5] The co-modified organopolysiloxane described in any one of [1] to [4], expressed by structural formula (1-1) below.

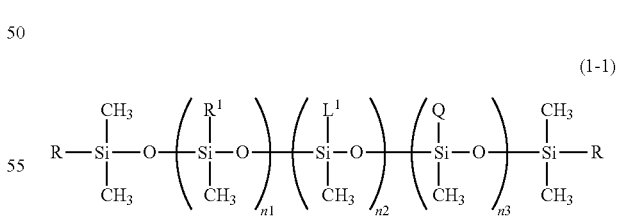

(1-1)

In structural formula (1-1), $R^1$, $L^1$, and Q are groups that are synonymous with those described above, and R is a group selected from $R^1$, $L^1$, and Q. However, when n2=0, at least one R is $L^1$; and when n3=0, at least one R is Q. (n1+n2+n3) is a number in a range from 3 to 2,000; and n1, n2, and n3 are numbers in a range from 0 to 2,000.

[6] The co-modified organopolysiloxane described in any one of [1] to [5], expressed by structural formula (1-1-1) or (1-1-2) below.

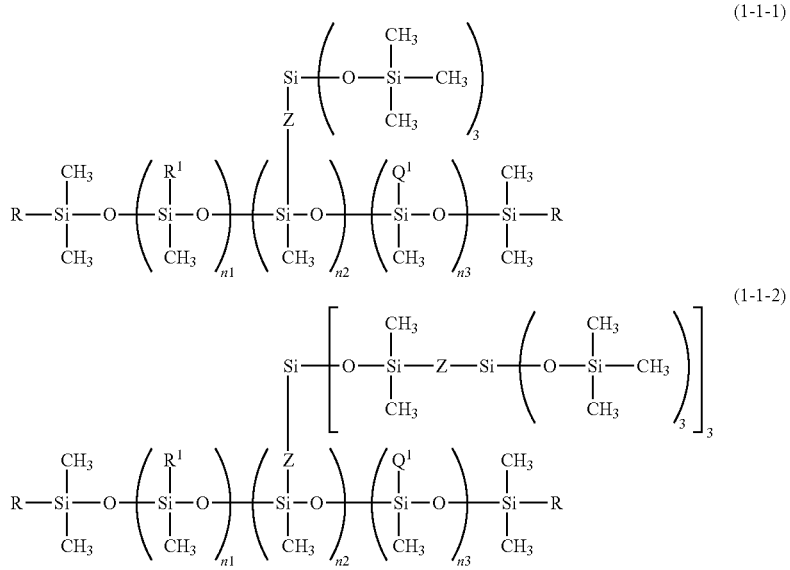

(1-1-1)

(1-1-2)

In these structural formulae, Z and $R^1$ are groups that are synonymous with those described above; R is a group selected from $R^1$, the $L^1$, and $Q^1$, described hereinafter; n1 is a number in a range from 10 to 1,000; n2 is a number in a range from 0 to 250; and n3 is a number in a range from 0 to 250. However, when n2=0, at least one R is $L^1$; and when n3=0, at least one R is $Q^1$.

$Q^1$ are each independently a hydrophilic group selected from the group consisting of structural formulae (4-1-2), (4-2-2), (4-3-2), and (4-4-2) below:

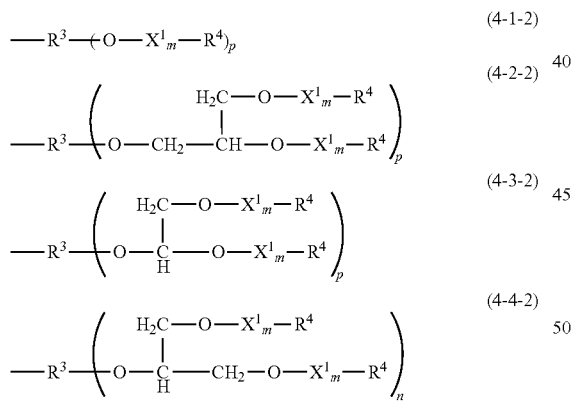

In these structural formulae, $R^3$ is an organic group having (p+1) valency, and p is a number that is greater than or equal to 1 and less than or equal to 3; X1 are each independently at least one hydrophilic unit selected from the hydrophilic units expressed by the general formulae (3-1) to (3-4) above, and m is a number in a range of 1 to 100; and R4 is a hydrogen atom or a group selected from the group consisting of glycidyl groups, acyl groups, and alkyl groups having from 1 to 20 carbons.

[7] The co-modified organopolysiloxane described in [6], wherein in the structural formula (1-1-1) or (1-1-2), Z are each independently a group selected from divalent organic groups expressed by general formulae (5-1) to (5-7) below.

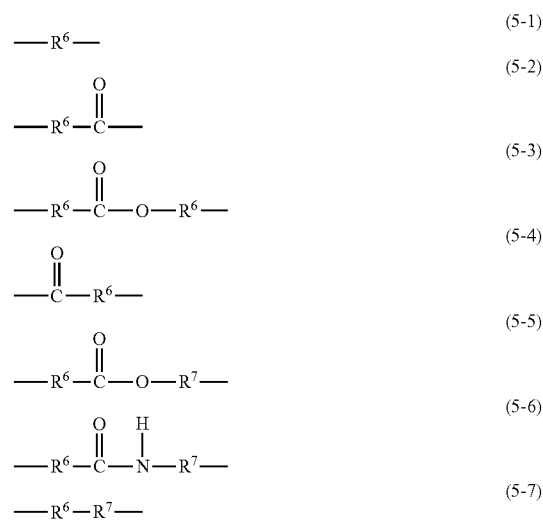

In these formulae, $R^6$ may have a substituent, and are each independently a straight or branched chain alkylene group or alkenylene group having from 2 to 22 carbons, or an arylene group having from 6 to 22 carbons; and $R^7$ is a group selected from divalent organic groups expressed by the following formulae.

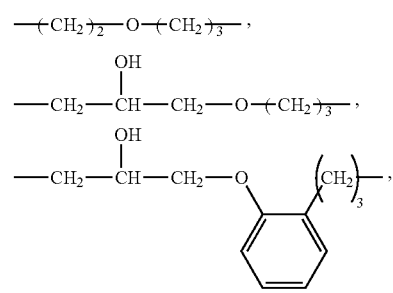

-continued

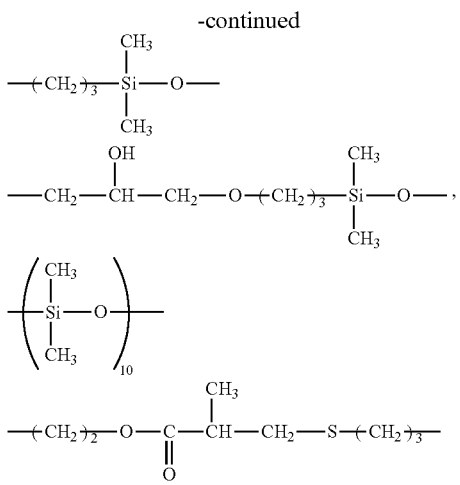

[8] The co-modified organopolysiloxane described in [6], wherein in the structural formulae (4-1-2), (4-2-2), (4-3-2), and (4-4-2), p is 1 and $R^3$ is a group selected from divalent organic groups expressed by general formula (5-1), (5-1-2), (5-1-3), or (5-2) below.

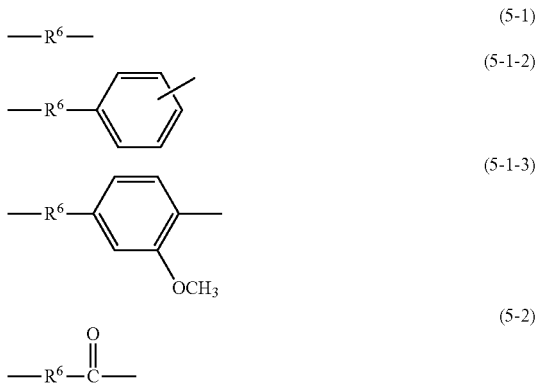

In these formulae, $R^6$ may have a substituent, and are each independently a straight or branched chain alkylene group or alkenylene group having from 2 to 22 carbons, or an arylene group having from 6 to 22 carbons.

Another object of the present invention is achieved by the invention of a surfactant and an emulsion composition comprising the co-modified organopolysiloxane described in [9] to [11-1] below.

[9] A surfactant comprising the co-modified organopolysiloxane described in any one of [1] to [8].

[10] A surfactant comprising: (A) the co-modified organopolysiloxane described in any one of [1] to [8], and (A2) a hydrophilic compound having a reactive functional group.

[11] An emulsion composition comprising: (A) the co-modified organopolysiloxane described in any one of [1] to [8], (B) water, and (C) at least one oil agent selected from a silicone oil, a hydrocarbon oil, or an ester oil that is a liquid at from 5 to 100° C.

[11-1] A method of adjusting transparency of the emulsion composition described in [11], comprising independently mixing an aqueous phase including the component (B) and an oil phase including the component (A) and the component (C) and, thereafter, adjusting a difference between refractive indexes at 25° C. of both phases so as to be less than or equal to 0.0020 units, and emulsifying.

Likewise, another object of the present invention is achieved by the invention of a powder treatment agent, a powder composition, and a powder in oil dispersion comprising the co-modified organopolysiloxane described in [12] to [17] below.

[12] A powder treatment agent comprising the co-modified organopolysiloxane described in any one of [1] to [8].

[13] A powder composition comprising: (A) the co-modified organopolysiloxane described in any one of [1] to [8], and (D) a powder or a powdered colorant.

[14] The powder composition described in [13], wherein from 1.0 to 30 parts by weight of (A) the co-modified organopolysiloxane described in any one of [1] to [8] per 100 parts by weight of (D) the powder or the powdered colorant are used to surface treat the component (D).

[15] The powder composition described in [13] or [14], wherein the component (D) is one or two or more selected from the group consisting of an inorganic pigment powder, an organic pigment powder, and a resin powder, having an average diameter in a range of 1 nm to 20 μm.

[16] The powder composition described in [13] or [14], wherein the component (D) is an inorganic body pigment.

[17] A powder in oil dispersion comprising: (A) the co-modified organopolysiloxane described in any one of [1] to [8], (D) a powder or a powdered colorant, and (C) at least one oil agent selected from a silicone oil, a nonpolar organic compound, and a low polarity organic compound, that is a liquid at from 5 to 100° C.

Furthermore, an object of the present invention is more preferably achieved by the invention of a topical composition, particularly the invention of a cosmetic composition, comprising the co-modified organopolysiloxane, the emulsion composition, and the powder composition or the powder in oil dispersion described in [18] to [29] below.

[18] A topical composition comprising the co-modified organopolysiloxane described in any one of [1] to [8].

[19] The topical composition described in [18] that is a cosmetic composition or a medicament.

[20] A cosmetic composition comprising the emulsion composition described in [11].

[21] A cosmetic composition comprising the powder composition described in any one of [13] to [16].

[22] A cosmetic composition comprising the powder in oil dispersion described in [17].

[23] A substantially water-free cosmetic composition comprising: the co-modified organopolysiloxane described in any one of [1] to [8], and an oil agent.

[24] The cosmetic composition described in any one of [18] to [23], further comprising: at least one selected from the group consisting of (E) a polyhydric alcohol or a lower monohydric alcohol, (F) an inorganic salt or an organic salt, and (G) a silicone-based surfactant (however, with the exception of the co-modified organopolysiloxane component (A)).

[25] The cosmetic composition described in any one of [18] to [24], further comprising: (H) at least one selected from the group consisting of a crosslinking organopolysiloxane, an organopolysiloxane elastomer spherical powder, a silicone resin, an acryl silicone dendrimer copolymer, a silicone raw rubber, a polyamide-modified silicone, an alkyl-modified silicone wax, and an alkyl-modified silicone resin wax.

[26] The cosmetic composition described in any one of [18] to [25], further comprising: (J) one or two or more selected from the group consisting of an anionic surfactant, a cationic surfactant, a nonionic surfactant (with the exception of silicone-based surfactants), an amphoteric surfactant, and a semipolar surfactant.

[27] The cosmetic composition described in any one of [18] to [26], further comprising: (K) a water-soluble polymer or (L) an ultraviolet light blocking component.

[28] The cosmetic composition described in any one of [18] to [27], wherein the cosmetic composition is a skin care product, a cosmetic product for hair, an anti-perspirant product, a makeup product, or an ultraviolet light blocking product.

[29] The cosmetic composition described in any one of [18] to [28], wherein a form of a product is liquid, milk-like, cream-like, solid, paste-like, gel-like, powder-like, multilayer, mousse-like, or spray-like.

Moreover, an object of the present invention is preferably achieved by a method in which the co-modified organopolysiloxane is manufactured via a hydrosilylation reaction. The manufacturing method is described in detail in [30] to [32] below.

[30] A method of manufacturing the co-modified organopolysiloxane described in any one of [1] to [8], wherein the co-modified organopolysiloxane is obtained by reacting at least: (a) an organohydrogensiloxane expressed by general formula (1') below,

$$R^1_a H_{b+c} SiO_{(4-a-b-c)/2} \qquad (1')$$

In this formula, $R^1$, a, b, and c are the same as recited above; (b) a hydrophilic derivative having one reactive unsaturated group in the molecule; and (c) a siloxane dendron having one reactive unsaturated group in the molecule; in the presence of a hydrosilylation reaction catalyst.

[31] The method of manufacturing a co-modified organopolysiloxane described in [30], wherein (b) the hydrophilic derivative having one reactive unsaturated group in the molecule, (c) the siloxane dendron having one reactive unsaturated group in the molecule, and (a) the organohydrogensiloxane expressed by the general formula (1') are reacted together, while the component (b) and the component (c) are at least in a state of coexistence.

[32] The method of manufacturing a co-modified organopolysiloxane described in [30] or [31], wherein: (c) the siloxane dendron having one reactive unsaturated group in the molecule is a compound expressed by general formula (2') below that has a siloxane dendron structure having one carbon-carbon double bond at a molecular terminal.

General Formula (2'):

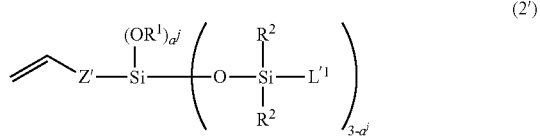

In general formula (2'), $L'^1$ is a methyl group or, when j=1, is a silylalkyl group expressed by general formula (2") below, and Z' is a divalent organic group.

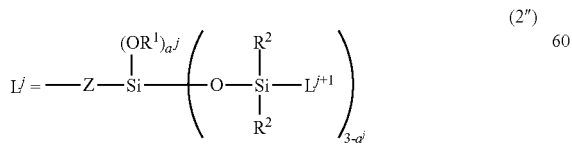

In general formula (2'), $R^2$ is a phenyl group or an alkyl group having from 1 to 6 carbons, and Z is a divalent organic group. j represents a generation of the silylalkyl group represented by $L^j$ and is an integer of 1 to c' when c' is a number of generations that is a number of repetitions of the silylalkyl group. The number of generations c' is an integer from 1 to 10, and $L^{j+1}$ is the silylalkyl group when j is less than c' and is a methyl group or a phenyl group when j=c'. $a^j$ is a number in a range from 0 to 3.

Effects of the Invention

According the present invention, a novel co-modified organopolysiloxane having a group that has a siloxane dendron structure and hydrophilic group in the molecule, that is easy to produce, is chemically stable, has superior utility, and in which separation into two phases and sedimentation of unreacted raw material following production occurs only minimally; and a method of manufacturing the same can be provided.

According to the present invention, a surfactant comprising the co-modified organopolysiloxane, which can stably emulsify various oil agents and impart a unique texture to an emulsion can be provided.

According to the present invention, a powder treatment agent comprising the co-modified organopolysiloxane that has excellent dispersion stability in mixed oil agent systems; and a powder in oil dispersion having superior stability in which the powder does not agglomerate or precipitate after preparing a powder composition obtained by treating the powder surface using a treatment agent, even when a method is used where the powder composition is dispersed in an oil agent dispersing medium, can be provided.

According to the present invention, an external use preparation of the co-modified organopolysiloxane, particularly for use as a raw material of a cosmetic composition, and a cosmetic composition comprising the organopolysiloxane can be provided. Specifically, a cosmetic composition that works to promote the effects of water and suppress oiliness in cases when compounded in a cosmetic composition comprising water and an oil agent and which, as a result, has superior effects of imparting silky-smooth moisturization to the skin and maintaining that feel can be provided. Particularly, a cosmetic composition that optionally ensures optical transparency and has superior storage stability when compounded in an emulsion-type cosmetic composition can be provided.

According to the present invention, a substantially water-free oil-based cosmetic composition that can impart a natural feeling on the skin without discomfort and sufficient moisturizing feel after application can be provided.

DETAILED DESCRIPTION OF THE INVENTION

A novel co-modified organopolysiloxane according to the present invention is a co-modified organopolysiloxane having a group that has a siloxane dendron structure and a hydrophilic group, and more specifically is a co-modified organopolysiloxane having a group ($-L^1$) that has a siloxane dendron structure and a hydrophilic group ($-Q$) expressed by the following general formula (1).

$$R^1_a L^1_b Q_c SiO_{(4-a-b-c)/2} \qquad (1)$$

(Hereinafter, the group represented by $L^1$ in general formula (1), which is a silylalkyl group expressed by the following general formula (2) when i=1, is also referred to as the "carbosiloxane dendrimer" and the "silylalkyl group having a siloxane dendron structure".)

First, a detailed description of the moieties $R^1$, $L^1$, and Q in general formula (1) will be given.

In general formula (1), $R^1$ is a monovalent organic group or a hydrogen atom. However, $R^1$ as a monovalent organic group does not include groups that correspond to $L^1$ or Q described above. Examples of the $R^1$ moiety include a hydrogen atom, a substituted or unsubstituted monovalent hydrocarbon group having from 1 to 30 carbons, an alkoxy group having from 1 to 30 carbons, a straight or branched polysiloxane chain, and the like. Examples of the substituted or unsubstituted monovalent hydrocarbon group include methyl groups, ethyl groups, propyl groups, butyl groups, pentyl groups, hexyl groups, heptyl groups, octyl groups, decyl groups, dodecyl groups, and other similar saturated aliphatic hydrocarbon groups; cyclopentyl groups, cyclohexyl groups, and similar saturated cycloaliphatic hydrocarbon groups; phenyl groups, tolyl groups, xylyl groups, naphthyl groups, and similar aromatic hydrocarbon groups; and groups wherein the hydrogen atoms bonded to the carbon atoms of these groups are substituted at least partially by fluorine or a similar halogen atom, or an organic group having an epoxy group, an acyl group, a carboxyl group, an amino group, a (meth)acryl group, a mercapto group, or the like. Examples of the alkoxy group include methoxy groups, ethoxy groups, isopropanoxy groups, higher alkoxy groups, and the like. The straight or branched polysiloxane chain is a straight or branched polysiloxane chain that does not correspond with $L^1$. Examples thereof include straight or branched polysiloxane chains having a polysiloxane chain structure that comprises a dimethylpolysiloxane unit that is bonded to the siloxane via a divalent linking group; where the dimethylpolysiloxane unit has a degree of polymerization of 1 to 100, and a silanol end, a trimethylsiloxy end, or an n-butyldimethylsiloxy end. Note that a portion of the methyl group of the polysiloxane chain may be substituted by a phenyl group, a fluorine or similar halogen atom, or an organic group including epoxy groups, acyl groups, carboxyl groups, amino groups, (meth)acryl groups, mercapto groups, and the like.

A modified group other than the group having a siloxane dendron structure (-$L^1$) and the hydrophilic group (-Q) can be introduced as $R^1$ or, alternately, the co-modified organopolysiloxane of the present invention can be designed in order to impart further functionality. Specifically, when $R^1$ is a substituted monovalent hydrocarbon group, a substituent can be suitably selected from the organic group examples described above in accordance with desired characteristics and uses. For example, when using the co-modified organopolysiloxane as a cosmetic raw material, a monovalent hydrocarbon group substituted with an amino group, an aminoethyl aminopropyl group, a carboxyl group, or the like can be selected as a substituent for the purpose of improving sensation during use, feeling to touch, and durability. Likewise, in addition to an alkyl group having from 1 to 4 carbons such as a methyl group or an ethyl group, an alkyl group having from 8 to 20 carbons can be selected as a portion of the $R^1$ moiety for the purpose of improving sensation during use, feel on the skin, and affinity with other components of a so-called medium chain alkyl group or long chain alkyl group.

Of these, $R^1$ is preferably a monovalent hydrocarbon group or a monovalent fluorinated hydrocarbon group having from 1 to 20 carbons. Examples of the monovalent hydrocarbon group not having unsaturated aliphatic bonds belonging to the $R^1$ moiety include methyl groups, ethyl groups, propyl groups, butyl groups, pentyl groups, hexyl groups, and similar alkyl groups; phenyl groups, tolyl groups, xylyl groups, and similar aryl groups; and aralkyl groups such as benzyl groups. Examples of the monovalent fluorinated hydrocarbon group include trifluoropropyl groups, pentafluoroethyl groups, and similar perfluoroalkyl groups. From an industrial perspective, $R^1$ is preferably a methyl group, an ethyl group, or a phenyl group, and more preferably from 90 to 100 mol % of all the $R^1$ moieties are selected from methyl groups, ethyl groups, or phenyl groups.

In general formula (1), the group represented by $L^1$ is a silylalkyl group having a siloxane dendron structure, and is defined as the silylalkyl group expressed by general formula (2) when i=1. The silylalkyl group having a siloxane dendron structure has a structure where a carbosiloxane unit is extended in the form of a dendrimer and, thus, compared to a linear or simply branched polysiloxane unit, is a functional group that exhibits high water repellency; and, due to a well balanced combination with hydrophilic groups, the silylalkyl group can provide superior surface activity to the co-modified organopolysiloxane according to the present invention. Additionally, the silylalkyl group having a siloxane dendron structure is chemically stable, and for this reason, the silylalkyl group is a functional group providing advantageous properties such as usability in combination with a wide range of cosmetic composition-use components.

In general formula (2), $R^2$ is a phenyl group or an alkyl group having from 1 to 6 carbons. Examples of the alkyl group having from 1 to 6 carbons include methyl, ethyl, n-propyl, i-propyl, n-butyl, i-butyl, s-butyl, pentyl, neopentyl, cyclopentyl, hexyl, and similar straight, branched, or cyclic alkyl groups. $R^1$ is a group that is synonymous with that described above and, in the general formula (2), is preferably a hydrogen atom, or a substituted or unsubstituted monovalent hydrocarbon group having from 1 to 30 carbons, and more preferably is a methyl group or a hydrogen atom.

In general formula (2), i represents a generation of the silylalkyl group represented by $L^i$, and is an integer of 1 to c when c is a number of generations that is a number of repetitions of the silylalkyl group. The number of generations c is an integer from 1 to 10, and $L^{i+1}$ is the silylalkyl group when i is less than c and is a methyl group or a phenyl group when i=c. $L^{i+1}$ is preferably a methyl group when i=c. $a^i$ is a number in a range of 0 to 3.

From a technical standpoint, the number of generations c is preferably an integer from 1 to 3, and more preferably is 1 or 2. In each of the number of generations, the group represented by $L^1$ is expressed as follows. In this formula, $R^2$ and Z are synonymous with the groups described above.

When the number of generations c=1, $L^1$ is expressed by the following general formula (2-1).

General Formula (2-1):

(2-1)

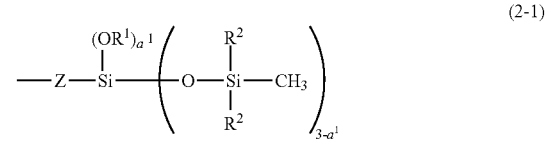

When the number of generations c=2, $L^1$ is expressed by the following general formula (2-2).

General Formula (2-2):

(2-2)

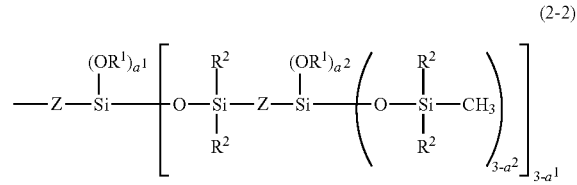

When the number of generations c=3, $L^1$ is expressed by the following general formula (2-3).

General Formula (2-3):

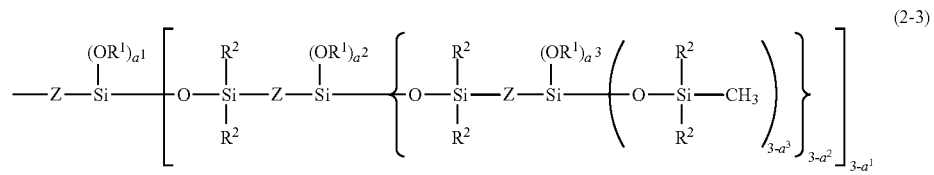

In formula (2), $a^i$ are each independently a number in a range from 0 to 3 and, in a structure expressed by formulae (2-1) to (2-3) where the number of generations is from 1 to 3, $a^1$, $a^2$, and $a^3$ are each independently a number in a range from 0 to 3. The $a^i$ moieties are preferably a number in a range from 0 to 1 and more preferably the $a^i$ moieties are 0.

In general formulae (2) and (2-1) to (2-3), Z are each independently a divalent organic group, and specific examples thereof include a divalent organic group formed by addition-reacting a silicon-bonded hydrogen atom and a functional group having an unsaturated hydrocarbon group such as an alkenyl group, an acryloxy group, a methacryloxy group, or the like at the terminal. Depending on the method for introducing the silylalkyl group having a siloxane dendron structure, the functional group can be appropriately selected and is not restricted to the functional groups described above. More specifically, Z are each independently a group selected from divalent organic groups expressed by the following general formulae (5-1) to (5-7). Of these, the Z in $L^1$ is preferably a divalent organic group expressed by general formula (5-1) that is introduced by a reaction between a silicon-bonded hydrogen atom and an alkenyl group. Likewise, Z is preferably a divalent organic group expressed by general formula (5-3) that is introduced by a reaction between a silicon-bonded hydrogen atom and an unsaturated carboxylic ester group. On the other hand, in the silylalkyl group represented by $L^i$ in which the number of generations c is 2 or more, and $L^i$ is $L^2$ to $L^c$, Z is preferably an alkylene group having from 2 to 10 carbons, more preferably a group selected from an ethylene group, a propylene group, a methylethylene group, and a hexylene group, and most preferably an ethylene group.

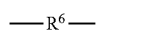 (5-1)

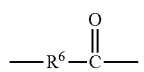 (5-2)

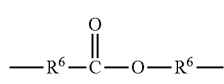 (5-3)

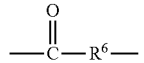 (5-4)

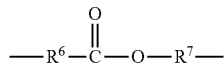 (5-5)

 (5-6)

—$R^6$—$R^7$— (5-7)

In these formulae (5-1) to (5-7), $R^6$ may have a substituent, and are each independently a straight or branched chain alkylene group or alkenylene group having from 2 to 22 carbons, or an arylene group having from 6 to 22 carbons; and More specifically, examples of $R^6$ include an ethylene group, a propylene group, a butylene group, a hexylene group, and similar straight alkylene groups; a methylmethylene group, a methylethylene group, a 1-methylpentylene group, a 1,4-dimethylbutylene group, and similar branched alkylene groups. $R^6$ is preferably a group selected from an ethylene group, a propylene group, a methylethylene group, and a hexylene group.

In formulae (5-5) to (5-7), $R^7$ is a group selected from divalent organic groups expressed by the following formulae.

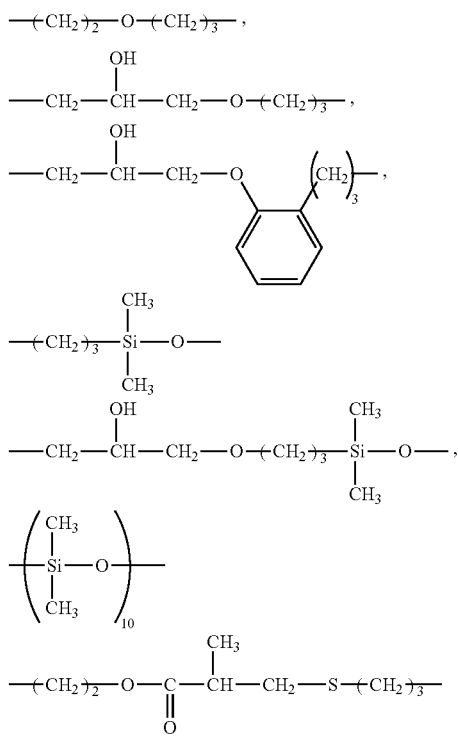

In general formula (1), Q is defined as a hydrophilic group bonded to the silicon atom via a linking group that is at least divalent, and comprises at least one hydrophilic unit selected from hydrophilic units expressed by the following structural formulae (3-1) to (3-4). Q as the hydrophilic group is a portion that imparts hydrophilicity to the co-modified organopolysiloxane according to the present application and, generally, is a functional group derived from a hydrophilic compound. Preferable examples of Q as defined above include at least monovalent alcohols, polyether-based compounds, polyglycerine-based compounds, polyglycidyl ether-based compounds, and functional groups derived from hydrophilic sugars, that may be partially capped at the molecular end by a hydrocarbon. Q is preferably a group derived from polyglycerin, and Q is more preferably a hydrophilic group having a triglycerin structure or a tetraglycerin structure.

Specifically, Q is a hydrophilic group bonded to the silicon atom via a linking group that is at least divalent, and comprises at least one hydrophilic unit selected from hydrophilic units expressed by the following structural formulae (3-1) to (3-4).

$$—C_rH_{2r}—O—$$ (3-1)

The hydrophilic unit expressed by formula (3-1) is an oxyalkylene unit. In this formula, r is a number in a range from 1 to 6, and is preferably a number in a range from 2 to 4. The hydrophilic unit expressed by formula (3-1) can have 1 or more hydrophilic groups (Q). Additionally, the hydrophilic unit expressed by (3-1) is preferably included in the hydrophilic group (Q) as a polyoxyalkylene unit where from 2 to 50 of the hydrophilic units expressed by formula (3-1) are linked and r are each independently from 2 to 4.

Particularly, from the standpoint of hydrophilicity, the hydrophilic unit expressed by formula (3-1) preferably is included in the hydrophilic group Q as 4 to 50 linked polyoxyalkylene units, and more preferably as one or more type of the polyoxyalkylene unit expressed by formula (3-1-1).

$$—(C_2H_4O)_{t1}(C_3H_6O)_{t2}—$$ (3-1-1)

In this formula, t1 and t2 are each numbers greater than or equal to 0, and (t1+t2) is a number in a range from 4 to 50 and preferably in a range from 8 to 30.

(3-2)

(3-3)

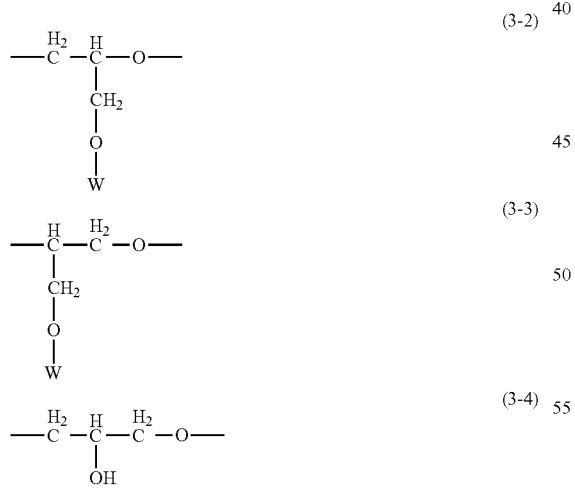
(3-4)

In formulae (3-2) to (3-4), W is a hydrogen atom or an alkyl group having from 1 to 20 carbons, and preferably is a hydrogen atom. Particularly, when W is a hydrogen atom, oxidation in air does not occur easily, and aldehydes such as formaldehyde and the like, and antigenic compounds such as formate esters and the like, are not easily produced over time while in storage. Therefore, when W is a hydrogen atom, there is a benefit of high environmental compatibility.

The hydrophilic units expressed by structural formulae (3-2) to (3-4) are hydrophilic units included in a hydrophilic group derived from a hydrophilic compound selected principally from polyhydric alcohols including glycerin, polyglycerines (also called "polyglycerols"), and polyglycidyl ethers or compounds in which terminal hydroxyl groups thereof are partially capped by hydrocarbon groups. However, the hydrophilic units are not limited thereto.

In general formula (1), Q may be, for example, a hydrophilic group that does not have a branched structure such as a straight polyoxyalkylene group, and may also be a hydrophilic group that has a partial branched structure in the functional group such as a polyglycerol group or a polyglycidylether group.

More specifically, Q may be a hydrophilic segment bonded to the silicon atom via a linking group that is at least divalent, comprising at least one linearly bonded hydrophilic unit selected from hydrophilic units expressed by the following structural formulae (3-1) to (3-4); or, furthermore, Q may be a hydrophilic segment bonded to the silicon atom via a linking group that is at least divalent, comprising not less than two of at least one hydrophilic unit selected from hydrophilic units expressed by structural formulae (3-1) to (3-4) above, and a branch unit selected from groups expressed by structural formulae (3-5) to (3-7) below.

(3-5)

(3-6)

(3-7)

The linking group that is at least divalent is a bonding site with respect to the silicon atom included in the hydrophilic group (Q), and a structure thereof is not particularly limited. Examples thereof include, ethylene groups, propylene groups, butylene groups, hexylene groups, and similar alkylene groups; ethylene phenylene groups, propylene phenylene groups, and similar alkylene phenylene groups; ethylene benzylene groups and similar alkylene aralkylene groups; ethyleneoxy phenylene groups, propyleneoxy phenylene groups, and similar alkyleneoxy phenylene groups; methyleneoxy benzylene groups, ethyleneoxy benzylene groups, propyleneoxy benzylene groups, and similar alkyleneoxy benzylene groups; and, furthermore, groups described below. Note that there are preferably from 0 to 3 and more preferably 0 or 1 ether bonds in the linking group that is at least divalent.

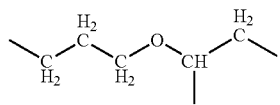

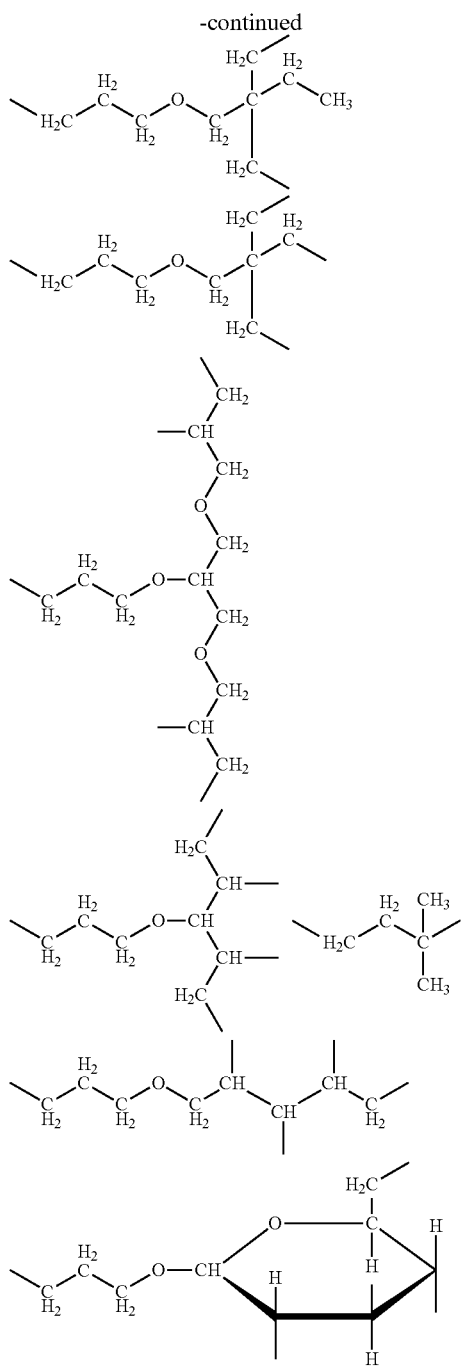

Q is more preferably a hydrophilic group expressed by the following general formulae (4-1) to (4-3).

General Formula (4-1):

$$-R^3(-O-X^1{}_m-R^4)_p \qquad (4\text{-}1)$$

In this formula, $R^3$ is an organic group having (p+1) valency, and p is a number that is greater than or equal to 1 and less than or equal to 3. Examples of $R^3$ include a group that is synonymous with the linking group that is at least divalent.

It is more preferable that p is equal to 1 and that $R^3$ is a group selected from divalent organic groups expressed by the following formula.

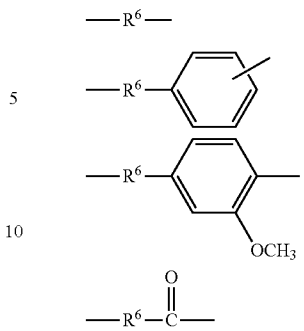

In this formula, $R^6$ may have a substituent, and are each independently a straight or branched chain alkylene group or alkenylene group having from 2 to 22 carbons, or an arylene group having from 6 to 22 carbons.

$X^1$ are each independently at least one hydrophilic unit selected from the hydrophilic units expressed by the general formulae (3-1) to (3-4) above, and m is a number in a range of 1 to 100. When $X^1$ is the hydrophilic unit (alkyleneoxy group) expressed by the general formula (3-1), m is preferably a number in a range from 4 to 50, and a structure expressed by $[-X^1{}_m-]$ is more preferably a polyoxyalkylene unit expressed by the formula (3-1-1). Additionally, when $X^1$ is the hydrophilic unit expressed by the general formulae (3-2) to (3-4), m is preferably a number in a range from 1 to 50, and more preferably is a number in a range from 1 to 15. $R^4$ is a hydrogen atom or a group selected from the group consisting of glycidyl groups, acyl groups, and alkyl groups having from 1 to 20 carbons, and preferably is a hydrogen atom or a methyl group.

General Formula (4-2):

$$-R^3(-O-X^2)_p \qquad (4\text{-}2)$$

In this formula, $R^3$ is a group synonymous with the groups described above, and p is a number synonymous with the number described above. $X^2$ is a hydrophilic group expressed by structural formula (4-2-1) below.

In this formula, the at least one hydrophilic unit selected from hydrophilic units expressed by the general formulae (3-1) to (3-4) is bonded to two oxygen atoms, each independently. The hydrophilic unit may further be bonded to a branch unit selected from groups expressed by structural formulae (3-5) to (3-7). Moreover the hydrophilic unit may be formed so as to have a dendroid-shape polyether structure, a polyglycerol structure, or a polyglycidyl ether structure obtained by branching into multiple generations.

In cases when the hydrophilic unit does not have other branch units, examples of the hydrophilic group expressed by general formula (4-2) include hydrophilic groups expressed by the following general formula (4-2-2). In this formula, p, $R^3$, $X^1$, $R^4$, and m are the same as described above.

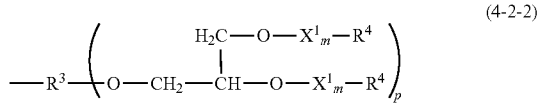
(4-2-2)

General Formula (4-3):

$$—R^3(—O—X^3)_p \quad (4\text{-}3)$$

In this formula, $R^3$ is a group synonymous with the groups described above, and p is a number synonymous with the number described above. $X^3$ is a hydrophilic group expressed by structural formula (4-3-1) below.

(4-3-1)

In this formula, the at least one hydrophilic unit selected from hydrophilic units expressed by the general formulae (3-1) to (3-4) is bonded to two oxygen atoms, each independently. The hydrophilic unit may further be bonded to a branch unit selected from groups expressed by structural formulae (3-5) to (3-7). Moreover the hydrophilic unit may be formed so as to have a dendroid-shape polyether structure, a polyglycerol structure, or a polyglycidyl ether structure obtained by branching into multiple generations.

In cases when the hydrophilic unit does not have other branch units, examples of the hydrophilic group expressed by general formula (4-3) include hydrophilic groups expressed by the following general formula (4-3-2). In this formula, p, $R^3$, $X^1$, $R^4$, and m are the same as described above.

(4-3-2)

General Formula (4-4):

$$—R^3(—O—X^4)_p \quad (4\text{-}4)$$

In this formula, $R^3$ is a group synonymous with the groups described above, and p is a number synonymous with the number described above. $X^4$ is a hydrophilic group expressed by structural formula (4-4-1) below.

(4-4-1)

In this formula, the at least one hydrophilic unit selected from hydrophilic units expressed by the general formulae (3-1) to (3-4) is bonded to two oxygen atoms, each independently. The hydrophilic unit may further be bonded to a branch unit selected from groups expressed by structural formulae (3-5) to (3-7). Moreover the hydrophilic unit may be formed so as to have a dendroid-shape polyether structure, a polyglycerol structure, or a polyglycidyl ether structure obtained by branching into multiple generations.

In cases when the hydrophilic unit does not have other branch units, examples of the hydrophilic group expressed by general formula (4-4) include hydrophilic groups expressed by the following general formula (4-4-2). In this formula, p, $R^3$, $X^1$, $R^4$, and m are the same as described above.

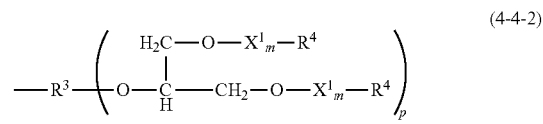
(4-4-2)

In general formula (1), a, b, and c are in ranges so that $1.0 \leq a \leq 2.5$, $0.001 \leq b \leq 1.5$, and $0.001 \leq c \leq 1.5$. In these numerical ranges, the co-modified organopolysiloxane according to the present application has a straight or branched polysiloxane backbone structure.

Preferable examples of the co-modified organopolysiloxane according to the present application include co-modified organopolysiloxanes expressed by the following structural formula (1-1).

Structural Formula (1-1):

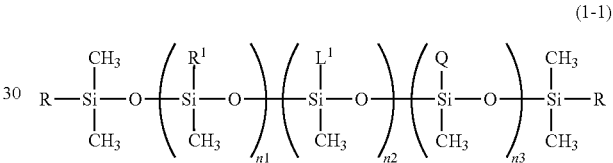
(1-1)

In structural formula (1-1), $R^1$, $L^1$, and Q are each independently groups that are synonymous with those described above, and R is a group selected from $R^1$, $L^1$, and Q. However, when n2=0, at least one R is $L^1$, and when n3=0, at least one R is Q. While 90 to 100 mol % of all the $R^1$ moieties are preferably groups selected from methyl groups, ethyl groups, and phenyl groups, for the purpose of designing a co-modified organopolysiloxane with higher functional properties, a long chain alkyl group or a monovalent hydrocarbon group in which a portion of the carbon-bonded hydrogen is substituted by a fluorine atom or other halogen atom or another organic group can be selected as a portion of $R^1$. Such a long chain alkyl group or a monovalent hydrocarbon group is preferable. Additionally, a hydrogen atom (—H) that is bonded to a silicon atom may be included as a portion of $R^1$.

In this formula, (n1+n2+n3) is a number in a range from 3 to 2,000, preferably in a range from 5 to 1,500, and more preferably a number in a range from 10 to 1,000. n1, n2, and n3 are numbers in a range from 0 to 2,000. n1 is preferably a number in a range from 10 to 1,000, n2 is preferably a number in a range from 1 to 250, and n3 is preferably a number in a range from 1 to 250.

Particularly, when using the co-modified organopolysiloxane according to the present application as a surfactant or a powder treatment agent, n1 is more preferably a number in a range from 10 to 1,000, n2 is more preferably a number in a range from 1 to 50, and n3 is more preferably a number in a range from 1 to 50.

Particularly preferable examples of the co-modified organopolysiloxane according to the present application include co-modified organopolysiloxanes expressed by the following structural formulae (1-1-1) and (1-1-2).

Structural Formula (1-1-1):

(1-1-1)

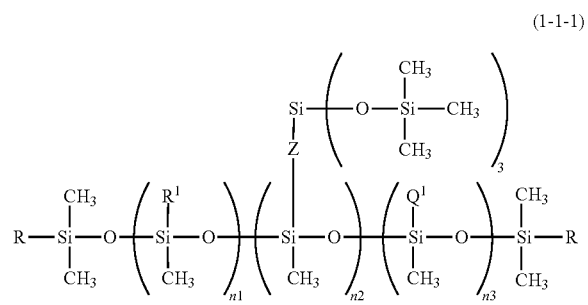

Structural Formula (1-1-2):

(1-1-2)

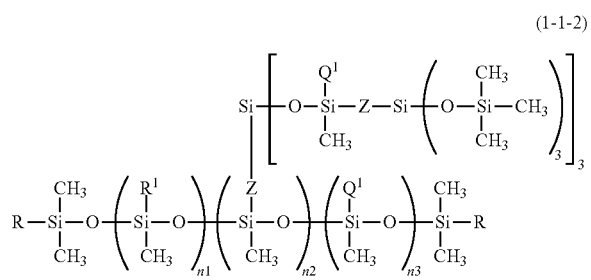

In the structural formulae (1-1-1) and (1-1-2), Z and $R^1$ are groups that are synonymous with those described above; R is a group selected from $R^1$, the $L^1$, and $Q^1$, described hereinafter. However, when n2=0, at least one R is $L^1$, and when n3=0, at least one R is $Q^1$. $Q^1$ are each independently a hydrophilic group selected from the group consisting of structural formulae (4-1-2), (4-2-2), (4-3-2), and (4-4-2) below. In this formula, $R^3$, $X^1$, and $R^4$ are groups synonymous with the groups described above, and p and m are numbers synonymous with the numbers described above.

(4-1-2)

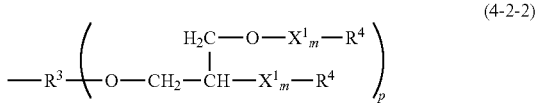
(4-2-2)

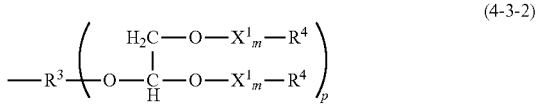
(4-3-2)

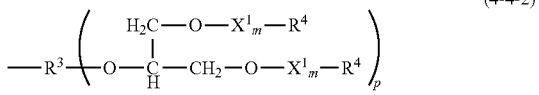
(4-4-2)

The co-modified organopolysiloxane according to the present application described above can be obtained by addition-reacting a hydrophilic compound, which has a reactive functional group and a compound with a siloxane dendron structure having one carbon-carbon double bond at one end of the molecular chain, with an organopolysiloxane that has a reactive functional group. The type of addition reaction is not particularly limited but, from the standpoint of reaction control, purity, and yield, the addition reaction is preferably performed in the presence of a hydrosilylation reaction catalyst.

Specifically, co-modified organopolysiloxane according to the present application can be obtained by reacting at least (a) an organohydrogensiloxane expressed by the following general formula (1');

(in this formula, $R^1$, a, b, and c are the same as recited above); (b) a hydrophilic derivative having one reactive unsaturated group in the molecule; and (c) a siloxane dendron having one reactive unsaturated group in the molecule; in the presence of a hydrosilylation reaction catalyst.

The co-modified organopolysiloxane according to the present application can be more preferably manufactured by reacting (b) the hydrophilic derivative having one reactive unsaturated group in the molecule, (c) the siloxane dendron having one reactive unsaturated group in the molecule, and (a) the organohydrogensiloxane expressed by the general formula (1') together, while the component (b) and the component (c) are at least in a state of coexistence. In a state where these components do not coexist, specifically, when a method is selected in which the component (C) is first reacted independently with the organohydrogenpolysiloxane and then the component (b) is reacted, an abundance ratio of the modified organopolysiloxane that is modified only by the group having the siloxane dendron structure increases, and compatibility with the surplus component (B) (specifically the polyglycerin monoallyl ether, and the like) becomes poor and, therefore, phase separation may occur. As a result, there are cases when a compound having the designed average composition formula, with respect to the content of the silicon-bonded hydrogen atom, cannot be obtained when introducing the functional group. On the other hand, in cases when only the component (B) is first independently reacted with the organohydrogenpolysiloxane, concentration of the hydrophilic group, particularly that of polyglycerines or similar polyhydric alcohol groups, with respect to the concentration of the Si—H groups in the reaction system reaches a state relatively higher when compared to the concentration of the unsaturated groups, which may lead to the entire system gelling during the dehydrogenation reaction or the like.

Preferably examples of the organohydrogensiloxane (a) expressed by general formula (1') include organohydrogensiloxanes expressed by the following structural formula (1-1)'.

Structural Formula (1-1)'

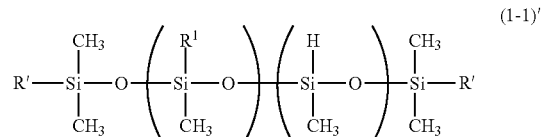

In this formula, $R^1$ are each independently a group that is synonymous with that described above, and R' is a group selected from $R^1$ and a hydrogen atom. n1, n2, and n3 are synonymous with the numbers described above. However, when (n2+n3)=0, at least one R' is a hydrogen atom.

The hydrophilic derivative (b) having one reactive unsaturated group in the molecule is a hydrophilic compound having a reactive functional group such as an alkenyl group on a molecular terminal, and examples thereof include an allyl polyether, an allyl polyglycerol, an allyl polyglycidyl ether, a polyglyceryl eugenol, a glycerin monoallyl ether, and the like. The hydrophilic derivative (b) can be synthesized according to a known method, or may be a commercially available product.

The siloxane dendron (c) having one reactive unsaturated group in the molecule is a compound expressed by the following general formula (2') that has a siloxane dendron structure having one carbon-carbon double bond at a molecular terminal.

General Formula (2')

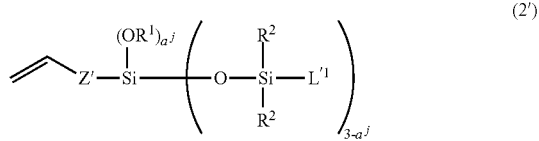

In general formula (2'), $L'^1$ is a methyl group or, when j=1, is a silylalkyl group expressed by general formula (2") below, and Z' is a divalent organic group.

General Formula (2")

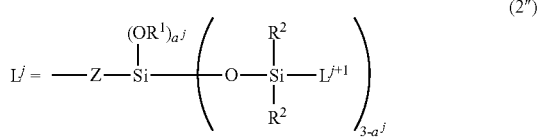

In general formula (2"), $R^2$ is a phenyl group or an alkyl group having from 1 to 6 carbons, and Z is a divalent organic group. j represents a generation of the silylalkyl group represented by $L^j$ and is an integer of 1 to c' when c' is a number of generations that is a number of repetitions of the silylalkyl group. The number of generations c' is an integer from 1 to 10, and $L^{j+1}$ is the silylalkyl group when j is less than c' and is a methyl group or a phenyl group when j=c'. $a^j$ is a number in a range of 0 to 3. $R^1$ is a group that is synonymous with that described above and, in the general formula (2"), is preferably a hydrogen atom, or a substituted or unsubstituted monovalent hydrocarbon group having from 1 to 30 carbons, and more preferably is a methyl group or a hydrogen atom.

The hydrosilylation reaction is preferably performed in the presence of a catalyst. Examples of the catalyst include platinum, ruthenium, rhodium, palladium, osmium, iridium, and similar compounds, and platinum compounds are particularly effective due to their high catalytic activity. Examples of the platinum compound include chloroplatinic acid; platinum metal; platinum metal supported on a carrier such as platinum supported on alumina, platinum supported on silica, platinum supported on carbon black, or the like; and a platinum complex such as platinum-vinylsiloxane complex, platinum phosphine complex, platinum-phosphite complex, platinum alcholate catalyst, or the like. A usage amount of the catalyst is about 0.5 to 100 ppm in terms of platinum metal, when using a platinum catalyst.

Additionally, the crude co-modified organopolysiloxane obtained via the addition reaction described above can be refined by performing a deodorizing treatment by a hydrogenation reaction in the presence of a hydrogenation catalyst in a solvent or without a solvent. This refined product can be preferably used in cases where the co-modified organopolysiloxane is used in an external use preparation application in which odor reduction and compatibility with other cosmetic composition components are needed. Moreover, the deodorizing treatment preferably has, as a pre-process or a post-process, a stripping process in which nitrogen gas is brought into contact with the crude co-modified organopolysiloxane or the hydrogenated product to remove light matter under reduced pressure.

In the hydrogenation reaction and stripping process, solvents, reaction conditions, pressure-reduction conditions, and the like used in the refining of conventional organopolysiloxane copolymers or polyether-modified silicones can be used or selected without any restrictions.

Alternately, the odor of the crude co-modified organopolysiloxane obtained via the addition reaction described above can easily be reduced by performing a stripping process in which light matter is removed by bringing nitrogen gas into contact with the crude product under reduced pressure, after an unreacted unsaturated compound is hydrolyzed by adding an acidic substance.

The co-modified organopolysiloxane according to the present invention that is obtained via the manufacturing method described above can be easily manufactured, and the degree of modification and type of modifying group can be easily controlled by simply changing the preparation of the raw material. Therefore, a functional molecular design is easy. Furthermore, the obtained co-modified organopolysiloxane is beneficial because it is chemically stable, has superior utility, and separation into two phases and sedimentation, or the like, of unreacted raw material following production occurs only minimally.

The novel co-modified organopolysiloxane according to the present invention (hereinafter, referred to as "component (A)") is particularly useful as a surfactant because it is hydrophobic, and has a silylalkyl group having a siloxane dendron structure that provides high water repellency and a hydrophilic group in the same molecule. The hydrophilic group is preferably a polyhydric alcohol such as polyether, glycerin, or the like, or a derivative thereof such as polyglycerine, polyglycidyl ether, or the like. Therefore, the novel co-modified organopolysiloxane of the present invention is particularly suited for use as a nonionic surfactant, and has the benefits of being able to stably emulsify various oil agents and impart unique texture and superior feeling to touch to an emulsion.

While applications as a surfactant are not particularly limited, the novel organopolysiloxane copolymer of the present invention displays superior surface activity effects (dispersibility, emulsifiability) at small amounts and, therefore is extremely useful as a surfactant for an external use preparation, and, particularly, other than cosmetic compositions, as a foam stabilizer used when manufacturing urethane foam, a release agent, an antifoam agent, a fiber treatment agent, an adhesive, an antifogging agent, a burnishing agent, a water repellant, a coating, a resin additive, an antistatic agent, and the like. Additionally, if a range of about 2 to 10 for the degree of polymerization of the polysiloxane chain portion is selected and a highly volatile polyether is used as the hydrophilic group, the novel organopolysiloxane copolymer of the present invention can be suitably used in applications such as cleaning electronics or electronic parts.

The novel co-modified organopolysiloxane (A) according to the present invention is, independently, a superior surfactant, but may also be suitably used in a mixture with a hydrophilic compound having a reactive functional group (A2) such as an alkenyl group at a molecular terminal, such as an allyl polyether, an allyl polyglycerol, an allyl polyglycidyl ether, or the like. From the standpoint of uniform miscibility, emulsifiability, and dispersibility with the co-modified organopolysiloxane (A), the hydrophilic compound having the reactive functional group is preferably exemplified by the same compound as the hydrophilic compound used in the manufacture of the novel co-modified organopolysiloxane according to the present invention.

In a composition obtained by mixing the novel co-modified organopolysiloxane (A) of the present invention and the hydrophilic compound having the reactive functional group (A2), a ratio expressed [component (A)/component (A2)] is preferably in a range of from 50/50 to 99.5/0.5, and more preferably in a range from 80/20 to 99/1.

Next, the emulsion composition including the co-modified organopolysiloxane (A) according to the present invention will be described. As described above, the co-modified organopolysiloxane (A) according to the present invention, or the mixture including the co-modified organopolysiloxane (A) and the hydrophilic compound having the reactive functional group (A2) is useful as a surfactant, and can also form an emulsion composition by stably emulsifying various oil agents and water. The emulsion composition can be in the form of an oil-in-water emulsion or a water-in-oil emulsion. Furthermore, emulsion compositions comprising such an emulsion as an inner phase (particulate material), such as O/W/O type emulsions and the like are encompassed in the scope of the present invention.

The emulsion composition according to the present invention preferably is an emulsion composition comprising (A) a co-modified organopolysiloxane, (B) water, and (C) an oil agent; and can be used as an external use preparation, particularly a raw material of a cosmetic composition.

Water (B) is free of ingredients that are harmful to the human body and needs only to be clean. Examples thereof include tap water, purified water, mineral water, deep sea water, and the like. In the emulsion composition of the present invention, an amount of water used and a compounding ratio thereof is not limited, but is preferably within a range from 5 to 99 wt. %, and more preferably within a range from 10 to 80 wt. % of the entire emulsion.

The oil agent is preferably one or more oil agents selected from (C) silicone oils, hydrocarbon oils, and ester oils that are liquid from 5 to 100° C. Note that, emulsification can be carried out by combining one or two or more commonly known vegetable oils and fats, animal oils and fats, higher alcohols, liquid triglyceride fatty acid, and artificial sebum with the oil agents described above.

Specific examples of the silicone oil component (C) include straight organopolysiloxanes expressed by the following general formula (1), cyclic organopolysiloxanes expressed by the general formula (2), and branched organopolysiloxanes expressed by the general formula (3).

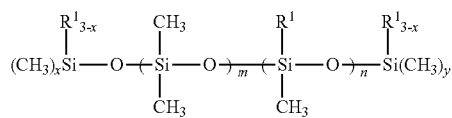

(1)

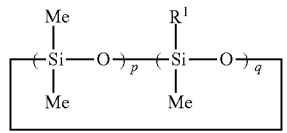

(2)

(3)

In general formulae (1) to (3) of the preceding paragraph, $R^1$ is a hydrogen atom, a hydroxyl group, or a group selected from an unsubstituted or fluorine substituted monovalent alkyl group having from 2 to 30 carbons, an aryl group, an amino substituted alkyl group, an alkoxy group, and a group expressed by $(CH_3)_3SiO\{(CH_3)_2SiO\}_uSi(CH_3)_2CH_2CH_2$—. Specific examples thereof include saturated aliphatic hydrocarbon groups such as ethyl groups, propyl groups, butyl groups, pentyl groups, hexyl groups, heptyl groups, octyl groups, decyl groups, dodecyl groups, and the like; unsaturated aliphatic hydrocarbon groups such as vinyl groups, allyl groups, hexenyl groups, and the like; saturated cycloaliphatic hydrocarbon groups such as cyclopentyl groups, cyclohexyl groups, and the like; aromatic hydrocarbon groups such as phenyl groups, tolyl groups, naphthyl groups, and the like; and groups wherein the hydrogen atoms bonded to the carbon atoms of these groups are substituted partially by an organic group having a halogen atom, an epoxy group, a carboxyl group, an amino group, a (meth)acryl group, a mercapto group, or the like, or a group substituted by a trimethylsiloxy group and bonded via a divalent hydrocarbon group and/or a straight polydimethyl siloxane bond. m is an integer from 0 to 1,000, n is an integer from 0 to 1,000, and m+n is an integer from 1 to 2,000. x and y are 0, 1, 2, or 3. p and q are integers from 0 to 8 such that $3 \leq p+q \leq 8$. r is an integer from 1 to 4 and u is an integer from 0 to 500.

Examples of silicone oils having the structure described above include cyclic organopolysiloxanes such as hexamethyl cyclotrisiloxane (D3), octamethyl cyclotetrasiloxane (D4), decamethyl cyclopentasiloxane (D5), dodecamethylcyclohexasiloxane (D6), 1,1-diethylhexamethyl cyclotetrasiloxane, phenylheptamethyl cyclotetrasiloxane, 1,1-diphenylhexamethyl cyclotetrasiloxane, 1,3,5,7-tetravinyltetramethyl cyclotetrasiloxane, 1,3,5,7-tetramethyl cyclotetrasiloxane, 1,3,5,7-tetracyclohexyltetramethyl cyclotetrasiloxane, tris(3,3,3-trifluoropropyl) trimethylcyclotrisiloxane, 1,3,5,7-tetra(3-methacryloxypropyl) tetramethyl cyclotetrasiloxane, 1,3,5,7-tetra(3-acryloxypropyl) tetramethyl cyclotetrasiloxane, 1,3,5,7-tetra(3-carboxypropyl) tetramethyl cyclotetrasiloxane, 1,3,5,7-tetra(3-vinyloxypropyl) tetramethyl cyclotetrasiloxane, 1,3,5,7-tetra(p-vinylphenyl) tetramethyl cyclotetrasiloxane, 1,3,5,7-tetra[3-(p-vinylphenyl) propyl] tetramethyl cyclotetrasiloxane, 1,3,5,7-tetra(N-acryloyl-N-methyl-3-aminopropyl) tetramethyl cyclotetrasiloxane, 1,3,5,7-tetra(N,N-bis(lauroyl)-3-aminopropyl) tetramethyl cyclotetrasiloxane, and the like. Examples of straight organopolysiloxanes include a dimethylpolysiloxane in which both molecular terminals are capped with trimethylsiloxy groups (dimethylsilicone with a low viscosity such as 2 cst or 6 cst to dimethylsilicone with a high viscosity such as 1,000,000 cst), an organohydrogenpolysiloxane, a methylphenylpolysiloxane in which both molecular terminals are capped with trimethylsiloxy groups, a copolymer of methylphenylsiloxane and dimethylsiloxane in which both molecular terminals are capped with trimethylsiloxy groups, a diphenylpolysiloxane in which both molecular terminals are capped with trimethylsiloxy groups, a copolymer of diphenylsiloxane and dimethylsiloxane in which both molecular terminals are capped with trimethylsiloxy groups, a trimethylpentaphenyltrisiloxane, a phenyl (trimethylsiloxy) siloxane, a methylalkylpolysiloxane in which both molecular terminals are capped with trimethylsiloxy groups, a copolymer of methylalkylsiloxane and dimethylpolysiloxane in which both molecular terminals are capped with trimethylsiloxy groups, a copolymer of methyl (3,3,3-trifluoropropyl) siloxane and dimethylsiloxane in which both molecular terminals are capped with trimethylsiloxy groups, an α,ω-dihydroxypolydimethylsiloxane, an α,ω-diethoxypolydimethylsiloxane, a 1,1,1,3,5,5,5-heptamethyl-3-octyltrisiloxane, a 1,1,1,3,5,5,5-heptamethyl-3-dodecyltrisiloxane, a 1,1,1,3,5,5,5-heptamethyl-3-hexadecyltrisiloxane, a tristrimethylsiloxymethylsilane, a tristrimethylsiloxyalkylsilane, a tetrakistrimethylsiloxysilane, a tetramethyl-1,3-dihydroxydisiloxane, an octamethyl-1,7-dihydroxytetrasiloxane, a hexamethyl-1,5-diethoxytrisiloxane, a hexamethyldisiloxane, an octamethyltrisiloxane, a higher alkoxy-modified silicone, a higher fatty acid-modified silicone, and the like.

Examples of the hydrocarbon oil component (C) include liquid paraffin, light liquid isoparaffin, heavy liquid isoparaffin, vaseline, n-paraffin, isoparaffin, isododecane, isohexadecane, polyisobutylene, hydrogenated polyisobutylene, polybutene, ozokerite, ceresin, microcrystalline wax, paraffin wax, polyethylene wax, polyethylene/polypropylene wax, squalane, squalene, pristane, polyisoprene, and the like.

Examples of the ester oil component (C) include hexyldecyl octanoate, cetyl octanoate, isopropyl myristate, isopropyl palmitate, butyl stearate, hexyl laurate, myristyl myristate, oleyl oleate, decyl oleate, octyldodecyl myristate, hexyldecyl dimethyloctanoate, cetyl lactate, myristyl lactate, diethyl phthalate, dibutyl phthalate, lanolin acetate, ethylene glycol monostearate, propylene glycol monostearate, propylene glycol dioleate, glyceryl monostearate, glyceryl monooleate, glyceryl tri(2-ethylhexanoate), trimethylolpropane tri(2-ethylhexanoate), ditrimethylolpropane triethylhexanoate, ditrimethylolpropane isostearate/sebacate, trimethylolpropane trioctanoate, trimethylolpropane triisostearate, diisopropyl adipate, diisobutyl adipate, 2-hexyldecyl adipate, di-2-heptyldecyl adipate, diisostearyl malate, hydrogenated castor oil monoisostearate, N-alkylglycol monoisostearate, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl gum ester, ethyl oleate, octyldodecyl oleate, neopentylglycol dicaprate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyloctyl sebacate, cetyl palmitate, octyldodecyl palmitate, octyl palmitate, 2-ethylhexyl palmitate, 2-hexyldecyl palmitate, 2-heptyldecyl palmitate, cholesteryl 12-hydroxystearate, dipentaerythritol fatty acid ester, 2-hexyldecyl myristate, ethyl laurate, 2-octyldodecyl N-lauroyl-L-glutamate, di(cholesteryl/behenyl/octyldodecyl) N-lauroyl-L-glutamate, di(cholesteryl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, isopropyl N-lauroylsarcosinate, diisostearyl malate, neopentylglycol dioctanoate, isodecyl neopentanoate, isotridecyl neopentanoate, isostearyl neopentanoate, isononyl isononanoate, isotridecyl isononanoate, octyl isononanoate, isotridecyl isononanoate, diethylpentanediol dineopentanoate, methylpentanediol dineopentanoate, tripropyleneglycol dineopentanoate, octyldodecyl neodecanoate, 2-butyl-2-ethyl-1,3-propanediol dioctanoate, pentaerythrityl tetraoctanoate, pentaerythrityl hydrogenated rosin, pentaerythrityl triethylhexanoate, dipentaerythrityl (hydroxystearate/stearate/rosinate), polyglyceryl tetraisostearate, polyglyceryl-10 nonaisostearate, polyglyceryl-8 deca(erucate/isostearate/ricinoleate), (hexyldecanoic acid/sebacic acid) diglyceryl oligoester, glycol distearate (ethylene glycol distearate), diisopropyl dimer dilinoleate, diisostearyl dimer dilinoleate, di(isostearyl/phytosteryl) dimer dilinoleate, (phytosteryl/behenyl) dimer dilinoleate, (phytosteryl/isostearyl/cetyl/stearyl/behenyl) dimer dilinoleate, dimer dilinoleyl dimer dilinoleate, dimer dilinoleyl diisostearate, dimer dilinoleyl hydrogenated rosin condensate, dimer dilinoleic acid hydrogenated castor oil, hydroxyalkyl dimer dilinoleyl ether, glyceryl triisooctanoate, glyceryl triisostearate, glyceryl trimyristate, glyceryl triisopalmitate, glyceryl trioctanoate, glyceryl trioleate, glyceryl diisostearate, glyceryl tri(caprylate/caprate), glyceryl tri(caprylate/caprate/myristate/stearate), hydrogenated rosin triglyceride (hydrogenated ester gum), rosin triglyceride (ester gum), glyceryl behenate eicosane dioate, glyceryl di-2-heptylundecanoate, diglyceryl myristate isostearate, cholesteryl acetate, cholesteryl nonanoate, cholesteryl stearate, cholesteryl isostearate, cholesteryl oleate, cholesteryl 12-hydroxystearate, cholesteryl ester of macadamia nut oil fatty acid, phytosteryl ester of macadamia nut oil fatty acid, phytosteryl isostearate, cholesteryl ester of soft lanolin fatty acid, cholesteryl ester of hard lanolin fatty acid, cholesteryl ester of long-chain branched fatty acid, cholesteryl ester of long-chain α-hydroxy fatty acid, octyldodecyl ricinoleate, octyldodecyl ester of lanolin fatty acid, octyldodecyl erucate, isostearic acid hydrogenated castor oil, ethyl ester of avocado fatty acid, isopropyl ester of lanolin fatty acid, and the like.

Examples of methods of dispersing/emulsifying the oil agent and water include using a mechanical force by means of an apparatus such as a homomixer, a paddle mixer, a Henschel mixer, a homo-disper, a colloid mill, a propeller stirrer, a homogenizer, an in-line type continuous emulsifier, an ultrasonic emulsifier, a vacuum kneader, or the like to disperse the composition in water.

The emulsion composition including the co-modified organopolysiloxane according to the present invention can be suitably used as a topical composition, particularly for a cosmetic composition or a cosmetic raw material. Other cosmetic raw material components (described hereinafter) can be compounded in the aqueous phase or the oil phase of the emulsion composition, and such an emulsion composition that comprises these cosmetic raw material components is encompassed in the present invention.

Furthermore, transparency of the emulsion composition including the co-modified organopolysiloxane of the present invention can be adjusted by mixing an aqueous phase including the component (B) independently with the component (A) and an oil phase including the oil agent component (C) and, thereafter, emulsifying so that a difference in refractive indexes at room temperature of both phases is less than or equal to 0.0020 units. More specifically, the method of adjusting the transparency of the emulsion composition of the present invention includes the following steps (i) to (iv).

(i) The co-modified organopolysiloxane (A) and the oil agent component (C) that is an oil component such as a volatile oil agent, a nonvolatile oil agent, a solubilization agent, or the like are mixed according to any method known in the art. Likewise, the aqueous phase component is mixed in a separate container.

(ii) The refractive index (RI) of each phase is measured separately at room temperature (25° C.).

(iii) The refractive index of each of the phases is adjusted so that the difference between the refractive indexes of these two phases is at least within 0.0020 units, and the optical transparency of the final mixture is obtained.

(iv) The two phases are emulsified. Emulsifying can be performed according to a desired emulsifying method but, ordinarily, the two phases are coalesced as an emulsion by gradually introducing the aqueous phase into the oil phase while agitating using mechanical means such as a shear mixer or the like.

The method of adjusting the transparency of the emulsion of the present invention can particularly be suitably used in cases of adjusting a water-in-oil emulsion composition. The obtained emulsion composition can be processed under high shear conditions using an appropriate apparatus such as a homogenizer or the like and, as a result, the transparency and stability thereof can be further enhanced. Additionally, in step (iii), in cases when adjusting a semi-transparent to high transparent emulsion, the difference in the refractive indexes of the two phases is within at least about 0.0020 refractive index (RI) units, preferably within about 0.00010 units, and most preferably, there is no difference between the refractive indexes of the two phases.

On the other hand, when preparing a milky emulsion or the like, in applications where transparency of the emulsion is not particularly needed, emulsification can be carried out without adjusting the refractive index of each phase, and an opaque emulsion composition can be obtained.

The adjusting of the refractive indexes can be performed by simply diluting the aqueous phase using an additional amount of water. Furthermore, a refractive index (RI) adjuster can be compounded in the aqueous phase or oil phase of the emulsion composition including the co-modified organopolysiloxane according to the present invention in order to adjust the difference between the refractive indexes of the oil phase and the aqueous phase. Thereby, optical transparency of the emulsion composition can be obtained. In other words, when the difference between the refractive indexes of both phases is 0 or extremely small, the entire emulsion composition is transparent or semi-transparent.

A type and amount used of the refractive index adjuster varies according to the refractive indexes of the aqueous phase and the oil phase and, generally, is present in an amount sufficient to adjust the refractive indexes of the aqueous phase and the oil phase so as to obtain optical transparency.

The refractive index adjuster is not particularly limited provided that it is a compound having the effect of increasing the refractive index value of the aqueous phase of the composition or is a component that lowers the refractive index value of the oil phase of the composition. Additionally, adding of the refractive index adjuster may be performed at any stage of the steps (i) to (iv), but from a practical standpoint, the refractive index of each phase is preferably adjusted in step (iii), using the refractive index adjuster.

Examples of the compound used as the refractive index adjuster of the aqueous phase include polyhydric alcohols and derivatives thereof, sugar alcohols and derivatives thereof, polyoxyalkylene group-containing alcohols, polyoxyalkylene group-containing ethers, silicone-polyether copolymers, various water soluble polar compounds, water soluble inorganic salts, organic salts, amino acids, and the like. Combinations of one or more of these aqueous phase refractive index adjusters may be used. A component that is a portion of components (E), (F), (G), and (K) described hereinafter can be suitably used as the aqueous phase refractive index adjuster.

Specific examples of the aqueous phase refractive index adjuster that can be used include propylene glycol, dipropylene glycol, glycerin, sorbitol, mannitol, xylitol, pentaerythritol, trimethylolpropane, hexylene glycol, octylene glycol, 1,2-butanediol, 1,2-pentanediol, 4-methyl-1,2-pentanediol, 2-methyl-1,2-pentanediol, 3,3-methyl-1,2-butanediol, 4-methyl-1,2-hexanediol, 1,2-heptanediol, 3-phenyl-1,2-propanediol, glycerol isopropyl ether, glycerol propyl ether, glycerol ethyl ether, glycerol methyl ether, glycerol butyl ether, glycerol isopentyl ether, diglycerol isopropyl ether, diglycerol isobutyl ether, triglycerol isopropyl ether, alkyl xylitol ether, alkyl sorbitol ether, 1,2,6-hexanetriol, 1,2-hexanediol, 1,2,4-butanetriol, 1,2-butylene glycol, 1,3-butylene glycol, diglycerin, triglycerin, tetraglycerin, polyglycerine, polyethyleneglycol, glycerin monoalkyl ether (e.g. hexyl alcohol, selachyl alcohol, batyl alcohol, and the like); sugar alcohols (e.g. maltitol, maltotriose, sucrose, erythritol, glucose, fructose, starch-decomposed products, maltose, xylitose, starch-decomposed sugar-reduced alcohols, and the like); glysolid; tetrahydrofurfuryl alcohol; POE-tetrahydrofurfuryl alcohol; POP-butyl ether; POP.POE-butyl ether; tripolyoxypropylene glycerin ether; POP-glycerin ether; POP-glycerin ether phosphate; POP.POE-pentane erythritol ether, silicone-polyether copolymers or various water soluble-polar substances; water soluble inorganic salts such as sodium chloride, or organic salts, amino acids, and the like.

Examples of components that can be used as the oil phase refractive index adjuster include the products described as examples of the component (C) of the "oil agent" of the present invention; oils and fats commonly used in cosmetic compositions, higher alcohols, higher fatty acids, organic-based oleophilic surfactants, and the like. However, because this component is used to adjust the oil phase refractive index, it is an oil agent that is different than the oil agent used as the base oil of the oil phase of the emulsion. Combinations of one or more of these oil phase refractive index adjusters may be used. Additionally, a mixture of two base oils may be used for the purpose of adjusting the refractive index of the oil phase.

Specific examples of the oil phase refractive index adjuster include silicone oils, lauryl myristate or diisopropyl sebacate, diisopropyl adipate, ester oils such as benzoic acid alkyls having 8 to 18 carbons, mineral oils or polydecenes, hydrogenated polyisobutene, and similar hydrocarbon oils, oleyl alcohol, batyl alcohol, lanolin alcohol, cholesterol, phytosterol, octyldodecanol, and similar long chain alcohols, PPG-3 myristyl ether or PPG-14 butyl ether, and POE(20) glyceryl triisostearate, or other mixtures.

When using the co-modified organopolysiloxane according to the present invention as a powder treatment agent, dispersion stability in mixed oil agent systems is excellent and, after preparing a powder composition obtained by treating the powder surface using a treatment agent, even when a method is used where the powder composition is dispersed in an oil agent dispersing medium, a powder in oil dispersion having superior stability is provided in which the powder does not agglomerate or precipitate.

The powder that can be used as the powder for treating the co-modified organopolysiloxane according to the present invention is a powder and/or a colorant for use in a cosmetic composition, and this powder and/or colorant can be any powder provided that it is normally used in cosmetic compositions, and is not limited as to form (sphere, bar, needle, plate, amorphous, spindle, or the like), particle size (aerosol, microparticle, pigment-grade particle, or the like), or particle structure (porous, nonporous, or the like) thereof. When compounding the powder and/or colorant as a pigment, preferably one or two or more selected from an inorganic pigment powder, an organic pigment powder, and a resin powder having an average diameter in a range of 1 nm to 20 μm is compounded.

Examples of the powder or powdered colorant component (D) include inorganic powders, organic powders, surfactant metal salt powders (metallic soaps), colored pigments, pearl pigments, metal powder pigments, and the like. In addition, compound products of the pigments can also be used. Specific examples of inorganic powders include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, black mica, lithia mica, silicic acid, silicic acid anhydride, aluminum silicate, sodium silicate, magnesium sodium silicate, magnesium silicate, aluminum magnesium silicate, calcium silicate, barium silicate, strontium silicate, metal salts of tungstic acid, hydroxyapatite, vermiculite, higilite, bentonite, montmorillonite, hectorite, zeolite, ceramic powder, calcium diphosphate, alumina, aluminum hydroxide, boron nitride, and the like. Examples of organic powders include polyamide powder, polyester powder, polyethylene powder, polypropylene powder, polystyrene powder, polyurethane powder, benzoguanamine powder, polymethylbenzoguanamine powder, polytetrafluoroethylene powder, poly(methyl methacrylate) powder, cellulose, silk powder, nylon powder, nylon 12, nylon 6, silicone powder, spherical silicone powder, silicone elastomer spherical particles surface-coated with polymethylsilsesquioxane, polymethylsilsesquioxane spherical particles, copolymers of styrene and acrylic acid, copolymers of divinylbenzene and styrene, vinyl resin, urea resin, phenol resin, fluorine resin, silicone resin, acrylic resin, melamine resin, epoxy resin, polycarbonate resin, microcrystalline fiber powder, starch powder, lauroyl lysine, and the like. Examples of surfactant metal salt powders include zinc stearate, aluminum stearate, calcium stearate, magnesium stearate, zinc myristate, magnesium myristate, zinc palmitate, zinc laurate, zinc cetylphosphate, calcium cetylphosphate, sodium zinc cetylphosphate, and the like. Examples of colored pigments include inorganic red pigments such as red iron oxide, iron oxide, iron hydroxide, iron titanate and the like; inorganic brown pigments such as gamma-iron oxide and the like; inorganic yellow pigments such as yellow iron oxide, ocher, and the like; inorganic black iron pigments such as black iron oxide, carbon black, and the like; inorganic purple pigments such as manganese violet, cobalt violet, and the like; inorganic green pigments such as chromium hydroxide, chromium oxide, cobalt oxide, cobalt titanate, and the like; inorganic blue pigments such as Prussian blue, ultramarine blue, and the like; laked pigments of tar pigments such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207, and the like, laked pigments of natural pigments such as carminic acid, laccaic acid, carthamin, brazilin, crocin, and the like. Examples of pearl pigments include titanium oxide-coated mica, titanium mica, iron oxide-treated titanium mica, titanium oxide-coated mica, bismuth oxychloride, titanium oxide-coated bismuth oxychloride, titanium oxide-coated talc, fish scale foil, titanium oxide-coated colored mica, and the like. Examples of the metal powder pigment include powders of metals such as aluminum, gold, silver, copper, platinum, stainless steel, and the like.

Additionally, a UV-ray absorptive scattering powder such as microparticle titanium oxide, microparticle iron-containing titanium oxide, microparticle zinc oxide, microparticle cerium oxide, compound products thereof, and the like may be used.

Furthermore, the powder and/or colorant is preferably subjected to a water-repellent treatment. Additionally, a product can be used in which these powders and/or colorants are compounded together; or subjected to surface treatment using a general oil agent, a silicone compound other than the co-modified organopolysiloxane according to the present invention, a fluorine compound, a surfactant, or the like. One type thereof or two or more types thereof can be used, as necessary.

Examples of other water-repellent treatments include various treatments in which the powder and/or colorant is surface treated with a water repellency agent. Specific examples thereof include organosiloxane treatments such as a methylhydrogenpolysiloxane treatment, a silicone resin treatment, a silicone gum treatment, an acryl silicone treatment, a fluorinated silicone treatment, and the like; metallic soap treatments such as a zinc stearate treatment and the like; silane treatments such as a silane coupling agent treatment, an alkylsilane treatment, and the like; fluorine compound treatments such as a perfluoroalkylsilane treatment, a perfluoroalkyl phosphate treatment, a perfluoro polyether treatment, and the like; amino acid treatments such as an N-lauroyl-L-lysine treatment and the like; oil agent treatments such as a squalane treatment and the like; acryl treatments such as an alkyl acrylate treatment and the like. The treatments described above can be used in combinations of one or more types thereof.

When using the co-modified organopolysiloxane according to the present invention as the powder surface treatment agent, a compounded amount of the co-modified organopolysiloxane and the powder and/or colorant is preferably in a range from 0.1 to 30 parts by weight, and more preferably from 0.5 to 10 parts by weight per 100 parts by mass of the powder and/or colorant. Furthermore, the compounded amount of the powder and/or colorant in a topical composition, particularly a cosmetic composition, is preferably in a range from 0.1 to 99 wt. % of the entire cosmetic composition. Particularly, the compounded amount when using in a powdered solid cosmetic composition is preferably in a range from 80 to 99 wt. % of the entire cosmetic composition.

The co-modified organopolysiloxane according to the present invention can be used to treat a powder surface using a conventional method. This method is not particularly limited, and an appropriate method from those described below can be selected.

1. A method in which the target powder is surface treated by being dispersed in a medium selected from organic solvents in which a treatment agent is compounded.

2. A method in which the powder and a powder treatment agent are mixed and, thereafter, surface treating is performed using a pulverizer such as a ball mill, a jet mill, or the like.

3. A treatment method in which a treatment agent is compounded in a solvent and adsorbed on a surface of the powder by dispersing the powder therein and, thereafter, dried and sintered.

Additionally, "powder in oil dispersion" as used in the present invention, refers to a product in which a powder composition obtained as described above is dispersed in an oil agent or, alternately, a product in which a co-modified organopolysiloxane is dissolved or dispersed in an oil agent, and then the powder is added by being mixed and dispersed therein; and a form thereof is that of a liquid dispersed product. The powder in oil dispersion of the present invention can be appropriately prepared according to a known method such as the methods described below.

1. A method in which the powder composition obtained as described above is added to and dispersed in an oil agent such as an ester oil, a silicone oil, or the like.

2. A method in which a co-modified organopolysiloxane is dissolved or dispersed in the oil agent described above, the powder is added thereto, and the mixing is performed using a dispersing apparatus such as a ball mill, a bead mill, a sand mill, or the like.

The obtained powder in oil dispersion can be compounded as-is in a cosmetic composition.

The powder composition and the powder in oil dispersion including the co-modified organopolysiloxane according to the present invention can be suitably used as a topical composition, particularly for a cosmetic composition or a cosmetic raw material.

The co-modified organopolysiloxane according to the present invention is particularly useful as a cosmetic raw material, a medicament raw material, or a topical composition, and cosmetic compositions including the co-modified organopolysiloxane provide a benefit of superior properties. Specifically, a cosmetic composition that works to promote the effects of water and suppress oiliness in cases when compounded in a cosmetic composition comprising water and an oil agent and which, as a result, has superior effects of imparting silky-smooth moisturization to the skin and maintaining that feel can be obtained. Furthermore, the co-modified organopolysiloxane according to the present invention is also useful as a cosmetic composition comprising the organopolysiloxane and an oil agent (also referred as "oil-based cosmetic composition"), which is substantially water-free. Examples of the oil agent used in this case include the same components described above.

Depending on the purpose thereof, the cosmetic composition of the present invention can include one or two or more polyhydric alcohols and/or lower monohydric alcohols as a component (E).

Examples of lower alcohols include ethanol, isopropanol, n-propanol, t-butanol, s-butanol, and the like. Examples of polyhydric alcohols include divalent alcohols such as 1,3-butylene glycol, 1,2-butylene glycol, propylene glycol, trimethylene glycol, tetramethylene glycol, 2,3-butylene glycol, pentamethylene glycol, 2-buten-1,4-diol, dibutylene glycol, pentyl glycol, hexylene glycol, octylene glycol, and the like; trivalent alcohols such as glycerol, trimethylol propane, 1,2,6-hexanetriol, and the like; polyhydric alcohols having 4 or more valences such as pentaerythritol, xylitol, and the like; and sugar alcohols such as sorbitol, mannitol, maltitol, maltotriose, sucrose, erythritol, glucose, fructose, a starch-decomposed product, maltose, xylitose, starch-decomposed sugar-reduced alcohol, and the like. Furthermore, examples other than low-molecule polyhydric alcohols include polyhydric alcohol polymers such as diethylene glycol, dipropylene glycol, triethylene glycol, polypropylene glycol, tetraethylene glycol, diglycerol, polyethylene glycol, triglycerol, tetraglycerol, polyglycerol, and the like. Of these, 1,3-butylene glycol, sorbitol, dipropylene glycol, glycerol, and polyethylene glycol are particularly preferable. A compounded amount thereof is preferably from 0.1 to 50 wt. % of the entire cosmetic composition. Additionally, polyhydric alcohol can be blended in order to improve storage stability of the cosmetic composition, in an amount ranging from about 5 to 30 wt. % of the entire cosmetic composition. This is an example of a preferable mode of the present invention.

Depending on the purpose thereof, the cosmetic composition of the present invention can include one or two or more inorganic salts and/or organic salts as a component (F). Examples of inorganic salts include hydrochloric acid, sulfuric acid, nitric acid, carbonic acid, phosphoric acid, and similar alkali metal salts, alkali earth metal salts, aluminum salts, zinc salts, ammonium salts, and the like. Preferable inorganic salts include sodium chloride, potassium chloride, magnesium chloride, calcium chloride, aluminium chloride, zinc chloride, ammonium chloride, and similar chlorides; sodium sulfate, potassium sulfate, magnesium sulfate, aluminium sulfate, zinc sulfate, ammonium sulfate, and other sulfides; sodium nitrate, potassium nitrate, magnesium nitrate, calcium nitrate, aluminum nitrate, zinc nitrate, ammonium nitrate, and similar nitrates; sodium carbonate, potassium carbonate, magnesium carbonate, calcium carbonate, and similar carbonates; and sodium phosphate, potassium phosphate, and similar phosphates. Of these, sodium chloride, potassium chloride, magnesium chloride, calcium chloride, sodium sulfate, potassium sulfate, magnesium sulfate, and aluminium sulfate are particularly preferable. Examples of organic salts include, in addition to sodium acetate, potassium acetate, and sodium ascorbate; sodium citrate, sodium lactate, sodium glycolate, sodium malate, sodium tartrate, and similar α-hydroxyacid salts; sodium aspartate, potassium aspartate, magnesium aspartate, calcium aspartate, sodium glutamate, potassium glutamate, magnesium glutamate, calcium glutamate, arginine-glutamate salts, ornithine-glutamate salts, lysine-glutamate salts, lysine-aspartate salts, ornithine-aspartate salts, and similar amino acid salts; sodium alginate; and the like. Of these, sodium acetate, sodium citrate, sodium lactate, and sodium glutamate are particularly preferable. A compounded amount thereof is from 0.1 to 8 wt. % and preferably from 0.5 to 5 wt. % of the entire cosmetic composition.

Depending on the purpose thereof, one or two or more silicone-based surfactants can be used as a component (G) (however, with the exception of the co-modified organopolysiloxane component (A)) in the cosmetic composition of the present invention. Such a silicone-based surfactant is not particularly limited, and preferable examples thereof include straight polyoxyalkylene-modified organopolysiloxane (polyether-modified silicone in which a polyoxyalkylene group is bonded at a sidechain and/or a terminal), a block copolymerized type polyoxyalkylene/dimethylpolysiloxane copolymer, and a straight polyoxyalkylene/alkyl-co-modified organopolysiloxane (alkyl/polyether-modified silicone in which a polyoxyalkylene group and an alkyl group are bonded at a sidechain and/or a terminal). Additional preferable examples of silicone-based surfactants include the specific elastomer silicone polyethers described in Japanese Patent No. 4080597 (Japanese Unexamined Patent Application Publication No. H-11-49957), Japanese Unexamined Patent Application Publication No. 2001-011281, and the like (examples of commercially available products include DC 9011 Silicone Elastomer Blend, manufactured by Dow Corning Corporation, in the USA).

Of the other silicone-based surfactants, examples of products that function as cleansing components or emulsifiers of oil agents include polyglyceryl-modified silicones, glyceryl-modified silicones, sugar-modified silicone fluorosurfactants, polyoxyethylene/polyoxypropylene block polymers, and alkylpolyoxyethylene/polyoxypropylene block polymer ethers.

Depending on the purpose thereof, the cosmetic composition of the present invention can include at least one selected from the group consisting of a crosslinking organopolysiloxane, an organopolysiloxane elastomer spherical powder, a silicone resin, an acryl silicone dendrimer copolymer, a silicone raw rubber, a polyamide-modified silicone, an alkyl-modified silicone wax, and an alkyl-modified silicone resin wax as a component (H). Each component is described hereinafter.

In the cosmetic composition of the present invention, the crosslinking organopolysiloxane used depending on the purpose of the cosmetic composition is an organopolysiloxane having a structure in which the organopolysiloxane chain is three-dimensionally crosslinked via a reaction with a crosslinking component or the like, and preferably does not have a hydrophilic portion such as a polyoxyalkylene unit or the like, and is non-emulsifiable. Any crosslinking organopolysiloxane can be used without limitations to physical modes or preparation methods such as dilution, properties, and the like, provided that it is a crosslinking organopolysiloxane. Particularly preferable examples include α,ω-diene crosslinking silicone elastomers (commercially available products include DC 9040 Silicone Elastomer Blend, DC 9041 Silicone Elastomer Blend, DC 9045 Silicone Elastomer Blend, and DC 9046 Silicone Elastomer Blend, manufactured by Dow Corning Corporation, in the USA) described in U.S. Pat. No. 5,654,362. Likewise, examples of partially crosslinking organopolysiloxane polymers include (dimethicone/vinyldimethicone) crosspolymers, (dimethicone/phenylvinyldimethicone) crosspolymers, (PEG-8 to 30/C6 to C30 alkyldimethicone) crosspolymers, (vinyldimethicone/C6 to C30 alkyldimethicone) crosspolymers, (dimethicone/polyglycerol) crosspolymers, and the like, using INCI names (International Nomenclature Cosmetic Ingredient labeling names).

In the case of being compounded as an emulsifiable crosslinking organopolysiloxane formed by crosslinking by means of a polyether compound as a component in a cosmetic composition, the co-modified organopolysiloxane according to the present invention functions as a surfactant or, alternately, a surfactant aid. For this reason, there is an advantage in that a uniform emulsification system can be formed. Furthermore, because the crosslinking organopolysiloxane functions as a surfactant, even when used in small amounts, a hydrous gel structure can be formed stably. This is advantageous because a water-containing cosmetic composition or emulsion cosmetic composition can be obtained that is soft and has superior water retention properties.

On the other hand, in the case of being compounded as a non-emulsifiable crosslinking organopolysiloxane, formed by crosslinking by means of an unsaturated hydrocarbon group such as a diene or an organopolysiloxane as a component, in a cosmetic composition, feel of adhesion to the skin can be improved. Furthermore, there are advantages in that excellent compatibility with other oil-based raw materials can be obtained, and the entire oil system can be uniformly and stably compounded in the cosmetic composition.

The organopolysiloxane elastomer spherical powder used in the cosmetic composition of the present invention depending on the purpose of the cosmetic composition is the same component as the spherical silicone powder described as the component (D), and may be subjected to powder treatment using the co-modified organopolysiloxane according to the present invention beforehand. However, the organopolysiloxane elastomer spherical powder is not limited thereto, and can also be used untreated. This organopolysiloxane elastomer spherical powder preferably has a primary particle size in a range from 0.1 to 50 μm. The organopolysiloxane elastomer spherical powder may be surface treated using silicone resin, silica, or the like. Examples of commercially available products of the organopolysiloxane elastomer spherical powder include Trefil E-506S, Trefil E-508, 9701 Cosmetic Powder, and 9702 Powder, manufactured by Dow Corning Toray Co., Ltd., and the like. Additionally, the organopolysiloxane elastomer spherical powder can be used in the cosmetic composition of the present invention in the form of an aqueous dispersion. Examples of commercially available products of the aqueous dispersion include BY 29-129 and PF-2001 PIF Emulsion, manufactured by Dow Corning Toray Co., Ltd., and the like. Adding a powdered silicone elastomer to the cosmetic composition according to the present invention is advantageous because a feeling to touch that is substantial, such as that obtained when an oil agent is dispersed, is imparted, unevennesses of the skin are concealed, and, in contrast with oil agents, a natural impression is given due to oily shininess of the skin and oily texture being suppressed.

One or two or more types of the silicone elastomer can be compounded depending on the purpose thereof. A compounded amount of the silicone elastomer is preferably in a range from 0.05 to 25 wt. % and more preferably in a range from 0.1 to 15 wt. % of the entire cosmetic composition, depending on purpose and compounding intention.

Preferable examples of silicone resins used in the cosmetic composition of the present invention depending on the purpose of the cosmetic composition include solid silicone net-like compounds such as MQ resin, MDQ resin, MTQ resin, MDTQ resin, TD resin, TQ resin, and TDQ resin formed from any combination of a trialkylsiloxy unit (M unit), a dialkylsiloxy unit (D unit), a monoalkylsiloxy unit (T unit), and a tetrafunctional siloxy unit (Q unit). Note that the substituent on the silicon of these silicone resins may include a substituted alkyl group, a phenyl group, an aryl group, or the like, in addition to the alkyl group. Of these, from the standpoint of obtaining superior usability, fluorine-modified silicone resins, trimethylsiloxy silicic acid (MQ resin), and dimethylsiloxy group-containing trimethylsiloxy silicic acid (MDQ resin) are particularly preferable. Compounding the silicone resin in conjunction with the co-modified organopolysiloxane according to the present invention is useful because the following improvement effects can be obtained due to the compounding of the silicone resin: improvements in feeling to touch of the cosmetic composition, uniform adhesion to the applied area, and adhesion of the powder to the skin.

Examples of acryl silicone dendrimer copolymers used in the cosmetic composition of the present invention depending on the purpose of the cosmetic composition include a vinyl-based polymer having a carbosiloxane dendrimer structure at the side chain such as that described in Japanese Patent No. 4009382 (Japanese Unexamined Patent Application Publication No. 2000-063225). Examples of commercially available products thereof include FA4001 CM Silicone Acrylate, FA4002 ID Silicone Acrylate (manufactured by Dow Corning Toray Co., Ltd.), and the like. When compounding the acryl silicone dendrimer copolymer alone, superior film formability can be obtained. Therefore, by compounding the dendrimer copolymer in the cosmetic composition according to the present invention, a strong cosmetic coating film can be formed on the applied part, and cosmetic durability such as sebum resistance, rubbing resistance, and the like can be significantly improved.

By using the co-modified organopolysiloxane together with the acryl silicone dendrimer copolymer, there are advantages in that a surface protective property such as sebum resistance can be improved due to strong water repellency provided by the carbosiloxane dendrimer structure; and at the same time, excellent feeling to touch and brightness are imparted when applying, and irregularities such as pores and wrinkles of the skin to which the cosmetic composition is applied can be effectively concealed due to the high emulsion stability of the present invention product being maintained. Moreover, the co-modified organopolysiloxane according to the present invention displays excellent miscibility with other oil agents, powders, the colorant, and the acryl silicone dendrimer copolymer and, therefore, there is an advantage in that makeup running or gathering on the skin can be controlled. Furthermore, when powders or colorants are treated in accordance with a conventional method by using the co-modified organopolysiloxane together with the acryl silicone dendrimer copolymer, a powder composition for use in a cosmetic composition with superior compounding stability can be prepared.

A compounded amount of the acryl silicone dendrimer copolymer can be suitably selected based on the purpose and compounding intent thereof, but is preferably in a range from 1 to 99 wt. % and more preferably in a range from 30 to 70 wt. % of the entire cosmetic composition.

The cosmetic composition of the present invention, depending on the purpose thereof, can include a silicone raw rubber (referred to also as "silicone gum"). Silicone raw rubber is differentiated from the oily silicones described above because the degree of polymerization of silicone raw rubber is high and, as a result, has a degree of plasticity that is measurable. Examples of such a silicone raw rubber include substituted or unsubstituted organopolysiloxanes having a dialkylsiloxy unit (D unit). Examples thereof include dimethylpolysiloxane, methylphenylpolysiloxane, methylfluoroalkylpolysiloxane, and the like, products that have a micro crosslinked structure thereof, and the like. Of these, a dimethylpolysiloxane raw rubber having a degree of polymerization from 3,000 to 20,000 is preferable.

Silicone gum has an ultra-high degree of polymerization and, therefore forms a protective film with superior breathability and retention on hair or skin. Therefore, the silicone gum is a component which can particularly provide glossiness and luster to hair and can impart a texture of firmness and body to the entire hair during use and after use.

A compounded amount of the silicone gum is from 0.05 to 30 wt. % and preferably from 1 to 15 wt. % of the entire cosmetic composition. When an emulsion composition prepared via a step of pre-emulsifying (including emulsion polymerization) is used, the silicone gum can easily be compounded, and can be stably compounded in the various cosmetic compositions of the present invention. Particularly, when the cosmetic composition of the present invention is a hair cosmetic composition or the like, an effect of imparting a specific feeling to touch or glossiness of the hair may be insufficient if the compounded amount of the silicone gum is less than the lower limit described above.

Examples of the polyamide-modified silicone used in the cosmetic composition of the present invention depending on the purpose of the cosmetic composition include a siloxane-based polyamide described in U.S. Pat. No. 5,981,680; and examples of commercially available products include 2-8178 Gellant, 2-8179 Gellant, and the like (manufactured by Dow Corning Corporation, in the USA). Such polyamide-modified silicones are useful as an oil-based raw material, and in particular, a thickening/gelling agent of a silicone oil, similar to an oil-soluble gelling agent described hereinafter.

Compatibility with the oil agent such as a silicone oil or the like can be further improved by using the polyamide-modified silicone together with the organosiloxane copolymer of the present invention. Thereby, the cosmetic composition according to the present invention delivers a superior sense of stability and adhesion, and excellent spreading and setting when applied to the skin or hair. Additionally, there are advantages from a quality standpoint such that a glossy, sheer sensation and superior luster can be provided, the viscosity or hardness (softness) of the entire cosmetic composition containing the oil-based raw material can be appropriately adjusted, and an oily sensation (oily and sticky feeling to touch) can be totally controlled. Moreover, because the polyamide-modified silicone and the co-modified organosiloxane of the present invention is used, dispersion stability of a perfume, a powder, and the like can be improved. Thereby, the obtained cosmetic composition is characterized by being able to maintain a uniform and fine cosmetic sensation for an extended period of time.

A compounded amount of the polyamide-modified silicone can be suitably selected based on the purpose and compounding intent thereof but, when using the polyamide-modified silicone as a gelling agent for an oil-based raw material, is in a range from 0.5 to 80 parts by weight and preferably in a range from 1 to 50 parts by weight per 100 parts by weight of the oil-based component such as the oil agent or the like.

The alkyl-modified silicone wax used in the cosmetic composition of the present invention depending on the purpose of the cosmetic composition needs only to be an alkyl-modified silicone wax in wax form at room temperature, and examples thereof include methyl (long chain alkyl) polysiloxanes having both molecular terminals capped with trimethylsiloxy groups, copolymers of a dimethylpolysiloxane having both molecular terminals capped with trimethylsiloxy groups and a methyl (long chain alkyl) siloxane, dimethylpolysiloxane modified with long chain alkyls at both terminals, and the like. Examples of commercially available products include AMS-C30 Cosmetic Wax, 2503 Cosmetic Wax, and the like (manufactured by Dow Corning Corporation, in the USA).

When using the co-modified organosiloxane according to the present invention in combination with the alkyl-modified silicone wax, compatibility with the oil-based raw material is improved, and superior formability and uniform dispersibility of the other components can be obtained and, thereby a cosmetic composition exhibiting superior storage stability over an extended period of time can be obtained. In particular, in a system containing a powder and a colorant, there is an advantage in that separation of the system including the alkyl-modified silicone wax, for the most part, does not occur, and an oil-based cosmetic composition having superior form-retaining strength and which spreads smoothly and uniformly when applied can be provided.

In the present invention, the alkyl-modified silicone wax preferably has a melting point of not lower than 60° C. because such will lead to cosmetic retainability effects and stability at high temperatures. A compounded amount thereof can be suitably selected based on the purpose and compounding intent thereof, and can be compounded in a range from 1 to 50 wt. % of the entire cosmetic composition. The compounded amount is preferably in a range from 5 to 40 wt. % because such leads to improvements in the formability and cosmetic retainability of the oil-based cosmetic composition. Additionally, the alkyl-modified silicone wax displays high compatibility with silicone oil having a long chain alkyl group such as the alkyl-modified silicone or the like and the crosslinking organopolysiloxanes and, therefore, is preferably used in combination with these optional components.

Examples of the alkyl-modified silicone resin wax used in the cosmetic composition of the present invention depending on the purpose of the cosmetic composition include the silsesquioxane resin wax described in Japanese Patent Application (Translation of PCT Application) No. 2007-532754.

As a result of using the alkyl-modified silicone resin wax in combination with the organosiloxane copolymer of the present invention and compounding these in the cosmetic composition of the present invention, there are advantages of conditioning effects on skin and hair being improved and fine texture and a moisturized feeling to touch being imparted.

In the present invention, a compounded amount of the alkyl-modified silicone resin wax can be suitably selected based on the purpose and compounding intent thereof, and can be compounded in a range from 0.5 to 50 wt. % of the entire cosmetic composition. The compounded amount is preferably in a range from 1 to 30 wt. % in order to attain sebum durability and a fine texture feeling to touch of the cosmetic composition.

The topical composition, cosmetic composition, cosmetic raw material, or the like of the present invention can, as necessary, further comprise another surfactant component (J). Particularly, one or two or more surfactants (J) selected from the group consisting of an anionic surfactant, a cationic surfactant, a nonionic surfactant, an amphoteric surfactant, and a semipolar surfactant can be used in combination for the purpose of dispersing the oil agent in water with higher stability. Furthermore, from the standpoint of being able to improve overall stability of the formulation, a silicone-based nonionic surfactant is preferably used. A compounded amount of these surfactants is in a range from 0.1 to 25 wt. % and preferably in a range from 0.5 to 10 wt. % of the entire cosmetic composition. However, in cases where the cosmetic composition according to the present invention is a cosmetic composition for cleansing skin or cleansing hair, for the purpose of improving cleansing properties, the compounded amount can be adjusted to within a range from 0.1 to 90 wt. % of the entire cosmetic composition and, from the standpoint of cleansing ability, the surfactant component is preferably compounded at an amount not less than 25 wt. % of the entire cosmetic composition.

Furthermore, in cases where the organopolysiloxane of the present invention is used in a cleansing agent, from the standpoint of cleansing activity, two or more types of surfactants can be preferably compounded.

More specifically, examples of anionic surfactants include saturated or unsaturated fatty acid salts (e.g. sodium laurate, sodium stearate, sodium oleate, sodium linolenate, and the like); alkylsulfuric acid salts; alkylbenzene sulfonic acids (e.g. hexylbenzenesulfonic acid, octylbenzenesulfonic acid, dodecylbenzenesulfonic acid, and the like) and salts thereof; polyoxyalkylene alkyl ether sulfuric acid salts; polyoxyalkylene alkenyl ether sulfuric acid salts; polyoxyethylene alkylsulfuric ester salts; sulfosuccinic acid alkyl ester salts; polyoxyalkylene sulfosuccinic acid alkyl ester salts; polyoxyalkylene alkylphenyl ether sulfuric acid salts; alkanesulfonic acid salts; octyltrimethylammonium hydroxide; dodecyltrimethylammonium hydroxide; alkyl sulfonates; polyoxyethylene alkylphenyl ether sulfuric acid salts; polyoxyalkylene alkyl ether acetic acid salts; alkyl phosphoric acid salts; polyoxyalkylene alkyl ether phosphoric acid salts; acylglutamic acid salts; α-acylsulfonic acid salts; alkylsulfonic acid salts; alkylallylsulfonic acid salts; α-olefinsulfonic acid salts; alkylnaphthalene sulfonic acid salts; alkanesulfonic acid salts; alkyl- or alkenylsulfuric acid salts; alkylamide sulfuric acid salts; alkyl- or alkenyl phosphoric acid salts; alkylamide phosphoric acid salts; alkyloylalkyl taurine salts; N-acylamino acid salts; sulfosuccinic acid salts; alkyl ether carboxylic acid salts; amide ether carboxylic acid salts; α-sulfofatty acid ester salts; alanine derivatives; glycine derivatives; and arginine derivatives. Examples of salts include alkali metal salts such as sodium salts and the like, alkaline earth metal salts such as magnesium salts and the like, alkanolamine salts such as triethanolamine salts and the like, and ammonium salts.

Examples of cationic surfactants include alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, distearyldimethylammonium chloride, dicocoyldimethylammonium chloride, dioctyldimethylammonium chloride, di(POE)oleylmethylammonium (2 EO) chloride, benzalkonium chloride, alkyl benzalkonium chloride, alkyl dimethylbenzalkonium chloride, benzethonium chloride, stearyl dimethylbenzylammonium chloride, lanolin derivative quaternary ammonium salt, diethylaminoethylamide stearate, dimethylaminopropylamide stearate, behenic acid amide propyldimethyl hydroxypropylammonium chloride, stearoyl colaminoformyl methylpyridinium chloride, cetylpyridinium chloride, tall oil alkylbenzyl hydroxyethylimidazolinium chloride, and benzylammonium salt.

Examples of nonionic surfactants include polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene (hydrogenated) castor oils, polyoxyalkylene alkyl phenols, polyoxyalkylene alkyl phenyl ethers, polyoxyalkylene phenyl phenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerol fatty acid esters, polyglycerol alkyl ethers, polyglycerol fatty acid esters, sucrose fatty acid esters, fatty acid alkanolamides, alkylglucosides, polyoxyalkylene fatty acid bisphenyl ethers, polypropylene glycol, diethyleneglycol, polyoxyalkylene-modified silicones, polyglyceryl-modified silicones, glyceryl-modified silicones, sugar-modified silicones, fluorine-based surfactants, polyoxyethylene/polyoxypropylene block polymers, and alkyl polyoxyethylene/polyoxypropylene block polymer ethers. A polyoxyalkylene-modified silicone, a polyglycerol-modified silicone, or a glycerol-modified silicone in which an alkyl branch, a straight silicone branch, or the like may be possessed together with a hydrophilic group at the same time, if necessary, can also be preferably used.

Examples of amphoteric surfactants include imidazoline-type, amidobetaine-type, alkylbetaine-type, alkylamidobetaine-type, alkylsulfobetaine-type, amidosulfobetaine-type, hydroxysulfobetaine-type, carbobetaine-type, phosphobetaine-type, aminocarboxylic acid-type, and amidoamino acid-type amphoteric surfactants. Specific examples thereof include imidazoline-type amphoteric surfactants such as sodium 2-undecyl-N,N,N-(hydroxyethylcarboxymethyl)-2-imidazoline, 2-cocoyl-2-imidazolinium hydroxide-1-carboxyethyloxy disodium salt, and the like; alkylbetaine-type amphoteric surfactants such as lauryl dimethylaminoacetic acid betaine, myristyl betaine, and the like; and amidobetaine-type amphoteric surfactants such as coconut oil fatty acid amidopropyl dimethylamino acetic acid betaine, palm kernel oil fatty acid amidopropyl dimethylamino acetic acid betaine, beef tallow fatty acid amidopropyl dimethylamino acetic acid betaine, hardened beef tallow fatty acid amidopropyl dimethylamino acetic acid betaine, lauric amidopropyl dimethylamino acetic acid betaine, myristic amidopropyl dimethylamino acetic acid betaine, palmitic amidopropyl dimethylamino acetic acid betaine, stearic amidopropyl dimethylamino acetic acid betaine, oleic amidopropyl dimethylamino acetic acid betaine, and the like; alkyl sulfobetaine-type amphoteric surfactants such as coconut oil fatty acid dimethyl sulfopropyl betaine and the like; alkylhydroxy sulfobetaine-type amphoteric surfactants such as lauryl dimethylaminohydroxy sulfobetaine and the like; phosphobetaine-type amphoteric surfactants such as laurylhydroxy phosphobetaine and the like; amidoamino acid-type amphoteric surfactants such as sodium N-lauroyl-N'-hydroxyethyl-N'-carboxymethyl ethylenediamine, sodium N-oleoyl-N'-hydroxyethyl-N'-carboxymethyl ethylenediamine, sodium N-cocoyl-N'-hydroxyethyl-N'-carboxymethyl ethylenediamine, potassium N-lauroyl-N'-hydroxyethyl-N'-carboxymethyl ethylenediamine, potassium N-oleoyl-N'-hydroxyethyl-N'-carboxymethyl ethylenediamine, sodium N-lauroyl-N-hydroxyethyl-N'-carboxymethyl ethylenediamine, sodium N-oleoyl-N-hydroxyethyl-N'-carboxymethyl ethylenediamine, sodium N-cocoyl-N-hydroxyethyl-N'-carboxymethyl ethylenediamine, monosodium N-lauroyl-N-hydroxyethyl-N',N'-dicarboxymethyl ethylenediamine, monosodium N-oleoyl-N-hydroxyethyl-N',N'-dicarboxymethyl ethylenediamine, monosodium N-cocoyl-N-hydroxyethyl-N',N'-dicarboxymethyl ethylenediamine, disodium N-lauroyl-N-hydroxyethyl-N',N'-dicarboxymethyl ethylenediamine, disodium N-oleoyl-N-hydroxyethyl-N',N'-dicarboxymethyl ethylenediamine, disodium N-cocoyl-N-hydroxyethyl-N',N'-dicarboxymethyl ethylenediamine, and the like.

Examples of semipolar surfactants include alkylamine oxide-type surfactants, alkylamine oxides, alkylamide amine oxides, alkylhydroxyamine oxides, and the like. Alkyldimethylamine oxides having from 10 to 18 carbons, alkoxyethyl dihydroxyethylamine oxides having from 8 to 18 carbons, and the like are preferably used. Specific examples thereof include dodecyldimethylamine oxide, dimethyloctylamine oxide, diethyldecylamine oxide, bis-(2-hydroxyethyl)dodecylamine oxide, dipropyltetradecylamine oxide, methylethylhexadecylamine oxide, dodecylamidopropyldimethylamine oxide, cetyldimethylamine oxide, stearyldimethylamine oxide, tallow dimethylamine oxide, dimethyl-2-hydroxyoctadecylamine oxide, lauryldimethylamine oxide, myristyldimethylamine oxide, isostearyldimethylamine oxide, coconut fatty acid alkyldimethylamine oxide, caprylic amide propyldimethylamine oxide, capric amide propyldimethylamine oxide, lauric amide propyldimethylamine oxide, myristic amide propyldimethylamine oxide, palmitic amide propyldimethylamine oxide, stearic amide propyldimethylamine oxide, isostearic amide propyldimethylamine oxide, oleic amide propyldimethylamine oxide, ricinoleic amide propyldimethylamine oxide, 12-hydroxystearic amide propyldimethylamine oxide, coconut fatty acid amide propyldimethylamine oxide, palm kernel oil fatty acid amide propyldimethylamine oxide, castor oil fatty acid amide propyldimethylamine oxide, lauric amide ethyldimethylamine oxide, myristic amide ethyldimethylamine oxide, coconut fatty acid amide ethyldimethylamine oxide, lauric amide ethyldiethylamine oxide, myristic amide ethyldiethylamine oxide, coconut fatty acid amide ethyldiethylamine oxide, lauric amide ethyldihydroxyethylamine oxide, myristic amide ethyldihydroxyethylamine oxide, and coconut fatty acid amide ethyldihydroxyethylamine oxide.

The cosmetic composition of the present invention can, depending on the purpose of the cosmetic composition, include one or two or more water-soluble polymers as a component (K). The water-soluble polymer can be compounded in order to prepare a cosmetic composition in the desired form and adjust the refractive index of and stabilize the aqueous phase. Additional compounding purposes include improving sensation during use of the cosmetic composition such as feeling to touch with respect to skin, hair, or the like, improving moisturizing effects, improving conditioning effects, and the like. Any of amphoteric, cationic, anionic, and nonionic polymers, and water-swellable clay minerals can be used provided that it is commonly used in a cosmetic product. The water-soluble polymers described above have an effect of thickening a hydrous component and, for this reason, are particularly useful in obtaining a gel-like hydrous cosmetic composition, a water-in-oil emulsion cosmetic composition, and an oil-in-water emulsion cosmetic composition. Examples of natural water-soluble polymers include vegetable-based polymers such as gum Arabic, tragacanth gum, galactan, guar gum, carob gum, karaya gum, carrageenan, pectin, agar, quince seed (*Cyclonia oblonga*), algal colloid (seaweed extract), starch (rice, corn, potato, or wheat), glycyrrhizinic acid, and the like; microorganism-based polymers such as xanthan gum, dextran, succinoglucan, pullulan, and the like; and animal-based polymers such as collagen, casein, albumin, gelatin, and the like. Additionally, examples of semisynthetic water-soluble polymers include starch-based polymers such as carboxymethyl starch, methylhydroxypropyl starch, and the like; cellulose-based polymers such as methylcellulose, nitrocellulose, ethylcellulose, methylhydroxypropylcellulose, hydroxyethylcellulose, sodium cellulose sulfate, hydroxypropylcellulose, sodium carboxymethylcellulose (CMC), crystalline cellulose, cellulose powder, and the like; and alginate-based polymers such as sodium alginate, propylene glycol alginate, and the like. Examples of synthetic water-soluble polymers include vinyl-based polymers such as polyvinylalcohol, polyvinyl methyl ether-based polymer, polyvinylpyrrolidone, carboxyvinyl polymer (CARBOPOL 940, CARBOPOL 941; manufactured by B.F. Goodrich Corporation), and the like; polyoxyethylene-based polymers such as polyethyleneglycol 20,000, polyethyleneglycol 6,000, polyethyleneglycol 4,000, and the like; copolymer-based polymers such as a copolymer of polyoxyethylene and polyoxypropylene, PEG/PPG-36/41 dimethylether, PEG/PPG-14/7 dimethylether, and the like; acryl-based polymers such as poly(sodium acrylate), poly(ethyl acrylate), polyacrylamide, and the like; polyethylene imines; cationic polymers; and the like. Examples of other cationic water-soluble polymers, in particular, as components which are preferably compounded in hair cosmetic compositions, include quaternary nitrogen-modified polysaccharides (e.g. cation-modified cellulose, cation-modified hydroxyethylcellulose, cation-modified guar gum, cation-modified locust bean gum, cation-modified starch, and the like); dimethyldiallylammonium chloride derivatives (e.g. a copolymer of dimethyldiallylammonium chloride and acrylamide, poly (dimethylmethylene piperidinium chloride), and the like); and vinylpyrrolidone derivatives (e.g. a copolymer of vinylpyrrolidone and dimethylaminoethyl methacrylic acid, a copolymer of vinylpyrrolidone and methacrylamide propyltrimethylammonium chloride, a copolymer of vinylpyrrolidone and methylvinylimidazolium chloride, and the like).

Depending on the purpose thereof, the cosmetic composition of the present invention can include one or two or more ultraviolet light blocking components as a component (L). Examples thereof include benzoic acid-based UV absorbers such as paraminobenzoic acid (hereinafter, referred to as "PABA"), PABA monoglycerol ester, N,N-dipropoxy-PABA ethyl ester, N,N-diethoxy-PABA ethyl ester, N,N-dimethyl-PABA ethyl ester, N,N-dimethyl-PABA butyl ester, and the like; anthranilic acid-based UV absorbers such as homomethyl-N-acetylanthranilate and the like; salicylic acid-based UV absorbers such as amyl salicylate, menthyl salicylate, homomethyl salicylate, octyl salicylate, phenyl salicylate, benzyl salicylate, p-isopropanolphenyl salicylate, and the like; cinnamic acid-based UV absorbers such as octyl cinnamate, ethyl-4-isopropylcinnamate, methyl-2,5-diisopropylcinnamate, ethyl-2,4-diisopropylcinnamate, methyl-2,4-diisopropylcinnamate, propyl-p-methoxycinnamate, isopropyl p-methoxycinnamate, isoamyl-p-methoxycinnamate, octyl-p-methoxycinnamate (2-ethylhexyl-p-methoxycinnamate), 2-ethoxyethyl-p-methoxycinnamate, cyclohexyl-p-methoxy cinnamate, ethyl-α-cyano-β-phenylcinnamate, 2-ethylhexyl-α-cyano-β-phenylcinnamate, glyceryl mono-2-ethylhexanoyl-diparamethoxycinnamate, 3-methyl-44-methylbis (trimethylsiloxy) silylbutyl 3,4,5-trimethoxycinnamate, and the like; benzophenone-based UV absorbers such as 2,4- dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenylbenzophenone-2-carboxylate, hydroxy-4-n-octoxybenzophenone, 4-hydroxy-3-carboxybenzophenone, and the like; benzotriazole-based UV absorbers such as 2-[4-(2-ethylhexyloxy)-2-hydroxyphenyl]-2H-benzotriazole, 2-(2-hydroxy-4-isobutoxyphenyl)-2H-benzotriazole, and the like; octrocrylene; 3-(4'-methylbenzylidene)-d,l-camphor; 3-benzylidene-d,l-camphor; urocanic acid; urocanic acid ethyl ester; 2-phenyl-5-methylbenzoxazole; 2,2'-hydroxy-5-methylphenyl benzotriazole; 2-(2'-hydroxy-5'-t-octylphenyl)benzotriazole; 2-(2'-hydroxy-5'-methylphenyl)benzotriazole; dibenzaladine; dianisoylmethane; 4-methoxy-4'-t-butyldibenzoylmethane; 5-(3,3-dimethyl-2-norbornylidene)-3-pentan-2-one; and the like. Generally, the organic-based UV absorber has high polarity and does not readily dissolve. Therefore, conventionally, it has been difficult to stably compound a desired (high) amount of the organic-based UV absorber in water-in-oil (W/O) emulsion cosmetic compositions. However, when using the co-modified organopolysiloxane of the present invention having a group that has a carbosiloxane dendron structure, a long chain alkyl group, and a hydrophilic group as an emulsifier and, when a medium polarity oil such as an ester oil or the like is combined therewith as a binding agent, a stable, UV absorber-containing W/O emulsion cosmetic composition can be obtained even when the oil phase includes a low polarity oil such as a silicone oil, a hydrocarbon oil, or the like. In this case, the compounded amount of the organic-based UV absorber is preferably in a range of 0.1 to 10 wt. % and a compounded amount of the binding agent is preferably in a range of 0.005 to 5 wt. %.

Depending on the purpose thereof, the cosmetic composition of the present invention can include an inorganic ultraviolet light blocking component in addition to the ultraviolet light blocking component described above. The inorganic ultraviolet light blocking component may be a component in which an inorganic powder or the like recited for the powder and/or colorant (D) is compounded. Examples thereof include metal oxides such as titanium oxide, zinc oxide, cerium oxide, titanium suboxide, iron-doped titanium oxides, and the like; metal hydroxides such as iron hydroxides and the like; metal flakes such as platy iron oxide, aluminum flake, and the like; and ceramics such as silicon carbide and the like. Of these, at least one type of a material selected from fine particulate metal oxides and fine particulate metal hydroxides with an average particle size in a range from 1 to 100 nm is preferable.

The powder is preferably subjected to, for example, a conventional surface treatment such as fluorine compound treatments, of which a perfluoroalkyl phosphate treatment, a perfluoroalkylsilane treatment, a perfluoropolyether treatment, a fluorosilicone treatment, or a fluorinated silicone resin treatment is preferable; silicone treatments, of which a methylhydrogenpolysiloxane treatment, a dimethylpolysiloxane treatment, or a vapor-phase tetramethyltetrahydrogen cyclotetrasiloxane treatment is preferable; silicone resin treatments, of which a trimethylsiloxysilicic acid treatment is preferable; pendant treatments which are methods of adding alkyl chains after a vapor-phase silicone treatment; silane coupling agent treatments; titanium coupling agent treatments; silane treatments, of which an alkylsilane treatment or an alkylsilazane treatment is preferable; oil agent treatments; N-acylated lysine treatments; polyacrylic acid treatments; metallic soap treatments in which a stearic acid salt or a myristic acid salt is preferably used; acrylic resin treatments; metal oxide treatments; and the like. Multiple treatments described above are preferably performed. For example, the surface of the fine particulate titanium oxide can be coated with a metal oxide such as silicon oxide, alumina, or the like and, thereafter, surface treating using an alkylsilane can be carried out. A total amount of material used for the surface treatment is preferably in a range from 0.1 to 50 wt. % of the weight of the powder.

In addition to the components described above, the cosmetic composition of the present invention may include fats or oils, higher alcohols, or higher fatty acids normally used in cosmetic compositions in addition to the oil agent used as the component (C) of the present invention, provided that such use does not impair the effects of the present invention. Additionally, in addition to the components described above, the cosmetic composition of the present invention may include various components including oil-soluble gelling agents, organo-modified clay minerals, aseptic antiseptic agents, bioactive components, skin beautifying components, pH adjusting agents, antioxidants, solvents, chelating agents, moisturizing components, perfumes, and the like, provided that such use does not impair the effects of the present invention.

Examples of such fats or oils, higher alcohols, or higher fatty acids include natural animal or vegetable fats and oils and semi-synthetic fats and oils such as avocado oil, linseed oil, almond oil, ibota wax, perilla oil, olive oil, cacao butter, kapok wax, kaya oil, carnauba wax, liver oil, candelilla wax, beef tallow, neatsfoot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shea butter, Chinese tung oil, cinnamon oil, jojoba wax, olive squalane, shellac wax, turtle oil, soybean oil, tea seed oil, camellia oil, evening primrose oil, corn oil, lard, rapeseed oil, Japanese tung oil, rice bran wax, germ oil, horse fat, persic oil, palm oil, palm kernel oil, castor oil, hydrogenated castor oil, castor oil fatty acid methyl ester, sunflower oil, grape oil, bayberry wax, jojoba oil, hydrogenated jojoba ester, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, reduced lanolin, lanolin alcohol, hard lanolin, lanolin acetate, lanolin fatty acid isopropyl ester, POE lanolin alcohol ether, POE lanolin alcohol acetate, lanolin fatty acid polyethylene glycol, POE hydrogenated lanolin alcohol ether, egg yolk oil, and the like. Herein, "POE" means "polyoxyethylene". Examples of higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, sitosterol, phytosterol, lanosterol, POE cholesterol ether, monostearyl glycerol ether (batyl alcohol), monooleyl glycerol ether (selachyl alcohol), and the like. Examples of higher fatty acids include lauric acid, myristic acid, palmitic acid, stearic acid, behenic acid, undecylenic acid, oleic acid, linolic acid, linolenic acid, arachidonic acid, eicosapentaenoic acid (EPA), docosahexaenoic acid (DHA), isostearic acid, 12-hydroxystearic acid, and the like.

Examples of the oil-soluble gelling agent include amino acid derivatives such as N-lauroyl-L-glutamic acid, α,γ-di-n-butylamine, and the like; dextrin fatty acid esters such as dextrin palmitate, dextrin stearate, dextrin 2-ethylhexanoate palmitate, and the like; sucrose fatty acid esters such as sucrose palmitate, sucrose stearate, and the like; fructooligosaccharide fatty acid esters such as inulin stearate, fructooligosaccharide 2-ethylhexanoate, and the like; benzylidene derivatives of sorbitol such as monobenzylidene sorbitol, dibenzylidene sorbitol, and the like; and the like.

Examples of the organo-modified clay mineral include dimethylbenzyl dodecylammonium montmorillonite clay, dimethyldioctadecylammonium montmorillonite clay, dimethylalkylammonium hectorite, benzyldimethylstearylammonium hectorite, distearyldimethylammonium chloride-treated aluminum magnesium silicate, and the like. Examples of commercially available products include Benton 27 (benzyldimethylstearylammonium chloride-treated hectorite, manufactured by Nationalred Co.), Benton 38 (distearyldimethylammonium chloride-treated hectorite, manufactured by Nationalred Co.), and the like.

Additionally, in cases where the cosmetic composition according to the present invention is an anti-perspirant or, alternately, depending on the purpose of the cosmetic composition, the cosmetic composition can include an anti-perspiration active component and/or a deodorant agent.

Examples of the anti-perspiration active component include astringent salts such as aluminum chlorohydrate, aluminum-zirconium tetrachlorohydrex glycine (ZAG), and the like; but aluminum, hafnium, zinc, and zirconium salts (e.g. aluminum halide, aluminum hydroxy halide, zirconium halide, zirconium oxyhalide, zirconium hydroxy halide, zirconyl hydroxide halide, aluminium chloride zirconium, zirconium lactate-aluminum, and basic aluminum halide) can be used. Examples thereof include $Al_2(OH)_5Cl$, aluminum bromide, buffer aluminium sulphate, alum, dried alum, various aqueous, alcohol, or glycine complexes thereof (e.g. a complex of an aluminum-zirconium chlorohydrate and glycine comprising aluminum, zirconium, and glycine (a ZAG complex), and the like. A single anti-perspiration active component may be used or a combination of two or more may be used. In cases where the anti-perspirant composition according to the present invention is a water-in-oil emulsion-type anti-perspirant composition, these anti-perspiration active components are an aqueous phase component. On the other hand, soybean extracts and isoflavones are known for their anti-perspirant effects; and, because they have low water solubility, are preferably used by dissolving them in the oil phase.

In the present invention, a compounded amount of the anti-perspiration active component is an amount sufficient to reduce perspiration, and restricting the compounded amount to a small amount can be beneficial in personal care compositions. Specifically, from the standpoints of anti-perspirant effects and feeling to touch, the compounded amount of the anti-perspiration active component in an anti-perspirant composition is preferably from 5 to 25 wt. % of the entire cosmetic composition. When using a water soluble anti-perspiration active component, from the standpoint of cost effectiveness, it is preferable to increase the proportion of water in the composition to a maximum limit, while maintaining anti-perspirant effects, but the anti-perspiration active component can also be added to the aqueous phase at amount near the saturation amount.

The cosmetic composition of the present invention, particularly the anti-perspirant composition, can include a deodorant agent in conjunction with or in place of the anti-perspirant component. Examples of the deodorant agent include deodorizers, perfumes, and substances that prevent or remove odors caused by perspiration. Such deodorant agents are antimicrobial agents (germicides or fungicides), bacteriostatic agents, odor absorbing substances, deodorizers, perfumes, or the like, and are compounded for the purpose of preventing underarm odor, odor from perspiration, foot odor, and other bodily odors. Note that these deodorant agents are useful in cosmetic compositions other than anti-perspirants and it goes without saying that they can be beneficially compounded in the cosmetic composition of the present invention.

Examples of antimicrobial agents include alkyltrimethylammonium bromide, cetylpyridinium chloride, benzethonium chloride, benzalkonium chloride, chlorhexidine hydrochloride, chlorhexidine gluconate, [[(diisobutylphenoxy)ethoxy]ethyl]dimethylbenzylammonium chloride, N-lauroyl sarcosine sodium, N-palmitoyl sarcosine sodium, N-myristoyl glycine, N-lauroyl sarcosine potassium, trimethyl ammonium chloride, aluminum chlorohydroxy sodium lactate, triethyl citrate, tricetyl methyl ammonium chloride, 1,5-pentanediol, 1,6-hexanediol, 2,4,4'-trichloro-2'-hydroxy diphenylether (triclosan), and 3,4,4'-trichlorocarbanilide(triclocarban); L-lysine hexadecylamide and similar diaminoalkylamidos; citric acid, salicylic acid, piroctose, and other heavy metal salts, preferably zinc salts and acids thereof; pyrithione heavy metal salts, preferably pyrithione zinc, phenol zinc sulfate, ethylparaben, butylparaben, hinokitiol, farnesol, phenoxyethanol, isopropyl methylphenol, propolis, lysozyme, lysozyme chloride, combinations of lysozyme and vitamin E or derivatives thereof, combinations of organic acids such as lysozyme and α-hydroxyacid and the like; and the like.

Examples of bacteriostatic agents include 1-heptyl glyceryl ether, 1-(2-ethylhexyl)glyceryl ether, 1-octyl glyceryl ether, 1-decyl glyceryl ether, 1-dodecyl glyceryl ether, and similar glyceryl monoalkyl ethers.

The odor absorbing substance is not particularly limited, provided that it absorbs odor causing substances and reduces odor, is constituted by a portion of the inorganic powders and organic polymers described above, and displays the same characteristics.

Examples of the odor absorbing substance include zinc oxide, magnesium oxide, zeolite, aluminometasilicate, silicic anhydride, colloidal silica, talc, mica, hydroxyapatite, cellulose, corn starch, silk, nylon powder, crosslinking organopolysiloxane powder, organopolysiloxane elastomer spherical powder, and the like. Likewise, carbonates such as alkali metal carbonates, alkali metal bicarbonate salts, and the like and hydrogen carbonates, ammonium salts, tetraalkylammonium salts, and the like can be used. Of these odor absorbing substances, sodium salts and potassium salts are more preferable. Additionally, organic or inorganic porous particles carrying silver, copper, zinc, cerium, or similar metal ions (e.g. silver ion-carrying zeolite, silver ion/zinc ion/ammonium ion-carrying zeolite), or aggregates of needle-like crystals including silver cancrinite can be used. Because these function as antimicrobial agents and odor absorbing substances, they can be used beneficially as the deodorant agent.

Furthermore, hydroxyalkylated cyclodextrin, sake cake extract containing rice fermenting liquid, and various extracts derived from animals, vegetables, microorganisms, fungi, and the like such as brown seaweed extract, cinnamon bark, clove, fennel, ginger, *mentha*, citron, gentiana lutea, apricot, eucalyptus, *Sophora flavescens*, mulberry, althea, sage, *Anthemis nobilis, Scutellaria* root, nutgall, gardenia, hamamelis, herbs, and the like can be used as the deodorant agent. A part of these components overlaps with a bioactive component described below, but selecting these extracts as the deodorant agent for the purpose of the functional effects thereof is both beneficial and preferable from the standpoint of the composition design of the cosmetic composition.

Preferably from 0.001 to 60 wt. %, more preferably from 0.01 to 30 wt. %, and yet more preferably from 0.01 to 3 wt. % of the odor absorbing substance is included in the entire composition. Provided that the compounded amount of the odor absorbing substance is within this range, there is an advantage that deodorizing performance can be improved while not negatively affecting the strength and feeling to touch of the formulation.

Suitable perfumes include known topical use substances, topical use substances that are effective in masking malodor accompanied by perspiration, and various topical use substances that provide a composition having a desired aroma. Examples thereof include the whole of perfumes and perfume chemicals such as perfume precursors, deodorizing fragrances, and the like that are suitable for topical application to the skin and, as necessary, may be a blended perfume component.

The cosmetic composition of the present invention can include a preservative for the purpose of preventing decomposition and the like. Examples of preservatives include alkyl paraoxybenzoates, benzoic acid, sodium benzoate, sorbic acid, potassium sorbate, phenoxyethanol, and the like. Examples of antimicrobial agents include benzoic acid, salicylic acid, carbolic acid, sorbic acid, alkyl paraoxybenzoates, parachlorometacresol, hexachlorophene, benzalkonium chloride, chlorhexidine chloride, trichlorocarbanilide, triclosan, photosensitizers, and the like. However, in cases where the cosmetic composition is a rouge, it is preferable that these are not included.

Examples of bioactive components include substances that impart some sort of bioactivity to the skin when applied on the skin. Examples thereof include anti-inflammatory agents, anti-aging agents, tightening agents, anti-oxidizing agents, hair regrowth agents, hair growth promoters, moisturizing agents, circulation promoters, antimicrobial agents, germicides, drying agents, cooling agents, warming agents, vitamins, amino acids, wound healing accelerators, irritation mitigation agents, analgesics, cell activating agents, enzyme components, and the like. Of these, natural vegetable extract components, seaweed extract components, and herbal medicine components are particularly preferable. In the present invention, a single bioactive component may be used or, preferably, two or more bioactive components are used.

Examples of the bioactive component include *Angelica keiskei* extract, avocado extract, *Hydrangea serrata* extract, *Althaea officinalis* extract, *Arnica montana* extract, aloe extract, apricot extract, apricot kernel extract, *Gingko biloba* extract, fennel fruit extract, turmeric root extract, oolong tea extract, *Rosa multiflora* extract, *Echinacea angustifolia* leaf extract, *Scutellaria baicalensis* root extract, *Phellodendron amurense* bark extract, *Coptis rhizome* extract, *Hordeum vulgare* seed extract, *Hypericum perforatum* extract, *Lamium album* extract, *Nasturtium officinale* extract, orange extract, dried sea water solution, seaweed extract, hydrolyzed elastin, hydrolyzed wheat powders, hydrolyzed silk, *Chamomilla recutita* extract, carrot extract, *Artemisia capillaris* flower extract, *Glycyrrhiza glabra* extract, *Hibiscus sabdariffa* extract, *Pyracantha fortuneana* extract, kiwi extract, *Cinchona succirubra* extract, cucumber extract, guanosine, *Gardenia florida* extract, *Sasa veitchii* extract, *Sophora angusti folia* extract, walnut extract, grapefruit extract, *Clematis vitalba* leaf extract, *chlorella* extract, *Morus alba* extract, *Gentiana lutea* extract, black tea extract, yeast extract, burdock extract, fermented rice bran extract, rice germ oil, *Symphytum officinale* leaf extract, collagen, *Vaccinum vitis idaea* extract, *Asiasarum sieboldi* extract, *Bupleurum falcatum* extract, umbilical extract, *Salvia* extract, *Crocus sativus* flower extract, sasa bamboo grass extract, *Crataegus cuneata* fruit extract, *Zanthoxylum piperitum* extract, *Corthellus shiitake* extract, *Rehmannia chinensis* root extract, *Lithospermum erythrorhizone* root extract, *Perilla ocymoides* extract, *Tilia cordata* extract, *Spiraea ulmaria* extract, *Paeonia albiflora* extract, *Acorns calamus* root extract, *Betula alba* extract, *Equisetum arvense* extract, *Hedera helix* extract, *Crataegus oxyacantha* extract, *Sambucus nigra* extract, *Achillea millefolium* extract, *Mentha piperita* leaf extract, sage extract, *Malva sylvestris* extract, *Cnidium officinale* root extract, *Swertia japonica* extract, soybean seed extract, *Zizyphus jujuba* fruit extract, thyme extract, *Camellia sinensis* leaf extract, *Eugenia caryophyllus* flower extract, *Imperata cylindrica* extract, *Citrus unshiu* peel extract, *Angelica acutiloba* root extract, *Calendula officinalis* extract, *Prunus persica* kernel extract, *Citrus aurantium* peel extract, *Houttuynia cordata* extract, tomato extract, natto extract, carrot extract, garlic extract, *Rosa canina* fruit extract, hibiscus extract, *Ophiopogon japonicus* root extract, *Nelumbo nucifera* extract, parsley extract, honey, *Hamamelis virginiana* extract, *Parietaria officinalis* extract, *Isodon trichocarpus* extract, bisabolol, *Eriojotrya japonica* extract, *Tussilago farfara* flower extract, *Petasites japonicus* extract, *Poria cocos* extract, *Ruscus aculeatus* root extract, grape extract, propolis, *Luffa cylindrica* fruit extract, safflower flower extract, peppermint extract, *Tillia miquellana* extract, *Paeonia suffruticosa* root extract, *Humulus lupulus* extract, *Pinus sylvestris* cone extract, horse chestnut extract, *Lysichiton camtschatcense* extract, *Sapindus mukurossi* peel extract, *Melissa officinalis* leaf extract, peach extract, *Centaurea cyanus* flower extract, *Eucalyptus globulus* leaf extract, *Saxifraga sarementosa* extract, *Citrus junos* extract, *Coix lacryma*-jobi seed extract, *Artemisia princeps* extract, lavender extract, apple extract, lettuce extract, lemon extract, *Astragalus sinicus* extract, rose extract, rosemary extract, Roman chamomile extract, royal jelly extract, and the like.

Additionally, examples of the bioactive component include biological macromolecules such as deoxyribonucleic acid, mucopolysaccharides, sodium hyaluronate, sodium chondroitin sulfate, collagen, elastin, chitin, chitosan, hydrolytic membrana testae, and the like; amino acids such as glycine, valine, leucine, isoleucine, serine, threonine, phenylalanine, arginine, lysine, aspartic acid, glutamic acid, cystine, cysteine, methionine, tryptophan, and the like; hormones such as estradiol, ethenyl estradiol, and the like; oil-based components such as sphingo lipid, ceramide, cholesterol derivatives, phosphatides, and the like; anti-inflammatory agents such as ε-aminocaproic acid, glycyrrhizinic acid, β-glycyrrhetic acid, lysozyme chloride, guai-azulene, hydrocortisone, allantoin, tranexamic acid, azulene, and the like; vitamins such as vitamin A, B2, B6, C, D, and E, calcium pantothenate, biotin, nicotinic acid amide, vitamin C esters, and the like; active components such as allantoin, diisopropyl amine dichloroacetate, 4-aminomethyl cyclohexanecarboxylic acid, and the like; anti-oxidizing agents such as carotenoid, flavonoid, tannin, lignan, saponin, and the like; cell activator agents such as α-hydroxyacid, β-hydroxyacid, and the like; circulation promoters such as γ-oryzanol, vitamin E derivatives, and the like; wound healing agents such as retinol, retinol derivatives, and the like; refreshing agents such as cepharanthine, licorice extract, capsicum tincture, hinokitiol, iodized garlic extract, pyridoxine hydrochloride, dl-α-tocopherol, dl-α-tocopherol acetate, nicotinic acid, nicotinic acid derivatives, calcium pantothenate, D-pantothenyl alcohol, acetyl pantothenyl ethyl ether, allantoin, isopropyl methylphenol, carpronium chloride, benzalkonium chloride, diphenhydramine hydrochloride, Takanal, camphor, vanillylamide nonylate, vanillylamide nonanoate, piroctone olamine, glyceryl pentadecanoate, l-menthol and the like; hair growth promoters such as mononitroguaiacol, resorcin, γ-aminobutyric acid, benzethonium chloride, mexiletine hydrochloride, auxin, female hormones, Cantharides tincture, cyclosporin, zinc pyrithione, hydrocortisone, Minoxidil, polyoxyethylene sorbitan monostearate, mentha oil, Sasanishiki extract, and the like; and the like.

Moreover, examples of skin beautifying components include whitening agents such as placenta extracts, arbutin, glutathione, saxifrageous extracts, and the like; cell activating agents such as royal jelly and the like; agents for ameliorating skin roughness; circulation promoters such as nonylic acid vanillylamide, benzyl nicotinate, beta-butoxyethyl nicotinate, capsaicin, zingerone, cantharide tincture, ichthammol, caffeine, tannic acid, α-borneol, tocopherol nicotinate, inositol hexanicotinate, cyclandelate, cinnarizine, tolazoline, acetylcholine, verapamil, cepharanthine, γ-oryzanol, and the like; astringents such as zinc oxide, tannic acid, and the like; antiseborrheic agents such as sulfur, thianthol, and the like; and the like. Examples of vitamins include vitamin As such as vitamin A oil, retinol, retinol acetate, retinol palmitate, and the like; vitamin Bs such as vitamin B2s such as riboflavin, riboflavin butyrate, flavin adenine dinucleotide, and the like; vitamin B6s such as pyridoxine hydrochloride, pyridoxine dioctanoate, pyridoxine tripalmitate, and the like; vitamin B12 and derivatives thereof; vitamin B15 and derivatives thereof, and the like; vitamin Cs such as L-ascorbic acid, L-ascorbyl dipalmitic acid esters, sodium L-ascorbyl 2-sulfate, dipotassium L-ascorbyl phosphoric acid diester, and the like; vitamin Ds such as ergocalciferol, cholecalciferol, and the like; vitamin Es such as α-tocopherol, β-tocopherol, γ-tocopherol, dl-α-tocopherol acetate, dl-α-tocopherol nicotinate, dl-α-tocopherol succinate, and the like; vitamin H; vitamin P; nicotinic acids such as nicotinic acid, benzyl nicotinate, and the like; pantothenic acids such as calcium pantothenate, D-pantothenyl alcohol, pantothenyl ethyl ether, acetyl pantothenyl ethyl ether, and the like; and the like.

Examples of pH adjusting agents include lactic acid, citric acid, glycolic acid, succinic acid, tartaric acid, dl-malic acid, potassium carbonate, sodium hydrogen carbonate, ammonium hydrogen carbonate, and the like.

Other than water, examples of the solvent include light isoparaffins, ethers, LPG, N-methylpyrrolidone, alternative chlorofluorocarbons, and the like.

Examples of the antioxidants include tocopherol, butylhydroxyanisole, dibutylhydroxytoluene, phytic acid, and the like. Examples of the chelating agent include alanine, sodium salt of edetic acid, sodium polyphosphate, sodium metaphosphate, phosphoric acid, and the like.

Examples of other moisturizing components include hyaluronic acid, chondroitin sulfate, pyrrolidone carboxylic acid salts, polyoxyethylene methylglucoside, polyoxypropylene methylglucoside, and the like. It goes without saying that the polyhydric alcohols and the like exhibit a function of retaining moisture on the skin or hair. With the cosmetic composition of the present invention, there are cases in which moisture retention properties of the moisturizing agent can be improved by using these moisturizing components in combination with other oil-based raw materials, selecting a gel-like formulation form for the cosmetic composition, or using the moisturizing components in combination with a membrane forming component.

The topical composition according to the present invention is not particularly limited, provided that it is a composition for application to the human body as a cosmetic composition or a medicament. Specific examples of products that the cosmetic composition of the present invention can be used for include skin cleansing agent products, skin care products, makeup products, anti-perspirant products, ultraviolet light blocking products, and similar skin use cosmetic products; hair use cleansing agent products, hair dressing products, hair use coloration products, hair growth products, hair rinsing products, hair conditioning products, hair treatment products, and similar hair use cosmetic products; and bath use cosmetic products. Examples of the medicament of the present invention include hair regrowth agents, hair growth promoters, analgesics, germicides, anti-inflammatory agents, refreshing agents, and skin anti-aging agents, but are not limited thereto.

The skin use cosmetic products can be used on any site of the entire body including the scalp, face (including lips, eyebrows, and cheeks), fingers, and fingernails. Specific examples thereof include cleansing gels, cleansing creams, cleansing foams, cleansing milks, cleansing lotions, face washing creams, eye makeup removers, face washing foams, liquid soaps (body soaps), hand soaps, gel-like soaps, bar soaps, facial rinses, body rinses, shaving creams, removers, acne treatment cosmetics, and similar skin cleansing agent products; skin creams, scalp treatments, skin milks, milk lotions, emulsions, toners, moisturizing liquids, beautifying liquids, facial packs, body powders, essences, shaving lotions, massage lotions, and similar skin care products; foundations, liquid foundations, oil-based foundations, makeup bases, powders, face powders, lipsticks, lip creams, muddy colored lipsticks or rouges, lip glosses, eye shadows, eye liners, eye creams, eyebrow pencils, eyelash cosmetic products, eyebrow pencils, eyebrow blushes, mascaras, blushers, cheek cosmetics (cheek color, cheek rouge), manicures, pedicures, nail colors, nail laquers, enamel removers, nail polishes, and similar makeup products; deodorants and similar anti-perspirants; and sunscreen agents, tanning use medicaments (sun tanning agent), and similar ultraviolet light blocking products.

Examples of scalp use cosmetic products include shampoos, rinse-in shampoos, and similar hair use cleansing agents; hair oils, hair waxes, hair use curl holding agents, setting agents, hair creams, hairsprays, hair liquids, and similar hair dressing products; hair coloring substances, hair color sprays, hair color rinses, hair color sticks, and similar hair use coloration products; hair tonics, hair treatment essences, hair packs, and similar hair growing products; and oil rinses, cream rinses, treatment rinses, hair conditioners, hair treatments, and similar hair rinse or hair conditioning products. Additionally, examples of the bath use cosmetic products include bath oils, bath salts, and bath foams.

The topical composition according to the present invention is not particularly limited to a cosmetic composition form, and can be preferably applied to liquid, W/O emulsion, O/W emulsion, W/O cream, O/W cream, solid (e.g. stick and the like), paste, gel, powder, multi-layer, mousse, mist, granule, flake, crushed stone, and similar forms. W/O emulsion, W/O cream, solid, paste, gel, and powder forms are particularly preferable.

A container of the cosmetic composition of the topical composition according to the present invention is not particularly limited either, and any container such as a jar, pump, tube, bottle, pressurized can dispensing container, pressure resistant aerosol container, light blocking container, compact container, cosmetic receptacle (kanazara), stick container, repeating container, spray container, divided container provided with a compound liquid dispensing opening, and the like can be filled with the cosmetic composition. Normal silicone-based formulations tend to separate easily in tubes, but the topical composition according to the present invention, particularly the cosmetic composition, has superior stability and, therefore, there is a benefit that the topical composition according to the present invention can be stored stably, even when charged into a tube container.

Anti-Perspirant Composition

As described above, the co-modified organopolysiloxane according to the present invention is a cosmetic raw material having superior applicability, and can be used widely as a composition to be applied as a cosmetic composition or a medicament to the human body. Next, a specific example of use as an anti-perspirant composition will be described. An anti-perspirant composition according to the present invention can be selected from any of a water-in-oil emulsion (water-based formulation), a stick form formulation, and a spray or similar aerosol formulation. Components thereof are dependent on the type of formulation selected, and can be appropriately selected from the cosmetic composition components described above. Particularly, the anti-perspiration active component compounded in an aqueous phase or an oil phase preferably optionally includes the deodorant component, as described above.

Water-in-Oil Emulsion-Type Anti-Perspirant Composition

In a water-in-oil emulsion-type anti-perspirant composition, which is one embodiment of the present invention, an oil phase component including the co-modified organopolysiloxane (e.g. co-modified organopolysiloxane, volatile oil agent, nonvolatile oil agent, solubilization agent, or the like) is mixed with an aqueous phase component according to an arbitrary method. Here, in order to ensure transparency, the refractive index of each phase is preferably adjusted as described in "the method of adjusting the transparency of an emulsion containing the co-modified organopolysiloxane of the present invention" in order to improve the stability and transparency of the water-in-oil emulsion-type anti-perspirant composition.

Moisturizing feel and a natural feeling on the skin without discomfort can be imparted by compounding the co-modified organopolysiloxane of the present invention in the water-in-oil emulsion-type anti-perspirant composition. Additionally, the co-modified organopolysiloxane of the present invention can also function as an emulsifier for stably emulsifying/dispersing the aqueous phase including the anti-perspiration active component in the oil phase. A compounded amount thereof is from 0.1 to 10 parts and preferably from 0.5 to 5 parts by weight, when the entire composition is considered to be 100 parts by weight. Furthermore, in the anti-perspirant of the present invention, by using the method of adjusting the transparency of the emulsion, there is a benefit in that a transparent water-in-oil emulsion-type anti-perspirant composition having superior transparency can be obtained.

A compounded amount of the volatile oil that is the base oil of the water-in-oil emulsion-type anti-perspirant composition is from 5 to 40 parts, preferably from 10 to 30 parts, and more preferably from 15 to 20 parts by weight, when the entire composition is considered to be 100 parts by weight. Those products of the examples recited for component (C) of the present invention that have a vapor pressure measured at 25° C. can be used as the volatile oil. Specifically, the vapor pressure at 25° C. of the volatile oil is from 0.01 to 8 hPa and preferably from 0.02 to 2.0 hPa; and the volatile oil has a boiling point at 1 atmosphere of less than 250° C.

In the water-in-oil emulsion-type anti-perspirant composition, the types and compounded amounts of the anti-perspiration active component and the deodorant component are as described above and can be suitably adjusted as desired.

Examples of the nonvolatile oil agent include those products that are not "volatile oils" recited for the oil agent component (C) in the present invention; the components recited for component (G) of the present invention; ether oils such as dioctyl ethers and the like; dioctyl carbonates, dioctadecyl carbonates, and similar carbonate ester oils; neopentyl glycol dicaprates and similar ester oils; polyalkylene glycol and derivatives thereof; and the like. Such nonvolatile oil agents have emollient effects and adjustment effects of the feeling to touch and form of the water-in-oil emulsion-type anti-perspirant composition. A compounded amount of the nonvolatile oil is, as described above, from 1 to 10 parts by weight and preferably from 2 to 8 parts by weight.

Additionally, a solubilization agent can be used in the water-in-oil emulsion-type transparent anti-perspirant composition of the present invention. These solubilization agents are selected from the products recited for the oil agent component (C) in the present invention, oils and fats normally used in cosmetic compositions, higher alcohols, higher fatty acids, organic-based oleophilic surfactants, and the like; and generally are selected from the oil agent used as the base oil, the oil agent used as the refractive index adjuster, and an oil agent different from the nonvolatile oil. However, the refractive index adjuster, base oil, or nonvolatile oil may function as the solubilization agent. A compounded amount of the solubilization agent is from about 0.1 to about 20 parts and preferably from 1.0 to 10.0 parts by weight of the entire composition.

Other components that may be present in the water-in-oil emulsion-type anti-perspirant composition of the present invention include the components (D) and (H) of the present invention. Proportions of these components are normally from 0 to 8 parts by weight, when the entire composition is considered to be 100 parts by weight, but are not limited thereto.

A surfactant may also be added to the water-in-oil emulsion-type anti-perspirant composition of the present invention. The surfactant is exemplified by the component (J) of the present invention and encompasses any hydrophilic emulsifier with an HLB greater than 8. A compounded amount thereof is generally from 0 to 2 parts by weight per 100 parts by weight of the entire composition. However, it is understood that adjusting this proportion based on the desired HLB of the system is obvious to one having ordinary skill in the art. Examples of hydrophilic nonionic surfactants preferable as the surfactant include POE-sorbitan fatty acid esters; POE sorbit fatty acid esters; POE-glycerin fatty acid esters; POE-fatty acid esters; POE-alkyl ethers; pluronic-types; POE-POP-alkyl ethers; tetra POE-tetra POP-ethylenediamine condensates; POE-castor oil hydrogenated castor oil derivatives; POE-beeswax-lanolin derivatives; alkanolamides; POE-propylene glycol fatty acid esters; POE-alkylamines; POE-fatty amides; sucrose fatty acid esters; alkylethoxydimethyl amine oxides; trioleyl phosphates; and the like.

Various components other than the components described above can be used in the external use preparation (e.g. the anti-perspirant composition) of the present invention, provided that such use does not impair the effects of the present invention. Examples thereof include thickening agents, oil-soluble gelling agents, organo-modified clay minerals, bioactive components, skin beautifying components, pH adjusting agents, antioxidants, solvents, chelating agents, moisturizing components, medicaments, and the like.

The anti-perspirant composition according to the present invention is used by applying an amount thereof to the underarms or other sites sufficient to suppress perspiration and/or odor. Preferably about 0.1 to 10 g, more preferably 0.1 to 5 g, and even more preferably 0.1 to 1 g is applied at the target site on the skin.

Nonaqueous Stick-Form Anti-Perspirant Composition

Next, a stick-form anti-perspirant composition, which is an embodiment of the present invention, will be described. The stick-form anti-perspirant composition is a configuration of a solid anti-perspirant composition and may be in a hydrous form such as a solid W/O emulsion or the like; and can also be a substantially water-free topical composition. Here, an example of a substantially water-free system will be described. The nonaqueous stick-form anti-perspirant composition is effective in obtaining superior stability and a dry sensation during use.

An oil phase component such as a co-modified organopolysiloxane, a volatile oil agent, a higher alcohol, a wax, a nonvolatile oil agent, or the like is mixed in the nonaqueous stick-form anti-perspirant composition, which is an embodiment of the present invention. The mixture is heated to the melting temperature (e.g. about 80° C.) of the solid component such as the higher alcohol, the wax, or the like, and agitated. Thus, a single liquid phase is formed. A temperature slightly higher than a solidification point of the system (e.g. about 65° C.) is maintained, the remaining components other than the anti-perspiration active component are added while agitating, and then the active component is added. After thoroughly mixing, the mixture is poured into a container and allowed to solidify at room temperature. Thus, the stick-form anti-perspirant composition is manufactured. Note that the agitating can be performed using a mechanical force by means of an apparatus such as a mixer or the like.

Moisturizing feel and a natural feeling on the skin free of discomfort can be imparted by compounding the co-modified organopolysiloxane of the present invention in the nonaqueous stick-form anti-perspirant composition. Therefore, in cases when a sensation of dryness is excessive, this sensation can be mitigated and a natural sensation during use can be obtained. Additionally, particle agglomeration can be suppressed due to the co-modified organopolysiloxane of the present invention being effectively adsorbed on the surface of the powder or solid microparticles and, therefore, the powder or solid microparticles can be stably and uniformly dispersed in the oil. As a result, the nonaqueous stick-form anti-perspirant composition including the co-modified organopolysiloxane of the present invention has the benefit that there is little white residue after application and drying. Furthermore, the co-modified organopolysiloxane of the present invention has excellent compatibility with higher alcohols, waxes, and similar solid oils and, therefore, the degree of hardness of the stick can be controlled and the generation of white deposit originating from the solid oil after application and drying can be mitigated. A compounded amount thereof is from 0.1 to 10 parts by weight and preferably from 0.5 to 5 parts by weight, when the entire composition is considered to be 100 parts by weight.

One or more types of volatile oil agents can be used in the nonaqueous stick-form anti-perspirant composition according to the present invention, and a compounded amount thereof is from 5 to 70 wt. % and, from the standpoint of obtaining excellent feeling to touch, is preferably from 10 to 60 wt. % of the entire composition.

In the nonaqueous stick-form anti-perspirant composition according to the present invention, any of the components described above can be used as the anti-perspiration active component without any particular restrictions. However, as the composition is a nonaqueous system, water soluble salts and the like are preferably used in their solid states and are dispersed in the composition as microparticles. An average diameter of the microparticles of the anti-perspiration active component is preferably from about 0.1 to 100 µm, more preferably from 0.1 to 20 µm, and even more preferably from 0.1 to 10 µm. On the other hand, by using relatively small particles having an average diameter in a range from 0.5 to 8 µm and relatively large particles having an average diameter in a range from 12 to 50 µm in combination, feeling to touch properties such as sliding feel and the like when applying the stick-form anti-perspirant composition can be improved.

One or more types of the anti-perspiration active component can be used in the nonaqueous stick-form anti-perspirant composition, and a compounded amount thereof is preferably from 10 to 70 wt. %, more preferably from 15 to 50 wt. %, and even more preferably from 15 to 25 wt. % of the entire composition because the effects of suppressing perspiration and odor can be sufficiently obtained and feeling to touch is excellent. Additionally, the deodorant agent described above can be compounded in conjunction with or in place of the anti-perspiration active component, and the type and compounded amount thereof are as described above.

The higher alcohol that can be used in the nonaqueous stick-form anti-perspirant composition according to the present invention has from 12 to 50 carbons, preferably from 16 to 30 carbons, and more preferably from 18 to 24 carbons. If the higher alcohol is within this range, excellent feeling to touch can be obtained. Specific examples thereof include cetyl alcohol, stearyl alcohol, arachidyl alcohol, behenyl alcohol, and the like. One or more types of higher alcohols can be used, and a compounded amount thereof is from 1 to 50 wt. %, preferably from 5 to 35 wt. %, and more preferably from 10 to 25 wt. % of the entire composition. If the higher alcohol is within this range, suitable formativeness and excellent feeling to touch can be obtained.

Examples of the nonvolatile oil agent that can be used in the nonaqueous stick-form anti-perspirant composition according to the present invention include those products that are not "volatile oils" recited for the oil agent component (C) in the present invention; various silicone oils; mineral oils and polydecenes; hydrogenated polyisobutene and similar hydrocarbon oils; the component (G) of the present invention; dioctyl ethers and similar ether oils; dioctyl carbonate, dioctadecyl carbonate, and similar carbonate ester oils; isopropyl palmitate, isopropyl myristate, lauryl myristate, diisopropyl sebacate, diisopropyl adipate, alkyl benzoic acids having from 8 to 18 carbons, and similar ester oils; PPG-3 myristyl ether, PPG-14 butyl ether, and similar polyalkylene glycols and derivatives thereof; isostearyl alcohol and oleyl alcohol; 2-ethylhexyl alcohol; organo-oleophilic surfactants; and the like. These oil agents have, in addition to emollient effects, effects of adjusting the feeling to touch and the form, and also may function as a compatibility accelerator of the oil phase. One or more types of nonvolatile oil agents can be used, and a compounded amount thereof is from 1 to 30 wt. % and preferably from 5 to 15 wt. % of the entire composition.

The nonaqueous stick-form anti-perspirant composition according to the present invention can further include a wax. This is preferable because stability at elevated temperatures will improve. Examples of the wax include the component (C) described above, oils and fats, and higher fatty acids, which are solid at room temperature. Other examples of the wax include products of the component (H) that are solid at room temperature.

Preferable examples include hydrogenated castor oil, fatty acid, wax-like modified silicones, and glycerol monostearate; 2-8178 Gellant, 2-8179 Gellant, and the like (manufactured by Dow Corning Corporation, in the USA); AMS-C30 Cosmetic Wax, 2503 Cosmetic Wax, and the like (manufactured by Dow Corning Corporation, in the USA); alkyl-modified silicone resin wax; and the like. Such products impart suitable hardness and stability to the obtained stick-form anti-perspirant composition.

One or more types of wax can be used, and a compounded amount thereof is from 1 to 10 wt. % and, from the perspective of obtaining excellent stability and excellent feeling to touch, is preferably from 2 to 8 wt. % of the entire composition.

Furthermore, in the nonaqueous stick-form anti-perspirant composition according to the present invention, a ratio of a total weight "X" of the oil phase component (except the volatile oil and the solid oil) to a total weight "Y" of the anti-perspiration active component and the deodorant agent is such that X/Y=1/7 to 5/6 and, from the standpoints of being able to further suppress white residue while maintaining high feeling to touch and anti-perspirant deodorant performance, is preferably such that X/Y=1/6 to 2/3.

Moreover, other components that can be present in the nonaqueous stick-form anti-perspirant composition according to the present invention include the components (D) and (H), and while proportions of these components are generally from about 0 parts to 8 parts per the total weight of the composition, said proportions are not limited thereto. Additionally, various components other than the components described above can be used provided that such use does not impair the effects of the present invention. Examples thereof include thickening agents, oil-soluble gelling agents, organo-modified clay minerals, bioactive components, skin beautifying components, pH adjusting agents, antioxidants, solvents, chelating agents, moisturizing components, medicaments, and the like.

The anti-perspirant composition according to the present invention is used by applying an amount thereof to the underarms or other sites sufficient to suppress perspiration and/or odor. Preferably about 0.1 to 10 g, more preferably 0.1 to 5 g, and even more preferably 0.1 to 1 g is applied at the target site on the skin. Additionally, the stick composition of the present invention is preferably applied once or twice per day in order to effectively suppress perspiration and/or odor.

Aerosol Anti-Perspirant Composition

Next, an aerosol anti-perspirant composition, which is a topical composition including the co-modified organopolysiloxane according to the present invention and is an embodiment of the present invention, will be described. The aerosol anti-perspirant composition may be in a hydrous form and can also be a substantially water-free topical composition. Nonaqueous aerosol anti-perspirant compositions provide an advantage of a dry sensation during use and, on the other hand, hydrous aerosol anti-perspirant compositions provide advantages of effectively suppressing perspiration and easily attaining a feeling of freshness.

The aerosol anti-perspirant composition according to the present invention can include a propellant, a powder component dispersed therein (e.g. an anti-perspiration active component, a deodorant agent, or a usage enhancing component), a co-modified organopolysiloxane, a liquid oil agent, and the like.

The anti-perspiration active component in the aerosol anti-perspirant composition according to the present invention may be in the form of a powder or a solution. When a powder, the anti-perspiration active component is preferably dispersed in the composition as microparticles. An average diameter of the microparticles is preferably from about 0.1 to 100 μm, more preferably from 0.1 to 20 μm, and even more preferably from 0.1 to 10 μm. When in the form of a solution, an aqueous solution can also be used, but in order to further enhance storage stability and the like of the composition, a material in which an AP active component is complexed with or dissolved in propylene glycol, polyethyleneglycol, an alkylglycerol ether, an alkyl etherified sugar, an alkyl etherified sugar alcohol, or a similar polyol is more preferably used. Examples of the anti-perspiration active component that can be used in the aerosol anti-perspirant composition according to the present invention include the same examples described above.

One or more types of the anti-perspiration active component can be used, and a compounded amount thereof is preferable from 0.001 to 20.0 wt. % and more preferably from 0.1 to 10.0 wt. % of the entire weight of the aerosol anti-perspirant composition.

Examples of a deodorant agent that can be used in conjunction with or in place of the anti-perspiration active component in the aerosol anti-perspirant composition according to the present invention include antimicrobial agents (germicides or fungicides), bacteriostatic agents, odor absorbing substances, deodorizers, perfumes, and the like. Specific examples thereof are as described above, and a compounded amount of the deodorant agent is preferably from 0.01 to 10.0 wt. % and more preferably from 0.1 to 3.0 wt. % of the entire weight of the aerosol anti-perspirant composition.

Additionally, because the aerosol anti-perspirant composition includes the co-modified organopolysiloxane of the present invention, particle agglomeration can be suppressed due to the co-modified organopolysiloxane of the present invention being effectively adsorbed on the surface of the powder or solid microparticles and, therefore, the powder or solid microparticles can be stably and uniformly dispersed in the system. As a result, with the aerosol anti-perspirant composition including the co-modified organopolysiloxane of the present invention, advantages are expected of reduced clogging of the aerosol valve, whiteness after use being not noticeable, and improved uniform adhesion to the skin. Additionally, depending on the AP active component and/or deodorant agent, drying or tightening of the skin may be felt after use, dry skin or declines in the elasticity of the skin may occur, or unnatural skin sensation may be experienced. However, these inconveniences are expected to be mitigated through use of the co-modified organopolysiloxane of the present invention. A compounded amount thereof is about 0.1 to about 10 parts and preferably from about 0.5 parts to about 5 parts.

In order to impart a dry feeling to touch to the skin, a particle size of the powder is preferably from 1 to 20 μm and more preferably from 5 to 15 μm. If the particle size is greater than 20 μm, abrasiveness will be felt, and if less than or equal to 1 μm, particle scattering may occur.

Examples of the propellant used in the present invention include gaseous vehicles. Specific examples include propane, n-butane, isobutane, isopentane, pentane, dimethylether, liquified petroleum gas (LPG), liquified natural gas, and the like. Of these, LPG, dimethylether, and isopentane are preferable. A single type of propellant may be used or two or more types may be combined. It is also possible to compound an alternative freon such as 1,1-difluoroethane or the like or a freon gas, but this is not preferable from an environmental standpoint. Additionally, from the standpoints of environment and safety, carbon dioxide gas or nitrogen gas can also be used. An amount of propellant charged is not particularly limited and can be determined appropriately according to conventional methods.

Exemplary powder components other than the AP active component and the deodorant agent that can be included in the aerosol anti-perspirant composition according to the present invention include usage enhancing components. Examples of usage enhancing components include products that have the ability to impart a feeling of dryness to the skin, such as silica gel, talc, bentonite, kaolinite, regular spherical shape silica, smectite, surface treated materials of the same, and similar inorganic powders; polyethylene powder, nylon powder, polystyrene powder, crosslinkable organopolysiloxane powder, organopolysiloxane elastomer spherical powder, silicone resin powder, and similar organic powders; composite powders such as inorganic powders including a metallic oxide; and the like. In other words the usage enhancing components can be the components (D) and (H) of the present invention. One of these usage enhancing components may be used or a combination of two or more may be used.

Examples of the liquid oil agent included in the aerosol anti-perspirant composition according to the present invention include those products recited for the oil agent component (C) in the present invention that are liquid at room temperature. The liquid oil agent has the effects of uniformly adhering the powder on the skin and enhancing sensation during use. Combinations of one or two or more of these liquid oil agents can be used. Not only from the perspective of feeling to touch, but also from the perspectives of emollient effect and formulation flexibility, it is preferable that the liquid oil agent include a silicone oil. In order to obtain a dry feeling to touch that is free of stickiness, a preferable range of the viscosity of the silicone oil is 100,000 cst (25° C.) or less, and a more preferable range is 100 cst (25° C.) or less. Note that a compounded amount of the liquid oil agent is preferably from 0.1 to 50 wt. % and more preferably from 0.5 to 25 wt. % of the entire weight of the aerosol anti-perspirant composition. If the compounded amount is less than 0.1 wt. %, a dry feeling to touch of the oil will not be displayed and compatibility on the skin will be poor; and if greater than 50 wt. %, sensation during use may decline due to non-adhesion to the skin and/or the stability of the formulation may be negatively affected.

When the aerosol anti-perspirant composition according to the present invention includes the liquid oil agent, the liquid oil agent can be pre-emulsified and compounded in the form of an O/W emulsion. This is effective in cases where dispersing the liquid oil agent as-is stably and uniformly in the aerosol anti-perspirant composition is difficult due to the viscosity of the liquid oil agent being high, and other reasons. Here, an O/W emulsion formulation provided with resistance to alcohols (described hereinafter) is preferable; and using a phosphate-based surfactant or a nonionic surfactant having an oleyl group as the surfactant (J) is effective from the standpoints of obtaining an O/W emulsion with excellent compounding stability. Additionally, an O/W emulsion with excellent compounding stability can be obtained by using a combination of a phosphate-based surfactant and a general nonionic surfactant.

The aerosol anti-perspirant composition according to the present invention can further include water, ethanol, IPA, a polyhydric alcohol, a surfactant, or the like for the purpose dissolving the anti-perspiration active component in the system and more effectively displaying perspiration suppression effects. However, when a compounded amount of ethanol, IPA, and similar lower monohydric alcohols and some polyhydric alcohols such as propylene glycol and 1,3-butylene glycol is great, there is a tendency for inflammation or irritation to occur at sites where the skin is sensitive, such as the armpits, during application and after application. Therefore, the compounded amount of the lower monohydric alcohol is preferably not more than 50 wt. % of the entire weight of the aerosol anti-perspirant composition. Additionally, the compounded amount of the polyhydric alcohol that tends to cause irritation and the like at sites where the skin is sensitive is preferably not more than 20 wt. % of the entire weight of the aerosol anti-perspirant composition. A preferable polyhydric alcohol is the component (E), which is the component recited as the "refractive index adjuster of the aqueous phase". Regarding water, a weight ratio of the anti-perspiration active component to water (anti-perspiration active component/water) is preferably in a range from 1/0.5 to 1/2. When the weight ratio is within this range, the following effects can be expected: further enhancing of perspiration suppression effects without a feeling of stickiness occurring, and rapid expression thereof.

Compounding the surfactant is effective in increasing the stability of hydrous aerosol anti-perspirant compositions. Specifically, nonaqueous aerosol anti-perspirant compositions are manufactured according to a conventional method in which a stock solution is prepared by first mixing the components other than the propellant and the powder; then, the powder is dispersed uniformly in this stock solution; and, thereafter, the propellant is charged. As a result, stability problems do not easily occur. On the other hand, when a hydrous aerosol anti-perspirant composition is manufactured according to the same method, there are problems in that the stability of the system declines when the liquified petroleum gas (LPG) or similar propellant is compounded, and the perspiration component and similar components are prone to separate as a deposit. Therefore, the type and amount of the liquid oil agent that can be compounded becomes limited, and countermeasures such as reducing the concentration of the anti-perspiration active component and increasing the compounded amount of the alcohol have become necessary. This has lead to a decrease in the degree of freedom of formulation. However, these problems can be mitigated by compounding an appropriate surfactant.

From the standpoints of the anti-perspiration active component being acidic and obtaining dispersion stability effects of the aerosol anti-perspirant composition system, the appropriate surfactant is preferably one or two or more types of nonionic or weakly acidic surfactants. Of these, polyoxyethylene polyoxypropylene cetyl ether phosphate and polyoxyethylene oleyl ether phosphate are preferable.

A compounded amount of this surfactant is preferably from 0.1 to 25 wt. % and more preferably from 0.1 to 10 wt. % of the entire weight of the aerosol anti-perspirant composition. If the compounded amount is less than 0.1 wt. %, the stability enhancing effect of the formulation will be poor and, taking into consideration the purpose of compounding, exceeding 25 wt. % is not cost effective and will lead to a decline in sensation during use.

Moreover, other components that can be present in the aerosol anti-perspirant composition according to the present invention include the components (F), (G), (H), and (J) of the present invention, and while proportions of these components are generally from about 0 parts to 8 parts per the total weight of the composition, said proportions are not limited thereto. Additionally, various components other than the components described above can be used provided that such use does not impair the effects of the present invention. Examples thereof include thickening agents, oil-soluble gelling agents, organomodified clay minerals, bioactive components, skin beautifying components, pH adjusting agents, antioxidants, solvents, chelating agents, moisturizing components, medicaments, and the like.

A conventional aerosol container can be used for the aerosol anti-perspirant composition according to the present invention. Alternately, the aerosol anti-perspirant composition according to the present invention can be sprayed using an aerosol container in which an inner surface thereof has been coated with a resin coating for the purpose of preventing rust or the like. The aerosol anti-perspirant composition according to the present invention can also be sprayed using a double-layer container that is provided with an inner pouch.

The anti-perspirant composition according to the present invention is used by applying an amount thereof to the underarms or other sites, by spraying, sufficient to suppress perspiration and/or odor. Preferably about 0.1 to 5 g, more preferably 0.1 to 3 g, and even more preferably 0.1 to 1 g is applied at the target site on the skin. Additionally, the aerosol anti-perspirant composition of the present invention is preferably applied by spraying once or twice per day in order to effectively suppress perspiration and/or odor.

EXAMPLES

Hereinafter, the present invention is described with reference to examples, but it should be understood that the present invention is not limited to these examples. In the following compositional formulae, "Me" represents a methyl (—$CH_3$) group, "M" represents a $Me_3SiO$ group (or an $Me_3Si$ group), "D" represents an $Me_2SiO$ group, "$M^H$" represents an MeHSiO group, and "$M^R$" and "$D^R$" respectively represent units in which a methyl group in "M" or "D" is modified by any substituent. Additionally, in the manufacturing examples, "IPA" represents isopropyl alcohol.

Practical Example 1

Synthesis of Silicone Compound No. 1

194.5 g of a methylhydrogenpolysiloxane expressed by the average composition formula $MD_{400}D^H{}_{10}M$, 18.8 g of a vinyl tris(trimethylsiloxy)silane expressed by the average composition formula $CH_2$=CH—$Si(OSiMe_3)_3$, 3.3 g of a glycerin monoallyl ether expressed by the structural formula $CH_2$=CH—$CH_2$—$OCH_2CH(OH)CH_2OH$, and 90 g of isopropyl alcohol (IPA) were placed in a reaction vessel, and heated to 50° C. while agitating under a nitrogen stream. 0.055 g of an IPA solution of a platinum-1,3-divinyl-1,1,3,3-tetramethyldisiloxane complex (Pt concentration: 4.5 wt. %) was added and the mixture was reacted for 2.5 hours at 80° C. Then, 2 g of the reaction liquid was sampled and it was confirmed that the reaction was complete through an alkali decomposition gas generation method (the remaining Si—H groups were decomposed using a KOH ethanol/water solution, and the reaction rate was calculated from the volume of the generated hydrogen gas). The reaction liquid was heated under reduced pressure to remove low-boiling components by distillation. Thus, a novel glycerin co-modified silicone having a siloxane dendron structure expressed by the average composition formula $MD_{400}D^{R*31}{}_7D^{R*21}{}_3M$ was obtained.

In this formula, $R^{*21}$ and $R^{*31}$ are as described below.

$R^{*21}$=—$C_3H_6OCH_2CH(OH)CH_2OH$ $R^{*31}$=—$C_2H_4Si(OSiMe_3)_3$

This product was a light yellow color uniform viscous liquid having semi-transparency.

Practical Example 2

Synthesis of Silicone Compound No. 2

196.6 g of a methylhydrogenpolysiloxane expressed by the average composition formula $MD_{400}D^H{}_{10}M$, 13.6 g of a vinyl tris(trimethylsiloxy)silane expressed by the average composition formula $CH_2$=CH—$Si(OSiMe_3)_3$, 5.5 g of a glycerin monoallyl ether expressed by the structural formula $CH_2$=CH—$CH_2$—$OCH_2CH(OH)CH_2OH$, and 90 g of IPA were placed in a reaction vessel, and heated to 70° C. while agitating under a nitrogen stream. 0.060 g of an IPA solution of a platinum-1,3-divinyl-1,1,3,3-tetramethyldisiloxane complex (Pt concentration: 4.5 wt. %) was added and the mixture was reacted for 5 hours at 80° C. Then, 2 g of the reaction liquid was sampled and it was confirmed that the reaction was complete through an alkali decomposition gas generation method. The reaction liquid was heated under reduced pressure to remove low-boiling components by distillation. Thus, a novel glycerin-modified silicone having a siloxane dendron structure expressed by the average composition formula $MD_{400}D^{R*31}{}_5D^{R*21}{}_5M$ was obtained.

In this formula, $R^{*21}$ and $R^{*31}$ are the same as described above.

This product was a light yellow color uniform viscous liquid having semi-transparency.

Practical Example 3

Synthesis of Silicone Compound No. 3

198.8 g of a methylhydrogenpolysiloxane expressed by the average composition formula $MD_{400}D^{11}{}_{10}M$, 8.2 g of a vinyl tris(trimethylsiloxy)silane expressed by the average composition formula $CH_2$=CH—$Si(OSiMe_3)_3$, 7.9 g of a glycerin monoallyl ether expressed by the structural formula $CH_2$=CH—$CH_2$—$OCH_2CH(OH)CH_2OH$, and 90 g of IPA were placed in a reaction vessel, and heated to 70° C. while agitating under a nitrogen stream. 0.060 g of an IPA solution of a platinum-1,3-divinyl-1,1,3,3-tetramethyldisiloxane complex (Pt concentration: 4.5 wt. %) was added and the mixture was reacted for 5 hours at 80° C. Then, 2 g of the reaction liquid was sampled and it was confirmed that the reaction was complete through an alkali decomposition gas generation method. The reaction liquid was heated under reduced pressure to remove low-boiling components by distillation. Thus, a novel glycerin-modified silicone having a siloxane dendron structure expressed by the average composition formula $MD_{400}D^{R*31}{}_3D^{R*21}{}_7M$ was obtained.

In this formula, $R^{*21}$ and $R^{*31}$ are the same as described above.

This product was a brown color uniform viscous liquid having semi-transparency.

Practical Example 4

Synthesis of Silicone Compound No. 4

177.5 g of a methylhydrogenpolysiloxane expressed by the average composition formula $MD_{72}D^H{}_{12}M$, 107.6 g of a vinyl tris(trimethylsiloxy)silane expressed by the average composition formula $CH_2$=CH—$Si(OSiMe_3)_3$, 14.7 g of a glycerin monoallyl ether expressed by the structural formula $CH_2$=CH—$CH_2$—$OCH_2CH(OH)CH_2OH$, and 90 g of IPA were placed in a reaction vessel, and heated to 40° C. while agitating under a nitrogen stream. 0.130 g of an IPA solution of a platinum-1,3-divinyl-1,1,3,3-tetramethyldisiloxane complex (Pt concentration: 4.5 wt. %) was added and the mixture was reacted for 3 hours at 80° C. Then, 2 g of the reaction liquid was sampled and it was confirmed that the reaction was complete through an alkali decomposition gas generation method. The reaction liquid was heated under reduced pressure to remove low-boiling components by distillation. Thus, a novel glycerin-modified silicone having a

Practical Example 5

Synthesis of Silicone Compound No. 5

198.7 g of a methylhydrogenpolysiloxane expressed by the average composition formula $MD_{400}D^{11}{}_{10}M$, 8.2 g of a vinyl tris(trimethylsiloxy)silane expressed by the average composition formula $CH_2=CH-Si(OSiMe_3)_3$, 5.6 g of a glycerin monoallyl ether expressed by the structural formula $CH_2=CH-CH_2-OCH_2CH(OH)CH_2OH$, 2.4 g of 1-decene, and 90 g of IPA were placed in a reaction vessel, and heated to 70° C. while agitating under a nitrogen stream. 0.050 g of an IPA solution of a platinum-1,3-divinyl-1,1,3,3-tetramethyldisiloxane complex (Pt concentration: 4.5 wt. %) was added and the mixture was reacted for 3 hours at 80° C. Then, 2 g of the reaction liquid was sampled and it was confirmed that the reaction was complete through an alkali decomposition gas generation method. The reaction liquid was heated under reduced pressure to remove low-boiling components by distillation. Thus, a novel glycerin-modified silicone having an alkyl group and a siloxane dendron structure expressed by the average composition formula $MD_{400}D^{R*11}{}_2D^{R*31}{}_3D^{R*21}{}_5M$ was obtained.

In this formula, $R^{*21}$ and $R^{*31}$ are the same as described above, and $R^{*11}=-C_{10}H_{21}$.

This product was a light yellowish-brown, semi-transparent uniform liquid

Practical Example 6

Synthesis of Silicone Compound No. 6

109.3 g of a methylhydrogenpolysiloxane expressed by the average composition formula $MD_{72}D^H{}_{12}M$, 66.3 g of a vinyl tris(trimethylsiloxy)silane expressed by the average composition formula $CH_2=CH-Si(OSiMe_3)_3$, 24.3 g of a polyglycerine monoallyl ether, 200 g of IPA, and 0.23 g of a 2.3 wt. % sodium acetate/methanol solution were placed in a reaction vessel, and heated to 50° C. while agitating under a nitrogen stream. 0.160 g of an IPA solution having 5 wt. % of chloroplatinic acid was added, and the mixture was reacted for 7 hours at 80° C. Then, 2 g of the reaction liquid was sampled and it was confirmed that the reaction was complete through an alkali decomposition gas generation method. The reaction liquid was heated under reduced pressure to remove low-boiling components by distillation. Thus, a novel polyglycerin-modified silicone having a siloxane dendron structure expressed by the average composition formula $MD_{72}D^{R*31}{}_9D^{R*22}{}_3M$ was obtained.

In this formula, $R^{*31}$ is the same as described above.

Here the polyglycerine monoallyl ether is synthesized by ring-opening polymerizing 3 molar equivalents of glycidol with 1 mole of a glycerin monoallyl ether. The glycerin monoallyl ether has two hydroxyl groups that are both reactable with the glycidol and, therefore, the polyglycerine portion includes not only a straight structure, but also a branched structure.

$R^{*22}$ is a hydrophilic group expressed by $-C_3H_6O-X$, where "X" is the tetraglycerin portion.

This product had a milky white uniform gum-like form.

Practical Example 7

Synthesis of Silicone Compound No. 7

105.5 g of a methylhydrogenpolysiloxane expressed by the average composition formula $MD_{72}D^H{}_{12}M$, 64.0 g of a vinyl tris(trimethylsiloxy)silane expressed by the average composition formula $CH_2=CH-Si(OSiMe_3)_3$, 30.5 g of polyglyceryl eugenol, and 200 g of IPA were placed in a reaction vessel, and heated to 60° C. while agitating under a nitrogen stream. 0.130 g of an IPA solution of a platinum-1,3-divinyl-1,1,3,3-tetramethyldisiloxane complex (Pt concentration: 4.5 wt. %) was added and the mixture was reacted for 3 hours at 80° C. Then, 2 g of the reaction liquid was sampled and it was confirmed that the reaction was complete through an alkali decomposition gas generation method. The reaction liquid was heated under reduced pressure to remove low-boiling components by distillation. Thus, a novel polyglycerin-modified silicone having a siloxane dendron structure expressed by the average composition formula $MD_{72}D^{R*31}{}_9D^{R*23}{}_3M$ was obtained.

In this formula, $R^{*31}$ is the same as described above.

Here, the polyglyceryl eugenol is synthesized by ring-opening polymerizing 4 molar equivalents of glycidol with 1 mole of eugenol. The polyglycerine portion that is constituted mainly by tetraglycerin can include not only a straight structure, but also a branched structure.

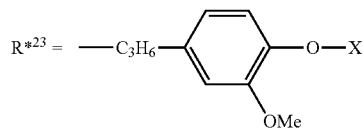

"X" is the tetraglycerin portion.

This product had a milky white uniform gum-like form.

Practical Example 8

Synthesis of Silicone Compound No. 8

112.3 g of a methylhydrogenpolysiloxane expressed by the average composition formula $MD_{72}D^H{}_{12}M$, 45.4 g of a vinyl tris(trimethylsiloxy)silane expressed by the average composition formula $CH_2=CH-Si(OSiMe_3)_3$, 32.5 g of polyglyceryl eugenol, and 200 g of IPA were placed in a reaction vessel, and heated to 55° C. while agitating under a nitrogen stream. 0.100 g of an IPA solution of a platinum-1,3-divinyl-1,1,3,3-tetramethyldisiloxane complex (Pt concentration: 4.5 wt. %) was added and the mixture was reacted for 2 hours at 80° C. Then, 2 g of the reaction liquid was sampled and it was confirmed that the reaction rate had reached from 75 to 80% through an alkali decomposition gas generation method. 9.9 g of 1-decene was added and the mixture was further reacted for 1 hour at 80° C. The reaction liquid was sampled again and confirmed, revealing that the reaction was complete. The reaction liquid was heated under reduced pressure to remove low-boiling components by distillation. Thus, a novel polyglycerin-modified silicone having an alkyl group and a siloxane dendron structure expressed by the average composition formula $MD_{72}D^{R*11}{}_3D^{R*31}{}_6D^{R*23}{}_3M$ was obtained.

In this formula, $R^{*31}$ and $R^{*23}$ are the same as described above, and $R^{*11}=-C_{10}H_{21}$.

This product had an off-white uniform gum-like form.

(Continuation from page 69:)

siloxane dendron structure expressed by the average composition formula $MD_{72}D^{R*31}{}_9D^{R*21}{}_3M$ was obtained.

In this formula, $R^{*21}$ and $R^{*31}$ are the same as described above.

This product was a nearly colorless uniform liquid having semi-transparency.

Practical Example 9

Synthesis of Silicone Compound No. 9

171.9 g of a methylhydrogenpolysiloxane expressed by the average composition formula $MD_{45}D^H{}_2M$, 19.9 g of a vinyl tris(trimethylsiloxy)silane expressed by the average composition formula $CH_2=CH-Si(OSiMe_3)_3$, 8.2 g of a glycerin monoallyl ether expressed by the structural formula $CH_2=CH-CH_2-OCH_2CH(OH)CH_2OH$, and 60 g of IPA were placed in a reaction vessel, and heated to 60° C. while agitating under a nitrogen stream. 0.04 g of an IPA solution of a platinum-1,3-divinyl-1,1,3,3-tetramethyldisiloxane complex (Pt concentration: 4.5 wt. %) was added and the mixture was reacted for 2 hours at 80° C. Then, 2 g of the reaction liquid was sampled and it was confirmed that the reaction was complete through an alkali decomposition gas generation method. The reaction liquid was heated under reduced pressure to remove low-boiling components by distillation. Thus, a novel glycerin-modified silicone having a siloxane dendron structure expressed by the average composition formula $MD_{45}D^{R*31}{}_1D^{R*21}{}_1M$ was obtained.

$R^{*21}=-C_3H_6OCH_2CH(OH)CH_2OH$

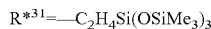

$R^{*31}=-C_2H_4Si(OSiMe_3)_3$

This product was a nearly colorless uniform liquid having semi-transparency.

Practical Example 10

Synthesis of Silicone Compound No. 10

160.9 g of a methylhydrogenpolysiloxane expressed by the average composition formula $MD_{45}D^H{}_2M$, 18.6 g of a vinyl tris(trimethylsiloxy)silane expressed by the average composition formula $CH_2=CH-Si(OSiMe_3)_3$, 20.5 g of a polyglycerine monoallyl ether, and 200 g of IPA were placed in a reaction vessel, and heated to 65° C. while agitating under a nitrogen stream. 0.067 g of an IPA solution of a platinum-1,3-divinyl-1,1,3,3-tetramethyldisiloxane complex (Pt concentration: 4.5 wt. %) was added and the mixture was reacted for 3 hours at 80° C. Then, 2 g of the reaction liquid was sampled and it was confirmed that the reaction was complete through an alkali decomposition gas generation method. The reaction liquid was heated under reduced pressure to remove low-boiling components by distillation. Thus, a novel polyglycerin-modified silicone having a siloxane dendron structure expressed by the average composition formula $MD_{45}D^{R*31}{}_1D^{R*22}{}_1M$ was obtained.

In this formula, $R^{*31}$ is the same as described above.

Here, the polyglycerine monoallyl ether is synthesized by ring-opening polymerizing 3 molar equivalents of glycidol with 1 mole of a glycerin monoallyl ether. The glycerin monoallyl ether has two hydroxyl groups that are both reactable with the glycidol and, therefore, the polyglycerine portion includes not only a straight structure, but also a branched structure.

$R^{*22}$ is expressed by $-C_3H_6O-X$, where "X" is the tetraglycerin portion.

This product was a milky white uniform viscous liquid.

Practical Example 11

Synthesis of Silicone Compound No. 11

124.1 g of a methylhydrogenpolysiloxane expressed by the average composition formula $MD_{45}D^H{}_2M$, 60.1 g of 3-methacryloxypropyl(tris(trimethylsiloxy)silylethyldimethylsiloxy)silane expressed by the following average composition formula (10), 15.8 g of polyglycerine monoallyl ether, 200 g of IPA, and 0.08 g of 4-t-butylcatechol (polymerization inhibitor) were placed in a reaction vessel, and heated to 30° C. while agitating under a nitrogen stream. 0.130 g of an IPA solution of a platinum-1,3-divinyl-1,1,3,3-tetramethyldisiloxane complex (Pt concentration: 4.5 wt. %) was added and the mixture was reacted for 7 hours at 80° C. Then, 2 g of the reaction liquid was sampled and it was confirmed that the reaction was complete through an alkali decomposition gas generation method. The reaction liquid was heated under reduced pressure to remove low-boiling components and the polymerization inhibitor by distillation. Thus a novel polyglycerin-modified silicone having a carbosiloxane dendrimer structure expressed by the average composition formula $MD_{45}D^{R*32}{}_1D^{R*22}{}_1M$ was obtained.

Compositional Formula (10):

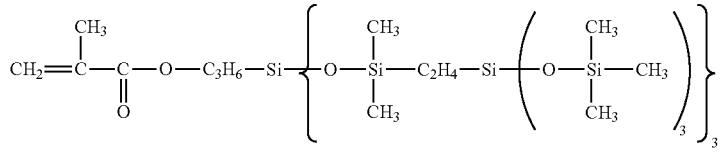

In the average composition formula $MD_{45}D^{R*32}{}_1D^{R*22}{}_1M$, $R^{*22}$ is the same as described above and $R^{*32}$ is the functional group described below.

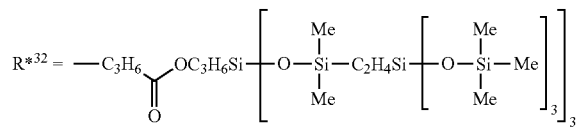

The obtained product was a milky white uniform viscous liquid.

Practical Example 12

Synthesis of Silicone Compound No. 12

156.1 g of a methylhydrogenpolysiloxane expressed by the average composition formula $MD_{45}D^H{}_2M$, 18.1 g of a vinyl tris(trimethylsiloxy)silane expressed by the average composition formula $CH_2=CH-Si(OSiMe_3)_3$, 25.9 g of polyglyceryl eugenol, and 200 g of IPA were placed in a reaction vessel, and heated to 70° C. while agitating under a nitrogen stream. 0.067 g of an IPA solution of a platinum-1,3-divinyl-1,1,3,3-tetramethyldisiloxane complex (Pt concentration: 4.5 wt. %) was added and the mixture was reacted for 3 hours at 80° C. Then, 2 g of the reaction liquid was sampled and it was confirmed that the reaction was complete through an alkali decomposition gas generation method. The reaction liquid was heated under reduced pressure to remove low-boiling components by distillation. Thus, a novel polyglycerin-modified silicone having a siloxane dendron structure expressed by the average composition formula $MD_{45}D^{R*31}{}_1D^{R*23}{}_1M$ was obtained.

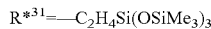

Here, the polyglyceryl eugenol is synthesized by ring-opening polymerizing 4 molar equivalents of glycidol with 1 mole of eugenol. The polyglycerine portion can include not only a straight structure, but also a branched structure.

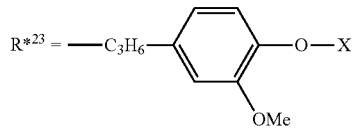

"X" is the tetraglycerin portion.

This product was a milky white uniform viscous liquid.

Practical Example 13

Synthesis of Silicone Compound No. 13

151.3 g of a methylhydrogenpolysiloxane expressed by the average composition formula $MD_{150}D^{11}{}_{10}M$, 26.7 g of a vinyl tris(trimethylsiloxy)silane expressed by the average composition formula $CH_2=CH-Si(OSiMe_3)_3$, 11.7 g of polyglycerine monoallyl ether, 10.2 g of diglycerin monoallyl ether, and 200 g of IPA were placed in a reaction vessel, and heated to 65° C. while agitating under a nitrogen stream. 0.100 g of an IPA solution of a platinum-1,3-divinyl-1,1,3,3-tetramethyldisiloxane complex (Pt concentration: 4.5 wt. %) was added and the mixture was reacted for 5 hours at 80° C. Then, 2 g of the reaction liquid was sampled and it was confirmed that the reaction was complete through an alkali decomposition gas generation method. The reaction liquid was heated under reduced pressure to remove low-boiling components by distillation. Thus, a novel polyglycerin-modified silicone having a siloxane dendron structure expressed by the average composition formula $MD_{150}D^{R*31}{}_5D^{R*22}{}_2D^{R*28}{}_3M$ was obtained.

In this formula, $R^{*31}$ is the same as described above.

$R^{*22}$ is also the same as described above, and is expressed by $-C_3H_6O-X$, where "X" is the tetraglycerin portion.

$R^{*28}=-C_3H_6O-X$, where "X" is the diglycerin portion.

This product was a milky white uniform viscous liquid.

Practical Example 14

Synthesis of Silicone Compound No. 14

100.0 g of a methylhydrogenpolysiloxane expressed by the average composition formula $MD_{43}D^H{}_7M$, 27.9 g of polyoxyethylene (10) monoallyl ether, and 0.055 g of natural vitamin E were placed in a reaction vessel, and heated to 65° C. while agitating under a nitrogen stream. 0.018 g of a toluene solution of a platinum-1,3-divinyl-1,1,3,3-tetramethyldisiloxane complex (Pt concentration: 2.2 wt. %) was added and the mixture was reacted for 3.5 hours at 80° C. Next, 54.7 g of a vinyl tris(trimethylsiloxy)silane expressed by the average composition formula $CH_2=CH-Si(OSiMe_3)_3$ was added, and 0.018 g of the same platinum catalyst solution described above was added. After reacting the mixture for 4 hours at 85° C., 2 g of the reaction liquid was sampled and it was confirmed that the reaction was complete through an alkali decomposition gas generation method. The reaction liquid was heated under reduced pressure to remove low-boiling components by distillation. Thus, a novel polyether-modified silicone having a siloxane dendron structure expressed by the average composition formula $MD_{43}D^{R*31}{}_5D^{R*24}{}_2M$ was obtained.

In this formula, $R^{*31}$ is the same as described above.

This product was a tan color uniform liquid that was substantially transparent.

Comparative Manufacturing Example 1

Synthesis of Silicone Compound No. 6-RE1

109.3 g of a methylhydrogenpolysiloxane expressed by the average composition formula $MD_{72}D^H{}_{12}M$, 66.3 g of a vinyl tris(trimethylsiloxy)silane expressed by the average composition formula $CH_2=CH-Si(OSiMe_3)_3$, 200 g of IPA, and 0.23 g of a 2.3 wt. % sodium acetate/methanol solution were placed in a reaction vessel, and heated to 50° C. while agitating under a nitrogen stream. 0.160 g of an IPA solution having 5 wt. % of chloroplatinic acid was added, and the mixture was reacted for 3 hours at 80° C. 2 g of the reaction liquid was sampled and it was confirmed that the reaction rate had exceeded 75%±5% and reached 85% of the target, through an alkali decomposition gas generation method. Next, 24.3 g of polyglycerine monoallyl ether was added, and the mixture was reacted for 4 hours at 80° C. 2 g of the reaction liquid was sampled and it was confirmed that the reaction was complete through an alkali decomposition gas generation method. The reaction liquid was heated under reduced pressure to remove low-boiling components by distillation. Thus, a novel polyglycerin-modified silicone having a siloxane dendron structure expressed by the average composition formula $MD_{72}D^{R*31}{}_{10}D^{R*22}{}_2M$ was obtained.

In this formula, $R^{*31}$ is the same as described above and is expressed by $-C_2H_4Si(OSiMe_3)_3$.

$R^{*22}$ is also the same as described above, and is expressed by $-C_3H_6O-X$, where "X" is the tetraglycerin portion.

This product had a liquid form that was off-white and extremely viscous throughout, and was not uniform, rather partial phase separation (of the viscous tan color phase) had occurred. The phase separation is thought to have occurred because an abundance ratio of the silicone modified only by the $-C_2H_4Si(OSiMe_3)_3$ increased due to first reacting only the vinyl tris(trimethylsiloxy)silane with the methylhydrogenpolysiloxane, and because of poor compatibility thereof with the excess polyglycerine monoallyl ether. In addition, another problem is that the compound expressed by the average composition formula $MD_{72}D^{R*31}{}_9D^{R*22}{}_3M$ (the original design) is difficult to obtain using this method.

Comparative Manufacturing Example 2

Synthesis of Silicone Compound No. 6-RE2

109.3 g of a methylhydrogenpolysiloxane expressed by the average composition formula $MD_{72}D^H{}_{12}M$, 24.3 g of a polyglycerine monoallyl ether, 200 g of IPA, and 0.23 g of a 2.3 wt. % sodium acetate/methanol solution were placed in a reaction vessel, and heated to 50° C. while agitating under a nitrogen stream. 0.160 g of an IPA solution having 5 wt. % of chloroplatinic acid was added, and the mixture was reacted for 3 hours at 80° C. 2 g of the reaction liquid was sampled and it was confirmed that the reaction rate had not reached the target 25% and was about 20%, through an alkali decomposition gas generation method. Then, 0.080 g of an IPA solution having 5 wt. % of chloroplatinic acid was added, the mixture was heated to 85 to 87° C., and the mixture was further reacted for 4 hours. As a result, the reaction liquid gellified and became entangled on the stirrer and, therefore, the planned addition of 66.3 g of a vinyl tris(trimethylsiloxy) silane expressed by the average composition formula $CH_2=CH-Si(OSiMe_3)_3$ was abandoned and production was terminated.

A reason for the gelling is thought to be as follows. The concentration of the polyhydric alcohol groups with respect to the concentration of the Si—H groups in the reaction system was in a state that was relatively greater than the concentration of the unsaturated groups due to first attempting to react only the polyglycerine monoallyl ether with the methylhydrogenpolysiloxane. Therefore the dehydrogenation reaction surpassed the side reaction suppression effects of the sodium acetate and, as a result, the reaction liquid gelled.

Comparative Example 1

Synthesis of Comparative Silicone Compound RE3

241.0 g of a methylhydrogenpolysiloxane expressed by the average composition formula $M^H D_{40} M^H$, 100.0 g of a bis-methallyl polyether expressed by the average composition formula $CH_2=C(CH_3)CH_2-O(C_2H_4O)_{10}(C_3H_6O)_7-CH_2-C(CH_3)=CH_2$, 102 g of IPA, 0.17 g of natural vitamin E, and 0.89 g of a 5 wt. % sodium acetate/methanol solution were placed in a reaction vessel, and heated to 50° C. while agitating under a nitrogen stream. 0.023 g of a toluene solution of a platinum-2,4,6,8-tetramethyl-2,4,6,8-tetravinyl tetrasiloxane complex (Pt concentration: 3.0 wt. %) was added and the mixture was reacted for 2.5 hours at 80° C. Then, 2 g of the reaction liquid was sampled and it was confirmed that the reaction was complete through an alkali decomposition gas generation method. The reaction liquid was heated under reduced pressure to remove low-boiling components by distillation. Thus, a block-type polyether-modified silicone expressed by the average composition formula $[D_{40}M^{R*25}_2]_3$ was obtained. Note that while the average composition formula is shown simplified, a molar ratio of the raw materials C=C groups and Si—H groups is approximately 4:3. Therefore, a form is obtained in which both ends of the modified silicone are capped by polyethers.

In this formula, $R^{*25}=-C_4H_8O(C_2H_4O)_{10}(C_3H_6O)_7-C_4H_8-$, in which the polyether portion is a random adduct of the ethylene oxide and the propylene oxide.

This product was a light yellow color uniform liquid that was transparent.

Comparative Example 2

Synthesis of Comparative Silicone Compound RE4

129.4 g of a methylhydrogenpolysiloxane expressed by the average composition formula $MD_{45}D^H_2M$, 40.0 g of polyoxyethylene (10) monoallyl ether, and 51 g of toluene were placed in a reaction vessel, and heated to 75° C. while agitating under a nitrogen stream. 0.017 g of an IPA solution having 10 wt. % of chloroplatinic acid was added and the mixture was reacted for 1.5 hours at 73 to 93° C. 2 g of the reaction liquid was sampled and it was confirmed that the reaction was complete through an alkali decomposition gas generation method. 0.51 g of sodium bicarbonate was added and the reaction liquid was heated under reduced pressure to remove low-boiling components by distillation. Furthermore, the mixture was filtered. Thus a polyether-modified silicone expressed by the average composition formula $MD_{45}D^{R*24}_2M$ was obtained.

$R^{*24}=-C_3H_6O(C_2H_4O)_{10}H$

This product was a nearly colorless uniform liquid that was transparent.

Comparative Example 3

Synthesis of Comparative Silicone Compound RE5

89.9 g of a methylhydrogenpolysiloxane expressed by the average composition formula $MD_{63}D^H_{22}M$, 36.4 g of polyoxyethylene (10) monoallyl ether, 73.7 g of 1-hexadecene, and 60 g of toluene were placed in a reaction vessel, and heated to 40° C. while agitating under a nitrogen stream. 0.06 g of an IPA solution of a platinum-1,3-divinyl-1,1,3,3-tetramethyldisiloxane complex (Pt concentration: 4.5 wt. %) was added and the mixture was reacted for 2.5 hours at 80 to 110° C. Then, 2 g of the reaction liquid was sampled and it was confirmed that the reaction was complete through an alkali decomposition gas generation method. The reaction liquid was heated under reduced pressure to remove low-boiling components by distillation. Thus, an alkyl/polyether co-modified silicone expressed by the average composition formula $MD_{63}D^{R*12}_{18}D^{R*24}_4M$ was obtained.

In this formula, $R^{*12}=-C_{16}H_{33}$ $R^{*24}=-C_3H_6O(C_2H_4O)_{10}H$

This product was a tan color uniform liquid having semi-transparency.

Comparative Example 4

Synthesis of Comparative Silicone Compound RE6

116.2 g of a methylhydrogenpolysiloxane expressed by the average composition formula $MD_{406}D^H_4M$, 34.0 g of an allyl polyether expressed by the average composition formula $CH_2=CH-CH_2-O(C_2H_4O)_{19}(C_3H_6O)_{19}H$, 45 g of IPA, 0.03 g of natural vitamin E, and 0.15 g of a 1.5 wt. % sodium acetate/methanol solution were placed in a reaction vessel, and heated to 50° C. while agitating under a nitrogen stream. 0.39 g of an IPA solution having 1 wt. % of chloroplatinic acid was added and the mixture was reacted for 4 hours at 80 to 85° C. 2 g of the reaction liquid was sampled and it was confirmed that the reaction was complete through an alkali decomposition gas generation method. 230 g of dimethylpolysiloxane diluent (2 cst) was added and dissolved and, thereafter, the mixture was heated under reduced pressure to remove the IPA and methanol by distillation. Thereby, a mixed liquid of a polyether-modified silicone expressed by the average composition formula $MD_{406}D^{R*26}_4M$ and a dimethylpolysiloxane (2 cst) was obtained as a weight ratio of 40:60.

In this formula, $R^{*26}=-C_3H_6O(C_2H_4O)_{19}(C_3H_6O)_{19}H$

This product was a slightly brown off-white viscous liquid.

Comparative Example 5

Synthesis of Comparative Silicone Compound RE7

92.7 g of a methylhydrogenpolysiloxane expressed by the average composition formula $MD_{37}D^H_{14}M$ was placed in a reaction vessel. Then a mixture comprising 19.2 g of a single-end vinyl-modified dimethylpolysiloxane expressed by the structural formula $CH_2=CH-SiMe_2(OSiMe_2)_6OSiMe_3$ and 0.10 g of a toluene solution of a platinum-1,3-divinyl-1,1,3,3-tetramethyldisiloxane complex (Pt concentration: 0.5 wt. %) was added dropwise, and the mixture was agitated at room temperature. Thus, a linear siloxane branched-type polysiloxane intermediate product was obtained.

30.9 g of polyoxyethylene (10) monoallyl ether, 57.3 g of 1-dodecene, 100 g of IPA, and 0.30 g of an IPA solution of a platinum-1,3-divinyl-1,1,3,3-tetramethyldisiloxane complex (Pt concentration: 0.5 wt. %) were placed in another reaction vessel, and while agitating under a nitrogen stream, the mixture was added dropwise to the previously synthesized linear siloxane branched-type polysiloxane in refluxing solvent. After the adding was completed, heating and agitating was continued for 1 hour. Then, 2 g of the reaction liquid was sampled and it was confirmed that the reaction was complete through an alkali decomposition gas generation method. The reaction liquid was heated under reduced pressure to remove low-boiling components by distillation. Furthermore the reaction liquid was filtered and, thereby, an alkyl/linear siloxane/polyether co-modified silicone expressed by the average composition formula $MD_{37}D^{R*13}{}_{11}D^{R*41}{}_{1}D^{R*24}{}_{2}M$ was obtained.

In this formula, $R^{*13}=-C_{12}H_{25}$ $R^{*41}=-C_2H_4SiMe_2(OSiMe_2)_6OSiMe_3$ $R^{*24}=-C_3H_6O(C_2H_4O)_{10}H$ This product was a nearly colorless uniform liquid having semi-transparency.

Comparative Example 6

Synthesis of Comparative Silicone Compound RE8

111.6 g of a methylhydrogenpolysiloxane expressed by the average composition formula $MD_{61}D^{H}{}_{15}M$ was placed in a reaction vessel. Then a mixture comprising 30.9 g of a single-end vinyl-modified dimethylpolysiloxane expressed by the structural formula $CH_2=CHSiMe_2(OSiMe_2)_6OSiMe_3$ and 0.10 g of a toluene solution of a platinum-1,3-divinyl-1,1,3,3-tetramethyldisiloxane complex (Pt concentration: 0.5 wt. %) was added dropwise, and the mixture was agitated at room temperature. Thus, a linear siloxane branched-type polysiloxane intermediate product was obtained.

Additionally, 7.0 g of triglycerin monoallyl ether, 50.4 g of 1-dodecene, 100 g of IPA, and 0.40 g of an IPA solution of a platinum-1,3-divinyl-1,1,3,3-tetramethyldisiloxane complex (Pt concentration: 0.5 wt. %) were placed in another reaction vessel, and while agitating under a nitrogen stream, the mixture was added dropwise to the previously synthesized linear siloxane branched-type polysiloxane in refluxing solvent. After the adding was completed, heating and agitating was continued for 3 hours. Then, 2 g of the reaction liquid was sampled and it was confirmed that the reaction was complete through an alkali decomposition gas generation method. The reaction liquid was heated under reduced pressure to remove low-boiling components by distillation. Furthermore the reaction liquid was filtered and, thereby, an alkyl/linear siloxane/polyglycerine co-modified silicone expressed by the average composition formula $MD_{61}D^{R*13}{}_{12}D^{R*41}{}_{2}D^{R*27}{}_{1}M$ was obtained.

In this formula, $R^{*13}=-C_{12}H_{25}$ $R^{*41}=-C_2H_4SiMe_2(OSiMe_2)_6OSiMe_3$ $R^{*27}=-C_3H_6O-X$, where "X" is the triglycerin portion.

This product was a nearly colorless uniform liquid having semi-transparency.

Comparative Example 7

Synthesis of Comparative Silicone Compound RE9

212.5 g of a methylhydrogenpolysiloxane expressed by the average composition formula $MD_{406}D^{H}{}_{4}M$, 4.9 g of a glycerin monoallyl ether expressed by the structural formula $CH_2=CH-CH_2-OCH_2CH(OH)CH_2OH$, and 90 g of IPA were placed in a reaction vessel, and heated to 70° C. while agitating under a nitrogen stream. 0.053 g of an IPA solution of a platinum-1,3-divinyl-1,1,3,3-tetramethyldisiloxane complex (Pt concentration: 4.5 wt. %) was added and the mixture was reacted for 3 hours at 80° C. Then, 2 g of the reaction liquid was sampled and it was confirmed that the reaction was complete through an alkali decomposition gas generation method. The reaction liquid was heated under reduced pressure to remove low-boiling components by distillation. Thus, a glycerin-modified silicone expressed by the average composition formula $MD_{406}D^{R*21}{}_{4}M$ was obtained.

In this formula, $R^{*21}=-C_3H_6OCH_2CH(OH)CH_2OH$

This product was a light-yellowish brown, semi-transparent uniform viscous liquid.

Comparative Example 8

Synthesis of Comparative Silicone Compound RE10

155.9 g of a methylhydrogenpolysiloxane expressed by the average composition formula $MD_{72}D^{H}{}_{12}M$, 13.0 g of a glycerin monoallyl ether expressed by the structural formula $CH_2=CH-CH_2-OCH_2CH(OH)CH_2OH$, 41.1 g of 1-decene, and 63 g of IPA were placed in a reaction vessel, and heated to 45° C. while agitating under a nitrogen stream. 0.055 g of an IPA solution of a platinum-1,3-divinyl-1,1,3,3-tetramethyldisiloxane complex (Pt concentration: 4.5 wt. %) was added and the mixture was reacted for 1 hour at 80° C. Then, 2 g of the reaction liquid was sampled and it was confirmed that the reaction was complete through an alkali decomposition gas generation method. The reaction liquid was heated under reduced pressure to remove low-boiling components by distillation. Thus, an alkyl/glycerin co-modified silicone expressed by the average composition formula $MD_{72}D^{R*11}{}_{9}D^{R*21}{}_{3}M$ was obtained.

In this formula, $R^{*11}=-C_{10}H_{21}$ $R^{*21}=-C_3H_6OCH_2CH(OH)CH_2OH.$

This product was a tan color liquid having semi-transparency.

Comparative Example 9

Synthesis of Comparative Silicone Compound RE11

134.6 g of a methylhydrogenpolysiloxane expressed by the average composition formula $MD_{72}D^{H}{}_{12}M$, 36.2 g of 1-decene, 29.9 g of a polyglycerine monoallyl ether, 200 g of IPA, and 0.25 g of a 2.3 wt. % sodium acetate/methanol solution were placed in a reaction vessel, and heated to 55° C. while agitating under a nitrogen stream. 0.160 g of an IPA solution having 5 wt. % of chloroplatinic acid was added, and the mixture was reacted for 7 hours at 80° C. Then, 2 g of the reaction liquid was sampled and it was confirmed that the reaction was complete through an alkali decomposition gas generation method. The reaction liquid was heated under reduced pressure to remove low-boiling components by distillation. Thus, an alkyl/polyglycerine co-modified silicone expressed by the average composition formula $MD_{72}D^{R*11}{}_9D^{R*22}{}_3M$ was obtained.

In this formula, $R^{*11}$ is the same as described above, $R^{*22}$ is also the same as described above, and is expressed by —$C_3H_6O$—X, where "X" is the tetraglycerin portion.

This product had a gum form that was off-white throughout, was not uniform but, rather, partial phase separation (of the gum form tan color phase) had occurred.

The average composition formulas of Silicone Compound No. 1 to Silicone Compound No. 14 according to the present invention, and Comparative Silicone Compound RE3 to Comparative Silicone Compound RE11 according to the comparative examples, synthesized according to the methods described above, are as follows.

TABLE 1

| Silicone compound | Average composition formula | Properties |
|---|---|---|
| Silicone compound No. 1 | $MD_{400}D^{R*31}{}_7D^{R*21}{}_3M$ | Light yellow, semi-transparent uniform viscous liquid |
| Silicone compound No. 2 | $MD_{400}D^{R*31}{}_5D^{R*21}{}_5M$ | Light yellow, semi-transparent uniform viscous liquid |
| Silicone compound No. 3 | $MD_{400}D^{R*31}{}_3D^{R*21}{}_7M$ | Brown, semi-transparent uniform viscous liquid |
| Silicone compound No. 4 | $MD_{72}D^{R*31}{}_9D^{R*21}{}_3M$ | Nearly colorless, semi-transparent uniform liquid |
| Silicone compound No. 5 | $MD_{400}D^{R*11}{}_2D^{R*31}{}_3D^{R*21}{}_5M$ | Light yellowish-brown, semi-transparent uniform liquid |
| Silicone compound No. 6 | $MD_{72}D^{R*31}{}_9D^{R*22}{}_3M$ | Milky white uniform gum-like form |
| Silicone compound No. 7 | $MD_{72}D^{R*31}{}_9D^{R*23}{}_3M$ | Milky white uniform gum-like form |
| Silicone compound No. 8 | $MD_{72}D^{R*11}{}_3D^{R*31}{}_6D^{R*23}{}_3M$ | Off-white uniform gum-like form |
| Silicone compound No. 9 | $MD_{45}D^{R*31}{}_1D^{R*21}{}_1M$ | Nearly colorless, semi-transparent uniform liquid |
| Silicone compound No. 10 | $MD_{45}D^{R*31}{}_1D^{R*22}{}_1M$ | Milky white uniform viscous liquid |
| Silicone compound No. 11 | $MD_{45}D^{R*32}{}_1D^{R*22}{}_1M$ | Milky white uniform viscous liquid |
| Silicone compound No. 12 | $MD_{45}D^{R*31}{}_1D^{R*23}{}_1M$ | Milky white uniform viscous liquid |
| Silicone compound No. 13 | $MD_{150}D^{R*31}{}_5D^{R*22}{}_2D^{R*28}{}_3M$ | Milky white uniform viscous liquid |
| Silicone compound No. 14 | $MD_{43}D^{R*31}{}_5D^{R*24}{}_2M$ | Tan, nearly transparent uniform liquid |

TABLE 2

| Comparative silicone compound RE3 | $[D_{40}M^{R*25}{}_2]_3$ *Block-type polyether-modified silicone capped at the ends with polyether | Light yellow, transparent uniform liquid |
|---|---|---|
| Comparative silicone compound RE4 | $MD_{45}D^{R*24}{}_2M$ | Colorless, transparent uniform liquid |
| Comparative silicone compound RE5 | $MD_{63}D^{R*12}{}_{18}D^{R*24}{}_4M$ | Tan, semi-transparent uniform liquid |
| Comparative silicone compound RE6 | $MD_{406}D^{R*26}{}_4M$ *Mixed liquid of a polyether-modified silicone expressed by the average composition formula described above and dimethylpolysiloxane (2 cst) at a weight ratio of 40:60 | Slightly brown off-white viscous liquid |
| Comparative silicone compound RE7 | $MD_{37}D^{R*13}{}_{11}D^{R*41}{}_1D^{R*24}{}_2M$ | Nearly colorless, semi-transparent uniform liquid |
| Comparative silicone compound RE8 | $MD_{61}D^{R*13}{}_{12}D^{R*41}{}_2D^{R*27}{}_1M$ | Nearly colorless, semi-transparent uniform liquid |
| Comparative silicone compound RE9 | $MD_{406}D^{R*21}{}_4M$ | Light yellowish-brown, semi-transparent uniform viscous liquid |
| Comparative silicone compound RE10 | $MD_{72}D^{R*11}{}_9D^{R*21}{}_3M$ | Tan, semi-transparent liquid |
| Comparative silicone compound RE11 | $MD_{72}D^{R*11}{}_9D^{R*22}{}_3M$ | Off-white gum form (not uniform but, rather, partially phase separated) |

In Tables 1 and 2, the structures and types of the functional groups are as follows.

Long chain alkyl group: $R^{*1}$

$R^{*11}$=—$C_{10}H_{21}$

$R^{*12}$=—$C_{16}H_{33}$

$R^{*13}$=—$C_{12}H_{25}$

Hydrophilic group: $R^{*2}$

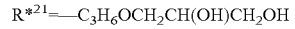
$R^{*21}$=—$C_3H_6OCH_2CH(OH)CH_2OH$ $R^{*22}$ is a hydrophilic group expressed by —$C_3H_6O$—X (where "X" is the tetraglycerin portion)

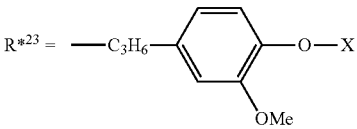

"X" is the tetraglycerin portion.

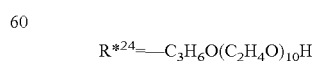
$R^{*24}$=—$C_3H_6O(C_2H_4O)_{10}H$ $R^{*25}$=—$C_4H_8O(C_2H_4O)_{10}(C_3H_6O)_7$—$C_4H_8$—, in which the polyether portion is a random adduct of the ethylene oxide and the propylene oxide.

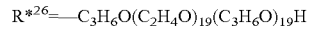
$R^{*26}$=—$C_3H_6O(C_2H_4O)_{19}(C_3H_6O)_{19}H$ $R^{*27}$ is a hydrophilic group expressed by —$C_3H_6O$—X (where "X" is the triglycerin portion)
$R^{*28}$ is a hydrophilic group expressed by —$C_3H_6O$—X (where "X" is the diglycerin portion)
Group having a siloxane dendron structure: $R^{*3}$

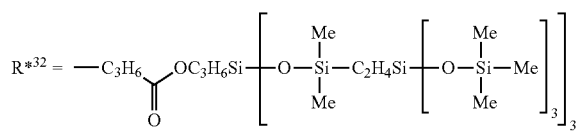

Group having a linear polysiloxane structure: $R^{*4}$

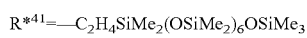

Practical Examples 15 to 23 and Comparative Examples 12 to 20

W/(Si+O), W/Si Emulsion Cosmetic Composition

W/(Si+O) and W/Si emulsions were prepared by mixing and emulsifying the components shown in the formulations in Tables 2 to 7 according to the following procedure. Note that in the description of the emulsion cosmetic composition, in the W/(Si+O) and/or W/Si emulsion, "W" is an abbreviation for "aqueous phase", "Si" is an abbreviation for "silicone-based oil agent", and "0" is an abbreviation for "other organic oil agent". Additionally, "Si+O" indicates an oil phase comprising a mixed oil of silicone oil and another organic oil agent.

Preparation Procedure

1. Dimethylpolysiloxane (2 cst) as a base oil, an oil agent for combination with the base oil, and a hydrophilic silicone compound as a surfactant were placed in a 200 mL container.

2. The mixture was mixed using a spatula in order to disperse and dissolve the surfactant in the oil agent. (oil phase A)

3. Saw teeth of a homo-disper were immersed in the oil phase A and the container was fixed. Then, the mixture was agitated. Agitation was continued until the entire mixture became a uniform solution.

4. Table salt and ion exchange water were placed in a separate cup. The table salt was dissolved by stirring using a spatula. (aqueous phase B)

5. Speed of the homo-disper was increased to 3,000 rpm and the aqueous phase B was poured into the oil phase A at a substantially constant rate over a period of about 40 seconds, while agitating the mixture.

6. Agitation was halted after agitating for two more minutes, the oil component adhered to the inner wall of the container was scraped off by using a spatula and mixed with the produced emulsion.

7. The mixture was agitated for 3 minutes at a speed of 3,000 rpm using the homo-disper. Thus the emulsion cosmetic composition was obtained.

The emulsion formulations (compositions) are shown in Tables 3 to 8 below.

Description of the Emulsion Formulations

200 Fluid 2 CS, manufactured by Dow Corning Corporation was used as the dimethylpolysiloxane (2 cst) base oil. (shown as "2 cst" in the tables)

Additionally, the following six types of oil agents were used as the oil agents combined with the base oil. (Six emulsions were prepared for each of the Practical Examples and Comparative Examples. Thus, a total of 108 emulsion samples were evaluated (9×6+9×6))

Combined Oil Agent

1) Dimethylpolysiloxane (6 cst); SH200 C FLUID 6CS, manufactured by Dow Corning Toray Co., Ltd. (shown as "6 cst" in the tables)

2) Caprylyl methicone; SS-3408 (alkyl-modified silicone), manufactured by Dow Corning Toray Co., Ltd. (shown as "SS-3408" in the tables)

3) Glyceryl tri(2-ethylhexanoate); IOTG (ester oil), manufactured by Nippon Fine Chemical Co., Ltd. (shown as "IOTG" in the tables)

4) Cetyl 2-ethylhexanoate; CEH (ester oil), manufactured by Kokyu Alcohol Kogyo Co., Ltd. (shown as "CEH" in the tables)

5) Isododecane (hydrocarbon oil (ID)); Marukazol R, manufactured by Maruzen Petrochemical Co., Ltd. (shown as "ID" in the tables)

6) Isoparaffin (hydrocarbon oil (IP)); ParLeam 4, manufactured by NOF corporation. (shown as "IP" in the tables)

TABLE 3

Practical Examples (Emulsion Formulation)

| | Practical Examples | | | |
|---|---|---|---|---|
| | 15-1 to 15-6 | 16-1 to 16-6 | 17-1 to 17-6 | 18-1 to 18-6 |
| Surfactant Name | Silicone compound No. 1 | Silicone compound No. 2 | Silicone compound No. 3 | Silicone compound No. 4 |
| Structure | $D/D^{R*31}/D^{R*21}$ 400/7/3 | $D/D^{R*31}/D^{R*21}$ 400/5/5 | $D/D^{R*31}/D^{R*21}$ 400/3/7 | $D/D^{R*31}/D^{R*21}$ 72/9/3 $D/D^{R*31}/D^{R*21}$ 72/9/3 (Low Mw) |
| Type | Siloxane dendron/glycerin co-modified (High Mw) | | | D/$D^{R*31}$/$D^{R*21}$ 72/9/3 (Low Mw) |
| Surfactant [g] | | 2 | | |
| 2 cst [g] | | 8 | | |
| Combined oil agent (6 cst, SS-3408, IOTG, CEH, ID, and IP) [g] | | 10 | | |
| Table salt [g] | | 1 | | |
| Ion exchange water [g] | | 79 | | |

TABLE 4

Practical Examples (Emulsion Formulation)

| | Practical Examples | | |
|---|---|---|---|
| | 19-1 to 19-6 | 20-1 to 20-6 | 21-1 to 21-6 |
| Surfactant Name | Silicone compound No. 5 | Silicone compound No. 6 | Silicone compound No. 7 |
| Structure | $D/D^{R*11}/D^{R*31}/D^{R*21}$ 400/2/3/5 | $D/D^{R*31}/D^{R*22}$ 72/9/3 | $D/D^{R*31}/D^{R*23}$ 72/9/3 |
| Type | Alkyl/siloxane dendron/glycerin co-modified (high Mw) | Siloxane dendron/polyglycerine co-modified (low Mw) | |

TABLE 4-continued

Practical Examples (Emulsion Formulation)

| | Practical Examples | | |
|---|---|---|---|
| | 19-1 to 19-6 | 20-1 to 20-6 | 21-1 to 21-6 |
| Surfactant [g] | | 2 | |
| 2 cst [g] | | 8 | |
| Combined oil agent (6 cst, SS-3408, IOTG, CEH, ID, and IP) [g] | | 10 | |
| Table salt [g] | | 1 | |
| Ion exchange water [g] | | 79 | |

TABLE 5

Practical Examples (Emulsion Formulation)

| | Practical Examples | |
|---|---|---|
| | 22-1 to 22-6 | 23-1 to 23-6 |
| Surfactant Name | Silicone compound No. 8 | Silicone compound No. 14 |
| Structure | $D/D^{R*11}/D^{R*31}/D^{R*23}$ 72/3/6/3 | $D/D^{R*31}/D^{R*24}$ 43/5/2 |
| Type | Alkyl/siloxane dendron/polyglycerine co-modified (high Mw) | Siloxane dendron/polyether co-modified (low Mw) |
| Surfactant [g] | 2 | |
| 2 cst [g] | 8 | |
| Combined oil agent (6 cst, SS-3408, IOTG, CEH, ID, and IP) [g] | 10 | |
| Table salt [g] | 1 | |
| Ion exchange water [g] | 79 | |

TABLE 6

Comparative Examples (Emulsion Formulation)

| | Comparative Examples | | |
|---|---|---|---|
| | 12-1 to 12-6 | 13-1 to 13-6 | 14-1 to 14-6 |
| Surfactant Name | Silicone compound RE3 | Silicone compound RE4 | Silicone compound RE5 |
| Structure | $[D/M^{R*25}]n[40/2]_3$ | $D/D^{R*24}$ 45/2 | $D/D^{R*12}/D^{R*24}$ 63/18/4 |
| Type | Block-type polyether modified | Polyether modified (low Mw) | Alkyl/polyether co-modified |
| Surfactant [g] | | 2 | |
| 2 cst [g] | | 8 | |
| Combined oil agent (6 cst, SS-3408, IOTG, CEH, ID, and IP) [g] | | 10 | |
| Table salt [g] | | 1 | |
| Ion exchange water [g] | | 79 | |

TABLE 7

Comparative Examples (Emulsion Formulation)

| | Comparative Examples | | |
|---|---|---|---|
| | 15-1 to 15-6 | 16-1 to 16-6 | 17-1 to 17-6 |
| Surfactant Name Structure and composition | Silicone compound RE6 $D/D^{R*26}$ = 406/4 (activity agent/2 cs = 40/60 solution) | Silicone compound RE7 $D/D^{R*13}/D^{R*41}/D^{R*24}$ 37/11/1/2 | Silicone compound RE8 $D/D^{R*13}/D^{R*41}/D^{R*27}$ 61/12/2/1 |
| Type | Polyether modified (high Mw) | Alkyl/linear siloxane branch/polyether co-modified | Alkyl/linear siloxane branch/polyglycerine co-modified |
| Surfactant [g] | 5 | | 2 |
| 2 cst [g] | 5 | | 8 |
| Combined oil agent (6 cst, SS-3408, IOTG, CEH, and IP) [g] | | 10 | |
| Table salt [g] | | 1 | |
| Ion exchange water [g] | | 79 | |

TABLE 8

Comparative Examples (Emulsion Formulation)

| | Comparative Examples | | |
|---|---|---|---|
| | 18-1 to 18-6 | 19-1 to 19-6 | 20-1 to 20-6 |
| Surfactant Name Structure and composition | Silicone compound RE9 $D/D^{R*21}$ 406/4 | Silicone compound RE10 $D/D^{R*11}/D^{R*21}$ 72/9/3 | Silicone compound RE11 $D/D^{R*11}/D^{R*22}$ 72/9/3 |
| Type | Glycerin modified (high Mw) | Alkyl/glycerin co-modified | Alkyl/polyglycerine co-modified |
| Surfactant [g] | | 2 | |
| 2 cst [g] | | 8 | |
| Combined oil agent (6 cst, SS-3408, IOTG, CEH, ID, and IP) [g] | | 10 | |
| Table salt [g] | | 1 | |
| Ion exchange water [g] | | 79 | |

Emulsion Evaluation

The emulsions obtained according to the formulations and preparation methods described above were evaluated for the following criteria.

1. Feeling to Touch 1-1: The emulsion was applied from the back of the hand to the finger tips (0.1 g×2 times) and to the arm (0.2 g×1 times; however when isododecane and isoparaffin were used as the oil agents in the emulsion, 0.2 g×2 times). Functional evaluations of feeling to touch and sensation during use when applying were performed regarding four aspects. Each aspect was scored from 0 (poor) to 5 (excellent) and ranking was determined.

Aspect 1: Feeling to touch when applying; from 0 (heavy oily feeling) to 5 (refreshing)

Aspect 2: Spreadability when applying; from 0 (high resistance when spreading) to 5 (no resistance when spreading)

Aspect 3: Smoothness when applying; from 0 (wrinkles and unevennesses in the skin are prominently felt) to 5 (smooth, wrinkles and unevennesses in the skin are hardly felt)

Aspect 4: Lightness when applying; from 0 (heavy, thick feeling when applied) to 5 (light, dry feeling)

1-2: Functional evaluations of skin sensation five minutes after application of the emulsion were performed regarding three aspects. Each aspect was scored from 0 (poor) to 5 (excellent) and ranking was determined. Furthermore, regarding the feeling of oil residue on the fingers, 0.05 g of the emulsion was placed on the index finger and the thumb and middle finger were rubbed against the index finger. The feeling of residue at this time was evaluated and scored in the same way as described above.

Aspect 5: Skin sensation after application; from 0 (sticky, high oily feeling) to 5 (high moisturizing feel)

Aspect 6: Skin sensation after application; from 0 (unnatural, unpleasant feeling of residue) to 5 (no discomfort, natural feel)

Aspect 7: Skin condition; from 0 (sebum dissolves and skin turns white, feeling of tightness or itching due to drying, high level of irritation) to 5 (no dissolution of sebum or drying)

Aspect 8: Feeling of oil residue on fingers; from 0 (persistent sliminess of the oil and unnatural slipperiness, feeling of oiliness on fingers remains) to 5 (very little feeling of oil residue)

1-3: The scores for each aspect of each of the emulsion samples and totals thereof were gathered into tables for each oil agent system (Tables 12 to 29). Furthermore, total scores (overall scores) of the feeling to touch evaluations of the emulsions were gathered into tables according to differences in oil agent systems and activity agents (Tables 9 to 11). Additionally, for each oil agent system and evaluation aspect, the total scores for the samples of Practical Example 9 and the total scores for the samples of Comparative Example 9 were collected in a table and compared. Thereby, the characteristics of the feeling to touch aspect, provided by the novel hydrophilic silicone used in the Practical Examples, were clarified (Tables 30 to 32).

2. Viscosity Stability 2-1: Emulsion viscosity was measured after preparation using a VISCONIC EMD E-type viscometer, manufactured by Tokyo Keiki, Inc. (cone rotor small: 3°×R9.7, 25° C., 2.5 rpm)

2-2: Next, a 25 g sample of the emulsion was placed in each of two 35 mL glass bottles and the bottles were sealed. Then one of the bottles was placed in a 0° C. and the other in a 40° C. high temperature chamber and allowed to sit at rest for two weeks. Thereafter, the bottles were removed from the chambers, returned to room temperature, and measured for viscosity the same as described above.

2-3: Viscosity values after the passage of time, which are relative values having an initial viscosity value set as 100%, are shown. These values were gathered into tables for each oil agent system (Tables 33 to 38).

3. Appearance

Appearance characteristics, that is, texture, of the emulsion was visually evaluated. Each group of Practical Example samples was divided into the two groups below and compared with a sample group in which the commercially available silicone activity agent of the Comparative Examples was used. Evaluation results were indicated by ⊚, ○, Δ, and x marks and are shown in Tables 38 to 41.

3-1: Imparted matte feel (samples having appearances without strong glossiness or shine were evaluated as "excellent")

If the glossiness of the emulsion is excessively strong, an oily glaze will easily form on the skin when applied and, therefore, there is value in suppressing the glossiness of the emulsion.

⊚ Not glossy, superior matte feel
○ Somewhat glossy, but excellent matte feel
Δ Minor matte feel
x High glossiness and no matte feel 3-2: Imparted pearl luster (samples having a beautiful, luxurious pearl-like luster were evaluated as excellent)

If the emulsion or cream can be provided with a beautiful pearl luster, product value from the standpoint of visual appearance will increase. Additionally, the skin can be provided with an elegant, calm brightness after application.

⊚ Luxurious, beautiful pearl-like luster
○ Pearl-like luster
Δ A small amount of pearl-like luster
x No pearl-like luster Evaluation Results Hereinafter, the total scores of the feeling to touch evaluation of the emulsions are gathered in tables according to differences in oil agent systems and activity agents.

TABLE 9

Feeling to touch evaluation summary

| oil agent system | Practical Example 15 | Practical Example 16 | Practical Example 17 | Practical Example 18 | Practical Example 19 | Practical Example 20 |
|---|---|---|---|---|---|---|
| 2cs + 6cs | 37 | 28 | 29 | 34 | 33 | 37 |
| 2cs + SS-3408 | 31 | 29 | 29 | 36 | 32 | 31 |
| 2cs + IOTG | 38 | 36 | 28 | 34 | 26 | 34 |
| 2cs + CEH | 38 | 32 | 30 | 37 | 35 | 35 |
| 2cs + ID | 33 | 34 | 25 | 34 | 31 | 36 |
| 2cs + IP | 37 | 37 | 27 | 35 | 30 | 34 |
| Total score | 214 | 196 | 168 | 210 | 187 | 207 |

TABLE 10

Feeling to touch evaluation summary (continued)

| oil agent system | Practical Example 21 | Practical Example 22 | Practical Example 23 | Comparative Example 12 | Comparative Example 13 | Comparative Example 14 |
|---|---|---|---|---|---|---|
| 2cs + 6cs | 38 | 36 | 33 | 22 | 29 | 22 |
| 2cs + SS-3408 | 32 | 30 | 30 | 22 | 26 | 23 |
| 2cs + IOTG | 37 | 32 | 30 | 21 | 22 | 26 |

TABLE 10-continued

Feeling to touch evaluation summary (continued)

| oil agent system | Practical Example 21 | Practical Example 22 | Practical Example 23 | Comparative Example 12 | Comparative Example 13 | Comparative Example 14 |
|---|---|---|---|---|---|---|
| 2cs + CEH | 38 | 36 | 31 | 22 | 26 | 21 |
| 2cs + ID | 32 | 30 | 26 | 13 | 17 | 19 |
| 2cs + IP | 31 | 28 | 32 | 18 | 23 | 20 |
| Total score | 208 | 192 | 182 | 118 | 143 | 131 |

TABLE 11

Feeling to touch evaluation summary (continued)

| oil agent system | Comparative Example 15 | Comparative Example 16 | Comparative Example 17 | Comparative Example 18 | Comparative Example 19 | Comparative Example 20 |
|---|---|---|---|---|---|---|
| 2cs + 6cs | 0 | 29 | 27 | 29 | 19 | 28 |
| 2cs + SS-3408 | 19 | 25 | 23 | 17 | 18 | 27 |
| 2cs + IOTG | 23 | 26 | 23 | 20 | 18 | 24 |
| 2cs + CEH | 23 | 27 | 26 | 20 | 20 | 27 |
| 2cs + ID | 14 | 30 | 26 | 25 | 18 | 22 |
| 2cs + IP | 16 | 23 | 23 | 18 | 17 | 25 |
| Total score | 95 | 160 | 148 | 129 | 110 | 153 |

The total scores of the Practical Example formulations were from 168 to 214 points. Compared with the Comparative Example formulations (top score of 160 points) the total scores (overall scores) of the feeling to touch and sensation during use of the Practical Example formulations were higher. It was found that even when various oil agent systems were used, stable emulsions with superior feeling to touch can be obtained. This is an effect of using the novel hydrophilic silicone having the siloxane dendron structure of the present invention as the emulsifier.

Next, detailed scores for the feeling to touch and sensation during use of each emulsion sample evaluated according to the eight aspects are shown.

TABLE 12

Feeling to touch evaluation detail (oil agent system (2cs + 6cs))

| Emulsion sample oil agent system (2cs + 6cs) | Practical Example 15-1 | Practical Example 16-1 | Practical Example 17-1 | Practical Example 18-1 | Practical Example 19-1 | Practical Example 20-1 |
|---|---|---|---|---|---|---|
| Aspect 1 (degree of refreshing feel) | 5 | 2 | 2 | 4 | 3 | 4 |
| Aspect 2 (spreadability) | 5 | 3 | 3 | 5 | 5 | 5 |
| Aspect 3 (smoothness) | 4 | 3 | 3 | 5 | 5 | 5 |
| Aspect 4 (lightness) | 5 | 2 | 3 | 5 | 4 | 5 |
| Aspect 5 (moisturizing feel) | 5 | 4 | 5 | 3 | 5 | 5 |
| Aspect 6 (natural feeling on skin) | 5 | 5 | 5 | 5 | 5 | 5 |
| Aspect 7 (minimal sebum dissolution) | 5 | 5 | 5 | 5 | 5 | 5 |
| Aspect 8 (minimal feeling of residue on fingers) | 3 | 4 | 3 | 2 | 1 | 3 |
| Total score | 37 | 28 | 29 | 34 | 33 | 37 |

TABLE 13

Feeling to touch evaluation (oil agent system (2cs + 6cs) continued)

| Emulsion sample oil agent system (2cs + 6cs) | Practical Example 21-1 | Practical Example 22-1 | Practical Example 23-1 | Comparative Example 12-1 | Comparative Example 13-1 | Comparative Example 14-1 |
| --- | --- | --- | --- | --- | --- | --- |
| Aspect 1 (degree of refreshing feel) | 4 | 4 | 3 | 1 | 2 | 1 |
| Aspect 2 (spreadability) | 5 | 5 | 5 | 4 | 4 | 4 |
| Aspect 3 (smoothness) | 5 | 5 | 5 | 4 | 4 | 3 |
| Aspect 4 (lightness) | 5 | 5 | 5 | 1 | 4 | 3 |
| Aspect 5 (moisturizing feel) | 5 | 4 | 3 | 1 | 3 | 1 |
| Aspect 6 (natural feeling on skin) | 5 | 5 | 4 | 4 | 4 | 3 |
| Aspect 7 (minimal sebum dissolution) | 5 | 5 | 5 | 5 | 5 | 5 |
| Aspect 8 (minimal feeling of residue on fingers) | 4 | 3 | 3 | 2 | 3 | 2 |
| Total score | 38 | 36 | 33 | 22 | 29 | 22 |

TABLE 14

Feeling to touch evaluation (oil agent system (2cs + 6cs) continued)

| Emulsion sample oil agent system (2cs + 6cs) | Comparative Example 15-1 | Comparative Example 16-1 | Comparative Example 17-1 | Comparative Example 18-1 | Comparative Example 19-1 | Comparative Example 20-1 |
| --- | --- | --- | --- | --- | --- | --- |
| Aspect 1 (degree of refreshing feel) | 0 | 4 | 3 | 3 | 1 | 4 |
| Aspect 2 (spreadability) | 0 | 5 | 4 | 5 | 3 | 4 |
| Aspect 3 (smoothness) | 0 | 4 | 5 | 5 | 3 | 4 |
| Aspect 4 (lightness) | 0 | 5 | 3 | 4 | 4 | 4 |
| Aspect 5 (moisturizing feel) | 0 | 2 | 2 | 3 | 1 | 2 |
| Aspect 6 (natural feeling on skin) | 0 | 3 | 4 | 3 | 1 | 4 |
| Aspect 7 (minimal sebum dissolution) | 0 | 5 | 5 | 5 | 5 | 5 |
| Aspect 8 (minimal feeling of residue on fingers) | 0 | 1 | 1 | 1 | 1 | 1 |
| Total score | 0 | 29 | 27 | 29 | 19 | 28 |

Note)
In Comparative Example 7-1, emulsifying was attempted but the aqueous phase and the oil phase separated and, as a result, the emulsion was not formed. Therefore, the scores for each of the eight evaluation aspects were determined to be 0.

TABLE 15

Feeling to touch evaluation detail (oil agent system (2cs + SS-3408))

| Emulsion sample oil agent system (2cs + SS-3408) | Practical Example 15-2 | Practical Example 16-2 | Practical Example 17-2 | Practical Example 18-2 | Practical Example 19-2 | Practical Example 20-2 |
| --- | --- | --- | --- | --- | --- | --- |
| Aspect 1 (degree of refreshing feel) | 5 | 2 | 3 | 4 | 4 | 4 |
| Aspect 2 (spreadability) | 5 | 4 | 4 | 5 | 3 | 5 |
| Aspect 3 (smoothness) | 3 | 4 | 3 | 5 | 4 | 4 |
| Aspect 4 (lightness) | 5 | 3 | 4 | 5 | 3 | 4 |
| Aspect 5 (moisturizing feel) | 2 | 4 | 4 | 4 | 5 | 3 |
| Aspect 6 (natural feeling on skin) | 3 | 4 | 4 | 5 | 5 | 4 |
| Aspect 7 (minimal sebum dissolution) | 4 | 4 | 4 | 4 | 4 | 4 |
| Aspect 8 (minimal feeling of residue on fingers) | 4 | 4 | 3 | 4 | 4 | 3 |
| Total score | 31 | 29 | 29 | 36 | 32 | 31 |

TABLE 16

Feeling to touch evaluation (oil agent system (2cs + SS-3408) continued)

| Emulsion sample oil agent system (2cs + SS-3408) | Practical Example 21-2 | Practical Example 22-2 | Practical Example 23-2 | Comparative Example 12-2 | Comparative Example 13-2 | Comparative Example 14-2 |
|---|---|---|---|---|---|---|
| Aspect 1 (degree of refreshing feel) | 4 | 3 | 3 | 1 | 2 | 1 |
| Aspect 2 (spreadability) | 4 | 4 | 5 | 4 | 5 | 5 |
| Aspect 3 (smoothness) | 5 | 4 | 4 | 4 | 4 | 5 |
| Aspect 4 (lightness) | 5 | 4 | 5 | 5 | 5 | 5 |
| Aspect 5 (moisturizing feel) | 4 | 4 | 3 | 1 | 2 | 1 |
| Aspect 6 (natural feeling on skin) | 5 | 4 | 3 | 2 | 2 | 1 |
| Aspect 7 (minimal sebum dissolution) | 4 | 4 | 4 | 4 | 4 | 4 |
| Aspect 8 (minimal feeling of residue on fingers) | 4 | 3 | 3 | 1 | 2 | 1 |
| Total score | 32 | 30 | 30 | 22 | 26 | 23 |

TABLE 17

Feeling to touch evaluation (oil agent system (2cs + SS-3408) continued)

| Emulsion sample oil agent system (2cs + SS-3408) | Comparative Example 15-2 | Comparative Example 16-2 | Comparative Example 17-2 | Comparative Example 18-2 | Comparative Example 19-2 | Comparative Example 20-2 |
|---|---|---|---|---|---|---|
| Aspect 1 (degree of refreshing feel) | 1 | 2 | 2 | 3 | 2 | 4 |
| Aspect 2 (spreadability) | 5 | 4 | 3 | 2 | 3 | 4 |
| Aspect 3 (smoothness) | 3 | 5 | 5 | 2 | 3 | 3 |
| Aspect 4 (lightness) | 4 | 5 | 4 | 3 | 4 | 4 |
| Aspect 5 (moisturizing feel) | 1 | 1 | 1 | 2 | 1 | 2 |
| Aspect 6 (natural feeling on skin) | 0 | 3 | 3 | 0 | 1 | 4 |
| Aspect 7 (minimal sebum dissolution) | 4 | 4 | 4 | 4 | 3 | 4 |
| Aspect 8 (minimal feeling of residue on fingers) | 1 | 1 | 1 | 1 | 1 | 2 |
| Total score | 19 | 25 | 23 | 17 | 18 | 27 |

TABLE 18

Feeling to touch evaluation detail (oil agent system (2cs + IOTG))

| Emulsion sample oil agent system (2cs + IOTG) | Practical Example 15-3 | Practical Example 16-3 | Practical Example 17-3 | Practical Example 18-3 | Practical Example 19-3 | Practical Example 20-3 |
|---|---|---|---|---|---|---|
| Aspect 1 (degree of refreshing feel) | 5 | 4 | 2 | 5 | 4 | 4 |
| Aspect 2 (spreadability) | 5 | 5 | 4 | 5 | 3 | 5 |
| Aspect 3 (smoothness) | 5 | 4 | 4 | 5 | 3 | 5 |
| Aspect 4 (lightness) | 4 | 4 | 2 | 4 | 3 | 4 |
| Aspect 5 (moisturizing feel) | 5 | 5 | 3 | 3 | 2 | 3 |
| Aspect 6 (natural feeling on skin) | 5 | 5 | 5 | 5 | 3 | 5 |
| Aspect 7 (minimal sebum dissolution) | 5 | 5 | 5 | 5 | 5 | 5 |
| Aspect 8 (minimal feeling of residue on fingers) | 4 | 4 | 3 | 2 | 3 | 3 |
| Total score | 38 | 36 | 28 | 34 | 26 | 34 |

TABLE 19-1

Feeling to touch evaluation (oil agent system (2cs + IOTG) continued)

| Emulsion sample oil agent system (2cs + IOTG) | Practical Example 21-3 | Practical Example 22-3 | Practical Example 23-3 | Comparative Example 12-3 | Comparative Example 13-3 | Comparative Example 14-3 |
|---|---|---|---|---|---|---|
| Aspect 1 (degree of refreshing feel) | 5 | 4 | 3 | 1 | 2 | 1 |
| Aspect 2 (spreadability) | 5 | 4 | 4 | 2 | 3 | 4 |
| Aspect 3 (smoothness) | 5 | 5 | 4 | 3 | 3 | 4 |
| Aspect 4 (lightness) | 4 | 3 | 4 | 2 | 1 | 4 |
| Aspect 5 (moisturizing feel) | 4 | 3 | 3 | 1 | 2 | 1 |
| Aspect 6 (natural feeling on skin) | 5 | 5 | 4 | 4 | 4 | 5 |
| Aspect 7 (minimal sebum dissolution) | 5 | 5 | 5 | 5 | 5 | 5 |
| Aspect 8 (minimal feeling of residue on fingers) | 4 | 3 | 3 | 3 | 2 | 2 |
| Total score | 37 | 32 | 30 | 21 | 22 | 26 |

TABLE 19-2

Feeling to touch evaluation (oil agent system (2cs + IOTG) continued)

| Emulsion sample oil agent system (2cs + IOTG) | Comparative Example 15-3 | Comparative Example 16-3 | Comparative Example 17-3 | Comparative Example 18-3 | Comparative Example 19-3 | Comparative Example 20-3 |
|---|---|---|---|---|---|---|
| Aspect 1 (degree of refreshing feel) | 1 | 3 | 3 | 3 | 1 | 3 |
| Aspect 2 (spreadability) | 4 | 4 | 3 | 2 | 2 | 3 |
| Aspect 3 (smoothness) | 3 | 4 | 5 | 2 | 3 | 3 |
| Aspect 4 (lightness) | 3 | 4 | 2 | 3 | 2 | 3 |
| Aspect 5 (moisturizing feel) | 1 | 2 | 1 | 2 | 1 | 1 |
| Aspect 6 (natural feeling on skin) | 4 | 3 | 3 | 2 | 2 | 4 |
| Aspect 7 (minimal sebum dissolution) | 5 | 4 | 5 | 5 | 5 | 5 |
| Aspect 8 (minimal feeling of residue on fingers) | 2 | 2 | 1 | 1 | 2 | 2 |
| Total score | 23 | 26 | 23 | 20 | 18 | 24 |

TABLE 20

Feeling to touch evaluation detail (oil agent system (2cs + CEH))

| Emulsion sample oil agent system (2cs + CEH) | Practical Example 15-4 | Practical Example 16-4 | Practical Example 17-4 | Practical Example 18-4 | Practical Example 19-4 | Practical Example 20-4 |
|---|---|---|---|---|---|---|
| Aspect 1 (degree of refreshing feel) | 4 | 3 | 3 | 5 | 5 | 4 |
| Aspect 2 (spreadability) | 5 | 4 | 4 | 5 | 5 | 5 |
| Aspect 3 (smoothness) | 5 | 4 | 2 | 5 | 3 | 5 |
| Aspect 4 (lightness) | 5 | 3 | 2 | 5 | 5 | 4 |
| Aspect 5 (moisturizing feel) | 4 | 4 | 5 | 4 | 5 | 4 |
| Aspect 6 (natural feeling on skin) | 5 | 5 | 5 | 5 | 5 | 5 |
| Aspect 7 (minimal sebum dissolution) | 5 | 5 | 5 | 5 | 5 | 5 |
| Aspect 8 (minimal feeling of residue on fingers) | 5 | 4 | 4 | 3 | 2 | 3 |
| Total score | 38 | 32 | 30 | 37 | 35 | 35 |

TABLE 22

Feeling to touch evaluation (oil agent system (2cs + CEH) continued)

| Emulsion sample oil agent system (2cs + CEH) | Practical Example 21-4 | Practical Example 22-4 | Practical Example 23-4 | Comparative Example 12-4 | Comparative Example 13-4 | Comparative Example 14-4 |
|---|---|---|---|---|---|---|
| Aspect 1 (degree of refreshing feel) | 5 | 4 | 3 | 2 | 2 | 1 |
| Aspect 2 (spreadability) | 5 | 5 | 5 | 2 | 4 | 4 |
| Aspect 3 (smoothness) | 4 | 5 | 4 | 2 | 4 | 2 |
| Aspect 4 (lightness) | 5 | 4 | 4 | 2 | 3 | 2 |
| Aspect 5 (moisturizing feel) | 5 | 4 | 3 | 2 | 1 | 2 |
| Aspect 6 (natural feeling on skin) | 5 | 5 | 4 | 4 | 4 | 4 |
| Aspect 7 (minimal sebum dissolution) | 5 | 5 | 5 | 5 | 5 | 5 |
| Aspect 8 (minimal feeling of residue on fingers) | 4 | 4 | 3 | 3 | 3 | 1 |
| Total score | 38 | 36 | 31 | 22 | 26 | 21 |

TABLE 23

Feeling to touch evaluation (oil agent system (2cs + CEH) continued)

| Emulsion sample oil agent system (2cs + CEH) | Comparative Example 15-4 | Comparative Example 16-4 | Comparative Example 17-4 | Comparative Example 18-4 | Comparative Example 19-4 | Comparative Example 20-4 |
|---|---|---|---|---|---|---|
| Aspect 1 (degree of refreshing feel) | 1 | 1 | 3 | 2 | 1 | 4 |
| Aspect 2 (spreadability) | 4 | 5 | 4 | 1 | 3 | 4 |
| Aspect 3 (smoothness) | 2 | 4 | 5 | 3 | 2 | 3 |
| Aspect 4 (lightness) | 2 | 5 | 2 | 2 | 3 | 4 |
| Aspect 5 (moisturizing feel) | 3 | 1 | 1 | 3 | 2 | 1 |
| Aspect 6 (natural feeling on skin) | 4 | 4 | 4 | 3 | 3 | 4 |
| Aspect 7 (minimal sebum dissolution) | 5 | 5 | 5 | 5 | 5 | 5 |
| Aspect 8 (minimal feeling of residue on fingers) | 2 | 2 | 2 | 1 | 1 | 2 |
| Total score | 23 | 27 | 26 | 20 | 20 | 27 |

TABLE 24

Feeling to touch evaluation detail (oil agent system (2cs + ID))

| Emulsion sample oil agent system (2cs + ID) | Practical Example 15-5 | Practical Example 16-5 | Practical Example 17-5 | Practical Example 18-5 | Practical Example 19-5 | Practical Example 20-5 |
|---|---|---|---|---|---|---|
| Aspect 1 (degree of refreshing feel) | 4 | 5 | 3 | 5 | 3 | 5 |
| Aspect 2 (spreadability) | 4 | 4 | 3 | 5 | 3 | 4 |
| Aspect 3 (smoothness) | 5 | 5 | 3 | 5 | 5 | 4 |
| Aspect 4 (lightness) | 4 | 4 | 3 | 5 | 3 | 5 |
| Aspect 5 (moisturizing feel) | 4 | 4 | 3 | 3 | 4 | 4 |
| Aspect 6 (natural feeling on skin) | 4 | 4 | 3 | 3 | 5 | 5 |
| Aspect 7 (minimal sebum dissolution) | 3 | 3 | 2 | 3 | 4 | 4 |
| Aspect 8 (minimal feeling of residue on fingers) | 5 | 5 | 5 | 5 | 4 | 5 |
| Total score | 33 | 34 | 25 | 34 | 31 | 36 |

TABLE 25

Feeling to touch evaluation (oil agent system (2cs + ID) continued)

| Emulsion sample oil agent system (2cs + ID) | Practical Example 21-5 | Practical Example 22-5 | Practical Example 23-5 | Comparative Example 12-5 | Comparative Example 13-5 | Comparative Example 14-5 |
|---|---|---|---|---|---|---|
| Aspect 1 (degree of refreshing feel) | 4 | 3 | 3 | 1 | 2 | 1 |
| Aspect 2 (spreadability) | 3 | 4 | 3 | 1 | 2 | 2 |
| Aspect 3 (smoothness) | 3 | 4 | 2 | 2 | 2 | 2 |
| Aspect 4 (lightness) | 5 | 5 | 5 | 5 | 5 | 5 |
| Aspect 5 (moisturizing feel) | 4 | 3 | 3 | 0 | 0 | 0 |
| Aspect 6 (natural feeling on skin) | 4 | 4 | 3 | 0 | 1 | 2 |
| Aspect 7 (minimal sebum dissolution) | 4 | 3 | 2 | 0 | 1 | 3 |
| Aspect 8 (minimal feeling of residue on fingers) | 5 | 4 | 5 | 4 | 4 | 4 |
| Total score | 32 | 30 | 26 | 13 | 17 | 19 |

TABLE 26

Feeling to touch evaluation (oil agent system (2cs + ID) continued)

| Emulsion sample oil agent system (2cs + ID) | Comparative Example 15-5 | Comparative Example 16-5 | Comparative Example 17-5 | Comparative Example 18-5 | Comparative Example 19-5 | Comparative Example 20-5 |
|---|---|---|---|---|---|---|
| Aspect 1 (degree of refreshing feel) | 1 | 4 | 4 | 3 | 5 | 4 |
| Aspect 2 (spreadability) | 3 | 3 | 2 | 3 | 2 | 3 |
| Aspect 3 (smoothness) | 2 | 5 | 5 | 3 | 2 | 2 |
| Aspect 4 (lightness) | 3 | 5 | 4 | 3 | 4 | 4 |
| Aspect 5 (moisturizing feel) | 0 | 3 | 1 | 3 | 0 | 1 |
| Aspect 6 (natural feeling on skin) | 1 | 4 | 3 | 4 | 1 | 2 |
| Aspect 7 (minimal sebum dissolution) | 1 | 2 | 3 | 2 | 1 | 2 |
| Aspect 8 (minimal feeling of residue on fingers) | 3 | 4 | 4 | 4 | 3 | 4 |
| Total score | 14 | 30 | 26 | 25 | 18 | 22 |

TABLE 27

Feeling to touch evaluation detail (oil agent system (2cs + IP))

| Emulsion sample oil agent system (2cs + IP) | Practical Example 15-6 | Practical Example 16-6 | Practical Example 17-6 | Practical Example 18-6 | Practical Example 19-6 | Practical Example 20-6 |
|---|---|---|---|---|---|---|
| Aspect 1 (degree of refreshing feel) | 5 | 5 | 2 | 4 | 2 | 4 |
| Aspect 2 (spreadability) | 5 | 5 | 5 | 4 | 4 | 5 |
| Aspect 3 (smoothness) | 4 | 4 | 4 | 4 | 5 | 4 |
| Aspect 4 (lightness) | 5 | 5 | 2 | 5 | 2 | 4 |
| Aspect 5 (moisturizing feel) | 5 | 5 | 4 | 5 | 4 | 4 |
| Aspect 6 (natural feeling on skin) | 5 | 5 | 5 | 5 | 5 | 5 |
| Aspect 7 (minimal sebum dissolution) | 4 | 4 | 3 | 4 | 4 | 4 |
| Aspect 8 (minimal feeling of residue on fingers) | 4 | 4 | 2 | 4 | 4 | 4 |
| Total score | 37 | 37 | 27 | 35 | 30 | 34 |

TABLE 28

Feeling to touch evaluation (oil agent system (2cs + IP) continued)

| Emulsion sample oil agent system (2cs + IP) | Practical Example 21-6 | Practical Example 22-6 | Practical Example 23-6 | Comparative Example 12-6 | Comparative Example 13-6 | Comparative Example 14-6 |
|---|---|---|---|---|---|---|
| Aspect 1 (degree of refreshing feel) | 4 | 3 | 4 | 1 | 4 | 1 |
| Aspect 2 (spreadability) | 3 | 3 | 5 | 2 | 4 | 3 |
| Aspect 3 (smoothness) | 3 | 4 | 4 | 3 | 3 | 3 |
| Aspect 4 (lightness) | 4 | 3 | 5 | 3 | 4 | 4 |
| Aspect 5 (moisturizing feel) | 4 | 3 | 3 | 1 | 2 | 2 |
| Aspect 6 (natural feeling on skin) | 5 | 5 | 4 | 4 | 4 | 3 |
| Aspect 7 (minimal sebum dissolution) | 4 | 4 | 3 | 1 | 1 | 2 |
| Aspect 8 (minimal feeling of residue on fingers) | 4 | 3 | 4 | 3 | 1 | 2 |
| Total score | 31 | 28 | 32 | 18 | 23 | 20 |

TABLE 29

Feeling to touch evaluation (oil agent system (2cs + IP) continued)

| Emulsion sample oil agent system (2cs + IP) | Comparative Example 15-6 | Comparative Example 16-6 | Comparative Example 17-6 | Comparative Example 18-6 | Comparative Example 19-6 | Comparative Example 20-6 |
|---|---|---|---|---|---|---|
| Aspect 1 (degree of refreshing feel) | 1 | 2 | 2 | 3 | 1 | 3 |
| Aspect 2 (spreadability) | 1 | 3 | 3 | 2 | 3 | 4 |
| Aspect 3 (smoothness) | 1 | 2 | 4 | 3 | 2 | 3 |
| Aspect 4 (lightness) | 2 | 3 | 3 | 1 | 4 | 3 |
| Aspect 5 (moisturizing feel) | 3 | 2 | 1 | 3 | 2 | 2 |
| Aspect 6 (natural feeling on skin) | 4 | 4 | 4 | 2 | 2 | 4 |
| Aspect 7 (minimal sebum dissolution) | 3 | 4 | 4 | 3 | 1 | 4 |
| Aspect 8 (minimal feeling of residue on fingers) | 1 | 3 | 2 | 1 | 2 | 2 |
| Total score | 16 | 23 | 23 | 18 | 17 | 25 |

From the results shown above, it is clear that when the novel hydrophilic silicone of the present invention is used as the emulsifier of a W/(Si+O) or W/Si emulsion, regardless of the oil agent system, a stable emulsion having superior feeling to touch and sensation during use can be obtained. The feeling to touch and sensation during use of such an emulsion liquid are affected the most by the type of oil agent, from the standpoint of the compounded amount, but are also affected by the chemical structure of the hydrophilic silicone emulsifier.

In order to clarify the characteristics related to feeling to touch of the novel hydrophilic silicone having the siloxane dendron structure of the present invention, the total scores of the samples of Practical Example 9 and the total score of the samples of Comparative Example 9 for each oil agent system and evaluation aspect were calculated. The differences therebetween (Practical Example total score–Comparative Example total score) were found and are shown in Tables 30 to 32.

TABLE 30

Comparison of Practical Example and Comparative Example (1)

| Feeling to touch and sensation during use Evaluation aspects | oil agent system | | | | | |
|---|---|---|---|---|---|---|
| | 2cs + 6cs | | | 2cs + SS-3408 | | |
| | Practical Example total score | Comparative Example total score | Difference | Practical Example total score | Comparative Example total score | Difference |
| 1: Degree of refreshing feel | 31 | 19 | +12 | 32 | 18 | +14 |

TABLE 30-continued

Comparison of Practical Example and Comparative Example (1)

| Feeling to touch and sensation during use Evaluation aspects | oil agent system | | | | | |
|---|---|---|---|---|---|---|
| | 2cs + 6cs | | | 2cs + SS-3408 | | |
| | Practical Example total score | Comparative Example total score | Difference | Practical Example total score | Comparative Example total score | Difference |
| 2: Spreadability | 41 | 33 | +8 | 39 | 35 | +4 |
| 3: Smoothness | 40 | 32 | +8 | 36 | 34 | +2 |
| 4: Lightness | 39 | 28 | +11 | 38 | 39 | −1 |
| 5: Moisturizing feel | 39 | 15 | +24 | 33 | 12 | +21 |
| 6: Natural feeling on skin | 44 | 26 | +18 | 37 | 16 | +21 |
| 7: Minimal sebum dissolution | 45 | 40 | +5 | 36 | 35 | +1 |
| 8: Minimal feeling of residue on fingers | 26 | 12 | +14 | 32 | 11 | +21 |

Low viscosity silicone oil having volatility that is not too high has an advantage of providing a dry, light feeling to touch when applying, but also has a problem in that an unnatural feeling of residue (discomfort) on the skin occurs after application. Therefore, in cases where the oil agent system comprises only this type of silicone oil, it is difficult to obtain a natural feeling on the skin after application of a W/Si emulsion.

However, it is clear that when using the novel hydrophilic silicone of the present invention as the emulsifier, there are significant differences compared to when a conventional silicone-based surfactant is used, in particular that it is easy to obtain a lasting moisturizing feel and a natural feeling on the skin. Moreover, it has also been shown that the product of the present invention is superior to conventional products in that the product of the present invention can reduce the feeling of residue on the fingers and impart a feeling of refreshment during application.

While ester oils have a problem in that they feel heavy and oily when applying, they have the advantage of providing a natural skin feel after application. However, due to its high degree of oiliness, oil agent systems comprising ester oils have problems attaining moisturizing feel after application or, in other words, providing a refreshing sensation when applying and maintaining that feel thereafter.

However, it is clear that when using the novel hydrophilic silicone of the present invention as the emulsifier, there are significant differences compared to when a conventional silicone-based surfactant is used, in particular that it is easy to obtain a refreshing feeling to touch when applying even when the oil agent system includes an ester oil and, furthermore, that it is easy to obtain lasting moisturizing feel. Moreover, it has also been shown that the product of the present invention is superior to conventional products in that the product of the present invention can reduce the feeling of residue on the fingers and improve spreadability during application.

TABLE 31

Comparison of Practical Example and Comparative Example (2)

| Feeling to touch and sensation during use Evaluation aspects | oil agent system | | | | | |
|---|---|---|---|---|---|---|
| | 2cs + IOTG | | | 2cs + CEH | | |
| | Practical Example total score | Comparative Example total score | Difference | Practical Example total score | Comparative Example total score | Difference |
| 1: Degree of refreshing feel | 36 | 18 | +18 | 36 | 17 | +19 |
| 2: Spreadability | 40 | 27 | +13 | 43 | 31 | +12 |
| 3: Smoothness | 40 | 30 | +10 | 37 | 27 | +10 |
| 4: Lightness | 32 | 24 | +8 | 37 | 25 | +12 |
| 5: Moisturizing feel | 31 | 12 | +19 | 38 | 16 | +22 |
| 6: Natural feeling on skin | 42 | 31 | +11 | 44 | 34 | +10 |
| 7: Minimal sebum dissolution | 45 | 44 | +1 | 45 | 45 | +0 |
| 8: Minimal feeling of residue on fingers | 29 | 17 | +12 | 32 | 17 | +15 |

TABLE 32

Comparison of Practical Example and Comparative Example (3)

| Feeling to touch and sensation during use Evaluation aspects | oil agent system | | | | | |
|---|---|---|---|---|---|---|
| | 2cs + ID | | | 2cs + IP | | |
| | Practical Example total score | Comparative Example total score | Difference | Practical Example total score | Comparative Example total score | Difference |
| 1: Degree of refreshing feel | 35 | 25 | +10 | 33 | 18 | +15 |
| 2: Spreadability | 33 | 21 | +12 | 39 | 25 | +14 |
| 3: Smoothness | 36 | 25 | +11 | 36 | 24 | +12 |
| 4: Lightness | 39 | 38 | +1 | 35 | 27 | +8 |
| 5: Moisturizing feel | 32 | 8 | +24 | 37 | 18 | +19 |
| 6: Natural feeling on skin | 35 | 18 | +17 | 44 | 31 | +13 |
| 7: Minimal sebum dissolution | 28 | 15 | +13 | 34 | 23 | +9 |
| 8: Minimal feeling of residue on fingers | 43 | 34 | +9 | 33 | 17 | +16 |

Generally, hydrocarbon oils with high volatility provide a refreshing, light feel when applied. However, hydrocarbon oils are prone to break down sebum, causing the skin to whiten after application, which, in some cases, leads to a feeling of pulling or itchiness due to desiccation, and irritation. Therefore, in cases where the oil agent system comprises only this type of hydrocarbon oil, it is difficult to obtain a natural feeling on the skin and lasting moisturizing feel after application of a W/(Si+O) emulsion.

However, it is clear that when using the novel hydrophilic silicone of the present invention as the emulsifier, there are significant differences compared to when a conventional silicone-based surfactant is used, in particular that it is easy to obtain lasting moisturizing feel and a natural feeling on the skin even when the oil agent system comprises a hydrocarbon oil with high volatility. Moreover, it has also been shown that the product of the present invention is superior to conventional products in that the product of the present invention can improve spreadability during application.

Viscosity Stability

As shown in the following Tables 33 to 38, the emulsion obtained by using the novel hydrophilic silicone having the siloxane dendron structure of the present invention as the emulsifier displays minimal change in viscosity over time or with temperature regardless of the type of oil agent system used, in particular that variation is held to within ±8% of the initial value. On the other hand, it was found that the emulsions obtained using a conventional silicone-based surfactant as the emulsifier displayed ±10% or more variation in viscosity from the initial value, depending on the type of oil agent system used.

TABLE 33

Change of emulsion viscosity over time (oil agent system (2cs + 6cs))

| oil agent system 2cs + 6cs | Practical Example 15 | Practical Example 16 | Practical Example 17 | Practical Example 18 | Practical Example 19 | Practical Example 20 |
|---|---|---|---|---|---|---|
| Initial viscosity [mPa·s] | 30500 | 36800 | 42900 | 14000 | 31700 | 15000 |
| 40° C., 2 W [%] | 98 | 94 | 93 | 100 | 94 | 99 |
| 0° C., 2 W [%] | 102 | 100 | 98 | 100 | 94 | 101 |
| oil agent system 2cs + 6cs | Practical Example 21 | Practical Example 22 | Practical Example 23 | Comparative Example 12 | Comparative Example 13 | Comparative Example 14 |
| Initial viscosity [mPa·s] | 17000 | 19000 | 6100 | 35600 | 6000 | 14000 |
| 40° C., 2 W [%] | 101 | 100 | 98 | 97 | 96 | 100 |
| 0° C., 2 W [%] | 100 | 100 | 95 | 98 | 88 | 100 |
| oil agent system 2cs + 6cs | Comparative Example 15 | Comparative Example 16 | Comparative Example 17 | Comparative Example 18 | Comparative Example 19 | Comparative Example 20 |
| Initial viscosity [mPa·s] | | 8900 | 9000 | 31700 | 14000 | 15000 |
| 40° C., 2 W [%] | | 102 | 98 | 98 | 96 | 95 |
| 0° C., 2 W [%] | | 100 | 99 | 98 | 86 | 95 |

TABLE 34

Change of emulsion viscosity over time (oil agent system (2cs + SS-3408))

| oil agent system 2cs + SS-3408 | Practical Example 15 | Practical Example 16 | Practical Example 17 | Practical Example 18 | Practical Example 19 | Practical Example 20 |
|---|---|---|---|---|---|---|
| Initial viscosity [mPa·s] | 20400 | 26000 | 27200 | 8900 | 19200 | 8300 |
| 40° C., 2 W [%] | 101 | 92 | 96 | 100 | 93 | 101 |
| 0° C., 2 W [%] | 101 | 99 | 102 | 100 | 93 | 100 |
| oil agent system 2cs + SS-3408 | Practical Example 21 | Practical Example 22 | Practical Example 23 | Comparative Example 12 | Comparative Example 13 | Comparative Example 14 |
| Initial viscosity [mPa·s] | 9500 | 10400 | 3700 | 22400 | 3600 | 9300 |
| 40° C., 2 W [%] | 100 | 101 | 100 | 100 | 101 | 100 |
| 0° C., 2 W [%] | 101 | 102 | 100 | 100 | 100 | 100 |
| oil agent system 2cs + SS-3408 | Comparative Example 15 | Comparative Example 16 | Comparative Example 17 | Comparative Example 18 | Comparative Example 19 | Comparative Example 20 |
| Initial viscosity [mPa·s] | 25000 | 5900 | 6300 | 19800 | 8800 | 8300 |
| 40° C., 2 W [%] | 98 | 103 | 107 | 87 | 95 | 105 |
| 0° C., 2 W [%] | 99 | 89 | 90 | 98 | 96 | 90 |

TABLE 35

Change of emulsion viscosity over time (oil agent system (2cs + IOTG))

| oil agent system 2cs + IOTG | Practical Example 15 | Practical Example 16 | Practical Example 17 | Practical Example 18 | Practical Example 19 | Practical Example 20 |
|---|---|---|---|---|---|---|
| Initial viscosity [mPa·s] | 14000 | 41700 | 52100 | 23900 | 28400 | 25400 |
| 40° C., 2 W [%] | 100 | 105 | 103 | 107 | 106 | 102 |
| 0° C., 2 W [%] | 93 | 101 | 99 | 100 | 108 | 100 |
| oil agent system 2cs + IOTG | Practical Example 21 | Practical Example 22 | Practical Example 23 | Comparative Example 12 | Comparative Example 13 | Comparative Example 14 |
| Initial viscosity [mPa·s] | 27800 | 29600 | 14000 | 62300 | 13000 | 35900 |
| 40° C., 2 W [%] | 101 | 100 | 94 | 88 | 89 | 99 |
| 0° C., 2 W [%] | 101 | 100 | 98 | 103 | 95 | 99 |
| oil agent system 2cs + IOTG | Comparative Example 15 | Comparative Example 16 | Comparative Example 17 | Comparative Example 18 | Comparative Example 19 | Comparative Example 20 |
| Initial viscosity [mPa·s] | 44300 | 19800 | 20600 | 25500 | 25200 | 27200 |
| 40° C., 2 W [%] | 96 | 101 | 105 | 101 | 110 | 106 |
| 0° C., 2 W [%] | 98 | 99 | 97 | 102 | 101 | 95 |

TABLE 36

Change of emulsion viscosity over time (oil agent system (2cs + CEH))

| oil agent system 2cs + CEH | Practical Example 15 | Practical Example 16 | Practical Example 17 | Practical Example 18 | Practical Example 19 | Practical Example 20 |
|---|---|---|---|---|---|---|
| Initial viscosity [mPa·s] | 23300 | 39300 | 46200 | 15100 | 28700 | 14800 |
| 40° C., 2 W [%] | 99 | 95 | 92 | 105 | 95 | 101 |
| 0° C., 2 W [%] | 100 | 93 | 97 | 99 | 103 | 100 |
| oil agent system 2cs + CEH | Practical Example 21 | Practical Example 22 | Practical Example 23 | Comparative Example 12 | Comparative Example 13 | Comparative Example 14 |
| Initial viscosity [mPa·s] | 16900 | 18100 | 12000 | 42300 | 12000 | 17900 |
| 40° C., 2 W [%] | 100 | 101 | 100 | 99 | 100 | 111 |
| 0° C., 2 W [%] | 100 | 100 | 101 | 99 | 100 | 99 |

TABLE 36-continued

Change of emulsion viscosity over time (oil agent system (2cs + CEH))

| oil agent system 2cs + CEH | Comparative Example 15 | Comparative Example 16 | Comparative Example 17 | Comparative Example 18 | Comparative Example 19 | Comparative Example 20 |
|---|---|---|---|---|---|---|
| Initial viscosity [mPa · s] | 39000 | 13000 | 13000 | 30500 | 16300 | 17400 |
| 40° C., 2 W [%] | 93 | 94 | 94 | 93 | 97 | 92 |
| 0° C., 2 W [%] | 100 | 82 | 84 | 90 | 112 | 84 |

TABLE 37

Change of emulsion viscosity over time (oil agent system (2cs + ID))

| oil agent system 2cs + ID | Practical Example 15 | Practical Example 16 | Practical Example 17 | Practical Example 18 | Practical Example 19 | Practical Example 20 |
|---|---|---|---|---|---|---|
| Initial viscosity [mPa · s] | 14000 | 16500 | 18200 | 5400 | 13000 | 5500 |
| 40° C., 2 W [%] | 103 | 99 | 99 | 96 | 96 | 99 |
| 0° C., 2 W [%] | 100 | 99 | 101 | 93 | 92 | 95 |

| oil agent system 2cs + ID | Practical Example 21 | Practical Example 22 | Practical Example 23 | Comparative Example 12 | Comparative Example 13 | Comparative Example 14 |
|---|---|---|---|---|---|---|
| Initial viscosity [mPa · s] | 5600 | 5700 | 2900 | 15500 | 3000 | 6900 |
| 40° C., 2 W [%] | 100 | 100 | 100 | 100 | 100 | 103 |
| 0° C., 2 W [%] | 99 | 98 | 98 | 99 | 93 | 99 |

| oil agent system 2cs + ID | Comparative Example 15 | Comparative Example 16 | Comparative Example 17 | Comparative Example 18 | Comparative Example 19 | Comparative Example 20 |
|---|---|---|---|---|---|---|
| Initial viscosity [mPa · s] | 16800 | 4100 | 4500 | 12000 | 5000 | 5300 |
| 40° C., 2 W [%] | 110 | 101 | 100 | 96 | 101 | 102 |
| 0° C., 2 W [%] | 101 | 93 | 90 | 100 | 102 | 95 |

TABLE 38

Change of emulsion viscosity over time (oil agent system (2cs + IP))

| oil agent system 2cs + IP | Practical Example 15 | Practical Example 16 | Practical Example 17 | Practical Example 18 | Practical Example 19 | Practical Example 20 |
|---|---|---|---|---|---|---|
| Initial viscosity [mPa · s] | 18900 | 23400 | 25800 | 7800 | 17000 | 8500 |
| 40° C., 2 W [%] | 101 | 97 | 93 | 101 | 105 | 100 |
| 0° C., 2 W [%] | 104 | 101 | 99 | 100 | 96 | 101 |

| oil agent system 2cs + IP | Practical Example 21 | Practical Example 22 | Practical Example 23 | Comparative Example 12 | Comparative Example 13 | Comparative Example 14 |
|---|---|---|---|---|---|---|
| Initial viscosity [mPa · s] | 8900 | 8900 | 3900 | 22400 | 3800 | 9000 |
| 40° C., 2 W [%] | 99 | 99 | 102 | 100 | 103 | 103 |
| 0° C., 2 W [%] | 99 | 100 | 95 | 98 | 90 | 101 |

| oil agent system 2cs + IP | Comparative Example 15 | Comparative Example 16 | Comparative Example 17 | Comparative Example 18 | Comparative Example 19 | Comparative Example 20 |
|---|---|---|---|---|---|---|
| Initial viscosity [mPa · s] | 23000 | 6300 | 6500 | 16500 | 7900 | 8500 |
| 40° C., 2 W [%] | 94 | 99 | 100 | 99 | 102 | 103 |
| 0° C., 2 W [%] | 101 | 90 | 101 | 103 | 101 | 101 |

Appearance

As is shown in Tables 39 to 42 below, the emulsions obtained using the novel hydrophilic silicone of the present invention as the emulsifier, compared to the emulsions of the Comparative Examples, can impart a matte feel or a luxurious pearl-like luster to various oil agent systems. The glossiness of the emulsion not being excessive is effective because such leads to the suppression of excessive oiliness and oily shine after application to the skin. In other words, it was discovered that the novel hydrophilic silicone of the present invention provides and emulsion with a unique, superior texture.

TABLE 39

Appearance evaluation (matte feel); Practical Examples

| oil agent system | Practical Example 15 | Practical Example 16 | Practical Example 17 | Practical Example 18 | Practical Example 19 |
|---|---|---|---|---|---|
| 2cs + 6cs | ◎ | ◎ | ○ | ○ | ◎ |
| 2cs + SS-3408 | ◎ | ○ | Δ | ○ | ○ |
| 2cs + IOTG | Δ | Δ | ○ | Δ | Δ |
| 2cs + CEH | ○ | ○ | Δ | Δ | Δ |
| 2cs + ID | ◎ | ◎ | ○ | ◎ | ◎ |
| 2cs + IP | ◎ | ◎ | ○ | ○ | ○ |

TABLE 40

Appearance evaluation (matte feel); Comparative Examples

| oil agent system | Comparative Example 12 | Comparative Example 13 | Comparative Example 14 | Comparative Example 15 | Comparative Example 16 | Comparative Example 17 |
|---|---|---|---|---|---|---|
| 2cs + 6cs | x | x | Δ | N.A. | x | Δ |
| 2cs + SS-3408 | x | x | x | Δ | x | Δ |
| 2cs + IOTG | x | x | x | x | x | x |
| 2cs + CEH | x | x | x | x | x | x |
| 2cs + ID | x | x | Δ | ○ | x | ○ |
| 2cs + IP | x | x | x | Δ | x | Δ |

TABLE 41

Appearance evaluation (pearl luster); Practical Examples

| oil agent system | Practical Example 20 | Practical Example 21 | Practical Example 22 |
|---|---|---|---|
| 2cs + 6cs | ◎ | ◎ | ◎ |
| 2cs + SS-3408 | ◎ | ◎ | ◎ |
| 2cs + IOTG | ○ | ◎ | ◎ |
| 2cs + CEH | ○ | ◎ | ◎ |
| 2cs + ID | ◎ | ◎ | ◎ |
| 2cs + IP | ◎ | ◎ | ◎ |

TABLE 42

Appearance evalusation (pearl luster); Comparative Examples, continued

| oil agent system | Comparative Example 12 | Comparative Example 13 | Comparative Example 14 | Comparative Example 15 | Comparative Example 16 | Comparative Example 17 |
|---|---|---|---|---|---|---|
| 2cs + 6cs | x | x | x | N.A. | x | x |
| 2cs + SS-3408 | x | x | x | ○ | x | ○ |
| 2cs + IOTG | x | x | x | x | x | ○ |
| 2cs + CEH | x | x | x | x | x | Δ |
| 2cs + ID | x | x | x | x | x | Δ |
| 2cs + IP | x | x | x | ○ | x | x |

Practical Examples 24 to 43

W/(Si+O) and W/Si Emulsion Cosmetic Compositions

W/(Si+O) and W/Si emulsions were prepared by mixing and emulsifying the components shown in the formulations in Tables 43 to 51 according to the following procedure.

Preparation Procedure

1. Dimethylpolysiloxane (2 cst) as a base oil, an oil agent for combination with the base oil, and a hydrophilic silicone compound as a surfactant were placed in a 200 mL container.

2. The mixture was mixed using a spatula in order to disperse and dissolve the surfactant in the oil agent. (oil phase A)

3. Saw teeth of a homo-disper were immersed in the oil phase A and the container was fixed. Then, the mixture was agitated. Agitation was continued until the entire mixture became a uniform solution.

4. Salts and ion exchange water were placed in a separate cup. The salts were dissolved by stirring using a spatula. Depending on the formulation, glycerin or ethanol was further added and dissolved in the mixture. (aqueous phase B)

5. Speed of the homo-disper was increased to 3,000 rpm and the aqueous phase B was poured into the oil phase A at a substantially constant rate over a period of about 40 seconds, while agitating the mixture.

6. Agitation was halted after agitating for two more minutes, the oil component adhered to the inner wall of the container was scraped off by using a spatula and mixed with the produced emulsion.

7. The mixture was agitated for 3 minutes at a speed of 3,000 rpm using the homo-disper. Thus the preparation procedure was completed.

Emulsion formulation: The numbers shown in Tables 41 to 49 below are shown in units of grams.

TABLE 43

Emulsion composition (1)

| | Practical Examples | | | | | | |
|---|---|---|---|---|---|---|---|
| | 24-1 | 24-2 | 24-3 | 25-1 | 25-2 | 25-3 | 26-1 |
| 2 cst | 8.0 | 8.0 | 8.0 | 8.0 | 8.0 | 8.0 | 8.0 |
| 6 cst | 10.0 | — | — | 10.0 | — | — | 10.0 |
| IOTG | — | 10.0 | — | — | 10.0 | — | — |
| ID | — | — | 10.0 | — | — | 10.0 | — |
| Silicone compound No. 3 | 2.0 | 2.0 | 2.0 | — | — | — | — |
| Silicone compound No. 5 | — | — | — | 2.0 | 2.0 | 2.0 | — |
| Silicone compound No. 14 | — | — | — | — | — | — | 2.0 |
| Glycerin | 2.0 | 2.0 | 2.0 | 2.0 | 2.0 | 2.0 | 2.0 |
| Ethanol | — | — | — | — | — | — | — |
| Sodium citrate | — | — | — | — | — | — | — |
| Table salt | 1.0 | 1.0 | 1.0 | 1.0 | 1.0 | 1.0 | 1.0 |
| Ion exchange water | 77.0 | 77.0 | 77.0 | 77.0 | 77.0 | 77.0 | 77.0 |

TABLE 44

Emulsion composition (2)

| | Practical Examples | | | | | | |
|---|---|---|---|---|---|---|---|
| | 26-2 | 26-3 | 27-1 | 27-2 | 27-3 | 28-1 | 28-2 |
| 2 cst | 8.0 | 8.0 | 8.0 | 8.0 | 8.0 | 8.0 | 8.0 |
| 6 cst | — | — | 10.0 | — | — | 10.0 | — |
| IOTG | 10.0 | — | — | 10.0 | — | — | 10.0 |
| ID | — | 10.0 | — | — | 10.0 | — | — |
| Silicone compound No. 6 | — | — | 2.0 | 2.0 | 2.0 | — | — |
| Silicone compound No. 7 | — | — | — | — | — | 2.0 | 2.0 |
| Silicone compound No. 8 | — | — | — | — | — | — | — |
| Silicone compound No. 14 | 2.0 | 2.0 | — | — | — | — | — |
| Glycerin | 2.0 | 2.0 | — | — | — | — | — |
| Ethanol | — | — | 2.0 | 2.0 | 2.0 | 2.0 | 2.0 |
| Sodium citrate | — | — | — | — | — | — | — |
| Table salt | 1.0 | 1.0 | 1.0 | 1.0 | 1.0 | 1.0 | 1.0 |
| Ion exchange water | 77.0 | 77.0 | 77.0 | 77.0 | 77.0 | 77.0 | 77.0 |

TABLE 45

Emulsion composition (3)

| | Practical Examples | | | | | | |
|---|---|---|---|---|---|---|---|
| | 28-3 | 29-1 | 29-2 | 29-3 | 30-1 | 30-2 | 30-3 |
| 2 cst | 8.0 | 8.0 | 8.0 | 8.0 | 8.0 | 8.0 | 8.0 |
| 6 cst | — | 10.0 | — | — | 10.0 | — | — |
| IOTG | — | — | 10.0 | — | — | 10.0 | — |
| ID | 10.0 | — | — | 10.0 | — | — | 10.0 |
| Silicone compound No. 2 | — | — | — | — | 2.0 | 2.0 | 2.0 |
| Silicone compound No. 7 | 2.0 | — | — | — | — | — | — |
| Silicone compound No. 8 | — | 2.0 | 2.0 | 2.0 | — | — | — |
| Glycerin | — | — | — | — | — | — | — |
| Ethanol | 2.0 | 2.0 | 2.0 | 2.0 | — | — | — |
| Sodium citrate | — | — | — | — | 0.2 | 0.2 | 0.2 |
| Table salt | 1.0 | 1.0 | 1.0 | 1.0 | — | — | — |
| Ion exchange water | 77.0 | 77.0 | 77.0 | 77.0 | 79.8 | 79.8 | 79.8 |

TABLE 46

Emulsion composition (4)

| | Practical Examples | | | | | | |
|---|---|---|---|---|---|---|---|
| | 31-1 | 31-2 | 31-3 | 32-1 | 32-2 | 32-3 | 33-1 |
| 2 cst | 8.0 | 8.0 | 8.0 | 8.0 | 8.0 | 8.0 | 8.0 |
| 6 cst | 10.0 | — | — | 10.0 | — | — | 10.0 |
| IOTG | — | 10.0 | — | — | 10.0 | — | — |
| ID | — | — | 10.0 | — | — | 10.0 | — |
| Silicone compound No. 1 | — | — | — | 1.0 | 1.0 | 1.0 | 1.0 |
| Silicone compound No. 4 | 2.0 | 2.0 | 2.0 | — | — | — | — |
| Silicone compound RE3 | — | — | — | 1.0 | 1.0 | 1.0 | — |
| Silicone compound RE4 | — | — | — | — | — | — | 1.0 |
| Silicone compound RE5 | — | — | — | — | — | — | — |
| Silicone compound RE6 | — | — | — | — | — | — | — |
| Glycerin | 2.0 | 2.0 | 2.0 | — | — | — | — |
| Ethanol | — | — | — | — | — | — | — |
| Sodium citrate | 0.2 | 0.2 | 0.2 | — | — | — | — |
| Table salt | — | — | — | 1.0 | 1.0 | 1.0 | 1.0 |
| Ion exchange water | 77.8 | 77.8 | 77.8 | 79.0 | 79.0 | 79.0 | 79.0 |

TABLE 47

Emulsion composition (5)

| | Practical Examples | | | | | | |
|---|---|---|---|---|---|---|---|
| | 33-2 | 33-3 | 34-1 | 34-2 | 34-3 | 35-1 | 35-2 |
| 2 cst | 8.0 | 8.0 | 8.0 | 8.0 | 8.0 | 8.0 | 8.0 |
| 6 cst | — | — | 10.0 | — | — | 10.0 | — |
| IOTG | 10.0 | — | — | 10.0 | — | — | 10.0 |
| ID | — | 10.0 | — | — | 10.0 | — | — |
| Silicone compound No. 1 | 1.0 | 1.0 | 1.0 | 1.0 | 1.0 | 1.0 | 1.0 |
| Silicone compound RE3 | — | — | — | — | — | — | — |
| Silicone compound RE4 | 1.0 | 1.0 | — | — | — | — | — |
| Silicone compound RE5 | — | — | 1.0 | 1.0 | 1.0 | — | — |
| Silicone compound RE6 | — | — | — | — | — | 1.0 | 1.0 |
| Table salt | 1.0 | 1.0 | 1.0 | 1.0 | 1.0 | 1.0 | 1.0 |
| Ion exchange water | 79.0 | 79.0 | 79.0 | 79.0 | 79.0 | 79.0 | 79.0 |

TABLE 48

Emulsion composition (6)

| | Practical Examples | | | | | | |
|---|---|---|---|---|---|---|---|
| | 35-3 | 36-1 | 36-2 | 36-3 | 37-1 | 37-2 | 37-3 |
| 2 cst | 8.0 | 8.0 | 8.0 | 8.0 | 8.0 | 8.0 | 8.0 |
| 6 cst | — | 10.0 | — | — | 10.0 | — | — |
| IOTG | — | — | 10.0 | — | — | 10.0 | — |
| ID | 10.0 | — | — | 10.0 | — | — | 10.0 |
| Silicone compound No. 1 | 1.0 | — | — | — | — | — | — |
| Silicone compound No. 6 | — | 1.4 | 1.4 | 1.4 | 1.4 | 1.4 | 1.4 |
| Silicone compound RE3 | — | 0.6 | 0.6 | 0.6 | — | — | — |
| Silicone compound RE4 | — | — | — | — | 0.6 | 0.6 | 0.6 |
| Silicone compound RE5 | — | — | — | — | — | — | — |
| Silicone compound RE6 | 1.0 | — | — | — | — | — | — |
| Table salt | 1.0 | 1.0 | 1.0 | 1.0 | 1.0 | 1.0 | 1.0 |
| Ion exchange water | 79.0 | 79.0 | 79.0 | 79.0 | 79.0 | 79.0 | 79.0 |

TABLE 49

Emulsion composition (7)

| | Practical Examples | | | | | | |
|---|---|---|---|---|---|---|---|
| | 38-1 | 38-2 | 38-3 | 39-1 | 39-2 | 39-3 | 40-1 |
| 2 cst | 8.0 | 8.0 | 8.0 | 8.0 | 8.0 | 8.0 | 8.0 |
| 6 cst | 10.0 | — | — | 10.0 | — | — | 10.0 |
| IOTG | — | 10.0 | — | — | 10.0 | — | — |
| ID | — | — | 10.0 | — | — | 10.0 | — |
| Silicone compound No. 6 | 1.4 | 1.4 | 1.4 | 1.4 | 1.4 | 1.4 | — |
| Silicone compound No. 7 | — | — | — | — | — | — | 1.4 |
| Silicone compound RE3 | — | — | — | — | — | — | 0.6 |
| Silicone compound RE4 | — | — | — | — | — | — | — |
| Silicone compound RE5 | 0.6 | 0.6 | 0.6 | — | — | — | — |
| Silicone compound RE6 | — | — | — | 0.6 | 0.6 | 0.6 | — |
| Table salt | 1.0 | 1.0 | 1.0 | 1.0 | 1.0 | 1.0 | 1.0 |
| Ion exchange water | 79.0 | 79.0 | 79.0 | 79.0 | 79.0 | 79.0 | 79.0 |

TABLE 50

Emulsion composition (8)

| | Practical Examples | | | | | | |
|---|---|---|---|---|---|---|---|
| | 40-2 | 40-3 | 41-1 | 41-2 | 41-3 | 42-1 | 42-2 |
| 2 cst | 8.0 | 8.0 | 8.0 | 8.0 | 8.0 | 8.0 | 8.0 |
| 6 cst | — | — | 10.0 | — | — | 10.0 | — |
| IOTG | 10.0 | — | — | 10.0 | — | — | 10.0 |
| ID | — | 10.0 | — | — | 10.0 | — | — |
| Silicone compound No. 7 | 1.4 | 1.4 | 1.4 | 1.4 | 1.4 | 1.4 | 1.4 |
| Silicone compound RE3 | 0.6 | 0.6 | — | — | — | — | — |
| Silicone compound RE4 | — | — | 0.6 | 0.6 | 0.6 | — | — |
| Silicone compound RE5 | — | — | — | — | — | 0.6 | 0.6 |
| Silicone compound RE6 | — | — | — | — | — | — | — |
| Table salt | 1.0 | 1.0 | 1.0 | 1.0 | 1.0 | 1.0 | 1.0 |
| Ion exchange water | 79.0 | 79.0 | 79.0 | 79.0 | 79.0 | 79.0 | 79.0 |

TABLE 51

Emulsion composition (9)

| | Practical Examples | | | |
|---|---|---|---|---|
| | 42-3 | 43-1 | 43-2 | 43-3 |
| 2 cst | 8.0 | 8.0 | 8.0 | 8.0 |
| 6 cst | — | 10.0 | — | — |
| IOTG | — | — | 10.0 | — |

TABLE 51-continued

Emulsion composition (9)

| | Practical Examples | | | |
|---|---|---|---|---|
| | 42-3 | 43-1 | 43-2 | 43-3 |
| ID | 10.0 | — | — | 10.0 |
| Silicone compound No. 7 | 1.4 | 1.4 | 1.4 | 1.4 |
| Silicone compound RE3 | — | — | — | — |
| Silicone compound RE4 | — | — | — | — |

TABLE 51-continued

Emulsion composition (9)

| | Practical Examples | | | |
|---|---|---|---|---|
| | 42-3 | 43-1 | 43-2 | 43-3 |
| Silicone compound RE5 | 0.6 | — | — | — |
| Silicone compound RE6 | — | 0.6 | 0.6 | 0.6 |
| Table salt | 1.0 | 1.0 | 1.0 | 1.0 |
| Ion exchange water | 79.0 | 79.0 | 79.0 | 79.0 |

The feeling to touch was evaluated and the appearance was observed of the emulsion samples of Practical Examples 24 to 43 following the evaluation method described for the Practical Examples 15 to 23 and the Comparative Examples 12 to 20 above.

Evaluation Results

1. Feeling to Touch Evaluation

Total scores of the feeling to touch evaluation of the emulsions are gathered in Tables 52 and 53 below, according to differences in oil agent systems and activity agent. In the Practical Examples, formulations are used in which the emulsifier comprises a combination of the novel hydrophilic silicone having the siloxane dendron structure of the present invention and a conventional silicone-based surfactant.

Note that Comparative Examples 17, 18, 19, and 20, which are formulations using a conventional (poly)glycerin-modified silicone as the emulsifier (see Table 11), are recited herein as the Comparative Examples.

TABLE 52

Feeling to touch evaluation summary; oil agent system and activity agent

| oil agent system | Practical Example 32 | Practical Example 33 | Practical Example 34 | Practical Example 35 | Practical Example 36 | Practical Example 37 | Practical Example 38 | Practical Example 39 |
|---|---|---|---|---|---|---|---|---|
| 2cs + 6cs | 32 | 34 | 30 | 34 | 32 | 38 | 30 | 33 |
| 2cs + IOTG | 30 | 31 | 32 | 31 | 30 | 32 | 34 | 33 |
| 2cs + ID | 29 | 29 | 28 | 28 | 31 | 30 | 31 | 30 |
| Total score | 91 | 94 | 90 | 93 | 93 | 100 | 95 | 96 |

TABLE 53

Feeling to touch evaluation summary; oil agent system and activity agent, continued

| oil agent system | Practical Example 40 | Practical Example 41 | Practical Example 42 | Practical Example 43 | Comparative Example 17 | Comparative Example 18 | Comparative Example 19 | Comparative Example 20 |
|---|---|---|---|---|---|---|---|---|
| 2cs + 6cs | 28 | 32 | 31 | 36 | 27 | 29 | 19 | 28 |
| 2cs + IOTG | 30 | 32 | 31 | 31 | 23 | 20 | 18 | 24 |
| 2cs + ID | 27 | 28 | 30 | 30 | 26 | 25 | 18 | 22 |
| Total score | 85 | 92 | 92 | 97 | 76 | 74 | 55 | 74 |

Compared with the Comparative Example formulations, the total scores (overall scores) of the feeling to touch and sensation during use of the Practical Example formulations were higher. It was found that even when various oil agent systems were used, stable emulsions with superior feeling to touch can be obtained.

The total scores of the feeling to touch evaluation of an emulsion including glycerin as the polyhydric alcohol, ethanol as the lower monohydric alcohol, and sodium citrate as the organic salt is shown in Table 54 below. For comparison, a portion of the feeling to touch evaluation of a Practical Example emulsion including an inorganic salt (table salt) is also shown in Table 54.

Additionally, as shown below, by comparing the Practical Example shown in Table 54 with the Practical Example shown directly thereunder in Table 55 on a one-to-one basis, the effects of the various additives are revealed. (e.g. Practical Example 27 (including additives) corresponds to the evaluation data of Practical Example 20 (no additives), located directly thereunder)

TABLE 54

Feeling to touch evaluation summary; effects of the additives

| oil agent system | Practical Example 24 | Practical Example 25 | Practical Example 26 | Practical Example 27 | Practical Example 28 | Practical Example 29 | Practical Example 30 | Practical Example 31 |
|---|---|---|---|---|---|---|---|---|
| 2cs + 6cs   | 33 | 35 | 36 | 38 | 39 | 38 | 31 | 38 |
| 2cs + IOTG  | 32 | 29 | 33 | 35 | 38 | 33 | 36 | 36 |
| 2cs + ID    | 29 | 33 | 32 | 36 | 35 | 31 | 34 | 36 |
| Total score | 94 | 97 | 101 | 109 | 112 | 102 | 101 | 110 |

TABLE 55

Feeling to touch evaluation summary; Practical Example data for comparison with Table 53

| oil agent system | Practical Example 17 | Practical Example 19 | Practical Example 23 | Practical Example 20 | Practical Example 21 | Practical Example 22 | Practical Example 16 | Practical Example 18 |
|---|---|---|---|---|---|---|---|---|
| 2cs + 6cs   | 29 | 33 | 33 | 37 | 38 | 36 | 28 | 34 |
| 2cs + IOTG  | 28 | 26 | 30 | 34 | 37 | 32 | 36 | 34 |
| 2cs + ID    | 25 | 31 | 26 | 36 | 32 | 30 | 34 | 34 |
| Total score | 82 | 90 | 89 | 107 | 107 | 98 | 98 | 102 |

It is clear from a vertical comparison of Tables 54 and 55 that in each group of Practical Examples 24 to 31, the total score of for feeling to touch was higher than the total score of the corresponding group of Practical Examples 17 to 23. In other words, it was discovered that feeling to touch can be further improved when the W/(Si+O) and W/Si emulsions according to the present invention comprise glycerin, ethanol, and sodium citrate as components, compared to when these components are not comprised.

Detailed scores for the feeling to touch and sensation during use of each emulsion sample evaluated according to the eight aspects are shown below.

TABLE 56

Feeling to touch evaluation detail (oil agent system (2cs + 6cs))

| Emulsion sample oil agent system (2cs + 6cs) | Practical Example 24-1 | Practical Example 25-1 | Practical Example 26-1 | Practical Example 27-1 | Practical Example 28-1 | Practical Example 29-1 | Practical Example 30-1 |
|---|---|---|---|---|---|---|---|
| Aspect 1 (degree of refreshing feel) | 4 | 4 | 4 | 5 | 5 | 5 | 3 |
| Aspect 2 (spreadability) | 4 | 5 | 5 | 5 | 5 | 5 | 3 |
| Aspect 3 (smoothness) | 4 | 5 | 5 | 5 | 5 | 5 | 3 |
| Aspect 4 (lightness) | 3 | 4 | 5 | 5 | 5 | 5 | 3 |
| Aspect 5 (moisturizing feel) | 5 | 5 | 4 | 5 | 5 | 5 | 5 |
| Aspect 6 (natural feeling on skin) | 5 | 5 | 5 | 5 | 5 | 5 | 5 |
| Aspect 7 (minimal sebum dissolution) | 5 | 5 | 5 | 5 | 5 | 5 | 5 |
| Aspect 8 (minimal feeling of residue on fingers) | 3 | 2 | 3 | 3 | 4 | 3 | 4 |
| Total score | 33 | 35 | 36 | 38 | 39 | 38 | 31 |

TABLE 57

Feeling to touch evaluation (oil agent system (2cs + 6cs) continued)

| Emulsion sample oil agent system (2cs + 6cs) | Practical Example 31-1 | Practical Example 32-1 | Practical Example 33-1 | Practical Example 34-1 | Practical Example 35-1 | Practical Example 36-1 | Practical Example 37-1 |
|---|---|---|---|---|---|---|---|
| Aspect 1 (degree of refreshing feel) | 5 | 3 | 4 | 3 | 5 | 3 | 3 |

TABLE 57-continued

Feeling to touch evaluation (oil agent system (2cs + 6cs) continued)

| Emulsion sample oil agent system (2cs + 6cs) | Practical Example 31-1 | Practical Example 32-1 | Practical Example 33-1 | Practical Example 34-1 | Practical Example 35-1 | Practical Example 36-1 | Practical Example 37-1 |
|---|---|---|---|---|---|---|---|
| Aspect 2 (spreadability) | 5 | 5 | 5 | 5 | 4 | 5 | 5 |
| Aspect 3 (smoothness) | 5 | 5 | 4 | 4 | 5 | 5 | 5 |
| Aspect 4 (lightness) | 5 | 3 | 5 | 4 | 4 | 3 | 5 |
| Aspect 5 (moisturizing feel) | 5 | 3 | 4 | 3 | 4 | 3 | 4 |
| Aspect 6 (natural feeling on skin) | 5 | 5 | 4 | 4 | 4 | 5 | 5 |
| Aspect 7 (minimal sebum dissolution) | 5 | 5 | 5 | 5 | 5 | 5 | 5 |
| Aspect 8 (minimal feeling of residue on fingers) | 3 | 3 | 3 | 2 | 3 | 3 | 3 |
| Total score | 38 | 32 | 34 | 30 | 34 | 32 | 38 |

TABLE 58

Feeling to touch evaluation (oil agent system (2cs + 6cs) continued)

| Emulsion sample oil agent system (2cs + 6cs) | Practical Example 38-1 | Practical Example 39-1 | Practical Example 40-1 | Practical Example 41-1 | Practical Example 42-1 | Practical Example 43-1 |
|---|---|---|---|---|---|---|
| Aspect 1 (degree of refreshing feel) | 3 | 4 | 3 | 4 | 3 | 4 |
| Aspect 2 (spreadability) | 4 | 4 | 4 | 4 | 4 | 5 |
| Aspect 3 (smoothness) | 5 | 5 | 4 | 4 | 4 | 5 |
| Aspect 4 (lightness) | 4 | 4 | 3 | 4 | 4 | 5 |
| Aspect 5 (moisturizing feel) | 3 | 4 | 3 | 4 | 3 | 4 |
| Aspect 6 (natural feeling on skin) | 4 | 4 | 4 | 4 | 5 | 5 |
| Aspect 7 (minimal sebum dissolution) | 5 | 5 | 5 | 5 | 5 | 5 |
| Aspect 8 (minimal feeling of residue on fingers) | 2 | 3 | 2 | 3 | 3 | 3 |
| Total score | 30 | 33 | 28 | 32 | 31 | 36 |

TABLE 59

Feeling to touch evaluation detail (oil agent system (2cs + IOTG))

| Emulsion sample oil agent system (2cs + IOTG) | Practical Example 24-2 | Practical Example 25-2 | Practical Example 26-2 | Practical Example2 7-2 | Practical Example 28-2 | Practical Example 29-2 | Practical Example 30-2 |
|---|---|---|---|---|---|---|---|
| Aspect 1 (degree of refreshing feel) | 3 | 4 | 5 | 5 | 5 | 4 | 4 |
| Aspect 2 (spreadability) | 4 | 3 | 4 | 5 | 5 | 4 | 5 |
| Aspect 3 (smoothness) | 5 | 4 | 4 | 5 | 5 | 5 | 4 |
| Aspect 4 (lightness) | 3 | 3 | 4 | 4 | 5 | 4 | 4 |
| Aspect 5 (moisturizing feel) | 4 | 3 | 4 | 3 | 4 | 3 | 5 |
| Aspect 6 (natural feeling on skin) | 5 | 4 | 4 | 5 | 5 | 5 | 5 |
| Aspect 7 (minimal sebum dissolution) | 5 | 5 | 5 | 5 | 5 | 5 | 5 |
| Aspect 8 (minimal feeling of residue on fingers) | 3 | 3 | 3 | 3 | 4 | 3 | 4 |
| Total score | 32 | 29 | 33 | 35 | 38 | 33 | 36 |

TABLE 60

Feeling to touch evaluation (oil agent system (2cs + IOTG) continued)

| Emulsion sample oil agent system (2cs + IOTG) | Practical Example 31-2 | Practical Example 32-2 | Practical Example 33-2 | Practical Example 34-2 | Practical Example 35-2 | Practical Example 36-2 | Practical Example 37-2 |
|---|---|---|---|---|---|---|---|
| Aspect 1 (degree of refreshing feel) | 5 | 3 | 4 | 3 | 3 | 3 | 4 |
| Aspect 2 (spreadability) | 5 | 3 | 4 | 4 | 3 | 4 | 4 |
| Aspect 3 (smoothness) | 5 | 5 | 4 | 5 | 5 | 4 | 4 |
| Aspect 4 (lightness) | 4 | 3 | 3 | 4 | 3 | 3 | 4 |
| Aspect 5 (moisturizing feel) | 5 | 3 | 4 | 3 | 4 | 3 | 3 |
| Aspect 6 (natural feeling on skin) | 5 | 5 | 4 | 5 | 5 | 5 | 5 |
| Aspect 7 (minimal sebum dissolution) | 5 | 5 | 5 | 5 | 5 | 5 | 5 |
| Aspect 8 (minimal feeling of residue on fingers) | 2 | 3 | 3 | 3 | 3 | 3 | 3 |
| Total score | 36 | 30 | 31 | 32 | 31 | 30 | 32 |

TABLE 61

Feeling to touch evaluation (oil agent system (2cs + IOTG) continued)

| Emulsion sample oil agent system (2cs + IOTG) | Practical Example 38-2 | Practical Example 39-2 | Practical Example 40-2 | Practical Example 41-2 | Practical Example 42-2 | Practical Example 43-2 |
|---|---|---|---|---|---|---|
| Aspect 1 (degree of refreshing feel) | 4 | 4 | 3 | 4 | 3 | 3 |
| Aspect 2 (spreadability) | 5 | 5 | 3 | 3 | 4 | 4 |
| Aspect 3 (smoothness) | 5 | 5 | 5 | 5 | 5 | 5 |
| Aspect 4 (lightness) | 4 | 3 | 3 | 3 | 3 | 3 |
| Aspect 5 (moisturizing feel) | 3 | 3 | 3 | 4 | 3 | 3 |
| Aspect 6 (natural feeling on skin) | 5 | 5 | 5 | 5 | 5 | 5 |
| Aspect 7 (minimal sebum dissolution) | 5 | 5 | 5 | 5 | 5 | 5 |
| Aspect 8 (minimal feeling of residue on fingers) | 3 | 3 | 3 | 3 | 3 | 3 |
| Total score | 34 | 33 | 30 | 32 | 31 | 31 |

TABLE 62

Feeling to touch evaluation detail (oil agent system (2cs + ID))

| Emulsion sample oil agent system (2cs + ID) | Practical Example 24-3 | Practical Example 25-3 | Practical Example 26-3 | Practical Example 27-3 | Practical Example 28-3 | Practical Example 29-3 | Practical Example 30-3 |
|---|---|---|---|---|---|---|---|
| Aspect 1 (degree of refreshing feel) | 4 | 4 | 4 | 5 | 5 | 4 | 5 |
| Aspect 2 (spreadability) | 3 | 3 | 4 | 4 | 4 | 4 | 4 |
| Aspect 3 (smoothness) | 4 | 5 | 3 | 4 | 4 | 4 | 5 |
| Aspect 4 (lightness) | 3 | 4 | 5 | 5 | 5 | 5 | 4 |
| Aspect 5 (moisturizing feel) | 4 | 4 | 4 | 4 | 4 | 3 | 4 |
| Aspect 6 (natural feeling on skin) | 3 | 5 | 4 | 5 | 4 | 4 | 4 |
| Aspect 7 (minimal sebum dissolution) | 3 | 4 | 3 | 4 | 4 | 3 | 3 |
| Aspect 8 (minimal feeling of residue on fingers) | 5 | 4 | 5 | 5 | 5 | 4 | 5 |
| Total score | 29 | 33 | 32 | 36 | 35 | 31 | 34 |

TABLE 63

Feeling to touch evaluation (oil agent system (2cs + ID) continued)

| Emulsion sample oil agent system (2cs + ID) | Practical Example 31-3 | Practical Example 32-3 | Practical Example 33-3 | Practical Example 34-3 | Practical Example 35-3 | Practical Example 36-3 | Practical Example 37-3 |
|---|---|---|---|---|---|---|---|
| Aspect 1 (degree of refreshing feel) | 5 | 3 | 4 | 3 | 3 | 4 | 4 |
| Aspect 2 (spreadability) | 5 | 3 | 3 | 3 | 4 | 3 | 3 |
| Aspect 3 (smoothness) | 5 | 4 | 3 | 4 | 4 | 4 | 3 |
| Aspect 4 (lightness) | 5 | 5 | 5 | 5 | 4 | 5 | 5 |
| Aspect 5 (moisturizing feel) | 4 | 3 | 3 | 2 | 3 | 3 | 3 |
| Aspect 6 (natural feeling on skin) | 4 | 3 | 3 | 3 | 3 | 4 | 4 |
| Aspect 7 (minimal sebum dissolution) | 3 | 3 | 3 | 3 | 3 | 3 | 3 |
| Aspect 8 (minimal feeling of residue on fingers) | 5 | 5 | 5 | 5 | 4 | 5 | 5 |
| Total score | 36 | 29 | 29 | 28 | 28 | 31 | 30 |

TABLE 64

Feeling to touch evaluation (oil agent system (2cs + ID) continued)

| Emulsion sample oil agent system (2cs + ID) | Practical Example 38-3 | Practical Example 39-3 | Practical Example 40-3 | Practical Example 41-3 | Practical Example 42-3 | Practical Example 43-3 |
|---|---|---|---|---|---|---|
| Aspect 1 (degree of refreshing feel) | 4 | 4 | 3 | 3 | 3 | 4 |
| Aspect 2 (spreadability) | 3 | 4 | 2 | 3 | 3 | 3 |
| Aspect 3 (smoothness) | 3 | 4 | 3 | 3 | 3 | 4 |
| Aspect 4 (lightness) | 5 | 4 | 5 | 5 | 5 | 4 |
| Aspect 5 (moisturizing feel) | 3 | 3 | 3 | 3 | 3 | 3 |
| Aspect 6 (natural feeling on skin) | 4 | 4 | 3 | 3 | 4 | 4 |
| Aspect 7 (minimal sebum dissolution) | 4 | 3 | 3 | 3 | 4 | 4 |
| Aspect 8 (minimal feeling of residue on fingers) | 5 | 4 | 5 | 5 | 5 | 4 |
| Total score | 31 | 30 | 27 | 28 | 30 | 30 |

In order to clarify the benefits for each feeling to touch aspect of the emulsion that are obtained by compounding glycerin, ethanol, and sodium citrate, the total scores of the eight samples of Practical Examples 24 to 31 and the total scores for the eight samples of the Practical Examples used for comparison (Practical Examples 16 to 23) in which an inorganic salt (table salt) was used for each oil agent system and evaluation aspect were calculated and the differences therebetween were found (Practical Example total score–Practical Example for comparison total score). The results thereof are shown in Table 65.

TABLE 65

Effect the use of the additives have on the feeling to touch aspects of the emulsion

| Feeling to touch and sensation during use Evaluation aspects | oil agent system | | | | | | | | |
|---|---|---|---|---|---|---|---|---|---|
| | 2cs + 6cs | | | 2cs + IOTG | | | 2cs + ID | | |
| | Practical Examples 24 to 31 Total | Practical Examples 16 to 23 Total | Difference | Practical Examples 24 to 31 Total | Practical Examples 16 to 23 Total | Difference | Practical Examples 24 to 31 Total | Practical Examples 16 to 23 Total | Difference |
| 1: Degree of refreshing feel | 35 | 26 | +9 | 35 | 31 | +4 | 36 | 31 | +5 |
| 2: Spreadability | 37 | 36 | +1 | 35 | 35 | 0 | 31 | 29 | +2 |
| 3: Smoothness | 37 | 36 | +1 | 37 | 35 | +2 | 34 | 31 | +3 |
| 4: Lightness | 35 | 34 | +1 | 31 | 28 | +3 | 36 | 35 | +1 |

TABLE 65-continued

Effect the use of the additives have on the feeling to touch aspects of the emulsion

| Feeling to touch and sensation during use Evaluation aspects | oil agent system | | | | | | | | |
|---|---|---|---|---|---|---|---|---|---|
| | 2cs + 6cs | | | 2cs + IOTG | | | 2cs + ID | | |
| | Practical Examples 24 to 31 Total | Practical Examples 16 to 23 Total | Difference | Practical Examples 24 to 31 Total | Practical Examples 16 to 23 Total | Difference | Practical Examples 24 to 31 Total | Practical Examples 16 to 23 Total | Difference |
| 5: Moisturizing feel | 39 | 34 | +5 | 31 | 26 | +5 | 31 | 28 | +3 |
| 6: Natural feeling on skin | 40 | 39 | +1 | 38 | 37 | +1 | 33 | 31 | +2 |
| 7: Minimal sebum dissolution | 40 | 40 | 0 | 40 | 40 | 0 | 27 | 25 | +2 |
| 8: Minimal feeling of residue on fingers | 25 | 23 | +2 | 25 | 25 | 0 | 38 | 38 | 0 |

As described above, by compounding at least one selected from the group consisting of glycerin (polyhydric alcohol), ethanol (lower monohydric alcohol), sodium citrate (organic salt) in an emulsion formulation including at least the novel hydrophilic silicone of the present invention, oil agent, and water, compared with a case in which table salt (an inorganic salt) is further compounded, it is clear that the degree of refreshing feel when applying and the moisturizing feel after application is improved. It is said that a polyhydric alcohol of similar polyol is prone to produce stickiness after application, but with the formulation used in the present invention, the benefits described above were obtained, free of such disadvantages. (See the evaluation results recited in the "emulsion evaluation" section. In "Aspect 5: Moisturizing feel," stickiness was also checked for.)

Additionally, there are cases where sebum dissolution, irritation, or similar unnatural sensations are obtained after application when a lower monohydric alcohol is compounded, but with the formulation used in the present invention, the benefits described above were obtained, free of such disadvantages. The fact that little difference is seen between aspects 6 and 7 in Table 65 supports this finding.

Evaluation Results
Appearance

As shown in the following Tables 66 and 67, even in cases when at least one additive of glycerin, ethanol, sodium citrate, table salt, and similar additive is compounded in an emulsion formulation including at least the novel hydrophilic silicone of the present invention, an oil agent, and water, it was discovered that the emulsion can be provided with a matte feel appearance or, alternately, a luxurious pearl-like luster.

Moreover, in the emulsion formulation described above, even where the novel hydrophilic silicone of the present invention is used in combination with an existing silicone-based surfactant such as a polyether-modified silicone or an alkyl/polyether-modified silicone as an emulsifier (activity agent), it was discovered that the emulsion can be provided with a matte feel appearance or, alternately, a luxurious pearl-like luster. The glossiness of the emulsion not being excessive is effective because such leads to the suppression of excessive oiliness and oily shine after application to the skin.

TABLE 66

Appearance evaluation (matte feel)

| oil agent system | Practical Example 24 | Practical Example 25 | Practical Example 30 | Practical Example 31 | Practical Example 32 | Practical Example 33 | Practical Example 34 | Practical Example 35 |
|---|---|---|---|---|---|---|---|---|
| 2cs + 6cs | ⊚ | ⊚ | ⊚ | ⊚ | ○ | ⊚ | ⊚ | ⊚ |
| 2cs + IOTG | ○ | ○ | ○ | Δ | Δ | Δ | Δ | ○ |
| 2cs + ID | ⊚ | ⊚ | ○ | ⊚ | ⊚ | ○ | ⊚ | ⊚ |

TABLE 67

Appearance evaluation (pearl luster)

| oil agent system | Practical Example 26 | Practical Example 27 | Practical Example 28 | Practical Example 29 | Practical Example 36 | Practical Example 37 |
|---|---|---|---|---|---|---|
| 2cs + 6cs | ⊚ | ⊚ | ⊚ | ⊚ | ⊚ | ⊚ |
| 2cs + IOTG | ⊚ | ⊚ | ⊚ | ⊚ | ○ | ○ |
| 2cs + ID | ⊚ | ⊚ | ⊚ | ⊚ | ⊚ | ⊚ |

| oil agent system | Practical Example 38 | Practical Example 39 | Practical Example 40 | Practical Example 41 | Practical Example 42 | Practical Example 43 |
|---|---|---|---|---|---|---|
| 2cs + 6cs | ⊚ | ⊚ | ⊚ | ⊚ | ⊚ | ⊚ |
| 2cs + IOTG | ⊚ | ⊚ | ⊚ | ⊚ | ⊚ | ⊚ |
| 2cs + ID | ⊚ | ⊚ | ⊚ | ⊚ | ⊚ | ⊚ |

Practical Examples 44 to 49 and Comparative Examples 21 to 28

Powder in Oil Dispersions

The compositions (formulations) in Table 68 (Practical Examples) and Table 69 (Comparative Examples) were mixed and dispersed according to the following procedure.

Thus, powder in oil dispersions were prepared. Note that in the formulations shown in Tables 68 and 69, the numbers are shown in units of grams.

Preparation Procedure

1. Decamethyl cyclopentasiloxane (D5) and the silicone compound (dispersing agent) were placed in a 200 mL glass bottle and mixed and dissolved.
2. A powder and zirconia beads ten-times the weight of the powder (YTZ balls, diameter: 0.8 mm) were placed in the glass bottle described above. The bottle was capped and the components were mixed by lightly shaking the bottle. The following were used as the powder.

Titanium oxide: MTY-100SAS (manufactured by Tayca Corporation)

Zinc oxide: MZY-505S (manufactured by Tayca Corporation)

3. The glass bottle was set in a paint shaker and shaken for 1 hour.
4. The obtained mixture was passed through a sieve in order to remove the zirconia beads. Thus, a powder in oil dispersion was obtained.

TABLE 68

Powder in oil dispersion formulations (1); Practical Examples 44 to 49

| Practical Examples | 44 | 45 | 46 | 47 | 48 | 49 |
|---|---|---|---|---|---|---|
| D5 | 35.7 | 35.7 | 35.7 | 35.7 | 35.7 | 35.7 |
| Silicone compound No. 9 | 5.7 | — | — | 5.7 | — | — |
| Silicone compound No. 10 | — | 5.7 | — | — | 5.7 | — |
| Silicone compound No. 12 | — | — | 5.7 | — | — | 5.7 |
| Titanium oxide | 28.6 | 28.6 | 28.6 | — | — | — |
| Zinc oxide | — | — | — | 28.6 | 28.6 | 28.6 |

Note:
In the table, the compounding weight ratio of D5 to the powder to the dispersing agent (silicone compound) was 50:40:8.

TABLE 69

Powder in oil dispersion formulations (2); Comparative Examples 21 to 28

| Comparative Examples | 21 | 22 | 23 | 24 | 25 | 26 | 27 | 28 |
|---|---|---|---|---|---|---|---|---|
| D5 | 35.7 | 35.7 | 35.7 | 35.7 | 35.7 | 35.7 | 35.7 | 35.7 |
| Silicone compound RE4 | 5.7 | — | — | — | 5.7 | — | — | — |
| Silicone compound RE7 | — | 5.7 | — | — | — | 5.7 | — | — |
| Silicone compound RE8 | — | — | 5.7 | — | — | — | 5.7 | — |
| Silicone compound RE10 | — | — | — | 5.7 | — | — | — | 5.7 |
| Titanium oxide | 28.6 | 28.6 | 28.6 | 28.6 | — | — | — | — |
| Zinc oxide | — | — | — | — | 28.6 | 28.6 | 28.6 | 28.6 |

Note:
In the table, the compounding weight ratio of D5 to the powder to the dispersing agent (silicone compound) was 50:40:8.

Practical Examples 50 to 53 and Comparative Examples 29 to 36

Powder Compositions

The compositions (formulations) in Table 70 (Practical Examples) and Table 71 (Comparative Examples) were treated according to the following procedure. Thus, powder compositions according to the present invention and powder compositions for the Comparative Examples were prepared.

Preparation procedure: Amounts of the silicone compounds (surface treatment agents) shown in the tables were dissolved in isopropyl alcohol. Then, the powder was added and dispersed therein. The solvent was then removed by distillation. Thus, powder compositions were prepared.

The following were used as the powder.

Titanium oxide: MTY-100SAS (manufactured by Tayca Corporation)

Zinc oxide: MZY-505S (manufactured by Tayca Corporation)

TABLE 70

Powder composition formulations (1): Practical Examples 50 to 53

| | Practical Examples | | | |
|---|---|---|---|---|
| | 50 | 51 | 52 | 53 |
| Silicone compound No. 9 | 7.1 | — | 7.1 | — |
| Silicone compound No. 11 | — | 7.1 | — | 7.1 |
| Titanium oxide | 28.6 | 28.6 | — | — |
| Zinc oxide | — | — | 28.6 | 28.6 |

TABLE 71

Powder composition formulations (2): Comparative Examples 29 to 36

| | Comparative Examples | | | | | | | |
|---|---|---|---|---|---|---|---|---|
| | 29 | 30 | 31 | 32 | 33 | 34 | 35 | 36 |
| Silicone compound RE4 | 7.1 | — | — | — | 7.1 | — | — | — |
| Silicone compound RE7 | — | 7.1 | — | — | — | 7.1 | — | — |
| Silicone compound RE8 | — | — | 7.1 | — | — | — | 7.1 | — |
| Silicone compound RE10 | — | — | — | 7.1 | — | — | — | 7.1 |
| Titanium oxide | 28.6 | 28.6 | 28.6 | 28.6 | — | — | — | — |
| Zinc oxide | — | — | — | — | 28.6 | 28.6 | 28.6 | 28.6 |

Evaluation Method of the Dispersibility of the Powder

1. Dispersion Stability in D5

The dispersibility of the powder when the prepared powder in oil dispersions and powder compositions were compounded with an oil agent was evaluated by evaluating the dispersion stability of the compositions in decamethyl cyclopentasiloxane (D5). Specifically, the powder dispersions and powder compositions of Practical Examples 44 to 53 and Comparative Examples 21 to 36 were mixed with D5 so that a concentration of the powder was 5.1 wt. %. This mixed liquid was placed in a 50 mL sedimentation tube. Sedimentation after two days was visually observed and evaluated according to the following standards. Evaluation results are shown in Table 71.

⊚: Sedimentation was 0.2% or less
○: Sedimentation was from 0.2% to 2.0%
Δ: Sedimentation was from 2.0% to 2.8%
x: Sedimentation was 2.8% or greater
xx: Properties of the sample made it impossible to conduct the dispersion stability test Note that in these evaluations, 35.0 g of D5 was compounded in 5.0 g of the powder dispersions, and 37.45 g of D5 was compounded in 2.55 g of the powder compositions.

TABLE 72

Results of the evaluation of dispersibility of the powders of the powder in oil dispersions/powder compositions (D5)

|  | Sedimentation (%) | Rating |
|---|---|---|
| Practical Example 44-1 | 0.2 | ⊚ |
| Practical Example 45-1 | 0.1 | ⊚ |
| Practical Example 46-1 | 0.1 | ⊚ |
| Practical Example 47-1 | 0.3 | ⊚ |
| Practical Example 48-1 | 0.2 | ⊚ |
| Practical Example 49-1 | 0.2 | ⊚ |
| Practical Example 50-1 | Less than 0.1 | ⊚ |
| Practical Example 51-1 | Less than 0.1 | ⊚ |
| Practical Example 52-1 | Less than 0.1 | ⊚ |
| Practical Example 53-1 | Less than 0.1 | ⊚ |
| Comparative Example 21-1 | 1.5 | ○ |
| Comparative Example 22-1 | 1.7 | ○ |
| Comparative Example 23-1 | 0.9 | ○ |
| Comparative Example 24-1 | —*) | xx |
| Comparative Example 25-1 | 1.9 | ○ |
| Comparative Example 26-1 | 2.1 | Δ |
| Comparative Example 27-1 | 1.0 | ○ |
| Comparative Example 28-1 | —*) | xx |
| Comparative Example 29-1 | 2.4 | Δ |
| Comparative Example 30-1 | 2.9 | x |
| Comparative Example 31-1 | 2.6 | Δ |
| Comparative Example 32-1 | —**) | xx |
| Comparative Example 33-1 | 2.7 | Δ |
| Comparative Example 34-1 | 3.5 | x |
| Comparative Example 35-1 | 3.1 | x |
| Comparative Example 36-1 | —**) | xx |

Notes regarding sedimentation of the Comparative Examples
Note *): Dispersion stability tests could not be conducted for Comparative Examples 24 and 28 because a liquid powder dispersant could not be obtained. Specifically, after shaking using the paint shaker, it was discovered that the powder dispersant had hardened in a paste-like form that covered the zirconia beads and, therefore, it was impossible to remove the zirconia beads.
Note **): Dispersion stability test for Comparative Examples 32 and 36 were not conducted because the powder composition had agglomerated to a high degree and solidified after the removal of the solvent, resulting in difficulties in re-dispersion.

Evaluation Method of the Dispersibility of the Powder
2. Dispersion Stability in a D5/IOTG Solution The dispersibility of the powder when the prepared powder in oil dispersions and powder compositions were compounded with an oil agent was evaluated by evaluating the dispersion stability of the compositions in a mixed oil of D5 and glyceryl tri(2-ethylhexanoate) (IOTG; compounding ratio: 70/30).

Specifically, the powder dispersions and powder compositions of Practical Examples 44 to 53 and Comparative Examples 21 to 36 were mixed with a D5/IOTG solution so that a concentration of the powder was 5.1 wt. %. This mixed liquid was placed in a 50 mL sedimentation tube. Sedimentation after two days was visually observed and evaluated according to the following standards. Evaluation results are shown in Table 72.

⊚: Sedimentation was 0.2% or less

○: Sedimentation was from 0.2% to 2.0%

Δ: Sedimentation was from 2.0% to 2.8% x: Sedimentation was 2.8% or greater xx: Properties of the sample made it impossible to conduct the dispersion stability test Note that in these evaluations, the D5/IOTG compounding ratio of the mixed oil was set at 70/30 and, therefore, a 23.6 g of D5 and 11.4 g of IOTG were compounded in 5.0 g of the powder dispersions. Additionally, 26.2 g of D5 and 11.2 g of IOTG were compounded in 2.55 g of the powder compositions.

TABLE 73

Results of the evaluation of dispersibility of the powders of the powder in oil dispersions/powder compositions (D5/IOTG)

|  | Sedimentation (%) | Rating |
|---|---|---|
| Practical Example 44-2 | 0.2 | ⊚ |
| Practical Example 45-1 | 0.1 | ⊚ |
| Practical Example 46-2 | 0.1 | ⊚ |
| Practical Example 47-2 | 0.4 | ⊚ |
| Practical Example 48-2 | 0.3 | ⊚ |
| Practical Example 49-2 | 0.6 | ⊚ |
| Practical Example 50-2 | 0.1 | ⊚ |
| Practical Example 51-2 | Less than 0.1 | ⊚ |
| Practical Example 52-2 | 0.1 | ⊚ |
| Practical Example 53-2 | 0.1 | ⊚ |
| Comparative Example 21-2 | 1.6 | ○ |
| Comparative Example 22-2 | 1.9 | ○ |
| Comparative Example 23-2 | 1.0 | ○ |
| Comparative Example 24-2 | —*) | xx |
| Comparative Example 25-2 | 2.1 | Δ |
| Comparative Example 26-2 | 2.4 | Δ |
| Comparative Example 27-2 | 1.3 | ○ |
| Comparative Example 28-2 | —*) | xx |
| Comparative Example 29-2 | 2.7 | Δ |
| Comparative Example 30-2 | 3.4 | x |
| Comparative Example 31-2 | 2.9 | x |
| Comparative Example 32-2 | —**) | xx |
| Comparative Example 33-2 | 2.9 | x |
| Comparative Example 34-2 | 3.7 | x |

TABLE 73-continued

Results of the evaluation of dispersibility of the powders of the powder in oil dispersions/powder compositions (D5/IOTG)

|  | Sedimentation (%) | Rating |
|---|---|---|
| Comparative Example 35-2 | 3.4 | x |
| Comparative Example 36-2 | —**) | xx |

Notes related to the Comparative Examples in Table 73
Note *): Dispersion stability tests could not be conducted for Comparative Examples 24 and 28 because a liquid powder dispersant could not be obtained. Specifically, after shaking using the paint shaker, it was discovered that the powder dispersant had hardened in a paste-like form that covered the zirconia beads and, therefore, it was impossible to remove the zirconia beads.
Note **): Dispersion stability test for Comparative Examples 32 and 36 were not conducted because the powder composition had agglomerated to a high degree and solidified after the removal of the solvent, resulting in difficulties in re-dispersion.

From the results of the experiments shown above, compared to powder dispersions prepared using a conventional silicone-based surfactant as the dispersing agent (see Comparative Examples 21 to 28), it is clear that the powder dispersions prepared using the novel co-modified organopolysiloxane having the siloxane dendron structure of the present invention as the dispersing agent (see Practical Examples 44 to 49) has less sedimentation at dilution and superior uniformity.

Furthermore, the powder compositions prepared using a conventional silicone-based surfactant as the surface treatment agent of the powder (see Comparative Examples 29 to 36) displayed insufficient dispersion stability when dispersed in the oil agent and also displayed non-uniformity caused by sedimentation of the powder. In contrast, it was discovered that the powder compositions prepared using the novel co-modified organopolysiloxane of the present invention as the surface treatment agent (see Practical Examples 50 to 53) displayed superior dispersion stability even when diluted in an oil agent and in the form of a powder in oil dispersion and, moreover, displayed little sedimentation of the powder and formed a uniform dispersion liquid.

The powder dispersion and powder composition of the present invention display excellent dispersion stability not only when the dispersing medium is decamethyl cyclopentasiloxane (a low viscosity silicone oil), but also when the dispersing medium is a mixed oil of decamethyl cyclopentasiloxane and glyceryl tri(2-ethylhexanoate) (IOTG; ester oil).

Hereinafter, usage form and technical benefits of a substantially water-free cosmetic composition (cosmetic composition according to the present invention) are shown using lip gloss and oil-based foundation Practical Examples.

Preparation and Evaluation of Oil-Based Cosmetic Composition (Lip Gloss):

Practical Examples 54 to 58 and Comparative Examples 37 to 40

Lip gloss was prepared as an example of a substantially water-free cosmetic composition (cosmetic composition according to the present invention). Results of evaluation the feeling to touch thereof is shown in Practical Examples 54 to 58 and Comparative Examples 37 to 40.

Lip gloss was prepared by mixing and molding the formulations (compositions) shown in Tables 74 to 76 according to the following procedure. The numbers in the tables are shown in wt. % units.

Preparation Procedure
1. Components 1 to 15 were heated at from 40 to 50° C. and were uniformly mixed and dispersed.
2. After degassing, lip gloss was molded by filling a mold with the mixture and allowing it to sit at rest at room temperature.

The obtained lip gloss was tested according to the following method and a functional evaluation thereof was performed. The obtained evaluation results are shown in Tables 73 to 75.

Test Procedure
1. 0.05 g of the obtained lip gloss was evenly applied to a 1 cm×3 cm section of cleansed skin (back of hand).
Note: Lip gloss tends to enter wrinkles of the lips and spread out from there. Therefore, the back of the hand was used as the test surface because, like the lips, many wrinkles and sensory nerves are concentrated on the back of the hand and visual observation thereof is easy.
2. One hour after application, the following five criteria were evaluated.

Tendency not to spread: Visually determined
Natural feeling on the skin with no discomfort and moisturizing feel durability: Determined by sensation of the skin where the lip gloss was applied
Effect of suppressing oiliness: Determined by feeling to touch
Degree of satisfaction: Overall evaluation Evaluation
Each criterion was evaluated based on the following guidelines.

Tendency not to spread: A film initially measuring 1 cm×3 cm was applied and the amount of expansion and spreading into surrounding areas over time was visually observed.
⊚ No spread of color or oil
○ Slight, insignificant spread of color or oil
Δ Some spreading of color or oil
x noticeable spreading of color and oil Natural feeling on the skin with no discomfort: Determined by sensation of the skin where the lip gloss was applied
⊚ Skin felt natural and no discomfort was experienced
○ Slight discomfort on the skin was experienced
Δ Skin felt slightly unnatural Moisturizing feel durability: Determined by sensation of the skin where the lip gloss was applied
⊚ An appropriate and pleasant sense of moisturization lasted on the surface of the skin
○ A sense of moisturization remained on the surface of the skin
Δ The skin felt dry Effect of suppressing oiliness: Degree of oily stickiness determined by feeling to touch
⊚ No oily stickiness was experienced
○ Very little oily stickiness was experienced
Δ Some oily stickiness was experienced
x noticeable oily stickiness was experienced Degree of satisfaction: Overall degree of satisfaction as a lip gloss was determined
⊚ Very satisfied
○ Satisfied
Δ Acceptable
x Not satisfied

TABLE 74

Lip gloss formulation and evaluation results (Practical Examples 54 to 56)

| No. | Component | Practical Example 54 | Practical Example 55 | Practical Example 56 |
|---|---|---|---|---|
| 1 | Dimer dilinoleyl hydrogenated rosin condensate | 5.0 | 5.0 | 5.0 |
| 2 | Dimer dilinoleyl diisostearate | 10.0 | 10.0 | 10.0 |
| 3 | Isotridecyl isononanoate | 10.0 | 10.0 | 10.0 |
| 4 | SH 556 Fluid | 5.0 | 5.0 | 5.0 |
| 5 | Hydrogenated polyisobutene | 35.5 | 35.5 | 35.5 |
| 6 | Hydrogenated polystyrene/isoprene copolymer, hydrogenated polydecene | 30.0 | 30.0 | 30.0 |
| 7 | Silicone compound No. 6 | 4.5 | — | — |
| 8 | Silicone compound No. 10 | — | 4.5 | — |
| 9 | Silicone compound No. 13 | — | — | 4.5 |
| | Total | 100.0 | 100.0 | 100.0 |
| Evaluation | Tendency not to spread | o~Δ | Δ | o |
| | Natural feeling on the skin with no discomfort | ⊚ | ⊚ | ⊚ |
| | Moisturizing feel durability | ⊚ | ⊚ | ⊚ |
| | Effect of suppressing oiliness | ⊚ | ⊚ | ⊚ |
| | Degree of satisfaction | ⊚~o | o | ⊚ |

TABLE 75

Lip gloss formulation and evaluation results (Practical Examples 57 and 58 and Comparative Example 37)

| No. | Component | Practical Example 57 | Practical Example 58 | Comparative Example 37 |
|---|---|---|---|---|
| 1 | Dimer dilinoleyl hydrogenated rosin condensate | 5.0 | 5.0 | 5.0 |
| 2 | Dimer dilinoleyl diisostearate | 10.0 | 10.0 | 10.0 |
| 3 | Isotridecyl isononanoate | 10.0 | 10.0 | 10.0 |
| 4 | SH 556 Fluid | 5.0 | 5.0 | 5.0 |
| 5 | Hydrogenated polyisobutene | 35.5 | 35.5 | 35.5 |
| 6 | Hydrogenated polystyrene/isoprene copolymer, hydrogenated polydecene | 30.0 | 30.0 | 30.0 |
| 10 | Silicone compound No. 7 | 4.5 | — | — |
| 11 | Silicone compound No. 8 | — | 4.5 | — |
| 12 | Silicone compound RE9 | — | — | 4.5 |
| | Total | 100.0 | 100.0 | 100.0 |
| Evaluation | Tendency not to spread | o | o | Δ |
| | Natural feeling on the skin with no discomfort | ⊚ | ⊚ | o |
| | Moisturizing feel durability | ⊚ | ⊚ | Δ |
| | Effect of suppressing oiliness | ⊚ | ⊚ | Δ |
| | Degree of satisfaction | ⊚ | ⊚ | Δ |

TABLE 76

Lip gloss formulation and evaluation results (Comparative Examples 38 to 40)

| No. | Component | Comparative Example 38 | Comparative Example 39 | Comparative Example 40 |
|---|---|---|---|---|
| 1 | Dimer dilinoleyl hydrogenated rosin condensate | 5.0 | 5.0 | 5.0 |
| 2 | Dimer dilinoleyl diisostearate | 10.0 | 10.0 | 10.0 |
| 3 | Isotridecyl isononanoate | 10.0 | 10.0 | 10.0 |
| 4 | SH 556 Fluid | 5.0 | 5.0 | 5.0 |
| 5 | Hydrogenated polyisobutene | 35.5 | 35.5 | 35.5 |
| 6 | Hydrogenated polystyrene/isoprene copolymer, hydrogenated polydecene | 30.0 | 30.0 | 30.0 |
| 13 | Silicone compound RE10 | 4.5 | — | — |
| 14 | Silicone compound RE11 | — | 4.5 | — |
| 15 | Silicone compound RE8 | — | — | 4.5 |
| | Total | 100.0 | 100.0 | 100.0 |
| Evaluation | Tendency not to spread | x | Δ | Δ~x |
| | Natural feeling on the skin with no discomfort | o~Δ | o~Δ | o |
| | Moisturizing feel durability | Δ | o | Δ |
| | Effect of suppressing oiliness | Δ~x | o~Δ | Δ~x |
| | Degree of satisfaction | x | o~Δ | Δ |

Preparation and Evaluation of Oil-Based Cosmetic Composition (Oil-Based Foundation):

Practical Examples 59 to 63 and Comparative Examples 41 to 44

Oil-based foundation was prepared as an example of a substantially water-free cosmetic composition (cosmetic composition according to the present invention). Results of evaluations of the characteristics thereof are shown in Practical Examples 59 to 63 and Comparative Examples 41 to 44.

Oil-based foundation was prepared by mixing and molding the formulations (compositions) shown in Tables 77 to 79 according to the following procedure. The numbers in the tables are shown in wt. % units. Preparation procedure 1. Components 1 to 14 were heated at 90° C. and melted.
2. Components 15 to 18 were added thereto and the components were uniformly mixed and degassed.
3. The mixture was poured into a mold and cooled to form the oil-based foundation.

Characteristics of the obtained oil-based foundation were tested according to the following method, and the results of functional evaluations thereof are shown in Tables 77 to 79.

Test Procedure 1. 0.15 g of the obtained oil-based foundation was uniformly applied, in the form of a circle having a diameter of about 5 cm using a puff, to clean skin (forearm) of which downy hair had been shaved beforehand. Spreadability on the skin was evaluated.

2. The following three criteria were evaluated at each of 10 minutes (initial stage), 4 hours, and 9 hours after application.

Beauty of Finish: Visually Determined

Adhesive sensation, natural feeling on the skin with no discomfort:

Determined by sensation of the skin where the oil-based foundation was applied

Evaluation

Each criterion was evaluated based on the following guidelines.

Spreadability: Ease of spreading when applying using a puff was evaluated

⊚ The foundation spread smoothly

○ The foundation spread normally

Δ Spreading required an added effort

Beauty of Finish: Visually Determined

⊚ Cover was complete and finish was extremely beautiful

○ Cover was complete, but grooves caused by small wrinkles were slightly noticeable x Some lack of evenness on application surface and noticeable coarseness was observed Adhesive sensation: Sensation of the applied film to the skin was determined by the feeling on the skin where the oil-based foundation was applied.

⊚ A distinct sensation of adhesion was felt

○ A sensation of adhesion was felt, but was only noticeable if a conscious effort was made to notice it x No sensation of adhesion was felt Natural feeling on the skin with no discomfort: Determined by sensation of the skin where the lip gloss was applied ⊚ Skin felt natural and no discomfort was experienced ○ Slight discomfort on the skin was experienced Δ Skin felt slightly unnatural

TABLE 77

Formulation and evaluation results of the oil-based foundations (1)

| No. | Component | Practical Example 59 | Practical Example 60 | Practical Example 61 |
|---|---|---|---|---|
| 1 | Liquid paraffin | 10.0 | 10.0 | 10.0 |
| 2 | Squalane | 7.0 | 7.0 | 7.0 |
| 3 | Branched fatty acid cholesteryl ester | 7.0 | 7.0 | 7.0 |
| 4 | Paraffin wax | 5.0 | 5.0 | 5.0 |
| 5 | Starch fatty acid ester | 5.0 | 5.0 | 5.0 |
| 6 | Silicone compound No. 6 | 10.0 | — | — |
| 7 | Silicone compound No. 10 | — | 10.0 | — |
| 8 | Silicone compound No. 13 | — | — | 10.0 |
| 15 | Titanium oxide (hydrophobization-treated) | 20.0 | 20.0 | 20.0 |
| 16 | Titanated mica (hydrophobization-treated) | 3.0 | 3.0 | 3.0 |
| 17 | Mica (hydrophobization-treated) | 30.0 | 30.0 | 30.0 |
| 18 | Inorganic coloration pigment (hydrophobization-treated) | 3.0 | 3.0 | 3.0 |
| | Total | 100.0 | 100.0 | 100.0 |
| Evaluation | Spreadability | ○ | ⊚~○ | ⊚ |
| | Beauty of finish (initial/4 hr/9 hr) | ⊚/○/Δ | ⊚/○/Δ | ⊚/○/○~Δ |
| | Adhesive sensation (initial/4 hr/9 hr) | ⊚/○/Δ | ⊚/○/Δ | ⊚/○/○~Δ |
| | Natural feeling on the skin with no discomfort (initial/4 hr/9 hr) | ⊚/○/○ | ⊚/○/○ | ⊚/○/○ |

TABLE 78

Formulation and evaluation results of the oil-based foundations (2)

| No. | Component | Practical Example 62 | Practical Example 63 | Comparative Example 41 |
|---|---|---|---|---|
| 1 | Liquid paraffin | 10.0 | 10.0 | 10.0 |
| 2 | Squalane | 7.0 | 7.0 | 7.0 |
| 3 | Branched fatty acid cholesteryl ester | 7.0 | 7.0 | 7.0 |
| 4 | Paraffin wax | 5.0 | 5.0 | 5.0 |
| 5 | Starch fatty acid ester | 5.0 | 5.0 | 5.0 |
| 9 | Silicone compound No. 7 | 10.0 | — | — |
| 10 | Silicone compound No. 8 | — | 10.0 | — |
| 11 | Silicone compound RE9 | — | — | 10.0 |
| 15 | Titanium oxide (hydrophobization-treated) | 20.0 | 20.0 | 20.0 |
| 16 | Titanated mica (hydrophobization-treated) | 3.0 | 3.0 | 3.0 |
| 17 | Mica (hydrophobization-treated) | 30.0 | 30.0 | 30.0 |
| 18 | Inorganic coloration pigment (hydrophobization-treated) | 3.0 | 3.0 | 3.0 |
| | Total | 100.0 | 100.0 | 100.0 |
| Evaluation | Spreadability | ⊚~○ | ⊚~○ | ○~Δ |
| | Beauty of finish (initial/4 hr/9 hr) | ⊚/○/○ | ⊚/○/○ | ○/Δ/x |
| | Adhesive sensation (initial/4 hr/9 hr) | ⊚/○/○ | ⊚/○/○Δ | ⊚/Δ/x |
| | Natural feeling on the skin with no discomfort (initial/4 hr/9 hr) | ○/○~Δ/Δ | ○/○~Δ/Δ | ○~Δ/○~Δ/Δ |

TABLE 79

Formulation and evaluation results of the oil-based foundations (3)

| No. | Component | Comparative Example 42 | Comparative Example 43 | Comparative Example 44 |
|---|---|---|---|---|
| 1 | Liquid paraffin | 10.0 | 10.0 | 10.0 |
| 2 | Squalane | 7.0 | 7.0 | 7.0 |
| 3 | Branched fatty acid cholesteryl ester | 7.0 | 7.0 | 7.0 |
| 4 | Paraffin wax | 5.0 | 5.0 | 5.0 |
| 5 | Starch fatty acid ester | 5.0 | 5.0 | 5.0 |
| 12 | Silicone compound RE10 | 10.0 | — | — |
| 13 | Silicone compound RE11 | — | 10.0 | — |
| 14 | Silicone compound RE8 | — | — | 10.0 |
| 15 | Titanium oxide (hydrophobization-treated) | 20.0 | 20.0 | 20.0 |
| 16 | Titanated mica (hydrophobization-treated) | 3.0 | 3.0 | 3.0 |
| 17 | Mica (hydrophobization-treated) | 30.0 | 30.0 | 30.0 |
| 18 | Inorganic coloration pigment (hydrophobization-treated) | 3.0 | 3.0 | 3.0 |
| | Total | 100.0 | 100.0 | 100.0 |
| Evaluation | Spreadability | Δ | ○~Δ | Δ~x |
| | Beauty of finish (initial/4 hr/9 hr) | ⊚/Δ/x | ⊚/Δ/Δ | ⊚/Δ/x |
| | Adhesive sensation (initial/4 hr/9 hr) | ○/Δ/x | ○/Δ/Δ | Δ/Δ~x/x |
| | Natural feeling on the skin with no discomfort (initial/4 hr/9 hr) | ○/Δ/Δ | ○Δ/Δ/Δ | ○/Δ/Δ |

Compared to the oil-based cosmetics in which conventional silicone-based surfactants were compounded, the lip gloss according to the present invention described in Practical Examples 54 to 58 and the oil-based foundation according to the present invention described in Practical Examples 59 to 63 in which the novel co-modified organopolysiloxane having the siloxane dendron structure of the present invention was compounded had superior test evaluations and, regarding their sensation during use, displayed suppressed oiliness and superior overall results in regards to the degree of satisfaction. It is shown through the results of the experiments described above that novel co-modified organopolysiloxane of the present invention is beneficial even in the field of cosmetic compositions that are substantially free of water.

Hereinafter, a synthesis example of silicone compound Nos. 15 and 16 (Practical Examples of the present invention) and other embodiments using the same are described.

Practical Example 64

Synthesis of Silicone Compound No. 15

Step 1: 94.5 g of a methylhydrogenpolysiloxane expressed by the average composition formula $MD_{37}D^H{}_{13}M$, and 8.3 g of a vinyl tris(trimethylsiloxy)silane expressed by the average composition formula $CH_2\!=\!CH\!-\!Si(OSiMe_3)_3$ were placed in a reaction vessel. Then, 0.25 g of an IPA solution of a platinum-1,3-divinyl-1,1,3,3-tetramethyldisiloxane complex (Pt concentration: 0.4 wt. %) was added at room temperature while agitating under a nitrogen stream. The mixture was reacted for one hour while heating in an oil bath set to a temperature of 65° C. Then, 2 g of the reaction liquid was sampled and it was confirmed that the reaction rate was not in error through an alkali decomposition gas generation method.

Step 2: 34.5 g of 1-hexadecene was added to the reaction liquid and the heat generated thereby caused the temperature to rise from 35° C. to 60° C. The mixture was reacted for 1.5 hours while heating in an oil bath set to a temperature of 65° C. and, thereafter, it was confirmed that the reaction rate was not in error through the same method described above.

Step 3: 28.1 g of polyoxyethylene(10)monoallyl ether, 0.02 g of natural vitamin E, and 60 g of IPA were added to the reaction liquid. Then, 0.25 g of the platinum catalyst solution described above was added. The temperature rose about 5° C. due to the generated heat. The mixture was reacted for one hour under the same conditions described above and, thereafter, it was confirmed that the reaction rate was not in error through the same method described above.

Step 4: 34.5 g of 1-hexadecene was added to the reaction liquid and the heat generated thereby caused the temperature of rise about 10° C. The mixture was reacted for three hours while heating in an oil bath set to a temperature of 85° C. and, thereafter, it was confirmed that the reaction was complete. The reaction liquid was heated under reduced pressure to remove low-boiling components by distillation, and then was filtered. Thus, a novel polyether-modified silicone having an long chain alkyl group and a siloxane dendron structure expressed by the average composition formula 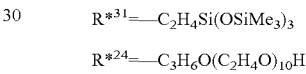 was obtained. In this formula, $R^{*12}\!=\!-C_{16}H_{33}$.

$R^{*31}\!=\!-C_2H_4Si(OSiMe_3)_3$ $R^{*24}\!=\!-C_3H_6O(C_2H_4O)_{10}H$

This product was a tan color uniform liquid that was substantially transparent.

Practical Example 65

Synthesis of Silicone Compound No. 16

Step 1: 94.6 g of a methylhydrogenpolysiloxane expressed by the average composition formula $MD_{330}D^H{}_{80}M$, and 10.4 g of a vinyl tris(trimethylsiloxy)silane expressed by the average composition formula $CH_2\!=\!CH\!-\!Si(OSiMe_3)_3$ were placed in a reaction vessel. Then, 0.25 g of an IPA solution of a platinum-1,3-divinyl-1,1,3,3-tetramethyldisiloxane complex (Pt concentration: 0.4 wt. %) was added at 35° C. while agitating under a nitrogen stream. After the temperature rise caused by generated heat leveled off, 10.4 g of the vinyl tris(trimethylsiloxy)silane (second adding) was added and the mixture was reacted in the same way. After the temperature rise caused by generated heat leveled off, 10.4 g of the vinyl tris(trimethylsiloxy)silane (third adding) was added and the mixture was reacted in the same way. Then, 2 g of the reaction liquid was sampled and it was confirmed that the reaction rate was not in error through an alkali decomposition gas generation method.

Step 2: 35.3 g of an allyl polyether expressed by the average composition formula $CH_2\!=\!CH\!-\!CH_2\!-\!O(C_2H_4O)_{19}(C_3H_6O)_{19}H$, 0.02 g of natural vitamin E, and 60 g of IPA were added to the reaction liquid. Then, 0.25 g of the platinum catalyst solution described above was added. After the temperature rise caused by generated heat leveled off, the mixture was reacted for two hours at from 65 to 80° C. and, thereafter, it was confirmed that the reaction rate was not in error through the same method described above.

Step 3: 13.0 g of 1-hexadecene was added to the reaction liquid that had a temperature of about 65° C. After the temperature rise caused by generated heat leveled off, 13.0 g of the 1-hexadecene (second adding) was added and the mixture was reacted in the same way. After the temperature rise caused by generated heat leveled off, 13.0 g of the 1-hexadecene (third adding) and 0.25 g of the platinum catalyst solution were added, and the mixture was reacted for three hours at from 65 to 80° C. Then, 2 g of the reaction liquid was sampled and it was confirmed that the reaction was complete through an alkali decomposition gas generation method.

Step 4: 200 g of a caprylyl methicone diluent (SS-3408) was added and dissolved and, thereafter, the mixture was heated under reduced pressure to remove the IPA and low-boiling components by distillation. The mixture was then filtered. Thus, a mixed liquid of a novel polyether-modified silicone having a long chain alkyl group and a siloxane dendron structure expressed by the average composition formula $MD_{330}D^{R*12}{}_{45}D^{R*31}{}_{30}D^{R*26}{}_{5}M$ and caprylyl methicone, at a weight ratio of 50:50, was obtained.

In this formula, $R^{*12} = -C_{16}H_{33}$

$R^{*31} = -C_2H_4Si(OSiMe_3)_3$

$R^{*26} = -C_3H_6O(C_2H_4O)_{19}(C_3H_6O)_{19}H$

This product was a gray-brown color uniform viscous liquid having semi-transparency.

Preparation and evaluation of the water-in-oil emulsion transparent anti-perspirant composition: Practical Examples 66 to 67 and Comparative Examples 45 to 46

Water-in-oil transparent anti-perspirant compositions were prepared as examples of cosmetic compositions according to the present invention. Results of evaluations of the characteristics thereof are described in Practical Examples 66 to 67 and Comparative Examples 45 to 46.

The water-in-oil emulsion anti-perspirant compositions were prepared by mixing and emulsifying the components shown in the formulations (compositions) in Table 80 according to the following procedure.

Preparation Procedure

1. Oil phase components were measured out into a 200 mL container according to the amounts shown in Table 80.

2. The mixture was mixed using a spatula in order to disperse and dissolve the surfactant (silicone compound) in the oil agent. (oil phase A)

3. Saw teeth of a homo-disper were immersed in the oil phase A and the container was fixed. Then, the mixture was agitated. Agitation was continued until the entire mixture became a uniform solution.

4. Specified amounts of the aqueous phase components were placed in another cup (with the exception of ion exchange water No. 14, shown last), and mixed and dissolved using a spatula. (aqueous phase B)

5. Two or three drops of each of these two phases were sampled, and refractive indexes (RI) of each at 25° C. was measured.

6. The up to 1.0 parts of ion exchange water (No. 14) shown last was added in small portions so that the RI value of the aqueous phase was within 0.0001 units and matched the RI of the oil phase. This process was repeated until the desired matching of the RI values was achieved.

7. Speed of the homo-disper was set to 3,000 rpm and the aqueous phase B was poured into the oil phase A at a substantially constant rate over a period of about two minutes, while agitating the mixture.

8. Agitation was halted after agitating for two more minutes, the oil component adhered to the inner wall of the container was scraped off by using a spatula and mixed with the produced emulsion.

9. The mixture was agitated for 3 minutes at a speed of 3,000 rpm using the homo-disper. Thus the preparation procedure was completed.

Characteristics of the obtained water-in-oil emulsion antiperspirant composition were tested according to the following method, and the results of functional evaluations thereof are shown in Table 80.

Test Procedure

1. Transparency of the appearance was visually observed.

2. The refractive index (RI) at 25° C. was measured.

3. The anti-perspirant composition was applied to the skin in order to conduct evaluations of handling, tactile sensation, and non-whitening performance. Handling and tactile sensation of the skin were measured via subjective comparison, and non-whitening was also determined via subjective comparison.

4. Two 35 mL glass bottles were prepared in which 25 g of the anti-perspirant composition was placed. The bottles were capped and one was placed in a 50° C. constant temperature bath and the other in a −5° C. constant temperature bath. After two weeks, the bottles were removed from the baths and returned to room temperature, Then, the anti-perspirant compositions were examined for changes in appearance.

Evaluation

Each criterion was evaluated based on the following guidelines.

Appearance: Transparency of the anti-perspirant composition visually determined through a 100 mL glass bottle.

RI: The refractive index at 25.0° C. of the obtained antiperspirant composition was measured using an RX-7000a digital refractometer (manufactured by ATAGO Co., Ltd.).

Handling: Confirmation of whether a desired amount (0.3 g) of the anti-perspirant composition could be easily extracted using the fingers without the composition immediately sliding off the fingers.

○ Desired amount easily extracted without immediate sliding x Desired amount could not be extracted because the product immediately slipped from the fingers Tactile sensation: A rating of "superior" or "inferior" was given regarding the feeling to touch (lack of stickiness) after a single application of 0.2 g of the anti-perspirant composition to the forearm.

○ No stickiness, not noticeable x Stickiness was noticeable

Non-whitening performance: Presence of whiteness was determined visually after a single application of 0.2 g of the anti-perspirant composition to the forearm and 15 minutes of drying.

○ No whiteness was observed

Δ Some whiteness was observed x Applied area appeared white

Stability: After a storage stability test (the condition is shown in the table), the appearance of the anti-perspirant composition was visually confirmed.

○ Semi-transparent to transparent, no noticeable change from initial appearance

Δ Slight decrease in transparency x Opaque or non-uniform appearance

TABLE 80

Formulation and evaluation results of the water-in-oil emulsion transparent anti-perspirant composition (1)

| No. | Component | Practical Example 66 | Practical Example 67 | Comparative Example 45 | Comparative Example 46 |
|---|---|---|---|---|---|
| — | Portion A: Oil phase | — | — | — | — |
| 1 | Dimethylpolysiloxane (2 cst) | 13.0 | 12.5 | 7.25 | 12.5 |
| 2 | SS-3408 | — | — | 3.5 | 3.5 |
| 3 | Dimethylpolysiloxane (20 cst) | 4.0 | 3.0 | 3.0 | 3.0 |
| 4 | Dimethylpolysiloxane (50 cst) | — | 1.0 | 1.0 | 1.0 |
| 5 | Isopropyl palmitate | 1.0 | 1.0 | 1.0 | 1.0 |
| 6 | Silicone compound No. 16 (Modified silicone:SS-3408 = 50:50 mixture) | 6.0 | 7.0 | — | — |
| 7 | silicone compound RE6 (Modified silicone:2 cst = 40:60 mixture) | — | — | 8.75 | — |
| 8 | Silicone compound RE7 | — | — | — | 3.5 |
| — | Portion B: Aqueous phase | — | — | — | — |
| 9 | Ion exchange water | 14.6 | 13.2 | 13.2 | 13.2 |
| 10 | Propylene glycol | 10.0 | 10.0 | 10.0 | 10.0 |
| 11 | POE (20) sorbitan monooleate | 0.66 | 0.66 | 0.66 | 0.66 |
| 12 | 50% aluminum chlorohydrate aqueous solution | 40.0 | 40.0 | 40.0 | 40.0 |
| 13 | 70% sorbitol aqueous solution | 13.4 | 13.4 | 13.4 | 13.4 |
| 14 | Ion exchange water (for balancing with the RI of Portion A) | 0.05 | 0.25 | 1.90 | 0.00 |
| | Total | ~100 | ~102 | ~102 | ~104 |
| Measurement | RI of portion A (at 25° C.) | 1.4021 | 1.4031 | 1.4012 | 1.4033 |
| | RI of portion B (at 25° C.) | 1.4021 | 1.4031 | 1.4012 | 1.4033 |
| | Final RI (at 25° C.) | 1.4023 | 1.4033 | 1.4017 | 1.4035 |
| Evaluation | Appearance | Transparent to semi-transparent | Transparent to semi-transparent | Transparent to semi-transparent | Transparent to semi-transparent |
| | Lack of stickiness when applying | ○ | ○ | ○ | x |
| | Non-whitening performance | ○ | ○ | ○ | ○ |
| | Emulsion stability (50° C., 2 weeks) | ○ | ○ | ○ | Δ |
| | Emulsion stability (−5° C., 2 weeks) | ○ | ○ | Δ | x |

Preparation and evaluation of the nonaqueous stick-form anti-perspirant composition: Practical Examples 68 to 69 and Comparative Examples 47 to 48

Nonaqueous stick-form anti-perspirant compositions were prepared as examples of cosmetic compositions according to the present invention. Results of evaluations of the characteristics thereof are described in Practical Examples 68 to 69 and Comparative Examples 47 to 48.

The nonaqueous stick-form anti-perspirant compositions were prepared by hot mixing→cooling/solidifying the components shown in the formulations (compositions) in Table 81 according to the following procedure.

Preparation Procedure

1. Components No. 1 to No. 8 were measured and placed in a 200 mL container. The mixture was heated to a temperature at which the higher alcohol and the wax melt (about 80° C.), and agitated. Thus, a single liquid phase was formed.

2. A temperature slightly higher than a solidification point of the system (e.g. about 65° C.) was maintained, and components No. 9 to No. 11 were added and dissolved in the mixture while agitating.

3. A temperature slightly higher than a solidification point of the system (e.g. about 65° C.) was maintained, and component No. 12 was added and uniformly dispersed by thoroughly agitating the mixture.

4. The mixture was poured into a container and allowed to solidify at room temperature.

Characteristics of the obtained nonaqueous stick-form anti-perspirant composition were tested according to the following method, and the results of functional evaluations thereof are shown in Table 81.

Test Procedure

1. The nonaqueous stick-form anti-perspirant composition was applied to the skin in order to conduct evaluations of sensation during use and non-whitening performance. Smoothness and appropriate dry sensation were evaluated via subjective comparison as the sensation during use when applying, and absence of stickiness was evaluated via subjective comparison as the sensation during use after application. Moreover, absence of white residue was evaluated via subjective comparison as the non-whitening performance after drying.

Evaluation

Each criterion was evaluated based on the following guidelines.

Smoothness: A rating of "superior" or "inferior" was given regarding the feeling to touch (smoothness when applying) after a single application of 0.2 g of the anti-perspirant composition to the back of the hand.

◎ Anti-perspirant composition was smoothly applied; unevennesses of the skin felt only slightly
○ Application was rather smooth
Δ Unsure
x Resistance was felt and smooth application was not possible Appropriate dry sensation: A rating of "superior" or "inferior" was given regarding the feeling to touch of the skin (dry sensation when applying) after a single application of 0.2 g of the anti-perspirant composition to the back of the hand.

○ Natural, appropriate dry sensation with no discomfort
Δ Natural and free of discomfort, but slightly lacking in dry sensation
x Discomfort was experienced Absence of stickiness: A rating of "superior" or "inferior" was given regarding the tactile sensation of the applied area (absence of stickiness) after a single application of 0.2 g of the anti-perspirant composition to the back of the hand.

◎ No sticking experienced
○ Almost no sticking experienced
Δ Some sticking experienced
x Noticeable sticking experienced Non-whitening performance: Presence of whiteness was determined visually after a single application of 0.2 g of the anti-perspirant composition to the forearm and 5 minutes of drying.

○ Nearly no noticeable whiteness
Δ Applied area appeared slightly white
x Applied area appeared white

TABLE 81

Formulation and evaluation results of the nonaqueous stick-form anti-perspirant compositions (1)

| No. | Component | Practical Example 68 | Practical Example 69 | Comparative Example 47 | Comparative Example 48 |
|---|---|---|---|---|---|
| 1 | Stearyl alcohol | 25.0 | 25.0 | 25.0 | 25.0 |
| 2 | Hydrogenated castor oil | 4.0 | 4.0 | 4.0 | 4.0 |
| 3 | Dimethylpolysiloxane (2 cst) | 37.0 | 33.0 | 31.0 | 37.0 |
| 4 | PPG-20 butyl ether | 7.0 | 7.0 | 7.0 | 7.0 |
| 5 | Sorbitan sesquiisostearate | 2.0 | 2.0 | 2.0 | 2.0 |
| 6 | Silicone compound No. 15 | 4.0 | 8.0 | — | — |
| 7 | Silicone compound RE6 (Modified silicone:2 cst = 40:60 mixture) | — | — | 10.0 | — |
| 8 | Silicone compound RE7 | — | — | — | 4.0 |
| 9 | L-menthol | 0.8 | 0.8 | 0.8 | 0.8 |
| 10 | BHT | 0.1 | 0.1 | 0.1 | 0.1 |
| 11 | 3-methyl-4-isopropylphenol | 0.1 | 0.1 | 0.1 | 0.1 |
| 12 | Dried alum | 20.0 | 20.0 | 20.0 | 20.0 |
| | Total | 100.0 | 100.0 | 100.0 | 100.0 |
| Evaluation | Smoothness | ◎ | ◎ | Δ | ○ |
| | Appropriate dry sensation | ○ | ○ | x | Δ |
| | Absence of stickiness | ◎ | ○ | Δ | ○ |
| | Absence of white residue | ○ | ○ | x | Δ |

Hereinafter, formulation examples of the cosmetic composition and the topical composition according to the present invention are described, but it is understood that the cosmetic composition and the topical composition according to the present invention are not limited to the types and compositions recited in these formulation examples. Note that in the formulation examples, all cosmetic raw materials that are described with a product number are products commercially available from Dow Corning Toray Co., Ltd.

Formulation Example 1

Emulsion Foundation

| Components | wt. % |
| --- | --- |
| 1. Decamethyl cyclopentasiloxane | 27.0 |
| 2. Dimethylpolysiloxane (6 cst) | 2.0 |
| 3. Methyl trimethicone (M3T) | 2.0 |
| 4. Composition of Practical Example 7 (composition containing silicone compound No. 7) | 2.0 |
| 5. Propylene glycol | 10.0 |
| 6. Ion exchange water | 30.0 |
| 7. Sodium L-aspartate | 2.0 |
| 8. Dextrin palmitate treated titanium dioxide | 10.0 |
| 9. Dextrin palmitate treated mica | 12.0 |
| 10. Dextrin palmitate treated talc | 2.0 |
| 11. Dextrin palmitate treated iron oxide | 1.0 |
| 12. Paraben | q.s. |
| 13. Antioxidant | q.s. |
| 14. Perfume | q.s. |

Manufacturing Method

A: Components 1 to 4 and components 12 and 13 are heated and dissolved at 50° C. Then, components 8 to 11 are added and dispersed into the mixture by agitating.

B: Meanwhile, components 5 to 7 and component 14 are mixed by agitating at 70° C., and dissolved.

C: A and B are both returned to room temperature. B is added to A, which was prepared first, while agitating using a homo-mixer, and the mixture is thoroughly agitated. Thereafter, the mixture is degassed and charged into a container. Thus, an emulsion foundation is obtained.

Effects

A unique sensation during use is obtained in which the emulsion foundation is extremely refreshing and spreads easily when applying; and has an appropriate lasting moisturizing feel without stickiness after application.

Stability over time of the product is also excellent.

Formulation Example 2

Liquid Foundation

| Components | wt. % |
| --- | --- |
| 1. Decamethyl cyclopentasiloxane | 25.0 |
| 2. Dimethylpolysiloxane (2 cst) | 18.0 |
| 3. Dimethylpolysiloxane (6 cst) | 2.0 |
| 4. Cetyl 2-ethylhexanoate | 5.0 |
| 5. Composition of Practical Example 8 (composition containing silicone compound No. 8) | 7.0 |
| 6. Ethanol | 8.0 |
| 7. Ion exchange water | 2.0 |
| 8. Polymethyl silsesquioxane powder | 13.0 |
| 9. Titanium dioxide | 13.0 |
| 10. Mica | 2.0 |
| 11. Iron oxide | 1.0 |

-continued

| Components | wt. % |
| --- | --- |
| 12. Polyethylene powder | 1.0 |
| 13. Polystyrene powder | 1.0 |
| 14. Cellulose powder | 1.0 |
| 15. Polyamide resin powder | 1.0 |
| 16. Paraben | q.s. |
| 17. Antioxidant | q.s. |
| 18. Perfume | q.s. |

Manufacturing Method

A: Components 1 to 5 and components 16 to 18 are mixed and dissolved at room temperature. Then, while agitating using a homo-mixer, component 6 is added and thoroughly mixed therewith.

B: Thereafter, component 7 is added while continuing to agitate using the homo-mixer.

C: Then, components 8 to 15 are added and the mixture is mixed and dispersed using the homo-mixer. Thereafter, the mixture is degassed and charged into a container. Thus, a liquid foundation is obtained.

Effects

Stickiness is absent when applying and the foundation spreads easily; and sliding feel is extremely superior. An appropriate moisturizing feel and a plain, natural sensation during use lasts after application. Stability over time of the product is superior and cosmetic retainability is excellent.

Formulation Example 3

Foundation

| Components | wt. % |
| --- | --- |
| 1. Decamethyl cyclopentasiloxane | 24.0 |
| 2. SS-3408 *1 | 5.0 |
| 3. Light liquid isoparaffin | 15.0 |
| 4. Neopentylglycol dicaprate | 3.0 |
| 5. Composition of Practical Example 6 (composition containing silicone compound No. 6) | 1.5 |
| 6. SS-2910 *2 | 0.5 |
| 7. Octadecyl dimethyl benzyl ammonium salt-modified montmorillonite | 4.0 |
| 8. Hydrophobization-treated titanium oxide *3 | 10.0 |
| 9. Hydrophobization-treated talc *3 | 6.0 |
| 10. Hydrophobization-treated mica *3 | 6.0 |
| 11. Hydrophobization-treated red iron oxide *3 | 1.6 |
| 12. Hydrophobization-treated yellow iron oxide *3 | 0.7 |
| 13. Hydrophobization-treated black iron oxide *3 | 0.2 |
| 14. Dipropylene glycol | 5.0 |
| 15. Paraoxy benzoic acid methyl ester | 0.3 |
| 16. Perfume | q.s. |
| 17. Purified water | 17.2 |

Note
*1 Caprylyl methicone
Note
*2 Polyether-modified silicone
Note
*3 Hydrophobization treatment: 2% methylhydrogenpolysiloxane was added to the powder and then heated.

Manufacturing Method

A: Components 1 to 7 are heated and mixed. Then, components 8 to 13 are added thereto and dispersed uniformly.

B: Components 14, 15, and 17 are heated and dissolved.

C: While agitating, B is added to A in small amounts and emulsified. Then, the mixture is cooled and component 16 is added. Thus, a foundation is obtained.

Effects

The foundation is very fine and spreads easily. A moist, clean natural sensation during use without discomfort lasts in which there is no stickiness or oiliness after application. Cosmetic retainability is excellent and stability is superior, having little variation due to changes in temperature or passage of time.

Formulation Example 4

Water-in-Oil Cream

| Components | wt. % |
| --- | --- |
| 1. Dimethyl distearyl ammonium hectorite | 1.0 |
| 2. Dioctadecyl methyl ammonium salt-modified montmorillonite | 1.0 |
| 3. Dimethylpolysiloxane (6 cst) | 5.0 |
| 4. 2-ethylhexyl paramethoxy cinnamate | 2.0 |
| 5. Diethylpentanediol dineopentanoate | 3.0 |
| 6. DC 9011 Silicone Elastomer Blend *4) | 6.0 |
| 7. Composition of Practical Example 2 (composition containing silicone compound No. 2) | 1.0 |
| 8. Dipropylene glycol | 10.0 |
| 9. Sodium citrate | 0.2 |
| 10. Ethanol | 3.0 |
| 11. Preservative | q.s. |
| 12. Perfume | q.s. |
| 13. Purified water | 67.8 |

Note
*4) Product in which crosslinking polyether-modified silicone is diluted using decamethyl cyclopentasiloxane (elastomer component: 15%)

Manufacturing Method

A: Components 1 to 7 are mixed.

B: Components 8 to 13 are mixed and dissolved, added to the aforementioned A, agitated, and emulsified. Thus, a water-in-oil cream is obtained.

Effects

Oiliness and stickiness is absent, spreading is easy, and a refreshing, clean sensation during use can be obtained. Compatibility with the skin is good and a rich moisturizing feel lasts. Also, a natural matted finish can be obtained. Stability over time of the product is also excellent.

Formulation Example 5

Water-in-Oil Emulsion Composition

| Components | wt. % |
| --- | --- |
| 1. Decamethyl cyclopentasiloxane | 4.2 |
| 2. Dimethylpolysiloxane (6 cst) | 3.0 |
| 3. Dimethylpolysiloxane (2 cst) | 2.0 |
| 4. Methyl trimethicone (M3T) | 2.0 |
| 5. SH 556 *5) | 3.0 |
| 6. Methylpentanediol dineopentanoate | 3.0 |
| 7. 9040 Silicone Elastomer Blend *6) | 5.0 |
| 8. Squalane | 5.8 |
| 9. Paraffin wax | 0.3 |
| 10. Palmitic acid | 0.2 |
| 11. Composition of Practical Example 13 (composition containing silicone compound No. 13) | 4.0 |
| 12. Quasi-sphingosine | 0.2 |
| 13. Quasi-ceramide | 5.0 |
| 14. Magnesium stearate | 1.0 |
| 15. Magnesium sulfate | 1.0 |
| 16. Methyl paraoxy benzoic acid | 0.2 |
| 17. Glycerin | 16.0 |
| 18. Dipropylene glycol | 0.5 |
| 19. Purified water | 43.6 |

Note
*5) Phenyl trimethicone

Note
*6) Product in which crosslinking organopolysiloxane (dimethicone crosspolymer) is diluted using decamethyl cyclopentasiloxane (elastomer component: 12%)

Manufacturing Method

A: Components 1 to 13 and component 16 are dissolved by heating and agitating at 80 to 90° C.

B: Component 14 is added to A and mixed therein by agitating, and dispersed uniformly.

C: Separately, component 15 and components 17 to 19 are mixed to form a solution.

D: C is added in small amounts while holding the temperature of B at 80° C. and mixing uniformly. Furthermore, the mixture is cooled to room temperature while agitating. Thus a water-in-oil emulsion composition is obtained.

Effects

The water-in-oil emulsion composition is suitable for skin care, particularly face care. A clean sensation when applying and a natural feeling on the skin, free of discomfort, can be obtained. The finish is somewhat matted and small wrinkles in the skin can be concealed. Furthermore, by compounding the silicone compound No. 13, promotion of transdermal absorption of the ceramides can be anticipated. Additionally, heightened efficacy of the ceramides themselves is expected due to the ceramides being transdermally absorbed.

Formulation Example 6

Water-in-Oil Emulsion Rouge (Liquid)

| Components | wt. % |
| --- | --- |
| 1. FA 4001 CM *7) | 20.0 |
| 2. BY 11-018 *8) | 25.0 |
| 3. Aerosol-form silicic anhydride | 0.1 |
| 4. Spherical urethane powder | 5.0 |
| 5. Composition of Practical Example 5 (composition containing silicone compound No. 5) | 5.0 |
| 6. Octyl methoxy cinnamate | 1.0 |
| 7. Red No. 202 | 0.5 |
| 8. Titanium oxide | 0.5 |
| 9. Titanated mica | 3.0 |
| 10. Perfume | 0.1 |
| 11. Ethanol | 10.0 |
| 12. Preservative | 0.2 |
| 13. Sodium chloride | 0.1 |
| 14. Purified water | 29.5 |

Note
*7) Decamethyl cyclopentasiloxane solution of (acrylates/polytrimethylsiloxy methacrylate) copolymer (active component: 30%)

Note
*8) Decamethyl cyclopentasiloxane solution of trimethylsiloxysilicate (active component: 30%)

Manufacturing Method

A: Components 1 to 10 are dispersed and mixed.

B: Separately, components 11 to 14 are uniformly dissolved.

C: B is added to A and the mixture is emulsified. After degassing, a container is filled with the mixture. Thus, a water-in-oil emulsion rouge is obtained.

Effects

Spreads easily and a sensation during use free of stickiness can be obtained. A sensation of tightness or stretching is not easily produced during use and moisturizing effects are enduring. Color spreading of the rouge is substantially absent due to the superior water resistance and water repellency of the product. Product stability over time is excellent.

Formulation Example 7

Liquid Rouge

| Components | wt. % |
|---|---|
| 1. Composition of Practical Example 14 (composition containing silicone compound No. 14) | 10.0 |
| 2. Silicic anhydride (average primary particle size: 10 nm) | 1.5 |
| 3. Diisostearyl malate | 15.0 |
| 4. Octyldodecanol | 4.0 |
| 5. Methyl trimethicone (M3T) | 1.0 |
| 6. Heavy liquid isoparaffin | 35.0 |
| 7. Squalane | 9.0 |
| 8. Sunflower oil | 5.0 |
| 9. Trioctanoin | 5.0 |
| 10. Vaseline | 5.0 |
| 11. Microcrystalline wax | 2.0 |
| 12. Red No. 202 | 0.8 |
| 13. Titanium oxide | 0.7 |
| 14. Titanium oxide covered glass powder | 2.0 |
| 15. Titanium oxide covered silica powder | 2.0 |
| 16. Nε-lauroyl-L-lysine | 2.0 |

Manufacturing Method

Components 3 to 9 are mixed and heated to 90° C. Thereafter, component 2 is added, and dispersed uniformly using a homo-mixer. Then, component 1 is added. Components 10 to 16 are added while maintaining the temperature at 90° C., the components are mixed using the homo-mixer, and then a container is filled with the mixture. Thereafter, the mixture is cooled. Thus a liquid rouge is obtained.

Effects

The liquid lipstick spreads smoothly and easily when applying and has a sensation during use that is free of stickiness. Luster on the lips is excellent as well.

Formulation Example 8

Rouge

| Components | wt. % |
|---|---|
| 1. Carnauba wax | 0.5 |
| 2. Candelilla wax | 5.0 |
| 3. Ceresin | 10.0 |
| 4. Squalane | 29.0 |
| 5. Methyl trimethicone (M3T) | 1.0 |
| 6. Glycerin triisostearate | 10.0 |
| 7. Glycerin diisostearate | 20.0 |
| 8. Hydroxypropyl-β-cyclodextrin | 1.0 |
| 9. Cholesterol stearate | 3.5 |
| 10. red iron oxide covered using the composition of Practical Example 9 (composition containing silicone compound No. 9) *9) | 0.2 |
| 11. Glycerin | 0.5 |
| 12. Purified water | 2.0 |
| 13. Coloring material | q.s. |
| 14. Perfume | q.s. |
| 15. Preservative | q.s. |

Note
*9) Product in which 3% silicone compound is added to red iron oxide and, thereafter, is heated.

Manufacturing Method

A: Component 9 is heated to 60° C. Component 10 is added thereto and is mixed and uniformly dispersed.

B: Separately, a product including 0.5% equivalent of component 8 and component 12 that are mixed, heated, and melted is prepared.

C: B is added to A and uniformly dispersed therein while agitating A.

D: Next, the balance of component 12 (1.5% equivalent) and component 11 are added to C and mixed therewith. Thus, a hydrate composition is obtained.

E: Components 1 to 7 are melted at 80° C. D is added thereto and uniformly dispersed while agitating.

F: Components 13 to 15 are added to E and dispersed therein by agitating. Then the mixture is molded. Thus, a rouge is obtained.

Effects

The hydroxypropylated β cyclodextrin, water, cholesterol ester, and hydrate composition covered with the silicone compound No. 9 are stably compounded in the rouge. As a result, the product displays high moisture retainability, has superior moisturizing durability, and high moisturizing effects.

Formulation Example 9

Sunscreen Emulsion

| Components | wt. % |
|---|---|
| 1. Decamethyl cyclopentasiloxane | 20.0 |
| 2. Methylphenylpolysiloxane | 3.0 |
| 3. Sorbitan monoisostearate | 1.0 |
| 4. SS-2910 *10) | 0.3 |
| 5. Composition of Practical Example 10 (composition containing silicone compound No. 10) | 0.3 |
| 6. Dioctadecyl methyl ammonium salt-modified montmorillonite | 0.2 |
| 7. BY 11-018 *11) | 1.0 |
| 8. Paramethoxy octyl cinnamate | 4.0 |
| 9. Fatty acid soap treated microparticle titanium dioxide | 8.0 |
| 10. Sorbitol | 2.0 |
| 11. Sodium chloride | 1.0 |
| 12. Preservative | q.s. |
| 13. Perfume | q.s. |
| 14. Purified water | 59.2 |

Note
*10) Polyether-modified silicone
Note
*11) Decamethyl cyclopentasiloxane solution of trimethylsiloxysilicate Manufacturing Method A: Components 1 to 8 are heated and mixed, and component 9 is uniformly dispersed therein.

B: Separately, components 10 to 12 and 14 are heated and mixed.

C: While agitating, B is added to A in small amounts and emulsified. Then, the mixture is cooled and component 13 is added. Thus, a sunscreen emulsion is obtained.

Effects

Stickiness and coarseness particular to suncare products are, for the most part, not felt when applying, and the emulsion is fine and is easily spread. A rich moisturizing feel lasts and cosmetic retainability is good. Therefore, ultraviolet light blocking effects last. Stability over time of the product is also excellent and agglomeration and the like of the powder does not easily occur.

Formulation Example 10

Emulsion

| Components | wt. % |
| --- | --- |
| 1. Decamethyl cyclopentasiloxane | 15.0 |
| 2. Methylphenylpolysiloxane | 5.0 |
| 3. Squalene | 5.0 |
| 4. Pentaerythritol tetra-2-ethylhexanoate | 5.0 |
| 5. Composition of Practical Example 8 (composition containing silicone compound No. 8) | 1.0 |
| 6. BY 22-008M *12) | 2.0 |
| 7. 9701 Cosmetic Powder *13) | 2.0 |
| 8. Hydrophobized silica | 0.5 |
| 9. Magnesium ascorbyl phosphate | 1.0 |
| 10. Sodium chloride | 1.0 |
| 11. Polyethyleneglycol 11000 | 1.0 |
| 12. Propylene glycol | 8.0 |
| 13. Preservative | q.s. |
| 14. Perfume | q.s. |
| 15. Purified water | bal. |

Note
*12) Decamethyl cyclopentasiloxane solution of polyether-modified silicone (active component: 12%)
Note
*13) organopolysiloxane elastomer spherical powder (silica-covered type)

Manufacturing Method

A: Components 1 to 6 are mixed uniformly, then components 7 and 8 are added and dispersed uniformly therein.

B: Components 9 to 11 are added to and dissolved in component 15. Then, components 12 and 13 are mixed uniformly and then added thereto.

C: B is added to A in small amounts and emulsified and then cooled. Then, component 14 is added. Thus, an emulsion is obtained.

Effects

An emulsion having a soft, puffy texture is obtained that spreads easily and is free of stickiness. A plain, discomfort free natural feeling on the skin and appropriate moisturizing feel last after application. Stability is superior, having little variation due to changes in temperature or passage of time.

Formulation Example 11

UV Blocking Cream

| Components | wt. % |
| --- | --- |
| 1. Decamethyl cyclopentasiloxane | 17.5 |
| 2. FA 4002 ID *14) | 12.0 |
| 3. Glyceryl triisooctanoate | 5.0 |
| 4. Paramethoxy octyl cinnamate | 6.0 |
| 5. SS-2910 *15) | 1.0 |
| 6. Composition of Practical Example 12 (composition containing silicone compound No. 12) | 0.5 |
| 7. Organo-modified bentonite | 0.2 |
| 8. Silicone treated zinc oxide | 20.0 |
| 9. 9702 Powder *16) | 3.0 |

-continued

| Components | wt. % |
| --- | --- |
| 10. Sodium chloride | 0.5 |
| 11. 1,3-butylene glycol | 2.0 |
| 12. Preservative | q.s. |
| 13. Perfume | q.s. |
| 14. Purified water | 32.3 |

Note
*14) Isododecane solution of (acrylates/polytrimethylsiloxy methacrylate) copolymer (active component: 40%)
Note
*15) Polyether-modified silicone
Note
*16) organopolysiloxane elastomer spherical powder (composite powder with mica)

Manufacturing Method

A: Component 2 is added to a portion of component 1 and uniformly mixed. Then, component 8 is added and dispersed using a bead mill.

B: The remainder of component 1 and components 3 to 7 are mixed and blended uniformly.

C: Components 9 to 11 and component 13 are mixed and dissolved.

D: C is added to B and emulsified. Then A and component 12 are added. Thus, a UV blocking cream is obtained.

Effects

The UV blocking cream is substantially free of stickiness, and spreads very easily. Additionally, while having superior adhesive sensation, a discomfort free natural feeling on the skin is obtained. The finish thereof is glossy and cosmetic retainability is extremely good. Moreover, the product is stable with respect to temperature and passage of time.

Formulation Example 12

UV Blocking Water-in-Oil Emulsion

| Components | wt. % |
| --- | --- |
| 1. Dimethylpolysiloxane (6 cst) | 5.0 |
| 2. DC 9011 Silicone Elastomer Blend *17) | 5.0 |
| 3. Glyceryl trioctanoate | 2.0 |
| 4. Dimethyl distearyl ammonium hectorite | 0.5 |
| 5. Octadecyl dimethyl benzyl ammonium salt-modified montmorillonite | 0.5 |
| 6. SS-2910 *18) | 1.0 |
| 7. Powder in oil dispersion of Practical Example 45 | 30.0 |
| 8. Powder in oil dispersion of Practical Example 48 | 30.0 |
| 9. Dipropylene glycol | 3.0 |
| 10. Sodium citrate | 0.2 |
| 11. Preservative | q.s. |
| 12. Perfume | q.s. |
| 13. Purified water | 22.8 |

Note
*17) Product in which crosslinking polyether-modified silicone is diluted using decamethyl cyclopentasiloxane (elastomer component: 15%)
Note
*18) Polyether-modified silicone Manufacturing method A: Components 1 to 6 are mixed.

B: Components 9 to 11 and component 13 are mixed and dissolved, then are added to A and agitated and emulsified.

C: Components 7, 8, and 12 are added to B and mixed uniformly.

Effects

The UV blocking water-in-oil emulsion spreads easily, is light on the skin, is free of stickiness and oiliness, has a feeling of sheerness, and has excellent cosmetic retainability. Additionally, UV blocking water-in-oil emulsion displays very little variation due to temperature or passage of time and has superior usability and stability.

Formulation Example 13

Sunscreen Agent

| Components | wt. % |
|---|---|
| 1. Dimethylpolysiloxane (6 cst) | 5.0 |
| 2. 9040 Silicone Elastomer Blend *19) | 5.0 |
| 3. Glyceryl triisooctanoate | 3.0 |
| 4. Methyl trimethicone | 2.5 |
| 5. SS-3408 *20) | 1.5 |
| 6. SS-2910 *21) | 1.0 |
| 7. Octyl methoxy cinnamate | 6.0 |
| 8. Decamethyl cyclopentasiloxane | 24.0 |
| 9. Powder composition of Practical Example 53 | 25.0 |
| 10. Sodium chloride | 0.5 |
| 11. 1,3-butylene glycol | 2.0 |
| 12. Purified water | 24.5 |
| 13. Perfume | q.s. |

Note
*19) Product in which crosslinking organopolysiloxane (dimethicone crosspolymer) is diluted using decamethyl cyclopentasiloxane (elastomer component: 12%)
Note
*20) Caprylyl methicone
Note
*21) Polyether-modified silicone Manufacturing Method A: Components 1 to 6 are mixed uniformly, and then components 8 and 9 are added.

B: Components 10 to 12 are mixed and dissolved, then are added to A and agitated and emulsified.

C: Component 7 is added to B and the mixture is mixed uniformly. Thus, a sunscreen agent is obtained.

Effects

The powder has excellent dispersion stability and does not easily agglomerate due to changes in temperature or passage of time. When applying, the sunscreen agent displays a smooth feeling to touch and spreads easily, and a cosmetic film with a feeling of sheerness and that is free of stickiness is obtained. Because cosmetic retainability is excellent, durability of sunscreen effects is superior.

Formulation Example 14

Water-in-Oil Emulsion Sunscreen

| Components | wt. % |
|---|---|
| 1. SH 556 *22) | 5.0 |
| 2. Octyl methoxy cinnamate | 5.0 |
| 3. Powder in oil dispersion of Practical Example 49 | 25.0 |
| 4. Composition of Practical Example 10 (composition containing silicone compound No. 10) | 1.0 |
| 5. Dipropylene glycol | 5.0 |
| 6. PEG(10)/PPG(14) dimethylether | 1.5 |
| 7. Sodium carboxymethylcellulose | 0.1 |
| 8. Succinoglycan | 0.3 |
| 9. Chelating agent | q.s. |
| 10. Preservative | q.s. |
| 11. Buffer | q.s. |
| 12. Purified water | 57.1 |

Note
*22) Phenyl trimethicone

Manufacturing Method

A: Components 1, 2, and 4 are mixed uniformly, and then component 3 is added.

B: Components 5 to 12 are mixed and dissolved, added to the aforementioned A, agitated, and emulsified. Thus, a water-in-oil emulsion sunscreen is obtained.

Effects

A natural finish with a feeling of sheerness is obtained and a rich moisturizing feel lasts. Moreover, the water-in-oil emulsion sunscreen has superior UV blocking effects in both the UVA band and the UVB band.

Formulation Example 15

O/W Cream

| Components | wt. % |
|---|---|
| 1. 2503 Cosmetic Wax *23) | 5.0 |
| 2. Cetanol | 1.0 |
| 3. Liquid paraffin | 10.0 |
| 4. Dimethylpolysiloxane (20 cst) | 5.0 |
| 5. Vaseline | 2.0 |
| 6. Candelilla wax | 2.0 |
| 7. Glyceryl triisostearate | 5.0 |
| 8. Stearic acid | 3.0 |
| 9. Glyceryl monostearate | 1.5 |
| 10. Composition of Practical Example 5 (composition containing silicone compound No. 5) | 10.0 |
| 11. Sorbitan sesquioleate | 0.5 |
| 12. Polyoxyethylene sorbitan monooleate | 1.0 |
| 13. Sodium hydroxide (1% aqueous solution) | 10.0 |
| 14. 1,3-butylene glycol | 5.0 |
| 15. Glycerin | 5.0 |
| 16. Preservative | q.s. |
| 17. Perfume | q.s. |
| 18. BY 29-129 *24) | 5.0 |
| 19. Purified water | 51.0 |

Note
*23) Stearyl dimethicone
Note
*24) Aqueous dispersion of organopolysiloxane elastomer spherical powder (active component: 63%)

Manufacturing Method

A: Components 1 to 12 are mixed, heated, and dissolved.

B: Components 13 to 16 and component 19 are mixed, heated, and dissolved.

C: B is added to A and emulsified, and the mixture is cooled to 40° C. Then, components 18 and 17 are added and mixed uniformly.

D: Then, the mixture is cooled to room temperature. Thus an O/W cream is obtained.

Effects

The O/W cream spreads easily, has superior adhesion to the skin, feels rich on the skin without being sticky, and has a dry feeling to touch. Moreover, with the O/W cream, the skin surface is free of oily glossiness and has a matted, natural finish. The O/W cream also provides a benefit of concealing small lines and wrinkles. Stability over time of the product itself is also excellent.

Formulation Example 16

Eye Shadow

| Components | wt. % |
| --- | --- |
| 1. Decamethyl cyclopentasiloxane | 13.0 |
| 2. Dimethylpolysiloxane (6 cst) | 10.0 |
| 3. Methyl trimethicone (M3T) | 2.0 |
| 4. Composition of Practical Example 1 (composition containing silicone compound No. 1) | 2.0 |
| 5. PEG(10)lauryl ether | 0.5 |
| 6. Silicone treated chromium oxide *25) | 6.2 |
| 7. Silicone treated ultramarine *25) | 4.0 |
| 8. Silicone treated titanium covered mica *25) | 6.0 |
| 9. Sodium chloride | 2.0 |
| 10. Propylene glycol | 8.0 |
| 11. Preservative | q.s. |
| 12. Perfume | q.s. |
| 13. Purified water | 46.3 |

Note
*25) Silicone treatment: 3% methylhydrogenpolysiloxane is added to the powder and then heated.

Manufacturing Method

A: Components 1 to 5 are mixed, components 6 to 8 are added and dispersed uniformly.

B: Components 9 to 11 and component 13 are dissolved uniformly.

C: While agitating, B is added to A in small amounts and emulsified.

Then, component 12 is added. Thus, an eye shadow is obtained.

Effects

The eye shadow spreads easily, is free of oiliness and powderiness, and has a refreshing, clean sensation during use that lasts. With the eye shadow, compatibility with the skin is good, moisture resistance, water repellency, and anti-perspirant properties are excellent. Therefore, make up does not smear easily. With this product, stability is superior, having little variation due to changes in temperature or passage of time.

Formulation Example 17

Mascara

| Components | wt. % |
| --- | --- |
| 1. Isododecane | 23.0 |
| 2. Methyl trimethicone (M3T) | 1.0 |
| 3. Dimethyl palmityl polysiloxane | 1.0 |
| 4. Dimethylpolysiloxane (100,000 cst) | 1.0 |
| 5. Microcrystalline wax | 5.0 |
| 6. Beeswax | 3.0 |
| 4. Composition of Practical Example 4 (composition containing silicone compound No. 4) | 3.0 |
| 8. Silicone covered black iron oxide | 14.0 |
| 9. Bentonite | 2.0 |
| 10. Nylon fiber (average length: 2 μm) | 2.0 |
| 11. Paraoxy benzoic acid ester | 0.5 |
| 12. Absolute ethanol | 2.5 |

-continued

| Components | wt. % |
| --- | --- |
| 13. Polyvinylalcohol | 0.5 |
| 14. Alkyl acrylate copolymer emulsion (50% dispersion liquid) | 19.5 |
| 15. Alkyl acrylate-styrene copolymer emulsion (50% dispersion liquid) | 8.0 |
| 16. Purified water | 14.0 |

Manufacturing Method

A: Components 1 to 7 are mixed and dissolved. Then, components 8 to 10 are added and uniformly dispersed while agitating using a homo-disper mixer.

B: Component 11 is dissolved in component 12, and the product thereof is added to component 16 and the mixture is mixed uniformly.

C: B is uniformly mixed with components 14 and 15. Then, component 13 is added and the mixture is mixed uniformly.

D: C is added in small amounts while agitating A using a homo-disper mixer. Thus, a mascara is obtained.

Effects

The mascara spreads easily and has a sensation during use that has little stickiness or oiliness. A mascara with superior durability can be obtained that has moisture resistance, water repellency, anti-perspirant properties, and that is not easily displaced due to light impacts. Additionally, stability is excellent with regards to the temperature and passage of time of the product itself.

Formulation Example 18

Mascara

| Components | wt. % |
| --- | --- |
| 1. Decamethyl cyclopentasiloxane | 19.4 |
| 2. Light liquid isoparaffin | 14.6 |
| 3. Methyl trimethicone (M3T) | 1.5 |
| 4. FA 4001 CM*26) | 31.0 |
| 5. Dextrin fatty acid ester | 15.0 |
| 6. Composition of Practical Example 3 (composition containing silicone compound No. 3) | 3.0 |
| 7. Organo-modified bentonite | 1.5 |
| 8. Hydrophobized silicic anhydride | 2.0 |
| 9. Nylon fiber (average length: 2 μm) | 2.0 |
| 10. Carbon black | 10.0 |

Note
*26) Decamethyl cyclopentasiloxane solution of (acrylates/polytrimethylsiloxy methacrylate) copolymer (active component: 30%)

Manufacturing Method

A: Components 1 to 10 are uniformly mixed. Then, a container is filled with the mixture. Thus, a mascara is obtained.

Effects

The mascara spreads easily and is free of stickiness and oiliness. Additionally, because the mascara has superior moisture resistance, water repellency, and anti-perspirant properties, cosmetic retainability is good. The product displays very little variation due to temperature or passage of time and has superior stability.

Formulation Example 19

Solid Powder Eye Shadow

| Components | wt. % |
|---|---|
| 1. Talc (hydrophobization-treated) | 16.0 |
| 2. Sericite (hydrophobization-treated) | 30.0 |
| 3. Titanated mica (hydrophobization-treated) | 35.0 |
| 4. Ultramarine (hydrophobization-treated) | 4.0 |
| 5. Iron oxide (hydrophobization-treated) | 2.0 |
| 6. SS-2910 *27) | 5.0 |
| 7. Composition of Practical Example 11 (composition containing silicone compound No. 11) | 5.0 |
| 8. Tetrakistrimethylsiloxysilane (M4Q) | 2.0 |
| 9. Liquid paraffin | 0.5 |
| 10. Paraffin | 0.5 |

Note
*27) Polyether-modified silicone

Manufacturing Method
A: Components 1 to 5 are agitated and mixed using a blender.
B: Components 6 to 10 are heated and dissolved.
C: B is blasted onto A and further agitated. Thereafter, the product is crushed and compression molded in a molding machine. Thus, a solid powder eye shadow is obtained.
Effects
Sensation during use and finish of the solid powder eye shadow are superior. Adhesion of the powder is excellent, and moisture resistance, water repellency, and anti-perspirant properties are superior. Therefore, the solid powder eye shadow has good cosmetic retainability.

Formulation Example 20

Pressed Powder Cosmetic

| Components | wt. % |
|---|---|
| 1. Silicone treated titanium oxide | 10.0 |
| 2. Silicone treated mica | 50.8 |
| 3. Silicone treated talc | 10.0 |
| 4. Silicone treated yellow iron oxide | 1.5 |
| 5. Silicone treated red iron oxide | 0.5 |
| 6. Silicone treated black iron oxide | 0.2 |
| 7. Paraffin wax | 2.0 |
| 8. Squalane | 1.4 |
| 9. 2-ethylhexyl palmitate | 2.0 |
| 10. Composition of Practical Example 9 (composition containing silicone compound No. 9) | 15.0 |
| 11. SS-3408 *28) | 2.6 |
| 12. Methyl trimethicone (M3T) | 1.0 |
| 13. Dimethylpolysiloxane | 3.0 |
| 14. Perfume | q.s. |

Note
*28) Caprylyl methicone

Manufacturing Method
A: Components 1 to 6 are mixed.
B: Components 7 to 13 are mixed and A is added.
C: Component 14 is added to B and press molded into a cosmetic receptacle.
Effects
The feeling to touch of the powder is dry and sensation during use is excellent. A natural feeling of application is obtained and compatibility with the skin is good. Additionally, moisture resistance, water repellency, and anti-perspirant properties are excellent.

Formulation Example 21

Powder Foundation

Components wt. %
1. Treated sericite *29) 42.0
2. Treated titanium oxide*29) 12.0
3. Treated talc *29) 24.0
4. Treated yellow iron oxide *29) 2.4
5. Treated red iron oxide *29) 0.8
6. Treated black iron oxide *29) 0.3
7. Dimethylpolysiloxane 1.8
8. Methyl trimethicone (M3T) 0.5
9. Liquid paraffin 6.2
10. Octyldodecanol 2.0
11. 9702 Powder *30) 8.0
12. Perfume q.s.
13. Preservative q.s.
Note *29) A modified powder obtained by: Mixing (in advance) sericite, titanium oxide, talc, yellow iron oxide, red iron oxide, and black iron oxide, all treated with 3% methylhydrogenpolysiloxane at the compounding ratio shown in Formulation Example 21; dispersing the unmodified powder obtained as described above in chloroform, adding the composition of Practical Example 11 (composition containing silicone compound No. 11) at an amount of 8% with respect to the powder, and agitating; and removing the chloroform under reduced pressure by distillation and crushing the product.
Note *30) organopolysiloxane elastomer spherical powder (composite powder with mica)
Manufacturing Method
A: Components 1 to 6 are mixed using a Henschel mixer.
B: Components 7 to 13 are mixed, added to A, and agitated.
C: B is crushed using an atomizer and, thereafter is stamped into a die.
Thus, a foundation is obtained.
Effects
With the foundation, while feeling to touch of the powder is extremely light and dry, a smooth and substantial sense of application can be obtained. The sense of coarseness particular to powders is reduced. Additionally, because the foundation has superior moisture resistance, water repellency, and anti-perspirant properties, cosmetic retainability is good.

Formulation Example 22

Pressed Foundation

| Components | wt. % |
|---|---|
| 1. Perfluoropolyether treated titanium oxide | 9.0 |
| 2. Perfluoropolyether treated zinc oxide | 3.0 |
| 3. Perfluoropolyether treated red iron oxide | 0.4 |
| 4. Perfluoropolyether treated yellow iron oxide | 4.0 |
| 5. Perfluoropolyether treated black iron oxide | 0.2 |
| 6. Perfluoropolyether treated talc | 15.0 |
| 7. Perfluoropolyether treated mica | 48.2 |
| 8. Perfluoropolyether treated titanated mica | 2.0 |
| 9. 9701 Cosmetic Powder *31) | 2.0 |
| 10. Squalane | 4.0 |
| 11. Dimethylpolysiloxane | 6.0 |
| 12. Vaseline | 2.0 |

-continued

| Components | wt. % |
|---|---|
| 13. Glyceryl triisooctanoate | 2.0 |
| 14. Composition of Practical Example 7 (composition containing silicone compound No. 7) | 2.0 |
| 15. Preservative | 0.1 |
| 16. Perfume | 0.1 |

Note
*31) organopolysiloxane elastomer spherical powder (silica-covered type)

Manufacturing Method

A: Components 1 to 9 are dispersed and mixed.

B: Components 10 to 14 are heated and uniformly mixed.

C: B is added to A and mixed. After crushing, the product is compression molded into a cosmetic receptacle. Thus, a pressed foundation is obtained.

Effects

The foundation is durable against impact and does not crack easily. Adhesion to the skin is excellent and sebum resistance, along with moisture resistance, water repellency, and anti-perspirant properties thereof is superior. Therefore, cosmetic retainability is very good.

Formulation Example 23

Cream

| Components | wt. % |
|---|---|
| 1. Hydrogenated soy phospholipid | 1.0 |
| 2. Cholesterol | 0.5 |
| 3. Dipropylene glycol | 10.0 |
| 4. Glycerin | 10.0 |
| 5. Purified water | 56.5 |
| 6. Sodium lactate | 1.0 |
| 7. Composition of Practical Example 6 (composition containing silicone compound No. 6) | 3.0 |
| 8. Decamethyl cyclopentasiloxane | 8.5 |
| 9. Methyl trimethicone (M3T) | 1.5 |
| 10. Glyceryl tri(2-ethylhexanoate) | 5.0 |
| 11. Meadowfoam oil | 3.0 |

Manufacturing Method

A: Components 1 to 4 are heated to 75° C.

B: Components 5 and 6 are heated to 75° C.

C: B is added to A and mixed. Then, the mixture is cooled to room temperature.

D: Components 7 to 11 are added in small amounts to C while agitating and mixed. Thus, a cream is obtained.

Effects

Based on the properties inherent in soy phospholipids, it is anticipated that a liposome having a lipid bilayer structure will be formed in the cream. This cream has good compatibility with the skin, is free of stickiness, has superior rich moisturizing feel after application, and has excellent stability over time.

Formulation Example 24

Foundation

| Components | wt. % |
|---|---|
| 1. Hydrogenated soy phospholipid | 0.5 |
| 2. Phytosterol | 0.1 |
| 3. Squalane | 1.0 |
| 4. Glycerin | 2.0 |
| 5. 1,3-butylene glycol | 2.0 |
| 6. Purified water | bal. |
| 7. Sodium chloride | 1.0 |
| 8. Methyl paraoxy benzoic acid | 0.3 |
| 9. Ethanol | 3.0 |
| 10. Composition of Practical Example 8 (composition containing silicone compound No. 8) | 2.0 |
| 11. SS-2910 *32) | 1.0 |
| 12. Diglyceryl diisostearate | 1.0 |
| 13. 2-ethylhexyl paramethoxy cinnamate | 3.0 |
| 14. Glyceryl tri(2-ethylhexanoate) | 5.0 |
| 15. Pentaerythritol rosinate | 0.1 |
| 16. Dextrin palmitate | 0.5 |
| 17. Inulin stearate | 0.5 |
| 18. Dimethyl distearyl ammonium hectorite | 1.0 |
| 19. Silicone treated titanium oxide | 10.0 |
| 20. Silicone treated red iron oxide | 0.3 |
| 21. Silicone treated yellow iron oxide | 1.5 |
| 22. Silicone treated black iron oxide | 0.05 |
| 23. Silicone treated fine particulate titanium oxide | 2.0 |
| 24. Nylon powder | 2.0 |
| 25. Decamethyl cyclopentasiloxane | 18.0 |

Note
*32) Polyether-modified silicone

Manufacturing Method

A: Components 1 to 5 are heated to 75° C.

B: Component 6 is heated to 75° C.

C: B is added to A and mixed. Then, the mixture is cooled to room temperature.

D: Components 7 to 9 are added to C and mixed.

E: Components 10 to 25 are mixed using a roll mill.

F: D is added to E while agitating and mixed. Thus, a foundation is obtained.

Effects

Based on the properties inherent in soy phospholipids, it is anticipated that a liposome having a lipid bilayer structure will be formed in the emulsion foundation. Adhesion to the skin is excellent and cosmetic retainability is superior. During use, the foundation is free of stickiness and a plain, natural feeling on the skin and appropriate moisturizing feel last. Stability over time of the product is excellent.

Formulation Example 25

Water-in-Oil Emulsion-Type Sunscreen

| Components | wt. % |
|---|---|
| 1. Silicone treated iron oxide-containing zinc oxide | 30.0 |
| 2. Composition of Practical Example 10 (composition containing silicone compound No. 10) | 6.0 |
| 3. Decamethyl cyclopentasiloxane | 25.0 |
| 4. Methyl trimethicone (M3T) | 5.0 |
| 5. Isononyl isononanoate | 2.0 |
| 6. Octyl methoxycinnamate | 7.0 |
| 7. Polymethyl silsesquioxane powder | 5.0 |
| 8. Purified water | 13.9 |

-continued

| Components | wt. % |
|---|---|
| 9. Ethanol | 2.0 |
| 10. Glycerin | 3.0 |
| 11. Carboxyvinyl powder (1% aqueous solution) | 1.0 |
| 12. Sodium chloride | 0.1 |

Manufacturing Method

A: Components 1 to 4 are uniformly mixed using three rollers.

B: A is added to components 5 to 7 and uniformly mixed.

C: Components 8 to 12 are added to B and uniformly mixed and emulsified.

D: C is degassed. Thus, a sunscreen is obtained.

Effects

Transparency of the cosmetic film is high and there is no ash-like color when applying. Stickiness particular to suncare products is reduced. Spreadability of the sunscreen is extremely good. Stability over time of the product is also excellent and agglomeration and the like of the powder does not easily occur.

Formulation Example 26

Lipstick

| Components | wt. % |
|---|---|
| 1. Polyethylene-polypropylene copolymer | 5.0 |
| 2. Candelilla wax | 5.0 |
| 3. Carnauba wax | 5.0 |
| 4. Vaseline | 10.0 |
| 5. Cetyl 2-ethylhexanoate | 10.0 |
| 6. Diglycerin diisostearate | 14.5 |
| 7. Macadamia nut oil | 7.0 |
| 8. Inulin stearate (Rheopearl ISK2; manufactured by Chiba Flour Milling Co., Ltd.) | 23.0 |
| 9. Composition of Practical Example 10 (composition containing silicone compound No. 10) | 2.0 |
| 10. Red No. 201 | 1.0 |
| 11. Red No. 202 | 3.0 |
| 12. Yellow No. 4, Aluminum Lake | 3.0 |
| 13. Titanium oxide | 1.0 |
| 14. Black iron oxide | 0.5 |
| 15. Iron oxide titanated mica | 10.0 |
| 16. Preservative | q.s. |
| 17. Perfume | q.s. |

Manufacturing Method

A: Components 1 to 9 are heated and dissolved. Then, components 10 to 16 are added and mixed uniformly.

B: Component 17 is added to A, and a container is filled with the mixture. Thus, a lipstick is obtained.

Effects

The lipstick has a rich feeling to touch and can be applied smoothly. During use, the lipstick is free of stickiness and prevents drying of the lips. With the lipstick, beautiful color development and luster is obtained and cosmetic retainability is excellent.

Formulation Example 27

Rouge

| Components | wt. % |
|---|---|
| 1. Microcrystalline wax | 10.0 |
| 2. Paraffin wax | 15.0 |
| 3. Carnauba wax | 5.0 |
| 4. Vaseline | 5.0 |
| 5. Diisostearyl malate | 7.0 |
| 6. Glyceryl triisostearate | 11.5 |
| 7. Propylene glycol dicaprate | 7.0 |
| 8. Inulin stearate (Rheopearl ISK2; manufactured by Chiba Flour Milling Co., Ltd.) | 2.0 |
| 9. Composition of Practical Example 8 (composition containing silicone compound No. 8) | 3.0 |
| 10. Decamethyl cyclopentasiloxane | 10.0 |
| 11. FA4001 CM *33) | 3.0 |
| 12. DC 593 *34) | 2.0 |
| 13. Red No. 201 | 1.0 |
| 14. Red No. 202 | 1.0 |
| 15. Yellow No. 4 | 2.0 |
| 16. Titanium oxide | 4.0 |
| 17. Black iron oxide | 0.5 |
| 18. Iron oxide titanated mica | 3.0 |
| 19. Titanated mica | 2.0 |
| 20. Purified water | 5.0 |
| 21. 1,3-butylene glycol | 1.0 |
| 22. Preservative | q.s. |
| 23. Perfume | q.s. |

Note
*33) Decamethyl cyclopentasiloxane solution of (acrylates/polytrimethylsiloxy methacrylate) copolymer (active component: 30 wt. %)
Note
*34) Dimethylpolysiloxane (100 cst) solution of trimethylsiloxysilicate (active component: 33%)

Manufacturing Method

A: Components 1 to 12 are heated and dissolved. Then, components 13 to 19 are added and mixed uniformly.

B: Components 20 to 22 are mixed uniformly and, thereafter, A is added and the mixture is mixed.

C: Component 23 is added to B, and a container is filled with the mixture. Thus, a rouge is obtained.

Effects

The rouge has a rich feeling to touch and can be applied smoothly. During use, the rouge is free of stickiness and prevents drying of the lips. Additionally, the emulsion stability of the product is very excellent.

Formulation Example 28

Foundation

| Components | wt. % |
|---|---|
| 1. Dimethylpolysiloxane (2 cst) | 10.0 |
| 2. Isododecane | 21.6 |
| 3. Isostearyl diglyceryl succinate | 0.6 |
| 4. SS-2910 *35) | 1.2 |
| 5. Composition of Practical Example 13 (composition containing silicone compound No. 13) | 0.6 |
| 6. BY25-320 *36) | 1.5 |
| 7. FZ-2250 *37) | 1.5 |
| 8. FA4002 ID *38) | 2.0 |
| 9. DC 593 *39) | 2.0 |

-continued

| Components | wt. % |
|---|---|
| 10. Covered iron oxide | 3.5 |
| 11. Covered titanium dioxide | 6.8 |
| 12. Nylon 12 | 8.0 |
| 13. Ion exchange water | 40.0 |
| 14. Magnesium sulfate | 0.7 |
| 15. Preservative | q.s. |

Note
*35) Polyether-modified silicone
Note
*36) Isoparaffin solution (20 wt. %) of dimethyl polysiloxane gum
Note
*37) Isoparaffin solution (35 wt. %) of polyether-silicone block copolymer
Note
*38) Isododecane solution of (acrylates/polytrimethylsiloxy methacrylate) copolymer (active component: 40 wt. %)
Note
*39) Dimethylpolysiloxane (100 cst) solution of trimethylsiloxysilicate (active component: 33%)

Manufacturing Method

A: Components 1 to 9 are mixed, and then components 10 to 12 are dispersed uniformly therein.

B: Components 13 to 15 are mixed and, thereafter, A is added and the mixture is emulsified. Thus, a foundation is obtained.

Effects

With the foundation, a cosmetic film that imparts a feeling of smoothness and substance can be obtained regardless of the foundation spreads smoothly and easily. A sensation of dryness or tightness or stretching is, for the most part, not felt after application, adhesion to the skin is excellent, and cosmetic retainability is superior.

Formulation Example 29

Anti-Perspirant Aerosolized Cosmetic Composition

| Components | wt. % |
|---|---|
| 1. Aluminumhydroxychloride | 3.0 |
| 2. Zinc oxide | 2.0 |
| 3. Silica | 3.0 |
| 4. Silver ion/zinc ion/ammonium ion-carrying zeolite | 1.0 |
| 5. Calcium stearate | 0.1 |
| 6. Dimethylpolysiloxane | 2.0 |
| 7. Cetyl octanoate | 1.0 |
| 8. Liquid paraffin | 1.0 |
| 9. Silicone compound No. 16 | 10.0 |
| 10. Sorbitan oleate | 1.0 |
| 11. Antioxidant | q.s. |
| 12. Perfume | q.s. |
| 13. Liquified petroleum gas | bal. |

Manufacturing Method

A: Components 6 to 11 (oil phase portion) are mixed and formed into a uniform liquid.

B: Components 1 to 5 (powder portion) are mixed with the oil phase portion, and uniformly dispersed therein.

C: Component 12 (propellant) is charged. Thus an anti-perspirant aerosolized cosmetic composition is obtained.

Effects

Adhesion of the powder is excellent, whiteness after use is not noticeable, and safety is high. The anti-perspirant aerosolized cosmetic composition is free of stickiness after application and provides an appropriate dry sensation. Moreover, a smooth, natural feeling on the skin can be obtained.

Formulation Example 30

Nonaqueous Pressurized Anti-Perspirant Product

| Components | wt. % |
|---|---|
| 1. 15 wt. % 1,2-hexanediol solution of aluminum chlorohydrate | 12.0 |
| 2. Dimethylpolysiloxane (10 cst) | 3.0 |
| 3. Decamethyl cyclopentasiloxane | 3.0 |
| 4. Silicone compound No. 15 | 3.0 |
| 5. Perfume | 1.0 |
| 6. Butane | 25.0 |
| 7. Isobutane | 30.0 |
| 8. Propane | 3.0 |
| 9. Dimethylether | 20.0 |

Manufacturing Method

A: Components 1 to 5 are mixed and formed into a uniform liquid.

B: Components 6 to 8 (propellants) are charged.

C: Lastly, component 9 (propellant) is charged. Thus, a nonaqueous pressurized anti-perspirant product is obtained.

Effects

A transparent, uniform, pressurized liquid can be obtained and, therefore, separation of the AP active components and the like does not occur and product life is long. The nonaqueous pressurized anti-perspirant product provides instant anti-perspirant effects and whiteness is not noticeable after use. After application, a moisturizing, natural feeling on the skin can be obtained.

Formulation Example 31

Aerosol Type Anti-Perspirant Composition

| Components | wt. % |
|---|---|
| 1. Aluminum hydroxy chloride *40) | 5.0 |
| 2. Aluminum hydroxy chloride *41) | 1.5 |
| 3. Purified water | 10.0 |
| 4. POE(10) POP(5) cetyl ether phosphate | 1.5 |
| 5. Magnesia silica | 1.0 |
| 6. Porous silica | 0.5 |
| 7. Polymethyl silsesquioxane powder | 1.0 |
| 8. Decamethyl cyclopentasiloxane | 2.0 |
| 9. Silicone compound No. 13 | 0.5 |
| 10. Isopropylmethylphenol | 0.05 |
| 11. Eucalyptus extract | 0.5 |
| 12. Soy extract | 0.1 |
| 13. Melissa officinalis leaf extract | 0.1 |
| 14. Apple extract | 0.1 |
| 15. Perfume M *42) | 0.15 |
| 16. Ethanol | 26.0 |
| 17. LPG (0.15 MPa/20° C.) | 50.0 |

Note
*40) REACH 101 MICRO-DRY (trade designation, manufactured by Reheis, Inc.)
Note
*41) REACH 501 MICRO-DRY (trade designation, manufactured by Reheis, Inc.)
Note
*42) Formulated according to the perfume composition shown in Table 82

Manufacturing Method

A: Components 1 to 4 are mixed and dissolved, and formed into a uniform liquid. (aqueous phase)

B: Separately, components 8 to 16 are mixed and dissolved, and formed into a uniform liquid. (ethanol phase)

C: The aqueous phase and the ethanol phase are thoroughly mixed, and formed into a uniform liquid. (stock solution)

D: Components 5 to 7 are mixed with the stock solution and uniformly dispersed therein.

E: Finally, component 17 is charged. Thus, an aerosol type anti-perspirant composition is obtained.

Effects

A transparent, uniform, pressurized liquid can be obtained and, therefore, separation of the anti-perspiration active components and the like does not occur and product life is long. Anti-perspirant effects are expressed rapidly, immediately after application to the skin. After application, a moisturizing, natural feeling on the skin that is free of stickiness can be obtained.

TABLE 82

Perfume composition example; Perfume M

| Component | Content (%) | Component | Content (%) |
|---|---|---|---|
| Aldehyde C-8 | 0.1 | Indole pure | 0.1 |
| Aldehyde C-9 | 0.1 | Ionone beta | 1.0 |
| Aldehyde C-10 | 0.1 | Jasmacyclene | 3.0 |
| Aldehyde C-11 Undecylenic | 0.1 | Juniper berry oil | 0.1 |
| Aldehyde C-12 lauric | 0.1 | Karanal | 0.1 |
| Allylheptanoate | 0.1 | Lemon oil | 10.0 |
| Ambroxane | 0.1 | Lemonile | 0.5 |
| Bergamot oil | 4.0 | Ligustral | 0.1 |
| Citral | 1.0 | Lilial | 2.0 |
| Citronellol | 8.0 | Lime oil | 2.0 |
| Citronellyl nitrile | 1.0 | Linalol | 5.0 |
| Cyclamen aldehyde | 0.5 | Linalyl acetate | 1.5 |
| Alpha-damascone | 0.1 | Lyral | 2.0 |
| Beta-damascone | 0.1 | Methyl heptenone | 1.0 |
| Dihydromyrcenol | 0.5 | Nerol 900 | 1.0 |
| Dipropylene glycol | 3.4 | Orange oil | 3.0 |
| Elemi Absolute | 3.0 | Orsolate | 0.5 |
| Ethyl vanillin | 0.1 | Pentalide | 1.0 |
| Eucalyptus oil | 0.5 | Phenylethyl phenylacetate | 0.5 |
| Galaxolide 50 benzyl benzoate | 12.0 | Phenylethyl alcohol | 1.0 |
| Gardamide | 0.3 | Pineapple base | 1.0 |
| Geranyl nitrile | 1.0 | Polysantole | 0.5 |
| Grapefruit oil | 5.5 | Rhubafuran | 0.5 |
| Hedione | 3.5 | Santalinol | 0.5 |
| Helional | 1.0 | Sweetie oil | 2.0 |
| Cis-3-hexenol | 0.1 | Terpineol | 3.0 |
| Cis-3-hexenyl isobutyrate | 0.1 | Tetrahydro muguol | 0.5 |
| Hexyl cinnamic aldehyde | 2.0 | Tonalide | 8.0 |
| Trans-2-hexenol | 0.2 | Total | 100.0 |

Formulation Example 32

Anti-Perspirant Lotion Composition

| Components | wt. % |
|---|---|
| 1. Aluminumhydroxychloride | 5.0 |
| 2. POE(15) POP(5) cetyl ether phosphate | 5.0 |
| 3. Purified water | 5.0 |
| 4. Talc | 0.4 |
| 5. Regular spherical shape silica | 0.4 |
| 6. Smectite | 0.4 |
| 7. Nylon powder | 0.4 |
| 8. Polyethylene powder | 0.4 |
| 9. Decamethyl cyclopentasiloxane | 1.0 |
| 10. SH 556 *43) | 1.0 |
| 11. Silicone compound No. 13 | 1.0 |
| 12. Triclosan | 0.1 |
| 13. Betula alba extract | 0.1 |
| 14. Rosemary extract | 0.1 |
| 15. Perfume | 1.0 |
| 16. Ethanol | bal. |

Note
*43) Phenyl trimethicone

Manufacturing Method

A: Components 9 to 16 are mixed and dissolved, and formed into a uniform liquid.

B: Components 1 to 3 are mixed and dissolved therein.

C: Furthermore, components 4 to 8 are mixed thoroughly and dispersed uniformly.

Effects

A transparent, uniform liquid agent can be obtained and, therefore, AP active components and the like do not separate and stability over time of the anti-perspirant lotion composition is excellent. Anti-perspirant effects are expressed rapidly, immediately after application to the skin. After application, a sensation of tightness or stretching caused by evaporation of the ethanol is suppressed, and a fresh, natural feeling on the skin, free of stickiness, is provided.

Formulation Example 33

W/O Emulsion-Type Skin External Use Preparation

| Components | wt. % |
|---|---|
| 1. Dimethylpolysiloxane (20 cst) | 10.0 |
| 2. Dimethylpolysiloxane (2 cst) | 20.0 |
| 3. Silicone compound No. 13 | 2.0 |
| 4. Ethanol | 20.0 |
| 5. Diisopropylamine dichloroacetate | 0.2 |
| 6. Purified water | 47.8 |

Manufacturing Method

A: Components 1 to 3 were heated and agitated at 70° C. and dissolved.

B: Separately, components 4 to 6 were mixed and formed into a solution. The solution was heated to 70° C.

C: B is added in small amounts while holding the temperature of A at 70° C. and mixing uniformly. Then, while agitating, the mixture is cooled to 30° C. Thus a W/O emulsion-type skin external use preparation is obtained.

Effects

As a result of compounding the silicone compound No. 13, an accelerated transdermal absorption rate of the diisopropylamine dichloroacetate (bioactive substance) is expected. Additionally, heightened medicinal efficacy of the bioactive component itself is expected due to the bioactive component being transdermally absorbed.

Formulation Example 34

Nonaqueous Anti-Perspirant Deodorant Stick Composition

| Components | wt. % |
|---|---|
| 1. Stearyl alcohol | 25.0 |
| 2. Behenyl alcohol | 0.5 |
| 3. Hydrogenated castor oil | 4.0 |
| 4. Polypropylene glycol (average molecular weight: 1,000) | 7.0 |
| 5. PPG-14 butyl ether | 1.0 |
| 6. Decamethyl cyclopentasiloxane | 33.0 |
| 7. Silicone compound No. 15 | 4.5 |
| 8. Aluminum-zirconium-tetrachlorohydrate-glycine | 25.0 |

Manufacturing Method

A: Components 1 to 3 and components 6 and 7 are dissolved by heating and agitating at 80° C.

B: A temperature of 65° C. is maintained and components 4 and 5 are added and dissolved while agitating.

C: A temperature of 65° C. is maintained and component 8 is added and dispersed uniformly by agitating.

D: The mixture is poured into a container and then allowed to solidify at room temperature.

Effects

The nonaqueous anti-perspirant deodorant stick composition can be applied to the skin smoothly and without resistance, and a pleasant, natural sensation during use can be obtained because a film thereof is free of stickiness and an appropriate degree of moisturizing feel is provided. White residue is, for the most part, unnoticeable after drying. Moreover, the durability of the anti-perspirant effects is excellent.

Formulation Example 35

W/O Solid Anti-Perspirant Stick Composition

| Components | wt. % |
|---|---|
| 1. Dimethylpolysiloxane (2 cst) | 22.5 |
| 2. $C_{12-15}$ alkyl benzoate | 12.5 |
| 3. Polydecene | 11.3 |
| 4. Silicone compound No. 15 | 1.9 |
| 5. β-sitosterol | 2.4 |
| 6. γ-oryzanol | 2.4 |
| 7. Aluminum-zirconium-pentachlorohydrate | 18.8 |
| 8. Purified water | 18.8 |
| 9. Glycerin | 9.4 |

Manufacturing Method

A: Components 1 to 4 are dissolved by heating and agitating at 80° C.

B: A temperature of 80° C. is maintained and components 5 and 6 are subsequently added and dissolved while agitating.

C: Separately, components 7 to 9 are mixed and dissolved and, thereafter, the mixture is heated to 65° C.

D: C is added in small amounts while holding the temperature of B at 65° C. and agitating.

E: After allowing the mixture to rest and performing degassing, the mixture is poured into a container and allowed to solidify at room temperature.

Effects

The W/O solid anti-perspirant stick composition has a semi-transparent, high-quality appearance and appropriate stick hardness. The sensation of application is extremely smooth and refreshing, and the durability of the anti-perspirant effects is excellent. Moreover, after application, there is no white residue.

Formulation Example 36

W/O Emulsion Type Anti-Perspirant Cream Composition

| Components | wt. % |
|---|---|
| 1. Mineral oil | 4.0 |
| 2. Cetearyl alcohol | 4.7 |
| 3. Glyceryl stearate | 2.0 |
| 4. PEG-20 stearate | 1.2 |
| 5. Silicone compound No. 15 | 1.5 |
| 6. Phenoxyethanol | 0.4 |
| 7. Titanium oxide | 0.2 |
| 8. Glycerin | 6.0 |
| 9. Aluminum-zirconium tetrachlorohydrex glycine | 15.0 |
| 10. Purified water | 65.0 |

Manufacturing Method

A: Components 1 to 6 are dissolved by heating and agitating at 80° C.

B: A temperature of 80° C. is maintained and component 7 is added while agitating and uniformly dispersed.

C: Separately, components 8 to 10 are mixed and dissolved and, thereafter, the mixture is heated to 65° C.

D: C is added in small amounts while holding the temperature of B at 65° C. and agitating.

Effects

The cream has a smooth, natural sensation of application that is free of discomfort. Balance between immediate effects and durability of anti-perspirant and moisturizing effects is excellent. The cream provides moisturization to the skin and restores elasticity. For the most part, there is no white residue after application.

Formulation Example 37

Mascara

| Components | wt. % |
|---|---|
| 1. FA4002 ID *44) | 19.0 |
| 2. Palmitic acid/dextrin ethylhexanoate | 8.0 |
| 3. Polyethylene wax | 3.5 |
| 4. Beeswax | 6.5 |
| 5. Lecithin | 0.5 |
| 6. SS-3408 *45) | 21.0 |
| 7. C11-12 Liquid isoparaffin | 19.0 |
| 8. Silicone compound No. 15 | 4.0 |
| 9. Iron oxide | 5.0 |
| 10. Aerosil RY200 *46) | 3.5 |
| 11. Talc | 10.0 |

Note
*44) Isododecane solution of (acrylates/polytrimethylsiloxy methacrylate) copolymer (active component: 40%)
Note
*45) Caprylyl methicone
Note
*46) Aerosil RY200 (manufactured by Nippon Aerosil Co., Ltd.): Hydrophobized silica Manufacturing Method A: Components 1 to 8 are mixed thoroughly and dissolved. As necessary, the mixture is heated to 40° C.

B: Components 9 to 11 are added to A and dispersed using a roller.

Effects

The mascara spreads easily, is free of stickiness and oiliness, has moisture resistance, water repellency, and anti-perspirant properties, and has excellent cosmetic retainability. The mascara also has superior stability, and does not vary with temperature or time.

Formulation Example 38

Aftershave Cream

| Components | wt. % |
|---|---|
| 1. SS-3408 *47) | 35.0 |
| 2. SS-2910 *48) | 2.9 |
| 3. Silicone compound No. 8 | 5.0 |
| 4. Polyethyleneglycol (molecular weight: 400) | 5.0 |
| 5. Sodium L-glutamate | 2.0 |
| 6. Allantoin | 0.1 |
| 7. Aloe extract | 0.1 |
| 8. Preservative | 0.1 |
| 9. Antioxidant | 0.1 |
| 10. Perfume | 0.7 |
| 11. Purified water | 49.0 |

Note
*47) Caprylyl methicone
Note
*48) Polyether-modified silicone

Manufacturing Method

A: Components 1 to 4 and component 10 are heated and mixed.

B: Components 5 to 9 and component 11 are heated and mixed.

C: B is added in small amounts to A and emulsified. Thus, an aftershave cream is obtained.

Effects

The aftershave cream has an appropriate viscosity and, therefore does not run when used, and also spreads easily and is free of stickiness. With the aftershave cream, irritation of the skin is minimal and, after application, a lasting moisturizing, but clean feel can be imparted. Additionally, the stability of the product is very excellent.

Formulation Example 39

Solid Foundation

| Components | wt. % |
|---|---|
| [Pigment portion] (38.2 wt. %) | |
| 1. Treated spherical titanium oxide (average primary particle size: 0.4 μm) *49) | 18.0 |
| 2. Treated iron oxide (mixture of black iron oxide, red iron oxide, and yellow iron oxide) *49) | 1.7 |
| 3. Treated talc *49) | 6.0 |
| 4. Treated mica *49) | 2.0 |
| 5. Nε-lauroyl-L-lysine | 3.5 |
| 6. Polyalkyl-methyl silsesquioxane (average primary particle size: 4 μm) | 5.0 |
| 7. Octyl silylated fine particulate titanium oxide (average primary particle size: 10 nm) | 2.0 |

| Components | wt. % |
|---|---|
| [Liquid portion] Volatile silicone (25 wt. %) | |
| 8. Decamethyl cyclopentasiloxane | 15.0 |
| 9. Methyl trimethicone | 10.0 |
| Polyol (6.5 wt. %) | |
| 10. 1,3-butylene glycol | 5.0 |
| 11. Maltitol | 1.0 |
| 12. Raffinose | 0.5 |
| Surfactant (2 wt. %) | |
| 13. Silicone compound No. 15 | 1.0 |
| 14. Sorbitan isostearate | 1.0 |
| Solid or paste-like oil agent (5 wt. %) | |
| 15. Paraffin | 5.0 |
| Purified water (12.7 wt. %) | |
| 16. Purified water | 12.7 |
| Oil agent (9.5 wt. %) | |
| 17. Dimethylpolysiloxane (6 cst) | 3.0 |
| 18. Methylphenylpolysiloxane | 2.0 |
| 19. Paramethoxy octyl cinnamate | 2.0 |
| 20. Propylene glycol dicaprylate | 2.0 |
| 21. Dipentaerythrityl hexahydroxystearate | 0.5 |
| Bioactive component | |
| 22. Cranberry extract | 1.0 |
| Preservative | |
| 23. Paraben | 0.1 |

Note
*49) Nε-lauroyl-L-lysine 5 wt. % treated pigment

Manufacturing Method

A: The oil-based liquid portion (components 8 to 9, components 13 to 15, components 17 to 21, and component 23) is uniformly mixed and dissolved at 80° C.

B: The pre-mixed and crushed pigment portion (components 1 to 7) is added thereto and uniformly dispersed at 80° C.

C: Then, the water-based liquid portion (components 10 to 12, component 16, and component 22) that was uniformly pre-mixed and dissolved at 80° C. is added to the mixture and emulsified and dispersed.

D: The obtained emulsion is degassed, pressed into a cosmetic receptacle, and set in a hermetic container. Thus, a solid foundation is obtained.

Effects

When applying, the solid foundation does not impart a feeling of dryness to the skin, and has superior compatibility with the skin. The solid foundation has reduced oiliness, and feels good when applied. Moreover cosmetic retainability is good. Stability of the formulation is also excellent and separation/agglomeration and the like does not easily occur.

Formulation Example 40

Daytime Use Skin-Lightening Cream

| Components | wt. % |
|---|---|
| 1. SS-2910 *50) | 1.0 |
| 2. Silicone compound No. 6 | 2.0 |
| 3. SH 556 *51) | 5.0 |
| 4. SS-3408 *52) | 6.0 |
| 5. Dimethylpolysiloxane (2 cst) | 6.0 |

-continued

| Components | wt. % |
|---|---|
| 6. Glycerin | 5.0 |
| 7. Dipropylene glycol | 10.0 |
| 8. Methyl paraoxy benzoic acid | 0.2 |
| 9. Sodium ascorbyl sulfate | 0.1 |
| 10. Sodium ascorbyl phosphate | 0.1 |
| 11. γ-aminobutyric acid | 0.1 |
| 12. Appleseed extract (antioxidizing agent) | 0.1 |
| 13. Sodium chloride | 0.9 |
| 14. Perfume | 0.1 |
| 15. Purified water | 63.4 |

Note
*50) Polyether-modified silicone
Note
*51) Phenyl trimethicone
Note
*52) Caprylyl methicone Manufacturing Method A: Components 1 to 5 are heated and dissolved at 60° C.
B: Components 6 to 15 are heated and dissolved at 60° C.
C: A is added to B while agitating and emulsifying/mixing is performed.
D: Next, the mixture is cooled to 30° C. while agitating, and a container is filled with the mixture. Thus, a daytime use skin-lightening cream is obtained.

Effects

The daytime use skin-lightening cream is free of discomfort such as a feeling of dryness when applying, spreads easily, and provides a superior moisturizing sensation during use. The moisturizing effect thereof is lasting and the skin does not become dry and coarse. The daytime use skin-lightening cream is prone to use as a cosmetic base.

Formulation Example 41

Sun Tanning Cream

| Components | wt. % |
|---|---|
| 1. SS-3408 | 12.0 |
| 2. Dimethylpolysiloxane (2 cst) | 3.0 |
| 3. Dimethylpolysiloxane (100 cst) | 5.0 |
| 4. Alkyl-modified silicone resin wax | 0.5 |
| 5. Silicone compound No. 10 | 2.2 |
| 6. Silicone compound No. 16 | 6.0 |
| 7. Palmitic acid | 0.2 |
| 8. Dimethyloctyl paraaminobenzoic acid | 0.5 |
| 9. 4-t-butyl-4'-methoxy-dibenzoylmethane | 0.5 |
| 10. Kaolin | 0.5 |
| 11. Red iron oxide | 0.2 |
| 12. Yellow iron oxide | 0.3 |
| 13. Black iron oxide | 0.1 |
| 14. Titanium oxide coated mica | 1.0 |
| 15. Sodium L-glutamate | 3.0 |
| 16. 1,3-butylene glycol | 5.0 |
| 17. Dioctadecyl dimethyl ammonium chloride | 0.1 |
| 18. Antioxidant | q.s. |
| 19. Preservative | q.s. |
| 20. Perfume | q.s. |
| 21. Purified water | bal. |

Manufacturing Method

A: Components 1 to 9 and components 18 and 19 are heated and dissolved.
B: Component 17 and a portion of component 21 are heated and agitated. Thereafter, components 10 to 14 are added and dispersed.
C: Components 15 and 16 and the remainder of component 21 are uniformly dissolved and mixed with B.
D: While agitating, C is added to A in small amounts and emulsified. Then, the mixture is cooled and component 20 is added. Thus, a sun tanning cream is obtained.

Effects

Not only does the sun tanning cream have superior stability in that it is free of variation such as separation or powder agglomeration due to temperature or the passing of time, but it also spreads easily and provides superior moisturizing feel.

Formulation Example 42

Polyol/O-Type Nonaqueous Emulsion Skin External Use Preparation

| Components | wt. % |
|---|---|
| 1. Dimethylpolysiloxane (20 cst) | 5.0 |
| 2. Dimethylpolysiloxane (2 cst) | 15.0 |
| 3. Liquid paraffin | 10.0 |
| 4. Cetyl 2-ethylhexanoate | 5.0 |
| 5. Silicone compound No. 16 | 3.0 |
| 6. Vitamin E | 0.1 |
| 7. Ascorbyl phosphate Mg | 0.2 |
| 8. Sodium chloride | 1.0 |
| 9. Glycerin | 25.0 |
| 10. 1,3-butylene glycol | 10.7 |
| 11. Dipropylene glycol | 25.0 |

Manufacturing Method

A: Components 1 to 6 were heated and agitated at 50° C. and dissolved.
B: Separately, components 7 to 11 were dissolved by agitating and mixing at 50° C.
C: B is added in small amounts while holding the temperature of A at 50° C. and mixing uniformly.

Then, while agitating, the mixture is cooled to 30° C. Thus a polyol/O-type nonaqueous emulsion skin external use preparation is obtained.

Effects

Because a stable emulsion of the nonaqueous system can be obtained, stability of the ascorbic acid derivative can be advantageously maintained and, as a result, it is expected that the benefits particular to vitamin C (the bioactive substance) will be displayed mildly and for an extended period of time on or within the skin.

Formulation Example 43

Polyol/O-Type Nonaqueous Emulsion Skin External Use Preparation

| Components | wt. % |
|---|---|
| 1. Dimethylpolysiloxane (20 cst) | 5.0 |
| 2. Dimethylpolysiloxane (2 cst) | 15.0 |
| 3. Liquid paraffin | 10.0 |
| 4. Cetyl 2-ethylhexanoate | 5.0 |
| 5. Silicone compound No. 16 | 3.0 |
| 6. Trisodium ascorbyl palmitate phosphate | 0.2 |
| 7. Vitamin E | 0.1 |
| 8. Sodium chloride | 1.0 |
| 9. Glycerin | 25.0 |
| 10. 1,3-butylene glycol | 10.7 |
| 11. Dipropylene glycol | 25.0 |

Manufacturing Method

A: Components 1 to 7 were heated and agitated at 50° C. and dissolved.

B: Separately, components 8 to 11 were dissolved by agitating and mixing at 50° C.

C: B is added in small amounts while holding the temperature of A at 50° C. and mixing uniformly.

Then, while agitating, the mixture is cooled to 30° C. Thus a polyol/O-type nonaqueous emulsion skin external use preparation is obtained.

Effects

Because a stable emulsion of the nonaqueous system can be obtained, stability of the trisodium ascorbyl palmitate phosphate can be advantageously maintained and, as a result, it is expected that effective transdermal absorption of the external use preparation will be obtained due to the properties particular to the substance, and that the benefits particular to vitamin C (the bioactive substance) will be displayed mildly and for an extended period of time on or within the skin.

The invention claimed is:

1. A co-modified organopolysiloxane having a group with a siloxane dendron structure and a hydrophilic group, expressed by the following general formula (1);

General Formula (1):

wherein, $R^1$ is a monovalent organic group with the exception of groups corresponding to $L^1$ or Q, or a hydrogen atom;

$L^1$ is a silylalkyl group having a siloxane dendron structure expressed by the following general formula (2) when i=1;

General Formula (2):

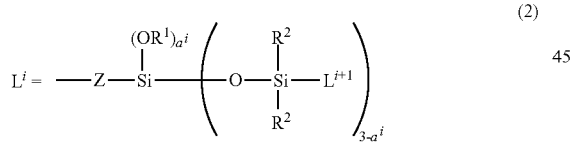

wherein, $R^1$ is synonymous with the group described above, $R^2$ is a phenyl group or an alkyl group having from 1 to 6 carbons, and Z is a divalent organic group; i represents a generation of the silylalkyl group represented by $L^i$, and is an integer of 1 to c when c is a number of generations that is a number of repetitions of the silylalkyl group, the number of generations c is an integer from 1 to 10, and $L^{i+1}$ is the silylalkyl group when i is less than c and is a methyl group or a phenyl group when i=c; $a^i$ is a number in a range of 0 to 3;

Q is a hydrophilic group derived from a hydrophilic compound selected from polyhydric alcohols comprising glycerin or polyglycerines, said hydrophilic group bonded to the silicon atom via a linking group that is at least divalent, and comprises at least one hydrophilic unit selected from hydrophilic units expressed by the following structural formulae (3-2) to (3-4):

wherein W is a hydrogen atom or an alkyl group having from 1 to 20 carbons;

wherein W is synonymous with the group described above; and

wherein a, b, and c are in a range so that $1.0 \leq a \leq 2.5$, $0.001 \leq b \leq 1.5$, and $0.001 \leq c \leq 1.5$.

2. The co-modified organopolysiloxane according to claim 1, wherein in the general formula (1), $L^1$ is a functional group expressed by the following general formula (2-1) or general formula (2-2):

General Formula (2-1):

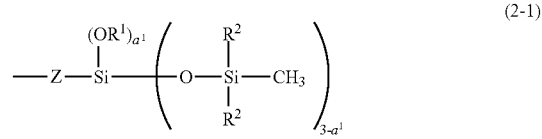

General Formula (2-2):

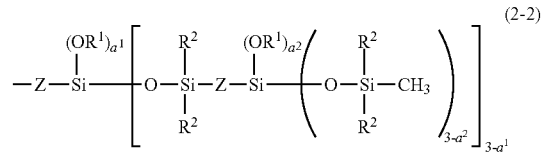

wherein $R^1$, $R^2$, and Z are synonymous with the groups described above, and $a^1$ and $a^2$ are each independently numbers in a range of 0 to 3.

3. The co-modified organopolysiloxane according to claim 1, expressed by structural formula (1-1) below,

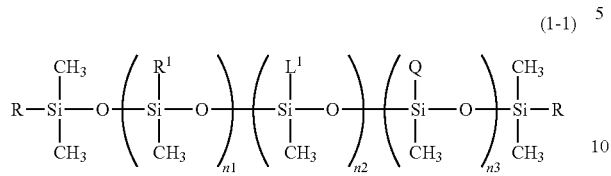
(1-1)

wherein $R^1$, $L^1$, and Q are groups that are synonymous with those described above, R is a group selected from $R^1$, $L^1$, and Q; however, when n2=0, at least one R is $L^1$; and when n3=0, at least one R is Q; (n1+n2+n3) is a number in a range from 3 to 2,000; and n1, n2, and n3 are numbers in a range from 0 to 2,000.

4. The co-modified organopolysiloxane according to claim 1, expressed by structural formula (1-1-1) or (1-1-2) below,

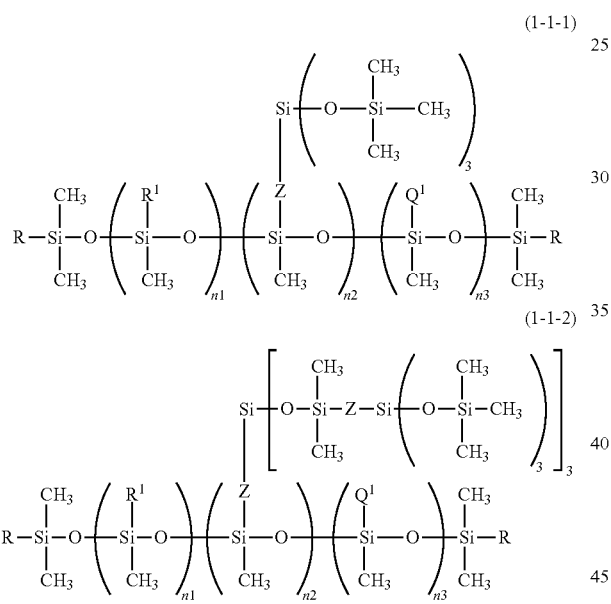
(1-1-1)
(1-1-2)

wherein Z and $R^1$ are groups that are synonymous with those described above; R is a group selected from $R^1$, the $L^1$, and $Q^1$, described hereinafter; n1 is a number in a range from 10 to 1,000; n2 is a number in a range from 0 to 250; n3 is a number in a range from 0 to 250; however, when n2=0, at least one R is $L^1$; and when n3=0, at least one R is $Q^1$;

$Q^1$ are each independently a hydrophilic group selected from the group consisting of structural formulae (4-1-2), (4-2-2), (4-3-2), and (4-4-2) below:

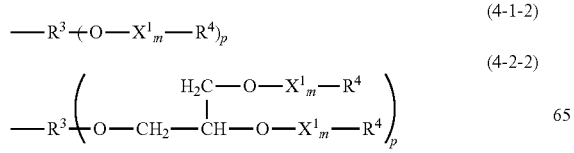
(4-1-2)
(4-2-2)

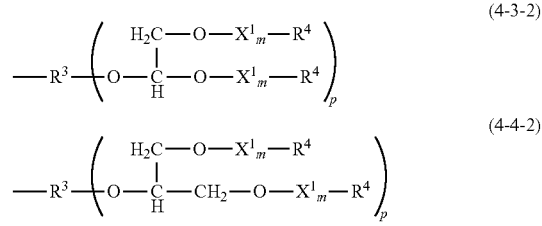
(4-3-2)
(4-4-2)

wherein $R^3$ is an organic group having (p+1) valency, and p is a number that is greater than or equal to 1 and less than or equal to 3; $X^1$ are each independently at least one hydrophilic unit selected from the hydrophilic units expressed by the general formulae (3-2) to (3-4) above, and m is a number in a range of 1 to 100; and $R^4$ is a hydrogen atom or a group selected from the group consisting of glycidyl groups, acyl groups, and alkyl groups having from 1 to 20 carbons.

5. The co-modified organopolysiloxane according to claim 4, wherein in the structural formula (1-1-1) or (1-1-2), Z are each independently a group selected from divalent organic groups expressed by general formulae (5-1) to (5-7) below:

(5-1)
(5-2)
(5-3)
(5-4)
(5-5)
(5-6)
(5-7)

wherein, $R^6$ may have a substituent, and are each independently a straight or branched chain alkylene group or alkenylene group having from 2 to 22 carbons, or an arylene group having from 6 to 22 carbons; and $R^7$ is a group selected from divalent organic groups expressed by the following formulae:

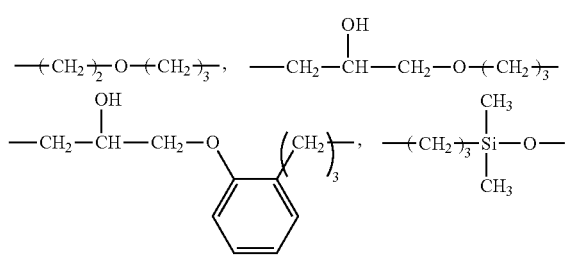

-continued

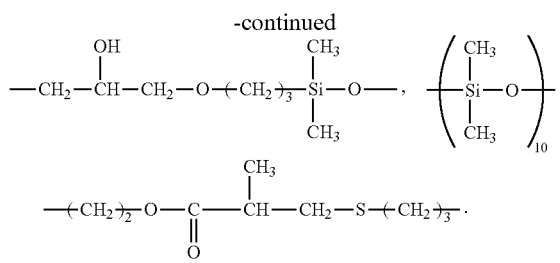

6. The co-modified organopolysiloxane according to claim 4, wherein in the structural formulae (4-1-2), (4-2-2), (4-3-2), and (4-4-2), p is 1 and $R^3$ is a group selected from divalent organic groups expressed by general formula (5-1), (5-1-2), (5-1-3), or (5-2) below:

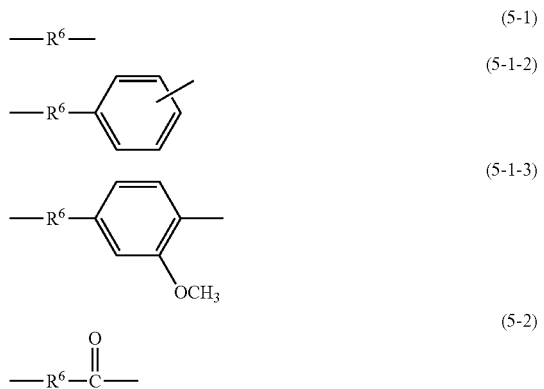

wherein, $R^6$ may have a substituent, and are each independently a straight or branched chain alkylene group or alkenylene group having from 2 to 22 carbons, or an arylene group having from 6 to 22 carbons.

7. A surfactant comprising the co-modified organopolysiloxane described in claim 1.

8. An emulsion composition comprising: (A) the co-modified organopolysiloxane described in claim 1, (B) water, and (C) at least one oil agent selected from silicone oil, hydrocarbon oil, or ester oil that is a liquid at from 5 to 100° C.

9. A method of adjusting transparency of the emulsion composition described in claim 8, comprising independently mixing an aqueous phase including the component (B) and an oil phase including the component (A) and the component (C) and, thereafter, adjusting a difference between refractive indexes at 25° C. of both phases so as to be less than or equal to 0.0020 units, and emulsifying.

10. A powder treatment agent comprising the co-modified organopolysiloxane described in claim 1.

11. A powder composition comprising: (A) the co-modified organopolysiloxane described in claim 1, and (D) a powder or a powdered colorant.

12. The powder composition according to claim 11, wherein the component (D) is one or two or more selected from the group consisting of an inorganic pigment powder, an organic pigment powder, and a resin powder, having an average diameter in a range of 1 nm to 20 μm.

13. A powder in oil dispersion comprising: (A) the co-modified organopolysiloxane described in claim 1, (D) a powder or a powdered colorant, and (C) at least one oil agent selected from a silicone oil, a nonpolar organic compound, or a low polarity organic compound, that is a liquid at from 5 to 100° C.

14. A topical composition comprising the co-modified organopolysiloxane described in claim 1.

15. A cosmetic composition comprising the emulsion composition described in claim 8.

16. A cosmetic composition comprising the powder composition described in claim 11.

17. A cosmetic composition comprising the powder in oil dispersion described in claim 13.

18. A substantially water-free cosmetic composition comprising: the co-modified organopolysiloxane described in claim 1, and an oil agent.

19. The topical composition according to claim 14 as a cosmetic composition, further comprising: at least one selected from the group consisting of (E) a polyhydric alcohol or a lower monohydric alcohol, (F) an inorganic salt or an organic salt, and (G) a silicone-based surfactant different than the co-modified organopolysiloxane component (A).

20. The topical composition according to claim 14 as a cosmetic composition, further comprising: (H) at least one selected from the group consisting of a crosslinking organopolysiloxane, an organopolysiloxane elastomer spherical powder, a silicone resin, an acryl silicone dendrimer copolymer, a silicone raw rubber, a polyamide-modified silicone, an alkyl-modified silicone wax, and an alkyl-modified silicone resin wax.

21. The topical composition according to claim 14 as a cosmetic composition, further comprising: (J) one or two or more selected from the group consisting of an anionic surfactant, a cationic surfactant, a nonionic surfactant with the exception of silicone-based surfactants, an amphoteric surfactant, and a semipolar surfactant.

22. The topical composition according to claim 14 as a cosmetic composition, further comprising: (K) a water-soluble polymer or (L) an ultraviolet light blocking component.

23. A method of manufacturing the co-modified organopolysiloxane described in claim 1, wherein the co-modified organopolysiloxane is obtained by reacting at least: (a) an organohydrogensiloxane expressed by general formula (1') below:

wherein $R^1$, a, b, and c are the same as described above; (b) a hydrophilic derivative having one reactive unsaturated group in the molecule; and (c) a siloxane dendron having one reactive unsaturated group in the molecule; in the presence of a hydrosilylation reaction catalyst.

24. The method of manufacturing a co-modified organopolysiloxane according to claim 23, wherein (b) the hydrophilic derivative having one reactive unsaturated group in the molecule, (c) the siloxane dendron having one reactive unsaturated group in the molecule, and (a) the organohydrogensiloxane expressed by the general formula (1') are reacted together, while the component (b) and the component (c) are at least in a state of coexistence.

25. The method of manufacturing a co-modified organopolysiloxane according to claim 23, wherein: (c) the siloxane dendron having one reactive unsaturated group in the molecule is a compound expressed by general formula (2') below that has a siloxane dendron structure having one carbon-carbon double bond at a molecular terminal:

(General Formula (2')):

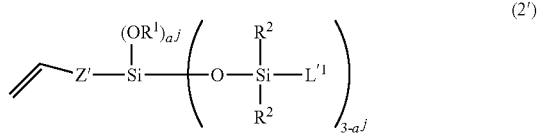

wherein, $R^1$ is a group that is synonymous with that described above, $L^{i1}$ is a methyl group or, when j=1, is a silylalkyl group expressed by general formula (2″) below, and Z′ is a divalent organic group;

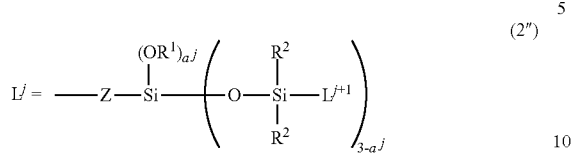

(2″)

wherein, $R^1$ is synonymous with the group described above, $R^2$ is a phenyl group or an alkyl group having from 1 to 6 carbons, and Z is a divalent organic group; j represents a generation of the silylalkyl group represented by $L^j$ and is an integer of 1 to c′ when c′ is a number of generations that is a number of repetitions of the silylalkyl group, the number of generations c′ is an integer from 1 to 10, and $L^{j+1}$ is the silylalkyl group when j is less than c′ and is a methyl group or a phenyl group when j=c′; and $a^j$ is a number in a range of 0 to 3.

* * * * *